(12) United States Patent
Berndt et al.

(10) Patent No.: US 9,238,631 B2
(45) Date of Patent: Jan. 19, 2016

(54) RADIOLABELED AMINO ACIDS FOR DIAGNOSTIC IMAGING

(75) Inventors: Mathias Berndt, Berlin (DE); Andre Muller, Berlin (DE); Heribert Schmitt-Willich, Berlin (DE); Timo Stellfeld, Berlin (DE); Georg Kettschau, Berlin (DE); Thomas Brumby, Berlin (DE); Keith Graham, Berlin (DE); Lutz Lehmann, Berlin (DE); Jorma Haβfeld, Dusseldorf (DE); Martin Kruger, Berlin (DE)

(73) Assignee: PIRAMAL IMAGING SA, Matran (CH)

( * ) Notice: Subject to any disclaimer, the term of this patent is extended or adjusted under 35 U.S.C. 154(b) by 0 days.

(21) Appl. No.: 14/115,471

(22) PCT Filed: Apr. 30, 2012

(86) PCT No.: PCT/EP2012/057925
§ 371 (c)(1),
(2), (4) Date: Apr. 2, 2014

(87) PCT Pub. No.: WO2012/150220
PCT Pub. Date: Nov. 8, 2012

(65) Prior Publication Data
US 2015/0011773 A1    Jan. 8, 2015

(30) Foreign Application Priority Data

May 3, 2011   (EP) ..................................... 11075076

(51) Int. Cl.
| | | |
|---|---|---|
| A61K 31/44 | (2006.01) |
| C07D 213/72 | (2006.01) |
| C07D 249/06 | (2006.01) |
| A61K 51/04 | (2006.01) |
| C07B 59/00 | (2006.01) |
| C07C 229/36 | (2006.01) |
| C07C 229/42 | (2006.01) |
| C07C 271/22 | (2006.01) |
| C07C 309/73 | (2006.01) |
| C07D 213/55 | (2006.01) |
| C07D 213/61 | (2006.01) |
| C07D 213/65 | (2006.01) |
| C07D 319/06 | (2006.01) |
| C07C 229/24 | (2006.01) |
| C07D 213/69 | (2006.01) |

(52) U.S. Cl.
CPC .......... *C07D 249/06* (2013.01); *A61K 51/0406* (2013.01); *C07B 59/00* (2013.01); *C07C 229/24* (2013.01); *C07C 229/36* (2013.01); *C07C 229/42* (2013.01); *C07C 271/22* (2013.01); *C07C 309/73* (2013.01); *C07D 213/55* (2013.01); *C07D 213/61* (2013.01); *C07D 213/65* (2013.01); *C07D 213/69* (2013.01); *C07D 319/06* (2013.01); *C07B 2200/05* (2013.01); *C07C 2101/04* (2013.01)

(58) Field of Classification Search
None
See application file for complete search history.

(56) References Cited

U.S. PATENT DOCUMENTS

| 2011/0064673 A1 | 3/2011 | Dinkelborg et al. |
| 2011/0104057 A1 | 5/2011 | Dinkelborg et al. |

FOREIGN PATENT DOCUMENTS

| WO | 2009141079 A1 | 11/2009 |
| WO | 2009141090 A1 | 11/2009 |

OTHER PUBLICATIONS

Lewis, Richard, "Hawley's Condensed Chemical Dictionary," 14th ed., NY John Wiley, 2002, on-line edition, excerpt.*
International Search Report and Written Opinion from PCT/EP2012/057925 dated Jul. 31, 2012.

\* cited by examiner

*Primary Examiner* — Heidi Reese
(74) *Attorney, Agent, or Firm* — Millen, White, Zelano, Branigan, P.C.

(57) ABSTRACT

This invention relates to novel compounds suitable for labeling by $^{18}F$ and to the corresponding $^{18}F$ labeled compounds themselves, $^{19}F$-fluorinated analogs thereof and their use as reference standards, methods of preparing such compounds, compositions comprising such compounds, kits comprising such compounds or compositions and uses of such compounds, compositions or kits for diagnostic imaging by Positron Emission Tomography (PET).

28 Claims, 8 Drawing Sheets

RADIOLABELED AMINO ACIDS FOR DIAGNOSTIC IMAGING

FIELD OF INVENTION

This invention relates to novel compounds suitable for $^{18}$F-labeling and to the corresponding $^{18}$F-labeled compounds, $^{19}$F-fluorinated analogues thereof and their use as reference standards, methods for preparing $^{18}$F-labeled compounds, methods for preparing $^{19}$F-fluorinated analogues, compositions comprising such compounds and/or analogues, kits comprising such compounds and/or analogues, and uses of $^{18}$F-labeled compounds for Positron Emission Tomography (PET) imaging of proliferative diseases such as tumor.

BACKGROUND

Molecular imaging has the potential to detect disease progression or therapeutic effectiveness earlier than most conventional methods in the fields of oncology, neurology and cardiology. Of the several promising molecular imaging technologies having been developed as optical imaging and MRI. PET is of particular interest for drug development because of its high sensitivity and ability to provide quantitative and kinetic data.

For example, positron emitting isotopes include carbon, iodine, fluorine, nitrogen, and oxygen. These isotopes can replace their non-radioactive counterparts in target compounds to produce tracers that function biologically and are chemically identical to the original molecules for PET imaging, or can be attached to said counterparts to give close analogues of the respective parent effector molecule. Among these isotopes $^{18}$F is the most convenient labeling isotope due to its relatively long half life (110 min) which permits the preparation of diagnostic tracers and subsequent study of biochemical processes. In addition, its high β+ yield and low β+ energy (635 keV) are also advantageous.

The $^{18}$F-fluorination reaction is of great importance for $^{18}$F-labeled radiopharmaceuticals which are used as in vivo imaging agents targeting and visualizing diseases, e.g. solid tumours or diseases of brain. A very important technical goal in using $^{18}$F-labeled radiopharmaceuticals is the rapid preparation and administration of the radioactive compound due to the fact that the $^{18}$F isotopes have a half-life of about 110 minutes that is beneficial for clinical use on the one hand, but is challenging for production processes of such compounds on the other hand.

The best known example for PET imaging of diseases is 2-[$^{18}$F]fluorodeoxyglucose ([$^{18}$F]FDG), which is the most widely used PET radiopharmaceutical [J Nucl Med (1978), 19: 1154-1161].

However, a number of pitfalls and artifacts have been ascribed to FDG imaging and more continue to surface as the worldwide experience with FDG increases. Altered FDG uptake in muscles, brown adipose tissue, bone marrow, the urinary tract, and the bowel is demonstrated in a significant proportion of patients, which can hide underlying malignant foci or mimic malignant lesions (Seminars in Nuclear Medicine, 40, 283 (2010)). Although PET is a sensitive tool for detecting malignancy. FDG uptake is not tumor specific. It can also be seen in healthy tissue or in benign disease as inflammation or posttraumatic repair and could be mistaken for cancer. The experienced nuclear medicine physician mostly manages to differentiate malignant from non-malignant FDG uptake, but some findings may remain ambiguous (Euro. Radio., 16, 1054 (2006)).

The area most common for interpretative pitfalls with FDG is related to uptake in active skeletal muscle. Many benign conditions can cause high accumulation of FDG creating the potential for false positive interpretation. Such pitfalls include variable physiologic FDG uptake in the digestive tract, thyroid gland, skeletal muscle, myocardium, bone marrow, and genitourinary tract and benign pathologic FDG uptake in healing bone, lymph nodes, joints, sites of infection, and cases of regional response to infection and aseptic inflammatory response. In many instances, these physiologic variants and benign pathologic causes of FDG uptake can be specifically recognized and properly categorized; in other instances, such as the lymph node response to inflammation or infection, focal FDG uptake is non-specific (J. Nucl. Med. Tech. 33, 145 (2005), Radiographics, 19, 61 (1999), Seminars in Nuclear Medicine, 34, 122 (2004); 34, 56 (2004), J. Nucl. Med. 45, 695 (2004)).

To overcome at least some of these limitations of FDG, other adaptations of the tumor metabolism beyond enhanced glycolysis need to be exploited to provide an improved PET imaging agent for tumors. Tumors in general often have to cope with severe conditions of oxidative stress. Thiol containing molecules like the amino acid L-cysteine and the tripeptide glutathione (GSH) are the major cellular components to overcome these conditions and are consumed for detoxification of reactive oxygen species (ROS) and other electrophiles, such as chemotherapeutics. Thus, a continuous supply of GSH and its precursors are critical for cell survival and provide a selective advantage for tumor growth. L-Cysteine plays a key role as reactive oxygen species scavenger by itself and is the rate-limiting building block for GSH biosynthesis. In the blood the oxidized dimer L-cystine is the dominant form and the availability of L-cysteine is limited. However, L-cysteine can be efficiently provided to cells via the cystine/glutamate exchanger xCT (SLC7A11). Subsequently L-cystine is reduced inside the cells to yield two molecules of L-cysteine. An increased xCT expression is found in many tumors. The xCT transporter was first described by Bannai and Kitamura in 1980 as a Na$^+$-independent, high-affinity transporter for L-cystine and L-glutamate in human fibroblasts (J. Biol. Chem. 255 (1980) 2372-2376). It is a heteromeric amino acid transporter for anionic amino acids and the main transporter for L-cystine (Pflugers Arch 442 (2001) 286-296, Pflugers Arch 447 (2004) 532-542). It is important to note that the xCT transporter is not able to discriminate between its natural substrates L-cystine and L-glutamate for the inward directed transport (Neuropharmacology 46 (2004) 273-284). Radiolabeled amino acid derivatives targeting the xCT transporter have been described before. [$^{18}$F]fluoroalkyl- and [$^{18}$F]fluoroalkoxy-substituted glutamic acid derivatives are disclosed in WO2008052788, WO2009141091, WO2009141090. Furthermore, WO2009141090 comprises fluorobenzyl- and fluoropyridylmethyl-substituted glutamic acid derivatives.

As one example, 4-(3-[$^{18}$F]fluoropropyl)glutamic acid was shown to be a promising agent for tumor imaging (WO2009141091, example 4). A biodistribution study in A549 tumor bearing nude mice demonstrated very good tumor targeting (1.6% ID/g at 1 h post injection), Kidney (6.4% ID/g at 30 min post injection) and pancreas (8.5% ID/g at 30 min post injection) were found to be the non-tumor organs with highest tracer uptake. Beside $^{18}$F labeled glutamic acid derivatives, also $^{18}$F labeled cystine derivatives were investigated regarding the potential to target xCT activity in tumors (WO2010125068). However, it is well known, that the uptake of L-cystine is pH dependent, with less uptake at low pH as typically found in tumor environment. In contrast, uptake of glutamate and its derivatives via xCT is independent of pH (J Biol Chem 256 (1981) 5770-5772).

Due to the half life of $^{18}F$ isotope of about 110 min, an $^{18}F$ radiopharmaceutical demands a daily production. Key factor for successful routine use of such radiotracer are a robust and high yield radiosynthesis on the one hand and reliable and fast analytical methods for determination of radiochemical purity, specific activity and by-products. Well established analytical methods comprise liquid chromatography (e.g. HPLC, UPLC) using radiodetector and UV-detector.

A drawback of the most promising $^{18}F$ labeled xCt substrates described so for is a missing chromophor to enable a standard detection by UV detectors. To measure specific activity or presence of by-products, derivatization methods (e.g. pre-column derivatization, post-column derivatization) using for example OPA, ACCQ, Fmoc, Ninhydrin reagents can be used. However, a simple direct analysis of the radiopharmaceutical compositions would be advantageous.

Problem to be Solved

PET imaging agents for detection of proliferative diseases such as tumors are needed that:
Have high tumor uptake and retention,
Have no or minor uptake in non-tumor tissue,
Provide improved specificity, e.g regarding tumor vs. inflammation,
Is synthesized in a simple and robust way to enable widespread use inclusive standard quality control methods for safe and simple release of the radiopharmaceuticals.

$^{18}F$ labeled substrates of the xCT transporter systems described so for showed moderate to good tumor uptake, but:
Showed retention in non-tumor tissues (e.g. pancreas, kidneys) as well and/or
Demand special analytical methods to for determination of specific activity and detection of non-radioactive (and non-UV active) by-products.

The new compounds described herein are specific xCT transporter substrates (see Example 71). The new radiolabeled derivatives show high tumor uptake and retention (e.g $[^{18}F]$-1, $[^{18}F]$-12, $[^{18}F]$-41 and $[^{18}F]$-52) with high contrast due to favorable clearance and low uptake in healthy tissues. In contrast to FDG used for tumor imaging so far, compounds described herein demonstrate reduced uptake in inflammatory lesions and improved washout (see Example 80).

Another feature of the compounds described herein is the possibility of using relatively simple and straight forward analytical methods due to the chromophor of the arylene or heteroarylene moieties within the chemical structures of the compounds of the present invention.

SUMMARY

The present invention provides novel compounds of Formula I, Formula II, Formula III, Formula IV, Formula V and Formula VI.

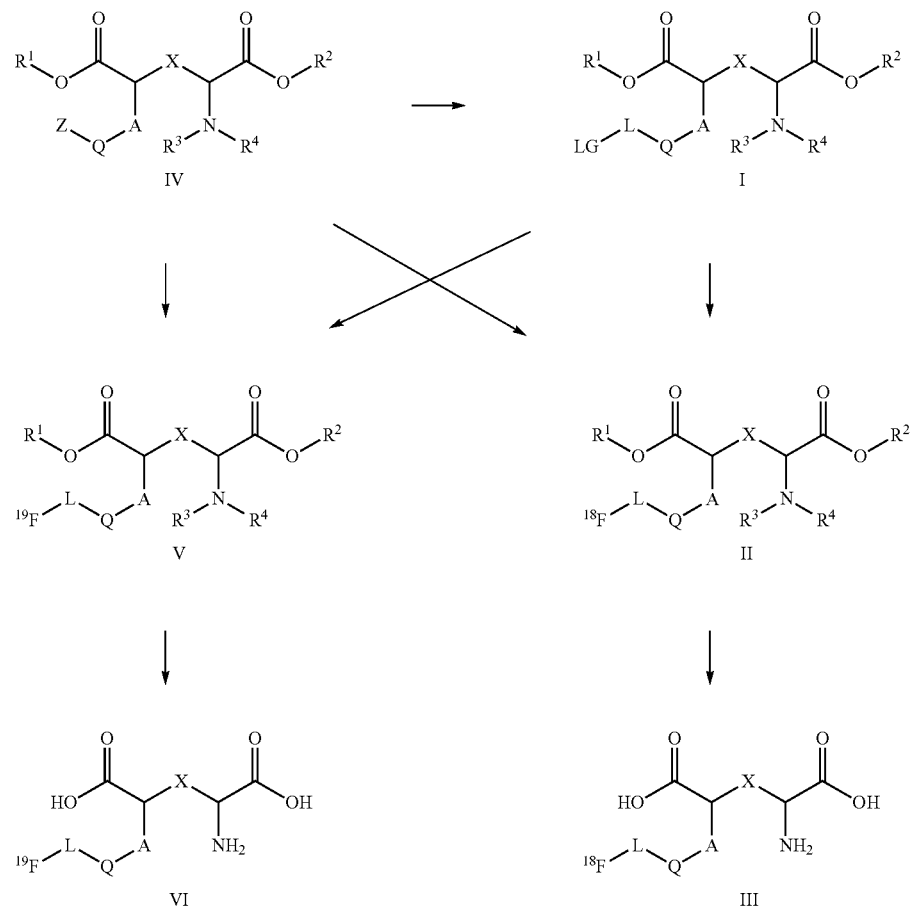

The invention furthermore provides a radiopharmaceutical composition of compounds of Formula III or pharmaceutically acceptable salts of an inorganic or organic acid or base thereof, hydrates, complexes, esters, amides, solvates and prodrugs thereof and optionally a pharmaceutically acceptable carrier, diluent, adjuvant or excipient.

The compounds of Formula III and Formula VI may exist as zwitterions. All forms of the compounds, including free acid, free-base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

The present invention also provides methods for manufacturing of compounds of Formula III:

Direct Method:

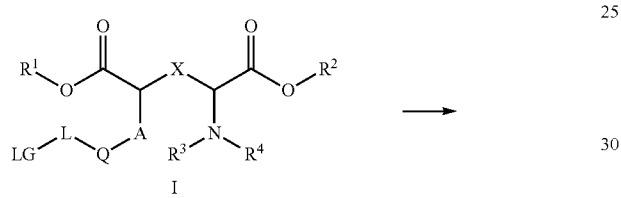

I

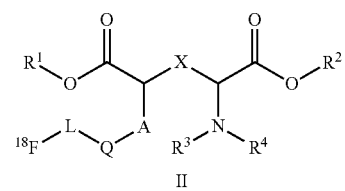

II

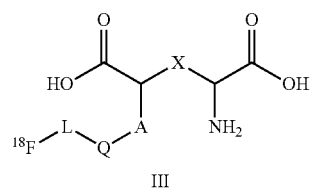

III $^{18}$F radiolabeling of compounds of Formula I to obtain compounds of Formula II, and Cleavage of protecting groups of compounds of Formula II to obtain compounds of Formula III.

Indirect Method:

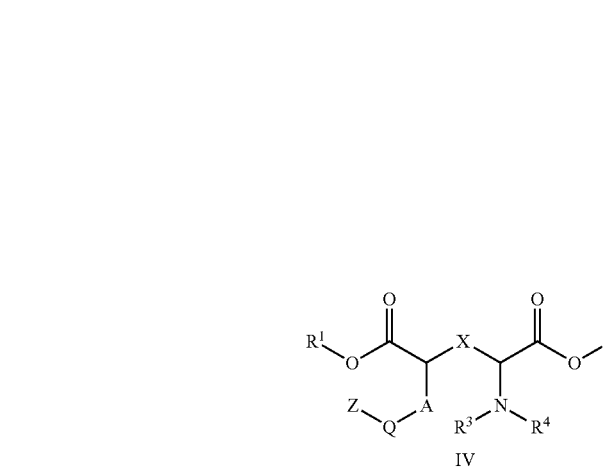

IV

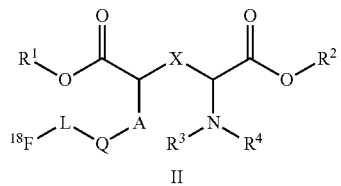

II if $R^1$ and $R^2$ and $R^3$ and $R^4$ are H

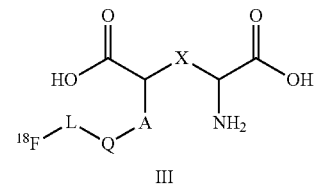

III

Reacting of compounds of Formula IV with a $^{18}$F radiolabeled building block, and Optionally, cleaving of protecting groups to obtain compounds of Formula III.

The present invention also provides methods for manufacturing of compounds of Formula VI:

Method 1:
$^{19}$F Fluorination of compounds of Formula I to obtain compounds of Formula V,
Cleavage of protecting groups of compounds of Formula V to obtain compounds of Formula VI.

Method 2:
Reacting of compound of Formula IV with a $^{19}$F fluorine reagent or $^{19}$F fluorinated building block,
Optionally, cleaving of protecting groups.

DETAILED DESCRIPTION

The first aspect of the present invention is directed to compounds of Formula I:

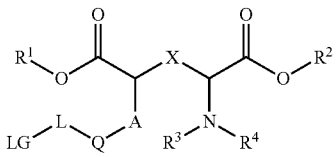

I wherein,
$R^1$ is a carboxyl protecting group,
$R^2$ is a carboxyl protecting group,
$R^3$ is hydrogen or an amine protecting group,
$R^4$ is hydrogen or an amine protecting group,
X is selected from the group comprising:
   a) $CH_2$,
   b) $CH_2$—$CH_2$,
   c) $CH_2$—$CH_2$—$CH_2$, and
   d) $CH_2$—$CH_2$—$CH_2$—$CH_2$.
A is alkylene.
Q is arylene or heteroarylene.
L is selected from the group comprising:
   a) alkylene,
   b) alkylene-O*,
   c) alkylene-N*H,
   d) cycloalkylene-O*,
   e) ($R^5$—O)-substituted alkylene,
   f) ($R^5$—O)-substituted alkylene-O*,
   g) ($R^6$—O), ($R^7$—O)-disubstituted alkylene,
   h) ($R^6$—O), ($R^7$—O)-disubstituted alkylene-O*, and
   i) $(CH_2CH_2O)_n$—$CH_2CH_2$—O* with n=1, 2 or 3,
* indicates the position of the bond to Q.
$R^5$ is
   a) hydrogen or
   b) hydroxyl protecting group,
$R^6$ is
   a) hydrogen or
   b) hydroxyl protecting group,
$R^7$ is
   a) hydrogen or
   b) hydroxyl protecting group,
LG is a leaving group, and
single isomers, tautomers, diastereomers, enantiomers, stereoisomers, stereoisomeric mixtures or mixtures thereof.

In a further embodiment, the invention is directed to compounds of Formula I:

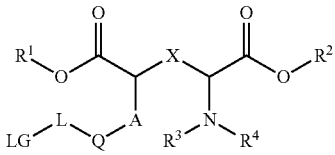

I wherein,
$R^1$ is a carboxyl protecting group,
$R^2$ is a carboxyl protecting group,
$R^3$ is hydrogen or an amine protecting group,
$R^4$ is hydrogen or an amine protecting group,
X is selected from the group comprising:
   a) $CH_2$,
   b) $CH_2$—$CH_2$, and
   c) $CH_2$—$CH_2$—$CH_2$.
A is alkylene.
Q is arylene or heteroarylene.
L is selected from the group comprising:
   a) alkylene,
   b) alkylene-O*,
   c) alkylene-N*H,
   d) cycloalkylene-O*,
   e) ($R^5$—O)-substituted alkylene,
   f) ($R^5$—O)-substituted alkylene-O*,
   g) ($R^6$—O), ($R^7$—O)-disubstituted alkylene,
   h) ($R^6$—O), ($R^7$—O)-disubstituted alkylene-O*, and
   i) $(CH_2CH_2O)_n$—$CH_2CH_2$—O* with n=1, 2 or 3,
* indicates the position of the bond to Q.
$R^5$ is
   a) hydrogen or
   b) hydroxyl protecting group,
$R^6$ is
   a) hydrogen or
   b) hydroxyl protecting group.
$R^7$ is
   a) hydrogen or
   b) hydroxyl protecting group.
LG is a leaving group, and
single isomers, tautomers, diastereomers, enantiomers, stereoisomers, stereoisomeric mixtures or mixtures thereof.

In a further embodiment, the invention is directed to compounds of Formula I:

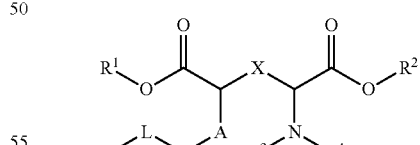

I wherein,
$R^1$ is a carboxyl protecting group,
$R^2$ is a carboxyl protecting group,
$R^3$ is hydrogen or an amine protecting group,
$R^4$ is hydrogen or an amine protecting group,
X is selected from the group comprising:
   a) $CH_2$, and
   b) $CH_2$—$CH_2$,
A is alkylene.
Q is arylene or heteroarylene.

L is selected from the group comprising:
a) alkylene,
b) alkylene-O*,
c) alkylene-N*H,
d) cycloalkylene-O*,
e) ($R^5$—O)-substituted alkylene,
f) ($R^5$—O)-substituted alkylene-O*,
g) ($R^6$—O), ($R^7$—O)-disubstituted alkylene,
h) ($R^6$—O), ($R^7$—O)-disubstituted alkylene-O*, and
i) $(CH_2CH_2O)_n$—$CH_2CH_2$—O* with n=1, 2 or 3,
* indicates the position of the bond to Q,
$R^5$ is
a) hydrogen or
b) hydroxyl protecting group,
$R^6$ is
a) hydrogen or
b) hydroxyl protecting group,
$R^7$ is
a) hydrogen or
b) hydroxyl protecting group,
LG is a leaving group, and
single isomers, tautomers, diastereomers, enantiomers, stereoisomers, stereoisomeric mixtures or mixtures thereof.

Preferred Features of Invention and Embodiments Thereof:

Preferably, $R^1$ is a carboxyl-protecting group selected from methyl, ethyl, propyl, butyl, tert-butyl, allyl, benzyl, 4-methoxybenzyl and 4-methoxyphenyl.

More preferably, $R^1$ is selected from the group comprising:
a) methyl,
b) ethyl, and
c) tert-butyl.

Even more preferably, $R^1$ is tert-butyl.

Preferably, $R^2$ is a carboxyl-protecting group selected from methyl, ethyl, propyl, butyl, tert-butyl, allyl, benzyl, 4-methoxybenzyl and 4-methoxyphenyl.

More preferably, $R^2$ is selected from the group comprising:
a) methyl,
b) ethyl, and
c) tert-butyl.

Even more preferably, $R^2$ is tert-butyl.

Preferably, $R^1$ and $R^2$ are identical.

Preferably, $R^3$ is hydrogen or an amine-protecting group.

The amine-protecting group is preferably carbobenzyloxy (Cbz), p-methoxybenzyl carbonyl (Moz or MeOZ), tert-butyloxycarbonyl (Boc), benzyl (Bn), p-methoxybenzyl (PMB), 3,4-dimethoxybenzyl (DMPM), p-methoxyphenyl (PMP), triphenylmethyl (Trityl) or methoxyphenyl diphenylmethyl (MMT).

Preferably $R^3$ is selected from the group comprising:
a) hydrogen,
b) tert-butyloxycarbonyl (Boc), and
c) triphenylmethyl (Trityl).

More preferably $R^3$ is selected from the group comprising:
a) tert-butyloxycarbonyl (Boc), and
b) triphenylmethyl (Trityl).

Preferably, Fe is hydrogen or an amine-protecting group.

The amine-protecting group is preferably carbobenzyloxy (Cbz), p-methoxybenzyl carbonyl (Moz or MeOZ), tert-butyloxycarbonyl (Boc), benzyl (Bn), p-methoxybenzyl (PMB), 3,4-dimethoxybenzyl (DMPM), p-methoxyphenyl (PMP), triphenylmethyl (Trityl) or methoxyphenyl diphenylmethyl (MMT).

Preferably $R^4$ is selected from the group comprising:
a) hydrogen,
b) tert-butyloxycarbonyl (Boc), and
c) triphenylmethyl (Trityl).

More preferably $R^4$ is selected from the group comprising:
a) tert-butyloxycarbonyl (Boc) and
b) triphenylmethyl (Trityl).

Additionally, $R^3$ and $R^4$ optionally form an amine-protecting group resulting in $NR^3R^4$ being 1,3-dioxo-1,3-dihydro-2H-isoindol-2-yl (phthalimido) or an azido group.

Preferably, $R^3$ is hydrogen and $R^4$ is an amine protecting group.

More preferably, $R^3$ is hydrogen and $R^4$ is tert-butyloxycarbonyl (Boc).

More preferably, $R^3$ is hydrogen and Fe is triphenylmethyl (Trityl).

Preferably, $R^3$ and $R^4$ are never Hydrogen at the same time.

Preferably, X is $CH_2$ or $CH_2$—$CH_2$.

More preferably, X is $CH_2$.

More preferably, X is $CH_2$—$CH_2$.

Preferably A is $C_1$-$C_6$ alkylene. More preferably, A is $C_1$-$C_3$ alkylene.

Even more preferably. A is methylene.

Even more preferably, A is ethylene.

Even more preferably, A is propylene.

Preferably, Q is phenylene, triazolylene or pyridylene.

Preferably, Q is phenylene or pyridylene.

More preferably, Q is phenylene.

More preferably, Q is pyridylene or triazolylene.

More preferably, Q is pyridylene.

Even more preferably, Q is a pyridylene as defined below

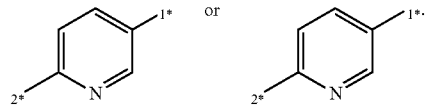

1* indicates the position of the bond to A and 2* indicates the position of the bond to L.

Preferably, L is selected from the group comprising:
a) $C_2$-$C_6$ alkylene,
b) $C_2$-$C_6$alkylene-O*,
c) $C_2$-$C_6$alkylene-N*H,
d) $C_3$-$C_6$cycloalkylene-O*,
e) ($R^5$—O)-substituted $C_2$-$C_6$alkylene,
f) ($R^5$—O)-substituted $C_3$-$C_6$alkylene-O*,
g) ($R^6$—O), ($R^7$—O)-disubstituted $C_3$-$C_6$alkylene,
h) ($R^6$—O), ($R^7$—O)-disubstituted $C_4$-$C_6$alkylene-O*, and
i) $(CH_2CH_2O)_n$—$CH_2CH_2$—O* with n=1, 2 or 3.
* indicates the position of the bond to Q.

More preferably, L is selected from the group comprising:
a) propylene,
b) propylene-O*,
c) ethylene-O*,
d) propylene-N*H,
e) cyclobutylene-O*,

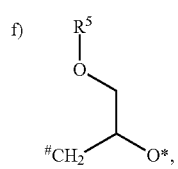

-continued g) 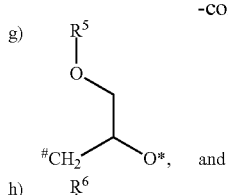 and h) 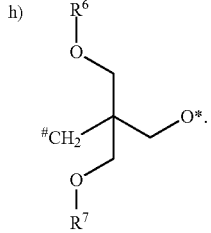

* indicates the position of the bond to Q and * indicates the position of the bond to LG.

If L is alkylene, L is preferably $C_1$ alkylene or linear or branched $C_2$-$C_6$ alkylene. More preferably, L is $C_2$-$C_3$ alkylene selected from ethylene and propylene.

Preferably, L is propylene.
Preferably, L is ethylene.
Preferably, L is methylene.

If L is alkylene-O* L is preferably $C_1$ alkylene-O* (methylene-O*) or linear or branched $C_2$-$C_6$ alkylene-O*. More preferably, L is $C_2$-$C_3$ alkylene-O* is selected from ethylene-O* and propylene-O*.

Preferably, L is propylene-O*.
Preferably, L is ethylene-O*.
Preferably, L is methylene-O*.

If L is alkylene-N*H L is preferably $C_1$ alkylene-N*H or linear or branched $C_2$-$C_6$ alkylene-N*H. More preferably, L is $C_2$-$C_3$ alkylene-N*H, selected from ethylene-N*H and propylene-N*H.

Preferably, L is propylene-N*H.
Preferably, L is ethylene-N*H.
Preferably, L is methylene-N*H.

"Alkylene" represents a linear or branched saturated bivalent chain of carbon atoms having 1 to 6, preferably 1 to 3 or 4 to 6, carbon atoms, by way of example and by preference methylene, ethylene and propylene. Preferably, alkylene is $C_1$ alkylene or $C_2$-$C_6$ alkylene. More preferably, alkylene is $C_2$-$C_3$ alkylene or $C_4$-$C_6$ alkylene.

The same applies to $C_2$-$C_6$alkylene-O* and $C_2$-$C_6$alkylene-NH*.

"Cycloalkylene" represents an alicyclic bivalent group of carbon atoms having 3 to 8, preferably 4 to 6, carbon atoms, by way of example and by preference cyclopropylene, cyclobutylene, cyclopentylene and cyclohexylene.

If L is cycloalkylene-O* L is preferably $C_3$-$C_6$ cycloalkylene-O* such as cyclopropylene-O*, cyclobutylene-O*, cyclopentylene-O* or cyclohexylene-O*.

Preferably, L is

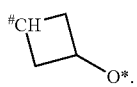

* indicates the position of the bond to LG.

If L is ($R^5$—O)-substituted $C_2$-$C_6$ alkylene, ($R^5$—O)-substituted $C_3$-$C_6$ alkylene-O*, ($R^6$—O), ($R^7$—O)-disubstituted $C_3$-$C_6$ alkylene, or ($R^6$—O), ($R^7$—O)-disubstituted $C_4$-$C_6$alkylene-O*, L is preferably an alkylene defined as above bearing one or two protected or unprotected hydroxyl groups.

Preferably, L is ($R^5$—O)-substituted $C_3$-$C_6$alkylene-O* selected from

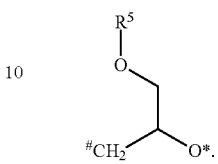

Preferably, L is ($R^6$—O), ($R^7$—O)-disubstituted $C_4$-$C_6$alkylene-O* selected from

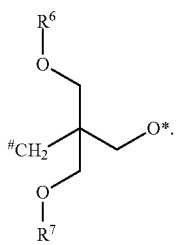

* indicates the position of the bond to Q, # indicates the position of the bond to LG.

Preferably, $R^5$ is a hydroxyl protecting group.
Preferably, $R^6$ and $R^7$ are hydroxyl protecting groups.
Additionally, $R^6$ and $R^7$ optionally form together one-diol protecting group.

Preferably, hydroxyl protecting group is selected from the group of t-butyl, benzyl, p-methoxybenzyl, p-nitrobenzyl, allyl, trityl, methoxymethyl, methoxyethoxymethyl, ethoxyethyl, 1-methyl-1-methoxyethyl, tetrahydropyranyl, trialkylsilyl; benzoyl, acetyl, and phenylacetyl. More preferably, hydroxyl protecting group is t-butyl.

Preferably LG is a leaving group selected from the group comprising:
a) sulfonate leaving group, and
b) halogen.

More Preferably LG is selected from the group comprising:
a) methylsulfonyloxy,
b) (4-methylphenyl)sulfonyloxy.

Even more preferably, LG is methylsulfonyloxy.
Even more preferably, LG is (4-methylphenyl)sulfonyloxy.

Compounds of Formula I are defined by the general formula and/or the combination of the preferred features as defined above.

In a first embodiment, compounds of the formula I are defined as compounds of Formula I-1, See structure in table A.

In a second embodiment, compounds of the formula I are defined as compounds of Formula I-2, See structure in table A.

In a third embodiment, compounds of the formula I are defined as compounds of Formula I-3, See structure in table A.

In a fourth embodiment, compounds of the formula I are defined as compounds of Formula I-4, See structure in table A.

In a fifth embodiment, compounds of the formula I are defined as encompassing single isomers or any mixture of at least two stereoisomers of Formula I-1, Formula I-2, Formula I-3 and Formula I-4 including racemates and diastereomeric mixtures.

Preferred features as disclosed above are incorporated herein for all embodiments.

TABLE A

Formula I stereoisomers

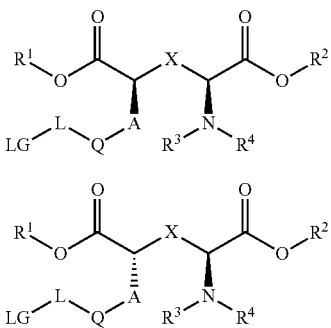

The compounds of Formula I-1, Formula I-2, Formula I-3 and, Formula I-4 furthermore encompass pharmaceutically acceptable salts of an inorganic or organic acid or base thereof, hydrates, complexes, esters, amides, and solvates thereof and optionally a pharmaceutically acceptable carrier, diluent, adjuvant or excipients.

A preferred compound of Formula I is di-tert-butyl N-(tert-butoxycarbonyl)-4-{4-[2-(tosyloxy)ethoxy]benzyl}glutamate:

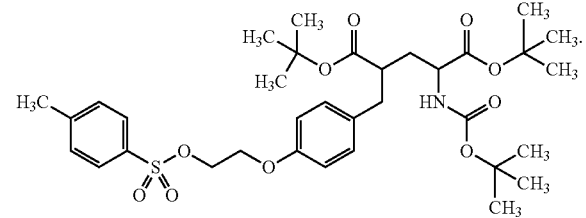

Another preferred compound of Formula I is di-tert-butyl N-(tert-butoxycarbonyl)-4-{4-[3-(tosyloxy)propoxy]benzyl}glutamate:

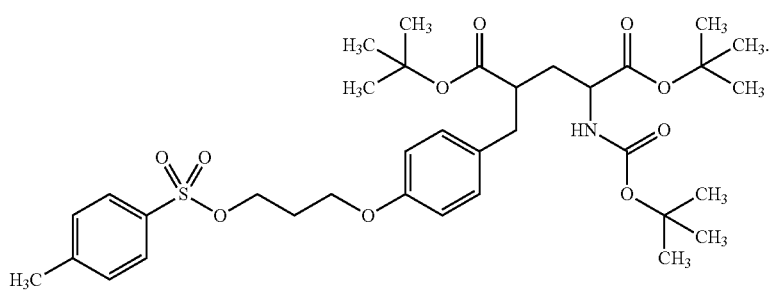 [SMILES: Cc1ccc(S(=O)(=O)OCCCOc2ccc(CC(CC(NC(=O)OC(C)(C)C)C(=O)OC(C)(C)C)C(=O)OC(C)(C)C)cc2)cc1]

Another preferred compound of Formula I is di-tert-butyl N-(tert-butoxycarbonyl)-4-{4-[3-(tosyloxy)propyl]benzyl}glutamate:

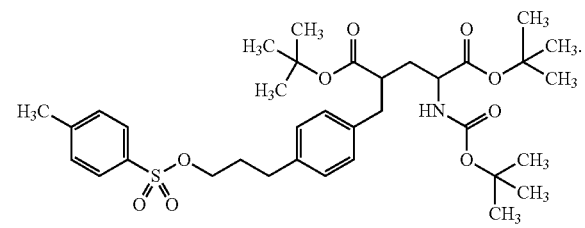 [SMILES: Cc1ccc(S(=O)(=O)OCCCc2ccc(CC(CC(NC(=O)OC(C)(C)C)C(=O)OC(C)(C)C)C(=O)OC(C)(C)C)cc2)cc1]

Another preferred compound of Formula I is di-tert-butyl N-(tert-butoxycarbonyl)-4-(4-{[3-(tosyloxy)propyl]amino}benzyl)glutamate:

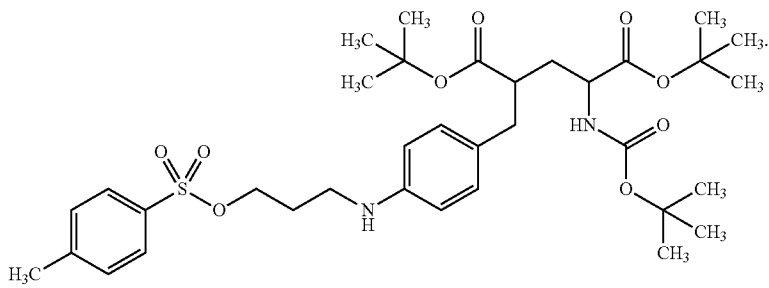 [SMILES: Cc1ccc(S(=O)(=O)OCCCNc2ccc(CC(CC(NC(=O)OC(C)(C)C)C(=O)OC(C)(C)C)C(=O)OC(C)(C)C)cc2)cc1]

Another preferred compound of Formula I is di-tert-butyl N-(tert-butoxycarbonyl)-4-(4-{[3-(tosyloxy)cyclobutyl]oxy}benzyl)glutamate:

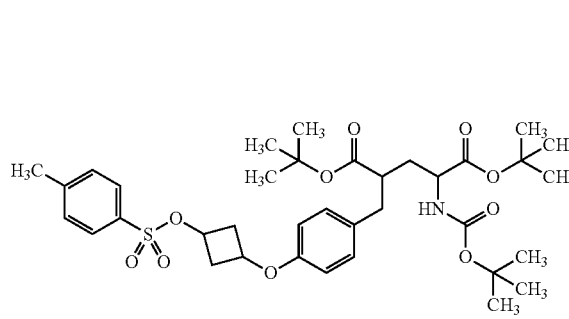

Another preferred compound of Formula I is di-tert-butyl N-(tert-butoxycarbonyl)-4-{4-[(1-hydroxy-3-{[(4-methylphenyl)sulfonyl]oxy}propan-2-yl)oxy]benzyl}glutamate:

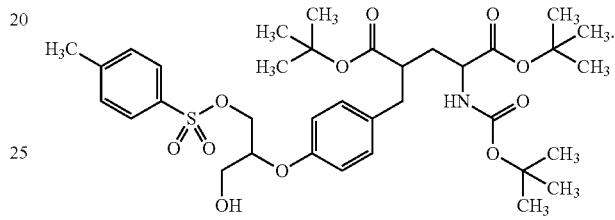

Another preferred compound of Formula I is di-tert-butyl N-(tert-butoxycarbonyl)-4-(3-{4-[2-(tosyloxy)ethoxy]phenyl}propyl)glutamate:

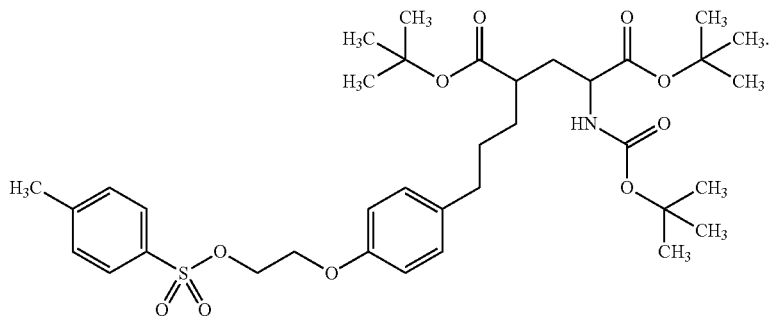 [SMILES: Cc1ccc(S(=O)(=O)OCCOc2ccc(CCCC(CC(NC(=O)OC(C)(C)C)C(=O)OC(C)(C)C)C(=O)OC(C)(C)C)cc2)cc1]

Another preferred compound of Formula I is di-tert-butyl N-(tert-butoxycarbonyl)-4-(3-{4-[3-(tosyloxy)propyl]phenyl}propyl)glutamate:

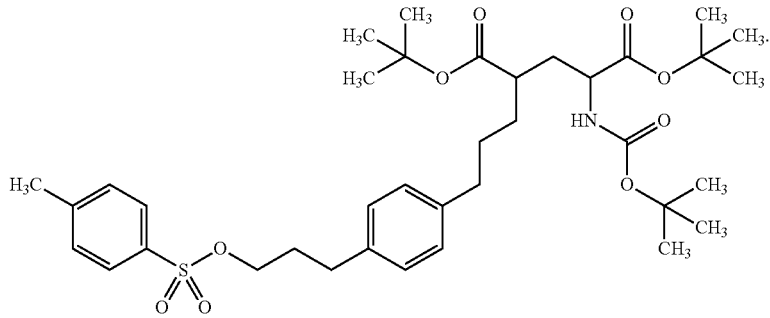 [SMILES: Cc1ccc(S(=O)(=O)OCCCc2ccc(CCCC(CC(NC(=O)OC(C)(C)C)C(=O)OC(C)(C)C)C(=O)OC(C)(C)C)cc2)cc1]

Another preferred compound of Formula I is di-tert-butyl 2-[(tert-butoxycarbonyl)amino]-5-{4-[2-(tosyloxy)ethoxy]benzyl}hexanedioate:

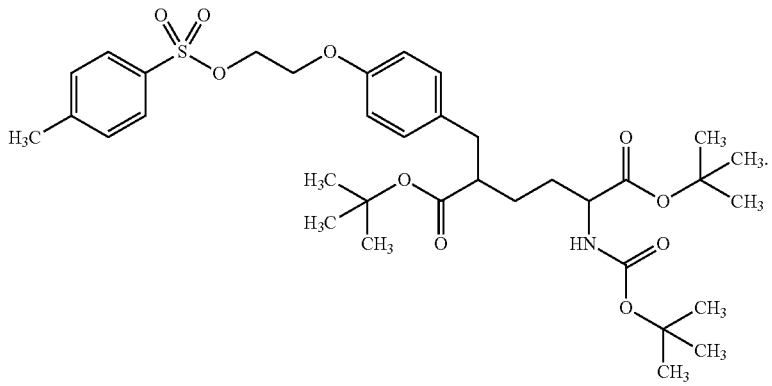 [SMILES: Cc1ccc(S(=O)(=O)OCCOc2ccc(CC(CCC(NC(=O)OC(C)(C)C)C(=O)OC(C)(C)C)C(=O)OC(C)(C)C)cc2)cc1]

Another preferred compound of Formula I is di-tert-butyl N-(tert-butoxycarbonyl)-4-({5-[3-(tosyloxy)propyl]pyridin-2-yl}methyl)-glutamate:

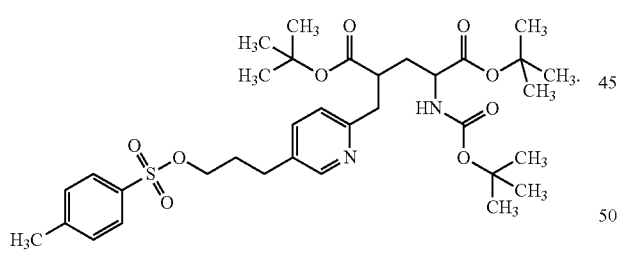

A more preferred compound of Formula I is di-tert-butyl (4S)—N-(tert-butoxycarbonyl)-4-{4-[2-(tosyloxy)ethoxy]benzyl}-L-glutamate:

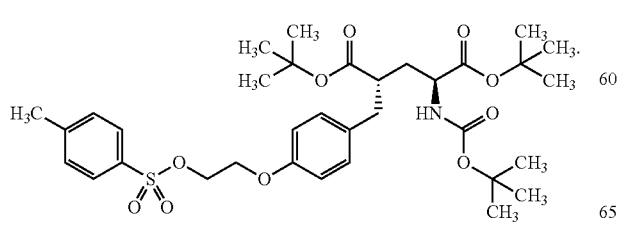

Another more preferred compound of Formula I is di-tert-butyl (4S)—N-(tert-butoxy-carbonyl)-4-{4-[3-(tosyloxy)propoxy]benzyl}-L-glutamate:

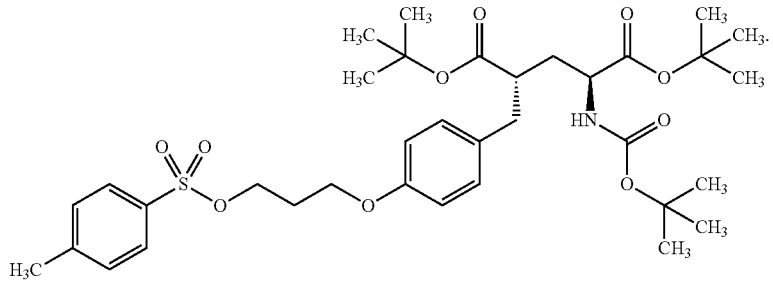 [SMILES: Cc1ccc(S(=O)(=O)OCCCOc2ccc(C[C@@H](C[C@H](NC(=O)OC(C)(C)C)C(=O)OC(C)(C)C)C(=O)OC(C)(C)C)cc2)cc1]

Another more preferred compound of Formula I is di-tert-butyl (4S)—N-(tert-butoxy-carbonyl)-4-{4-[3-(tosyloxy)propyl]benzyl}-L-glutamate:

Another more preferred compound of Formula I is di-tert-butyl (4S)—N-(tert-butoxy-carbonyl)-4-(4-{[3-(tosyloxy)propyl]amino}benzyl)-L-glutamate:

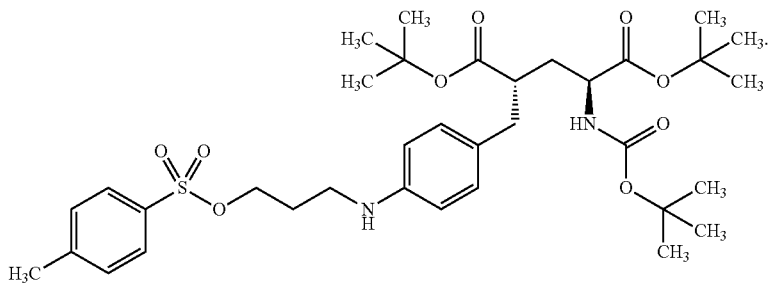 [SMILES: Cc1ccc(S(=O)(=O)OCCCNc2ccc(C[C@@H](C[C@H](NC(=O)OC(C)(C)C)C(=O)OC(C)(C)C)C(=O)OC(C)(C)C)cc2)cc1]

Another more preferred compound of Formula I is di-tert-butyl (4S)—N-(tert-butoxy-carbonyl)-4-(4-{trans-[3-(tosyloxy)cyclobutyl]oxy}benzyl)-L-glutamate:

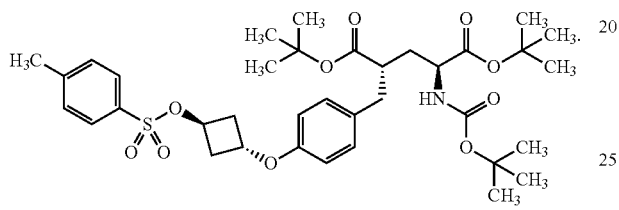

Another more preferred compound of Formula I is di-tert-butyl (4S)—N-(tert-butoxy-carbonyl)-4-(3-{4-[2-(tosyloxy)ethoxy]phenyl}propyl)-L-glutamate:

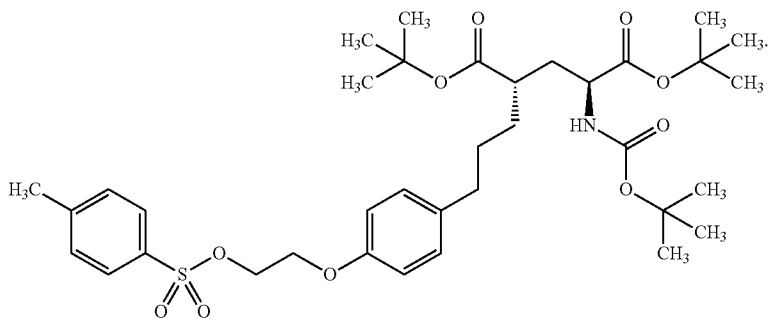 [SMILES: Cc1ccc(S(=O)(=O)OCCOc2ccc(CCC[C@@H](C[C@H](NC(=O)OC(C)(C)C)C(=O)OC(C)(C)C)C(=O)OC(C)(C)C)cc2)cc1]

Another more preferred compound of Formula I is di-tert-butyl (4S)—N-(tert-butoxy-carbonyl)-4-(3-{4-[3-(tosyloxy)propyl]phenyl}propyl)-L-glutamate:

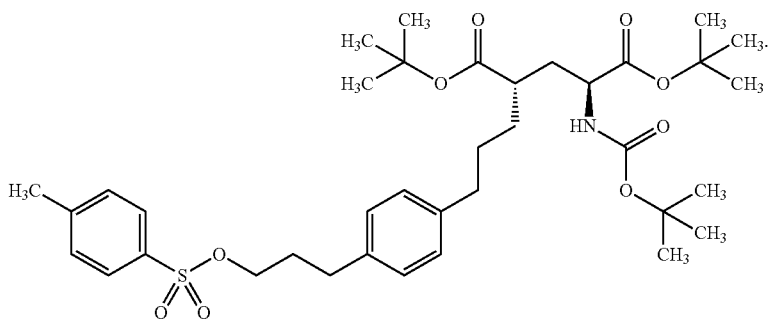 [SMILES: Cc1ccc(S(=O)(=O)OCCCc2ccc(CCC[C@@H](C[C@H](NC(=O)OC(C)(C)C)C(=O)OC(C)(C)C)C(=O)OC(C)(C)C)cc2)cc1]

Another more preferred compound of Formula I is di-tert-butyl (2S)-2-[(tert-butoxy-carbonyl)amino]-5-{4-[2-(tosyloxy)ethoxy]benzyl}hexanedioate:

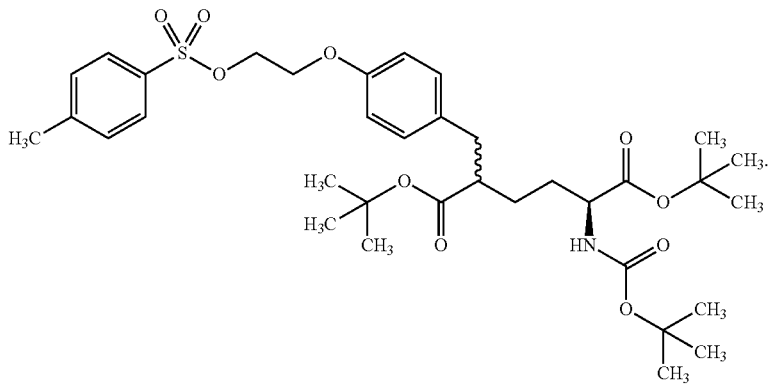 [SMILES: Cc1ccc(S(=O)(=O)OCCOc2ccc(CC(CC[C@H](NC(=O)OC(C)(C)C)C(=O)OC(C)(C)C)C(=O)OC(C)(C)C)cc2)cc1]

Another more preferred compound of Formula I is di-tert-butyl (2R)-2-[(tert-butoxy-carbonyl)amino]-5-{4-[2-(tosyloxy)ethoxy]benzyl}hexanedioate:

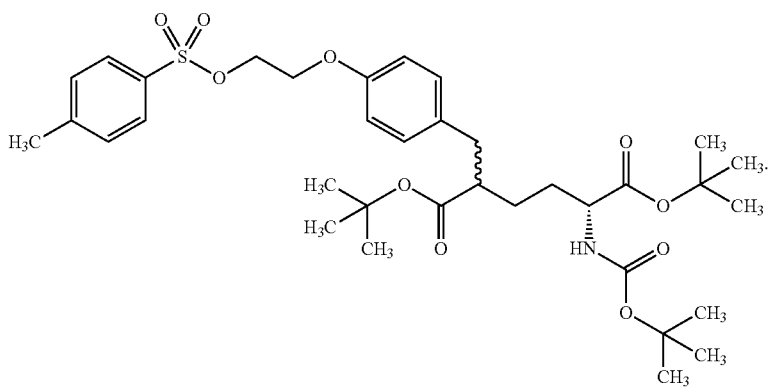 [SMILES: Cc1ccc(S(=O)(=O)OCCOc2ccc(CC(CC[C@@H](NC(=O)OC(C)(C)C)C(=O)OC(C)(C)C)C(=O)OC(C)(C)C)cc2)cc1]

Another more preferred compound of Formula I is di-tert-butyl (4R)—N-(tert-butoxycarbonyl)-4-({5-[3-(tosyloxy)propyl]pyridin-2-yl}methyl)-L-glutamate:

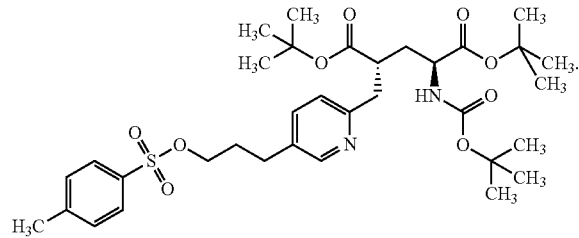 [SMILES: Cc1ccc(S(=O)(=O)OCCCc2ccc(C[C@@H](C[C@H](NC(=O)OC(C)(C)C)C(=O)OC(C)(C)C)C(=O)OC(C)(C)C)nc2)cc1]

The second aspect of the present invention is directed to compounds of Formula III:

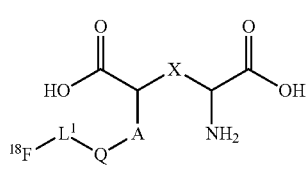

wherein
X is selected from the group comprising
 a) $CH_2$,
 b) $CH_2$—$CH_2$,
 c) $CH_2$—$CH_2$—$CH_2$, and
 d) $CH_2$—$CH_2$—$CH_2$—$CH_2$—,
A is alkylene.
Q is arylene or heteroarylene.
$L^1$ is selected from the group comprising:
 a) alkylene,
 b) alkylene-O*,
 c) alkylene-N*H,
 d) cycloalkylene-O*,
 e) monohydroxyalkylene,
 f) monohydroxyalkylene-O*,
 g) dihydroxyalkylene,
 h) dihydroxyalkylene-O*, and
 i) $(CH_2CH_2O)_n$—$CH_2CH_2$—O* with n=1, 2 or 3,
* indicates the position of the bond to Q, and
single isomers, tautomers, diastereomers, enantiomers, stereoisomers, stereoisomeric mixtures or mixtures thereof.

In a further embodiment, the invention is directed to compounds of Formula III:

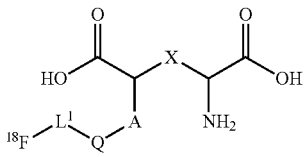

III wherein
X is selected from the group comprising
  a) $CH_2$,
  b) $CH_2$—$CH_2$, and
  c) $CH_2$—$CH_2$—$CH_2$.
A is alkylene.
Q is arylene or heteroarylene,
$L^1$ is selected from the group comprising:
  a) alkylene,
  b) alkylene-O*,
  c) alkylene-N*H,
  d) cycloalkylene-O*,
  e) monohydroxyalkylene,
  f) monohydroxyalkylene-O*,
  g) dihydroxyalkylene,
  h) dihydroxyalkylene-O*, and
  i) $(CH_2CH_2O)_n$—$CH_2CH_2$—O* with n=1, 2 or 3,
* indicates the position of the bond to Q, and
single isomers, tautomers, diastereomers, enantiomers, stereoisomers, stereoisomeric mixtures or mixtures thereof.

In a further embodiment, the invention is directed to compounds of Formula III:

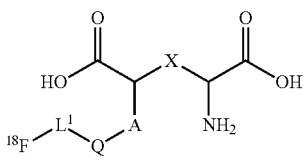

III wherein
X is selected from the group comprising
  a) $CH_2$, and
  b) $CH_2$—$CH_2$.
A is alkylene.
Q is arylene or heteroarylene,
$L^1$ is selected from the group comprising:
  a) alkylene,
  b) alkylene-O*,
  c) alkylene-N*H,
  d) cycloalkylene-O*,
  e) monohydroxyalkylene,
  f) monohydroxyalkylene-O*,
  g) dihydroxyalkylene,
  h) dihydroxyalkylene-O*, and
  i) $(CH_2CH_2O)_n$—$CH_2CH_2$—O* with n=1, 2 or 3,
* indicates the position of the bond to Q, and
single isomers, tautomers, diastereomers, enantiomers, stereoisomers, stereoisomeric mixtures or mixtures thereof.
Preferred Features of Invention and Embodiments Thereof:
  Preferably, X is $CH_2$ or $CH_2$—$CH_2$.
  More preferably, X is $CH_2$.
  More preferably, X is $CH_2$—$CH_2$.
  Preferably, A is $C_1$-$C_6$ alkylene. More preferably, A is $C_1$-$C_3$ alkylene.

Even more preferably. A is methylene.
Even more preferably. A is ethylene.
Even more preferably, A is propylene.
Preferably, Q is phenylene, triazolylene or pyridylene.
Preferably, Q is phenylene or pyridylene.
More preferably, Q is phenylene.
More preferably, Q is pyridylene or triazolylene.
More preferably, Q is pyridylene.
Even more preferably, Q is a pyridylene as defined below

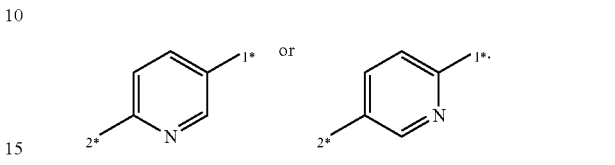

1* indicates the position of the bond to A and 2* indicates the position of the bond to $L^1$.
Preferably, $L^1$ is selected from the group comprising:
  a) $C_2$-$C_6$ alkylene,
  b) $C_2$-$C_6$alkylene-O*,
  c) $C_2$-$C_6$alkylene-N*H,
  d) $C_3$-$C_6$cycloalkylene-O*,
  e) monohydroxy $C_2$-$C_6$alkylene,
  f) monohydroxy $C_3$-$C_6$alkylene-O*,
  g) dihydroxy $C_3$-$C_6$alkylene,
  h) dihydroxy $C_4$-$C_6$alkylene-O*, and
  i) $(CH_2CH_2O)_n$—$CH_2CH_2$—O* with n=1, 2 or 3.
* indicates the position of the bond to Q.
More preferably, $L^1$ is selected from the group comprising:
  a) propylene,
  b) propylene-O*,
  c) ethylene-O*,
  d) propylene-N*H,
  e) cyclobutylene-O*, f)

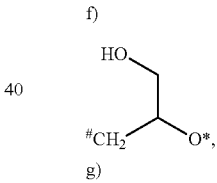

g)

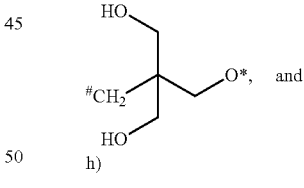, and h)

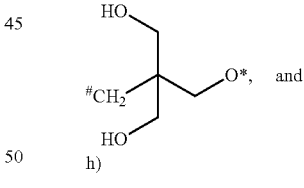

indicates the position of the bond to Q and * indicates the position of the bond to $^{18}F$.
If $L^1$ is alkylene. $L^1$ is preferably linear or branched $C_2$-$C_6$ alkylene. More preferably, $L^1$ is $C_2$-$C_3$ alkylene selected from ethylene and propylene.
Preferably, $L^1$ is propylene.
Preferably, L is ethylene.
Preferably, L is methylene.
If $L^1$ is alkylene-O* $L^1$ is preferably $C_1$ alkylene-O* (methylene-O*) or linear or branched $C_2$-$C_6$ alkylene-O*. More preferably, $L^1$ is $C_2$-$C_3$ alkylene-O* is selected from ethylene-O* and propylene-O*.

Preferably, $L^1$ is propylene-O*.
Preferably, $L^1$ is ethylene-O*.
Preferably, L is methylene-O*.
If $L^1$ is alkylene-N*H $L^1$ is preferably $C_1$ alkylene-N*H or linear or branched $C_2$-$C_6$ alkylene-N*H. More preferably, $L^1$ is $C_2$-$C_3$ alkylene-N*H, selected from ethylene-N*H and propylene-N*H.
Preferably, $L^1$ is propylene-N*H.
Preferably, L is ethylene-N*H.
Preferably, L is methylene-N*H.
"Alkylene" represents a linear or branched saturated bivalent chain of carbon atoms having 1 to 6, preferably 1 to 3 or 4 to 6, carbon atoms, by way of example and by preference methylene, ethylene and propylene. Preferably, alkylene is $C_1$ alkylene or $C_2$-$C_6$ alkylene. More preferably, alkylene is $C_2$-$C_3$ alkylene or $C_4$-$C_6$ alkylene.
The same applies to $C_2$-$C_6$alkylene-O* and $C_2$-$C_6$alkylene-NH*.
"Cycloalkylene" represents an alicyclic bivalent group of carbon atoms having 3 to 8, preferably 4 to 6, carbon atoms, by way of example and by preference cyclopropylene, cyclobutylene, cyclopentylene and cyclohexylene.
If $L^1$ is cycloalkylene-O* $L^1$ is preferably $C_3$-$C_6$ cycloalkylene-O* such as cyclopropylene-O*, cyclobutylene-O*, cyclopentylene-O* or cyclohexylene-O*.
Preferably, $L^1$ is

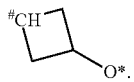

# indicates the position of the bond to $^{18}$F.
If $L^1$ is a monohydroxy $C_2$-$C_6$ alkylene, monohydroxy $C_3$-$C_6$alkylene-O*, dihydroxy $C_3$-$C_6$ alkylene, or dihydroxy $C_4$-$C_6$ alkylene-O*, $L^1$ is preferably an alkylene as defined above bearing one or two hydroxyl groups.
Preferably, $L^1$ is monohydroxy $C_3$-$C_6$alkylene-O* selected from

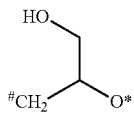

Preferably, $L^1$ is dihydroxy $C_4$-$C_6$alkylene-O* selected from

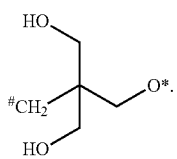

* indicates the position of the bond to Q, # indicates the position of the bond to $^{18}$F.
Compounds of Formula III are defined by the general formula and/or the combination of the preferred features as defined above.
In a first embodiment, compounds of the formula III are defined as compounds of Formula III-1, See structure in table B.

In a second embodiment, compounds of the formula III are defined as compounds of Formula III-2, See structure in table B.
In a third embodiment, compounds of the formula III are defined as compounds of Formula III-3, See structure in table B.
In a fourth embodiment, compounds of the formula III are defined as compounds of Formula III-4, See structure in table B.
In a fifth embodiment, compounds of the formula III are defined as encompassing single isomers or any mixture of at least two stereoisomers of Formula III-1, Formula III-2, Formula III-3 and Formula III-4 including racemates and diastereomeric mixtures.
Preferred features as disclosed above are incorporated herein for all embodiments.

TABLE B

Formula III stereoisomers

| | |
|---|---|
| ![III-1 structure] | III-1 |
| ![III-2 structure] | III-2 |
| ![III-3 structure] | III-3 |
| ![III-4 structure] | III-4 |

The compounds of Formula III-1, Formula III-2, Formula III-3, Formula III-4 furthermore encompass pharmaceutically acceptable salts of an inorganic or organic acid or base thereof, hydrates, complexes, esters, amides, and solvates thereof and optionally a pharmaceutically acceptable carrier, diluent, adjuvant or excipients.

The compounds of Formula III may exist as zwitterions. All forms of the compounds, including free acid, free-base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

A preferred compound of Formula III is 4-[4-(2-[¹⁸F]fluoroethoxy)benzyl]glutamic acid:

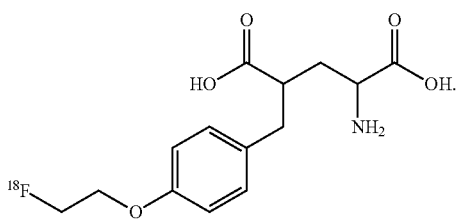 [SMILES: NC(CC(Cc1ccc(OCC[18F])cc1)C(=O)O)C(=O)O]

Another preferred compound of Formula III is 4-[4-(3-[¹⁸F]fluoropropoxy)benzyl]glutamic acid:

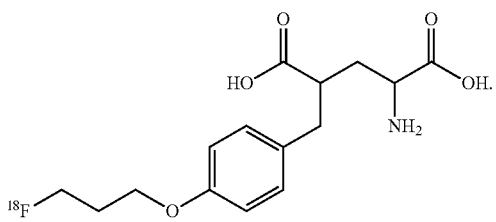 [SMILES: NC(CC(Cc1ccc(OCCC[18F])cc1)C(=O)O)C(=O)O]

Another preferred compound of Formula III is 4-[4-(3-[¹⁸F]fluoropropyl)benzyl]glutamic acid:

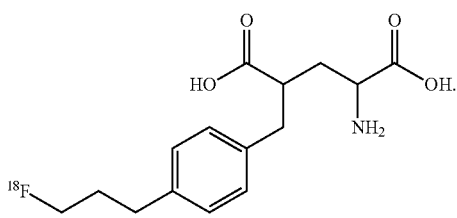 [SMILES: NC(CC(Cc1ccc(CCC[18F])cc1)C(=O)O)C(=O)O]

Another preferred compound of Formula III is 4-{4-[(3-[¹⁸F]fluoropropyl)amino]benzyl}-glutamic acid:

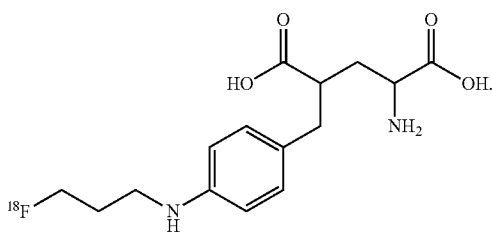 [SMILES: NC(CC(Cc1ccc(NCCC[18F])cc1)C(=O)O)C(=O)O]

Another preferred compound of Formula III is 4-{4-[(3-[¹⁸F]fluorocyclobutyl)oxy]benzyl}-glutamic acid:

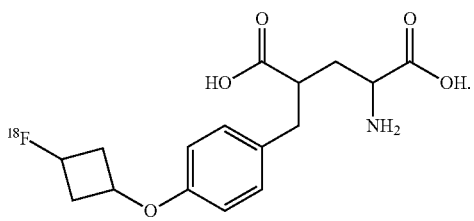 [SMILES: NC(CC(Cc1ccc(OC2CC([18F])C2)cc1)C(=O)O)C(=O)O]

Another preferred compound of Formula III is 4-{3-[4-(2-[¹⁸F]fluoroethoxy)phenyl]-propyl}glutamic acid:

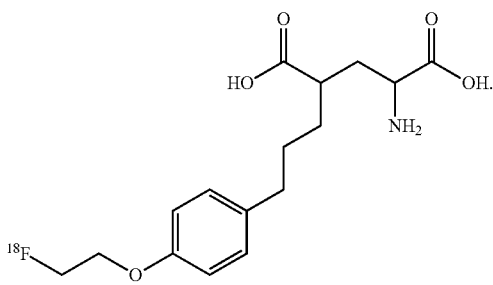 [SMILES: NC(CC(CCCc1ccc(OCC[18F])cc1)C(=O)O)C(=O)O]

Another preferred compound of Formula III is 2-amino-5-[4-(2-[¹⁸F]fluoroethoxy)-benzyl]hexanedioic acid:

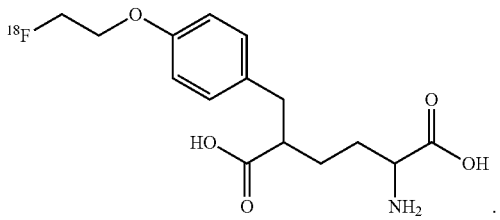 [SMILES: NC(CCC(Cc1ccc(OCC[18F])cc1)C(=O)O)C(=O)O]

A more preferred compound of Formula III is 4-[4-(2-[¹⁸F]fluoroethoxy)benzyl]-L-glutamic acid:

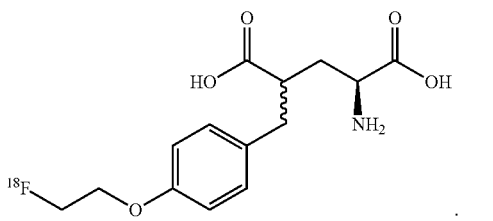

Another more preferred compound of Formula III is 4-[4-(3-[¹⁸F]fluoropropoxy)benzyl]-L-glutamic acid:

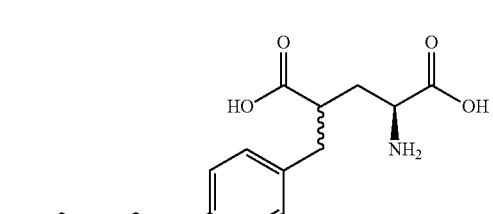

Another more preferred compound of Formula III is 4-[4-(3-[¹⁸F]fluoropropyl)benzyl]-L-glutamic acid:

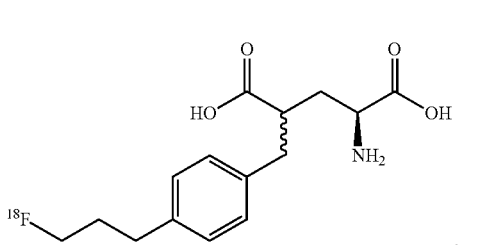

Another more preferred compound of Formula III is 4-{4-[(3-[$^{18}$F]fluoropropyl)-amino]benzyl}-L-glutamic acid:

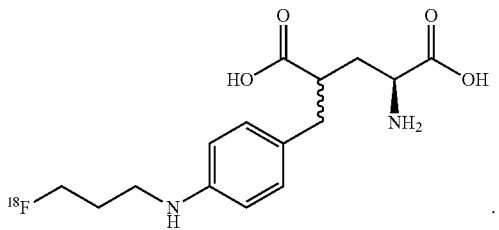

Another more preferred compound of Formula III is 4-{4-[(cis-3-[$^{18}$F]fluorocyclobutyl)-oxy]benzyl}-L-glutamic acid:

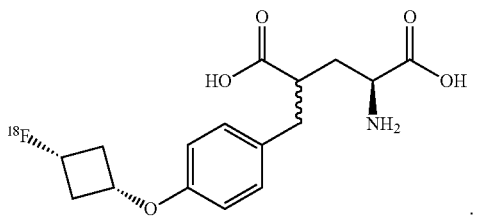 [SMILES: N[C@@H](CC(Cc1ccc(O[C@H]2C[C@@H]([18F])C2)cc1)C(=O)O)C(=O)O]

Another more preferred compound of Formula III is (4S)-4-{3-[4-(2-[$^{18}$F]fluoroethoxy)-phenyl]propyl}-L-glutamic acid:

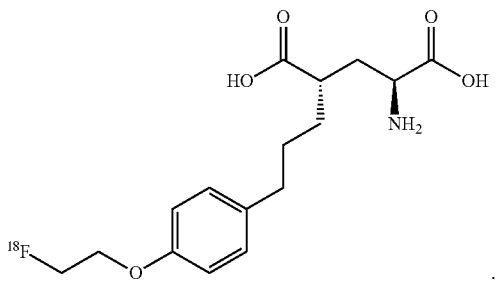 [SMILES: N[C@@H](C[C@H](CCCc1ccc(OCC[18F])cc1)C(=O)O)C(=O)O]

Another more preferred compound of Formula III is (2S)-2-amino-5-[4-(2-[$^{18}$F]fluoro-ethoxy)benzyl]hexanedioic acid:

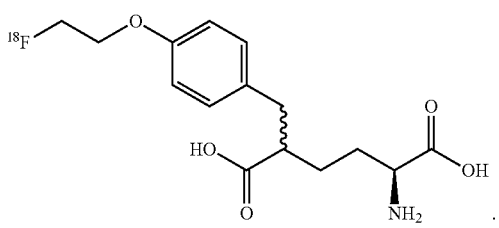 [SMILES: N[C@@H](CCC(Cc1ccc(OCC[18F])cc1)C(=O)O)C(=O)O]

Another more preferred compound of Formula III is (2R)-2-amino-5-[4-(2-[$^{18}$F]fluoro-ethoxy)benzyl]hexanedioic acid:

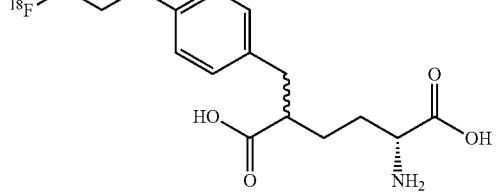

Another more preferred compound of Formula III is (4-{[5-(2-[$^{18}$F]fluoroethoxy)pyridin-2-yl]methyl}-L-glutamic acid:

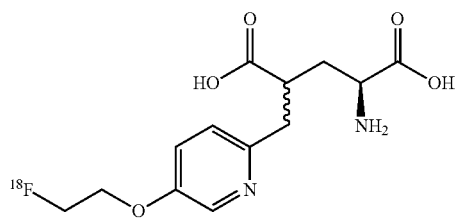

Another more preferred compound of Formula III is (2S)-2-Amino-5-{[5-(2-[$^{18}$F]fluoroethoxy)pyridin-2-yl]methyl}hexanedioic acid:

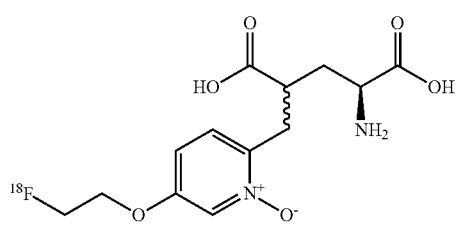

Another more preferred compound of Formula III is 4-{[5-(2-[$^{18}$F]fluoroethoxy)-1-oxidopyridin-2-yl]methyl}-L-glutamic acid:

Another more preferred compound of Formula III is (2S)-2-amino-5-{2-[4-(2-[$^{18}$F]fluoroethoxy)phenyl]ethyl}hexanedioic acid:

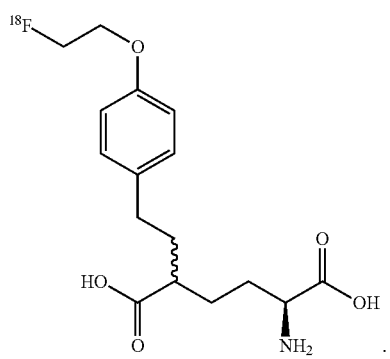

Another more preferred compound of Formula III is (2S)-2-amino-5-[4-([$^{18}$F]fluoromethoxy)benzyl]hexanedioic acid:

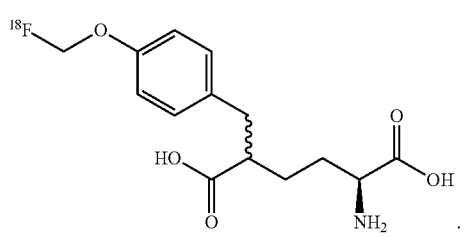

Another more preferred compound of Formula III is (2S, 5R)-2-amino-5-[4-([$^{18}$F]fluoromethoxy)benzyl]hexanedioic acid:

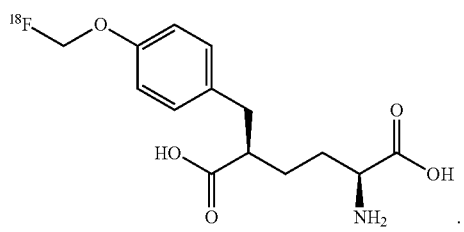 [SMILES: N[C@@H](CC[C@H](Cc1ccc(OC[18F])cc1)C(=O)O)C(=O)O]

Another more preferred compound of Formula III is (2S, 5S)-2-amino-5-[4-([$^{18}$F]fluoromethoxy)benzyl]hexanedioic acid:

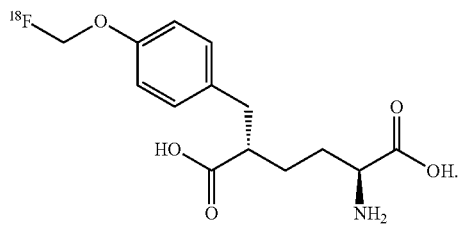

Another more preferred compound of Formula III is 4-[4-(2-[$^{18}$F]fluoroethoxy)-3-hydroxybenzyl]-L-glutamic acid:

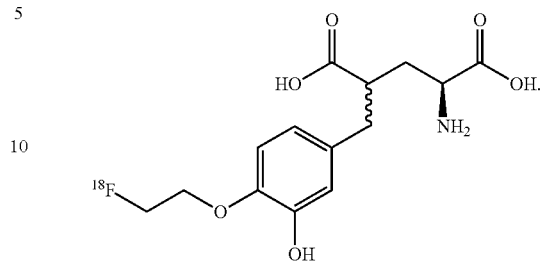

Another more preferred compound of Formula III is (4S)-4-{4-[($^{18}$F)fluoromethoxy]benzyl}-L-glutamic acid:

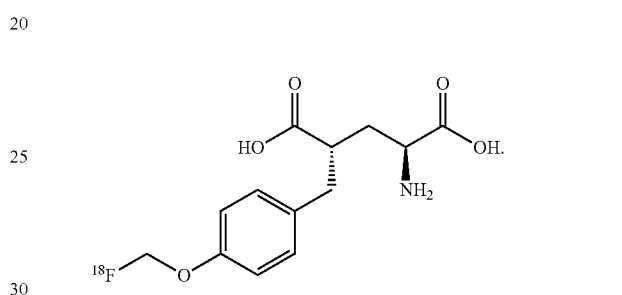

Another more preferred compound of Formula III is (4R)-4-{4-[($^{18}$F)fluoromethoxy]benzyl}-L-glutamic acid:

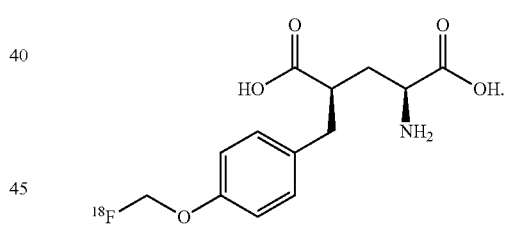

Another more preferred compound of Formula III is (2S)-2-amino-5-(4-{[2-($^{18}$F)fluoroethyl]amino}benzyl)hexanedioic acid:

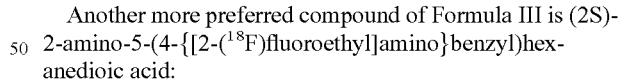
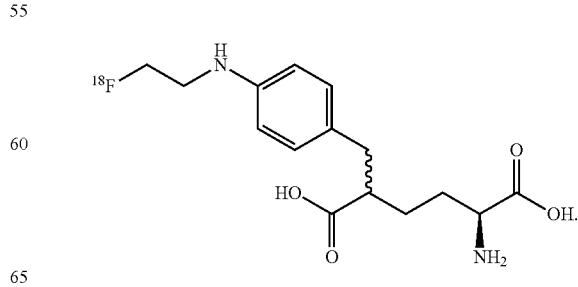

Another more preferred compound of Formula III is (2S)-2-amino-5-(4-{[(2S,3R)-4-($^{18}$F)fluoro-2,3-dihydroxybutyl]oxy}benzyl)hexanedioic acid:

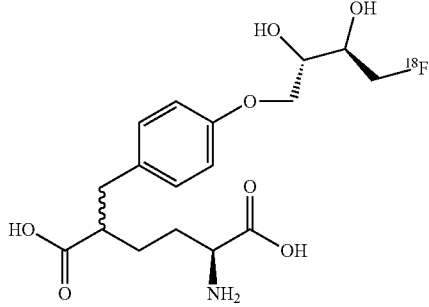 [SMILES: N[C@@H](CCC(Cc1ccc(OC[C@H](O)[C@@H](O)C[18F])cc1)C(=O)O)C(=O)O]

Another more preferred compound of Formula III is 4-({6-[2-($^{18}$F)fluoroethoxy]pyridin-3-yl}methyl)-L-glutamic acid:

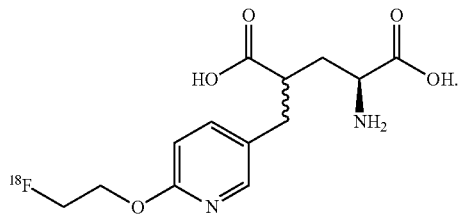

Another more preferred compound of Formula III is 4-(4-{[(2S,3R)-4-($^{18}$F)fluoro-2,3-dihydroxybutyl]oxy}benzyl)-L-glutamic acid:

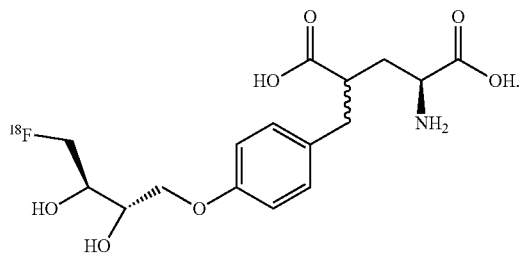 [SMILES: N[C@@H](CC(Cc1ccc(OC[C@H](O)[C@@H](O)C[18F])cc1)C(=O)O)C(=O)O]

Another more preferred compound of Formula III is 4-(4-{[1-($^{18}$F)fluoro-3-hydroxypropan-2-yl]oxy}benzyl)-L-glutamic acid:

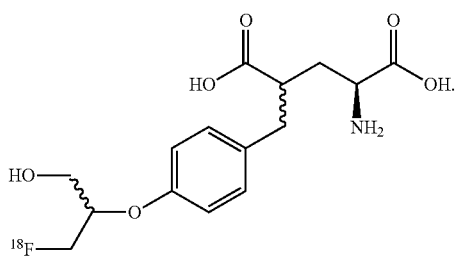 [SMILES: N[C@@H](CC(Cc1ccc(OC(CO)C[18F])cc1)C(=O)O)C(=O)O]

Another more preferred compound of Formula III is 4-({1-[2-($^{18}$F)fluoroethyl]-1H-1,2,3-triazol-4-yl}methyl)-L-glutamic acid:

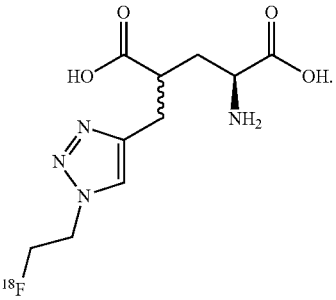 [SMILES: N[C@@H](CC(Cc1cn(CC[18F])nn1)C(=O)O)C(=O)O]

Another more preferred compound of Formula III is (2S,5R)-2-amino-5-[4-([$^{18}$F]fluoroethoxy)benzyl]hexanedioic acid:

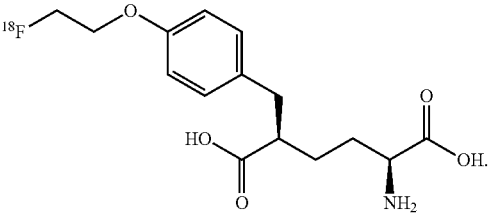 [SMILES: N[C@@H](CC[C@H](Cc1ccc(OCC[18F])cc1)C(=O)O)C(=O)O]

Another more preferred compound of Formula III is (2S,5S)-2-amino-5-[4-([$^{18}$F]fluoroethoxy)benzyl]hexanedioic acid:

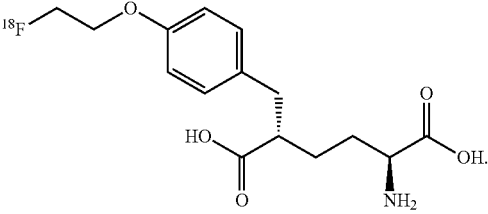

Another more preferred compound of Formula III is 4-{4-[($^{18}$F)fluoromethyl]benzyl}-L-glutamic acid:

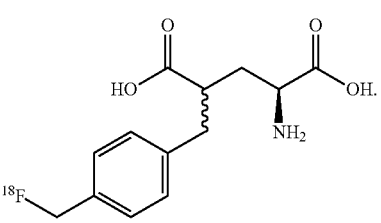 [SMILES: N[C@@H](CC(Cc1ccc(C[18F])cc1)C(=O)O)C(=O)O]

The third aspect of the present invention is directed to compounds of Formula II:

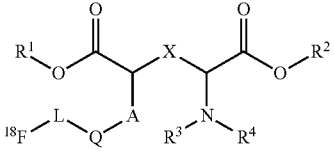

II wherein,
$R^1$ is hydrogen or a carboxyl protecting group,
$R^2$ is hydrogen or a carboxyl protecting group,
$R^3$ is hydrogen or an amine protecting group,
$R^4$ is hydrogen or an amine protecting group,
wherein at least one of $R^1$, $R^2$, $R^3$ and $R^4$ is not hydrogen,
X is selected from the group comprising:
  a) $CH_2$,
  b) $CH_2$—$CH_2$,
  c) $CH_2$—$CH_2$—$CH_2$, and
  d) $CH_2$—$CH_2$—$CH_2$—$CH_2$—,
A is alkylene.
Q is arylene or heteroarylene.
L is selected from the group comprising:
  a) alkylene,
  b) alkylene-O*,
  c) alkylene-N*H,
  d) cycloalkylene-O*,
  e) ($R^5$—O)-substituted alkylene,
  f) ($R^5$—O)-substituted alkylene-O*,
  g) ($R^6$—O), ($R^7$—O)-disubstituted alkylene,
  h) ($R^6$—O), ($R^7$—O)-disubstituted alkylene-O*, and
  i) $(CH_2CH_2O)_n$—$CH_2CH_2$—O* with n=1, 2 or 3,
* indicates the position of the bond to Q.
$R^5$ is
  a) hydrogen or
  b) hydroxyl protecting group,
$R^6$ is
  a) hydrogen or
  b) hydroxyl protecting group,
$R^7$ is
  a) hydrogen or
  b) hydroxyl protecting group, and
single isomers, tautomers, diastereomers, enantiomers, stereoisomers, stereoisomeric mixtures or mixtures thereof.

In a further embodiment, the invention is directed to compounds of Formula II:

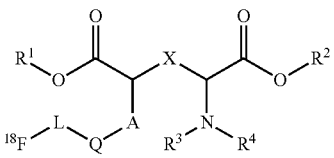

II wherein,
$R^1$ is hydrogen or a carboxyl protecting group.
$R^2$ is hydrogen or a carboxyl protecting group,
$R^3$ is hydrogen or an amine protecting group,
$R^4$ is hydrogen or an amine protecting group,
wherein at least one of $R^1$, $R^2$, $R^3$ and $R^4$ is not hydrogen.

X is selected from the group comprising:
  a) $CH_2$,
  b) $CH_2$—$CH_2$, and
  c) $CH_2$—$CH_2$—$CH_2$.
A is alkylene.
Q is arylene or heteroarylene.
L is selected from the group comprising:
  a) alkylene,
  b) alkylene-O*,
  c) alkylene-N*H,
  d) cycloalkylene-O*,
  e) ($R^5$—O)-substituted alkylene,
  f) ($R^6$—O)-substituted alkylene-O*,
  g) ($R^6$—O), ($R^7$—O)-disubstituted alkylene,
  h) ($R^6$—O), ($R^7$—O)-disubstituted alkylene-O*, and
  i) $(CH_2CH_2O)_n$—$CH_2CH_2$—O* with n=1, 2 or 3,
* indicates the position of the bond to Q.
$R^5$ is
  a) hydrogen or
  b) hydroxyl protecting group.
$R^6$ is
  a) hydrogen or
  b) hydroxyl protecting group,
$R^7$ is
  a) hydrogen or
  b) hydroxyl protecting group, and
single isomers, tautomers, diastereomers, enantiomers, stereoisomers, stereoisomeric mixtures or mixtures thereof.

In a further embodiment, the invention is directed to compounds of Formula II:

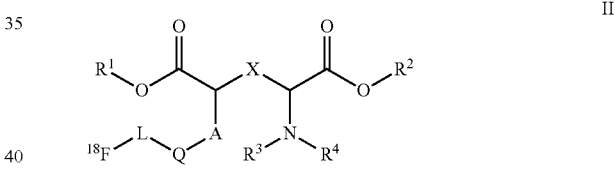

II wherein,
$R^1$ is hydrogen or a carboxyl protecting group,
$R^2$ is hydrogen or a carboxyl protecting group,
$R^3$ is hydrogen or an amine protecting group,
$R^4$ is hydrogen or an amine protecting group,
wherein at least one of $R^1$, $R^2$, $R^3$ and $R^4$ is not hydrogen,
X is selected from the group comprising:
  a) $CH_2$, and
  b) $CH_2$—$CH_2$,
A is alkylene.
Q is arylene or heteroarylene.
L is selected from the group comprising:
  a) alkylene,
  b) alkylene-O*,
  c) alkylene-N*H,
  d) cycloalkylene-O*,
  e) ($R^5$—O)-substituted alkylene,
  f) ($R^5$—O)-substituted alkylene-O*,
  g) ($R^5$—O), ($R^7$—O)-disubstituted alkylene,
  h) ($R^5$—O), ($R^7$—O)-disubstituted alkylene-O*, and
  i) $(CH_2CH_2O)_n$—$CH_2CH_2$—O* with n=1, 2 or 3,
* indicates the position of the bond to Q.
$R^5$ is
  a) hydrogen or
  b) hydroxyl protecting group, $R^6$ is
  a) hydrogen or
  b) hydroxyl protecting group,
$R^7$ is
  a) hydrogen or
  b) hydroxyl protecting group, and
single isomers, tautomers, diastereomers, enantiomers, stereoisomers, stereoisomeric mixtures or mixtures thereof.

Preferred Features of Invention and Embodiments Thereof:

Preferably, $R^1$ is a carboxyl-protecting group.

The carboxyl-protecting group is preferably selected from methyl, ethyl, propyl, butyl, tert-butyl, allyl, benzyl, 4-methoxybenzyl and 4-methoxyphenyl.

More preferably, $R^1$ is selected from the group comprising:
  a) methyl,
  b) ethyl, and
  c) tert-butyl.

Even more preferably, $R^1$ is tert-butyl.

Preferably, $R^1$ is selected from the group comprising: hydrogen, methyl, ethyl, propyl, butyl, tert-butyl, allyl, benzyl, 4-methoxybenzyl and 4-methoxyphenyl.

More preferably, $R^1$ is selected from the group comprising:
  a) hydrogen,
  b) methyl,
  c) ethyl, and
  d) tert-butyl.

Preferably, $R^2$ is a carboxyl-protecting group.

The carboxyl-protecting group is preferably selected from methyl, ethyl, propyl, butyl, tert-butyl, allyl, benzyl, 4-methoxybenzyl and 4-methoxyphenyl.

More preferably, $R^2$ is selected from the group comprising:
  a) methyl,
  b) ethyl, and
  c) tert-butyl.

Even more preferably. $R^2$ is tert-butyl.

Preferably, $R^2$ is selected from the group comprising: hydrogen, methyl, ethyl, propyl, butyl, tert-butyl, allyl, benzyl, 4-methoxybenzyl and 4-methoxyphenyl.

More preferably, $R^2$ is selected from the group comprising:
  a) hydrogen,
  b) methyl,
  c) ethyl, and
  d) tert-butyl.

Preferably, $R^1$ and $R^2$ are both a carboxyl protecting group.

Preferably, $R^3$ is hydrogen or an amine-protecting group.

The amine-protecting group is preferably carbobenzyloxy (Cbz), p-methoxybenzyl carbonyl (Moz or MeOZ), tert-butyloxycarbonyl (Boc), benzyl (Bn), p-methoxybenzyl (PMB), 3,4-dimethoxybenzyl (DMPM), p-methoxyphenyl (PMP), triphenylmethyl (Trityl) or methoxyphenyl diphenylmethyl (MMT).

Preferably $R^3$ is selected from the group comprising:
  a) hydrogen,
  b) tert-butyloxycarbonyl (Boc), and
  c) triphenylmethyl (Trityl).

More preferably $R^3$ is selected from the group comprising:
  a) tert-butyloxycarbonyl (Boc), and
  b) triphenylmethyl (Trityl).

Preferably, $R^4$ is hydrogen or an amine-protecting group.

The amine-protecting group is preferably carbobenzyloxy (Cbz), p-methoxybenzyl carbonyl (Moz or MeOZ), tert-butyloxycarbonyl (Boc), benzyl (Bn), p-methoxybenzyl (PMB), 3,4-dimethoxybenzyl (DMPM), p-methoxyphenyl (PMP), triphenylmethyl (Trityl) or methoxyphenyl diphenylmethyl (MMT).

Preferably $R^4$ is selected from the group comprising:
  a) hydrogen,
  b) tert-butyloxycarbonyl (Boc), and
  c) triphenylmethyl (Trityl).

More preferably $R^4$ is selected from the group comprising:
  a) tert-butyloxycarbonyl (Boc) and
  b) triphenylmethyl (Trityl).

Additionally, $R^3$ and $R^4$ optionally form an amine-protecting group, resulting in $NR^3R^4$ being 1,3-dioxo-1,3-dihydro-2H-isoindol-2-yl (phthalimido) or an azido group.

Preferably, $R^3$ is hydrogen and $R^4$ is an amine protecting group.

More preferably, $R^3$ is hydrogen and $R^4$ is tert-Butyloxycarbonyl (Boc).

More preferably, $R^3$ is hydrogen and $R^4$ is triphenylmethyl (Trityl).

Preferably, $R^3$ and $R^4$ are never Hydrogen at the same time.

Preferably, $R^1$ and $R^2$ are both a carboxyl protecting group, $R^3$ is hydrogen and $R^4$ is an amine protecting group.

Preferably, X is $CH_2$ or $CH_2$—$CH_2$.

More preferably, X is $CH_2$.

More preferably, X is $CH_2$—$CH_2$.

Preferably, A is $C_1$-$C_6$ alkylene. More preferably, A is $C_1$-$C_3$ alkylene.

Even more preferably, A is methylene.

Even more preferably, A is ethylene.

Even more preferably, A is propylene.

Preferably, Q is phenylene, triazolylene or pyridylene.

Preferably, Q is phenylene or pyridylene.

More preferably, Q is phenylene.

More preferably, Q is pyridylene or triazolylene.

More preferably, Q is pyridylene.

Even more preferably, Q is a pyridylene as defined below

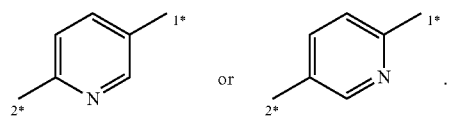

1* indicates the position of the bond to A and 2* indicates the position of the bond to L.

Preferably, L is selected from the group comprising:
  a) $C_2$-$C_6$ alkylene,
  b) $C_2$-$C_6$alkylene-O*,
  c) $C_2$-$C_6$alkylene-N*H,
  d) $C_3$-$C_6$cycloalkylene-O*,
  e) ($R^5$—O)-substituted $C_2$-$C_6$ alkylene,
  f) ($R^5$—O)-substituted $C_3$-$C_6$alkylene-O*,
  g) ($R^6$—O), ($R^7$—O)-disubstituted $C_3$-$C_6$ alkylene,
  h) ($R^6$—O), ($R^7$—O)-disubstituted $C_4$-$C_6$ alkylene-O*, and
  i) $(CH_2CH_2O)_n$—$CH_2CH_2$—O* with n=1, 2 or 3.

* indicates the position of the bond to Q.

More preferably, L is selected from the group comprising:
  a) propylene,
  b) propylene-O*,
  c) ethylene-O*,
  d) propylene-N*H,
  e) cyclobutylene-O*,

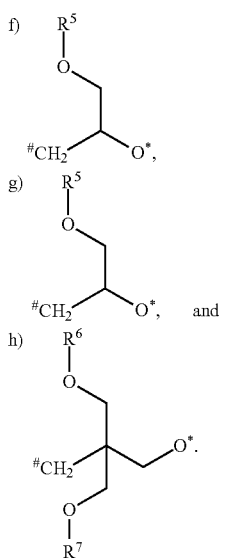

f)

g) and h)

\* indicates the position of the bond to Q and # indicates the position of the bond to $^{18}$F.

If L is alkylene, L is preferably linear or branched $C_2$-$C_6$ alkylene. More preferably, L is $C_2$-$C_3$ alkylene selected from ethylene and propylene.

Preferably, L is propylene.
Preferably, L is ethylene.
Preferably, L is methylene.

If L is alkylene-O\* L is preferably $C_1$ alkylene-O\* (methylene-O\*) or linear or branched $C_2$-$C_6$ alkylene-O\*. More preferably, L is $C_2$-$C_3$ alkylene-O\* is selected from ethylene-O\* and propylene-O\*.

Preferably, L is propylene-O\*.
Preferably, L is ethylene-O\*.
Preferably, L is methylene-O\*.

If L is alkylene-N\*H L is preferably $C_1$ alkylene-N\*H or linear or branched $C_2$-$C_6$ alkylene-N\*H. More preferably, L is $C_2$-$C_3$ alkylene-N\*H, selected from ethylene-N\*H and propylene-N\*H.

Preferably, L is propylene-N\*H.
Preferably, L is ethylene-N\*H.
Preferably, L is methylene-N\*H.

"Alkylene" represents a linear or branched saturated bivalent chain of carbon atoms having 1 to 6, preferably 1 to 3 or 4 to 6, carbon atoms, by way of example and by preference methylene, ethylene and propylene. Preferably, alkylene is $C_1$ alkylene or $C_2$-$C_6$ alkylene. More preferably, alkylene is $C_2$-$C_3$ alkylene or $C_4$-$C_6$ alkylene. The same applies to $C_2$-$C_6$alkylene-O\* and $C_2$-$C_6$alkylene-NH\*.

"Cycloalkylene" represents an alicyclic bivalent group of carbon atoms having 3 to 8, preferably 4 to 6, carbon atoms, by way of example and by preference cyclopropylene, cyclobutylene, cyclopentylene and cyclohexylene.

If L is cycloalkylene-O\* L is preferably $C_3$-$C_6$ cycloalkylene-O\* such as cyclopropylene-O\*, cyclobutylene-O\*, cyclopentylene-O\* or cyclohexylene-O\*.

Preferably, L is

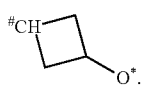

# indicates the position of the bond to $^{18}$F.

If L is ($R^5$—O)-substituted $C_2$-$C_6$ alkylene, ($R^5$—O)-substituted $C_3$-$C_6$ alkylene-O\*, ($R^6$—O), ($R^7$—O)-disubstituted $C_3$-$C_6$alkylene, or ($R^6$—O), ($R^7$—O)-disubstituted $C_4$-$C_6$alkylene-O\*, L is preferably an alkylene defined as above bearing one or two protected or unprotected hydroxyl groups.

Preferably, L is ($R^5$—O)-substituted $C_3$-$C_6$alkylene-O\* selected from

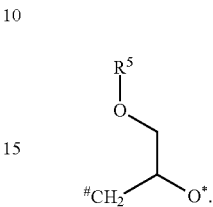

Preferably, L is ($R^6$—O), ($R^7$—O)-disubstituted $C_4$-$C_6$alkylene-O\* selected from

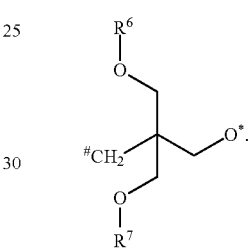

\* indicates the position of the bond to Q, # indicates the position of the bond to $^{18}$F.

Preferably, $R^5$ is a hydroxyl protecting group.

Preferably, $R^6$ and $R^7$ are hydroxyl protecting groups.

Additionally, $R^6$ and $R^7$ optionally form together one-diol protecting group.

Compounds of Formula II are defined by the general formula and/or the combination of the preferred features as defined above.

In a first embodiment, compounds of the formula II are defined as compounds of Formula II-1, See structure in table C.

In a second embodiment, compounds of the formula II are defined as compounds of Formula II-2, See structure in table C.

In a third embodiment, compounds of the formula II are defined as compounds of Formula II-3, See structure in table C.

In a fourth embodiment, compounds of the formula II are defined as compounds of Formula II-4, See structure in table C.

In a fifth embodiment, compounds of the formula II are defined as encompassing single isomers or any mixture of at least two stereoisomers of Formula II-1, Formula II-2, Formula II-3 and Formula II-4 including racemates and diastereomeric mixtures.

Preferred features as disclosed above are incorporated herein for all embodiments.

TABLE C

Formula II stereoisomers

II-1

II-2

II-3

II-4

The compounds of Formula II-1. Formula II-2, Formula II-3, Formula II-4 furthermore encompass pharmaceutically acceptable salts of an inorganic or organic acid or base thereof, hydrates, complexes, esters, amides, and solvates thereof and optionally a pharmaceutically acceptable carrier, diluent, adjuvant or excipients.

A preferred compound of Formula II is di-tert-butyl N-(tert-butoxycarbonyl)-4-[4-(2-[$^{18}$F]fluoroethoxy)benzyl] glutamate:

Another preferred compound of Formula II is di-tert-butyl N-(tert-butoxycarbonyl)-4-[4-(3-[$^{18}$F]fluoropropoxy)benzyl]glutamate:

Another preferred compound of Formula II is di-tert-butyl N-(tert-butoxycarbonyl)-4-[4-(3-[$^{18}$F]fluoropropyl)benzyl] glutamate:

Another preferred compound of Formula II is di-tert-butyl N-(tert-butoxycarbonyl)-4-(4-{[3-[$^{18}$F]fluoropropyl] amino}benzyl)glutamate:

Another preferred compound of Formula II is di-tert-butyl N-(tert-butoxycarbonyl)-4-(4-{cis-[3-[$^{18}$F]fluorocyclobutyl]oxy}benzyl)glutamate:

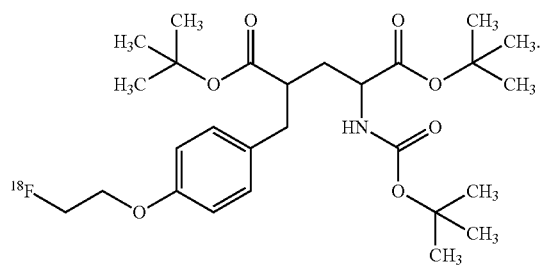 [SMILES: CC(C)(C)OC(=O)NC(CC(Cc1ccc(OCC[18F])cc1)C(=O)OC(C)(C)C)C(=O)OC(C)(C)C]

Another preferred compound of Formula II is di-tert-butyl N-(tert-butoxycarbonyl)-4-{3-[4-(2-[$^{18}$F]fluoroethoxy)phenyl]propyl}glutamate:

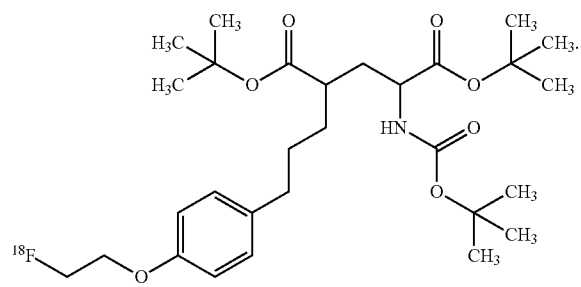 [SMILES: CC(C)(C)OC(=O)NC(CC(CCCc1ccc(OCC[18F])cc1)C(=O)OC(C)(C)C)C(=O)OC(C)(C)C]

Another preferred compound of Formula II is di-tert-butyl 2-[(tert-butoxycarbonyl)amino]-5-[4-(2-[$^{18}$F]fluoroethoxy)benzyl]hexanedioate:

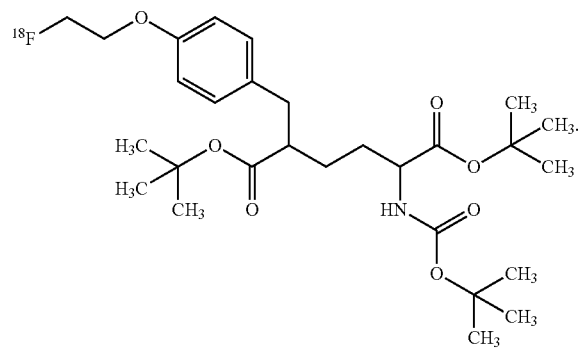 [SMILES: CC(C)(C)OC(=O)NC(CCC(Cc1ccc(OCC[18F])cc1)C(=O)OC(C)(C)C)C(=O)OC(C)(C)C]

A more preferred compound of Formula II is di-tert-butyl N-(tert-butoxycarbonyl)-4-[4-(2-[$^{18}$F]fluoroethoxy)benzyl]-L-glutamate:

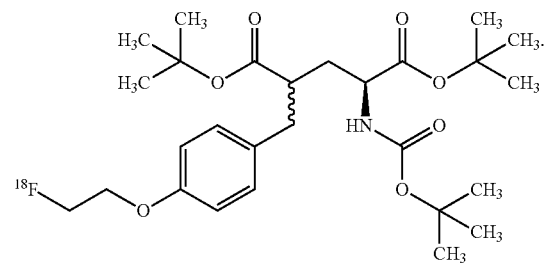 [SMILES: CC(C)(C)OC(=O)N[C@@H](CC(Cc1ccc(OCC[18F])cc1)C(=O)OC(C)(C)C)C(=O)OC(C)(C)C]

Another more preferred compound of Formula II is di-tert-butyl N-(tert-butoxycarbonyl)-4-[4-(3-[$^{18}$F]fluoropropoxy)benzyl]-L-glutamate:

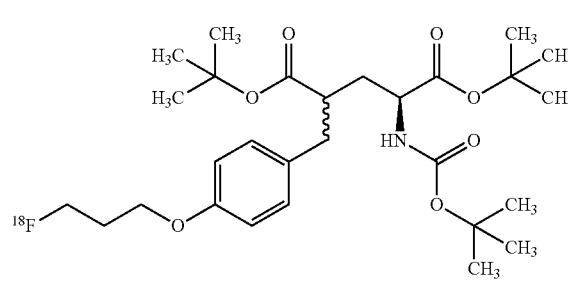

Another more preferred compound of Formula II is di-tert-butyl N-(tert-butoxycarbonyl)-4-[4-(3-[$^{18}$F]fluoropropyl)benzyl]-L-glutamate:

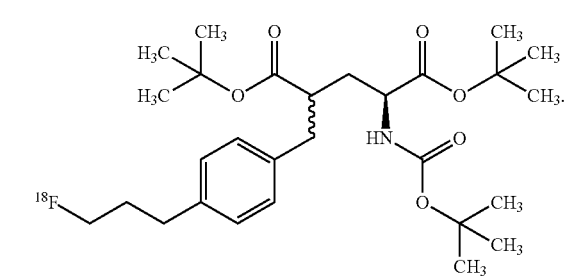 [SMILES: CC(C)(C)OC(=O)N[C@@H](CC(Cc1ccc(CCC[18F])cc1)C(=O)OC(C)(C)C)C(=O)OC(C)(C)C]

Another more preferred compound of Formula II is di-tert-buty N-(tert-butoxycarbonyl)-4-(4-{[3-[$^{18}$F]fluoropropyl]amino}benzyl)-L-glutamate:

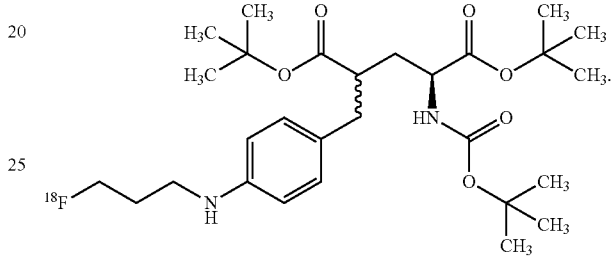

Another more preferred compound of Formula II is di-tert-buty N-(tert-butoxycarbonyl)-4-(4-{cis-[3-[$^{18}$F]fluorocyclobutyl]oxy}benzyl)-L-glutamate:

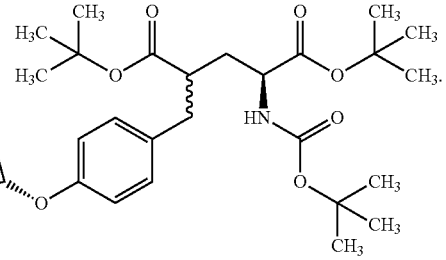

Another more preferred compound of Formula II is di-tert-butyl (4S)—N-(tert-butoxycarbonyl)-4-{3-[4-(2-[$^{18}$F]fluoroethoxy)phenyl]propyl}-L-glutamate:

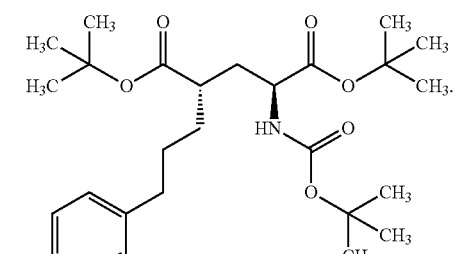

Another more preferred compound of Formula II is di-tert-butyl (2S)-2-[(tert-butoxycarbonyl)amino]-5-[4-(2-[$^{18}$F]fluoroethoxy)benzyl]hexanedioate:

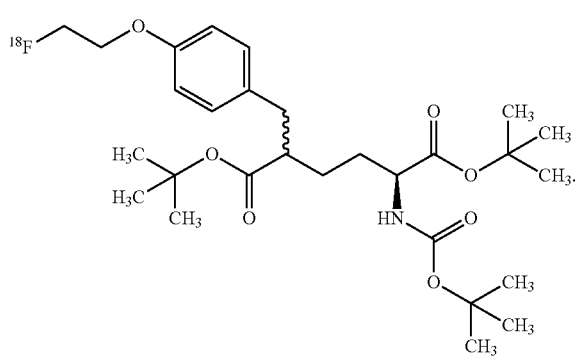 [SMILES: CC(C)(C)OC(=O)N[C@@H](CCC(Cc1ccc(OCC[18F])cc1)C(=O)OC(C)(C)C)C(=O)OC(C)(C)C]

Another more preferred compound of Formula II is di-tert-butyl (2R)-2-[(tert-butoxy-carbonyl)amino]-5-[4-(2-[18F]fluoroethoxy)benzyl]hexanedioate:

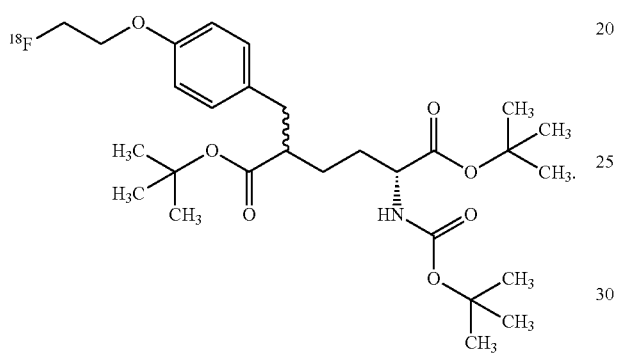

Another more preferred compound of Formula II is di-tert-butyl N-(tert-butoxycarbonyl)-4-({5-[2-(18F)fluoroethoxy]pyridin-2-yl}methyl)-L-glutamate:

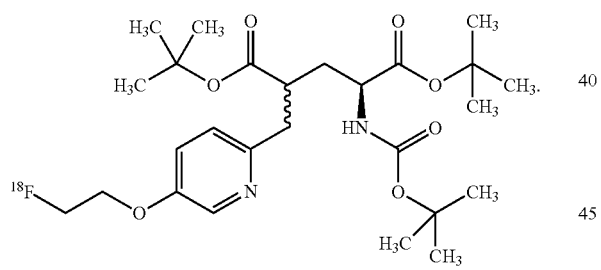

Another more preferred compound of Formula II is di-tert-butyl (2S)-2-[(tert-butoxycarbonyl)amino]5-{[5-(2-[18F]fluoroethoxy)pyridin-2-yl]methyl}hexanedioate:

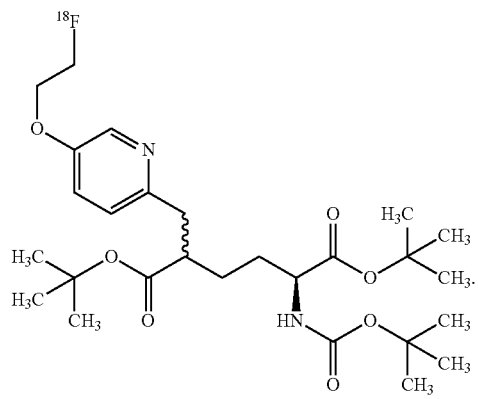 [SMILES: CC(C)(C)OC(=O)N[C@@H](CCC(Cc1ccc(OCC[18F])cn1)C(=O)OC(C)(C)C)C(=O)OC(C)(C)C]

Another more preferred compound of Formula II is di-tert-Butyl N-(tert-butoxycarbonyl)-4-{[5-(2-[18F]fluoroethoxy)-1-oxidopyridin-2-yl]methyl}-L-glutamate:

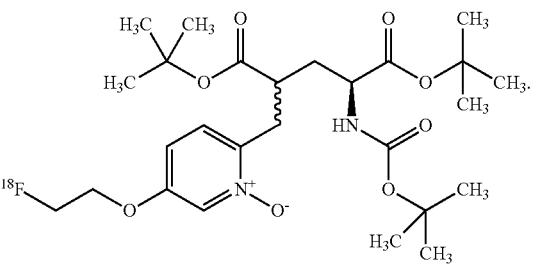 [SMILES: CC(C)(C)OC(=O)N[C@@H](CC(Cc1ccc(OCC[18F])c[n+]1[O-])C(=O)OC(C)(C)C)C(=O)OC(C)(C)C]

Another more preferred compound of Formula II is (2S)-2-tert-butoxycarbonylamino-5-{2-[4-(2-[18F]fluoroethoxy)-phenyl]-ethyl}-hexanedioic acid di-tert-butyl ester:

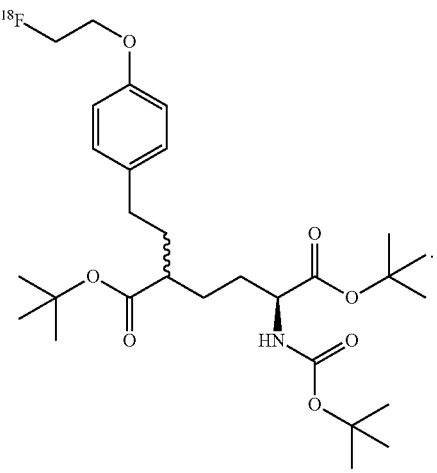 [SMILES: CC(C)(C)OC(=O)N[C@@H](CCC(CCc1ccc(OCC[18F])cc1)C(=O)OC(C)(C)C)C(=O)OC(C)(C)C]

Another more preferred compound of Formula II is di-tert-butyl-N-(tert-butoxycarbonyl)-4-[3-tert-butoxy-4-(2-[18F]fluoroethoxy)benzyl]-L-glutamate:

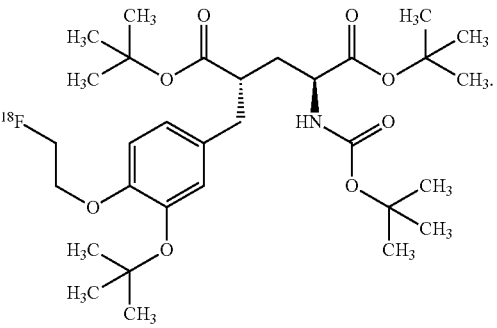 [SMILES: CC(C)(C)OC(=O)N[C@@H](C[C@H](Cc1ccc(OCC[18F])c(OC(C)(C)C)c1)C(=O)OC(C)(C)C)C(=O)OC(C)(C)C]

Another more preferred compound of Formula II is di-tert-butyl (2S)-2-[(tert-butoxycarbonyl)amino]-5-(4-{(tert-butoxycarbonyl)[2-(18F)fluoroethyl]amino}benzyl)hexanedioate:

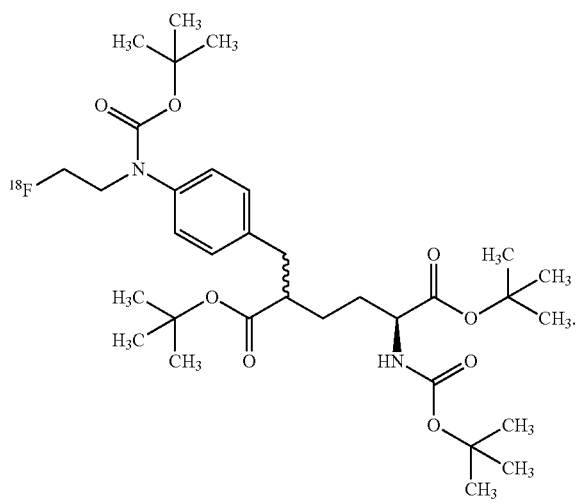 [SMILES: CC(C)(C)OC(=O)N[C@@H](CCC(Cc1ccc(N(CC[18F])C(=O)OC(C)(C)C)cc1)C(=O)OC(C)(C)C)C(=O)OC(C)(C)C]

Another more preferred compound of Formula II is di-tert-butyl (2S)-2-[(tert-butoxycarbonyl)amino]-5-[4-({(4S,5R)-5-[($^{18}$F)fluoromethyl]-2,2-dimethyl-1,3-dioxolan-4-yl}methoxy)benzyl]hexanedioate:

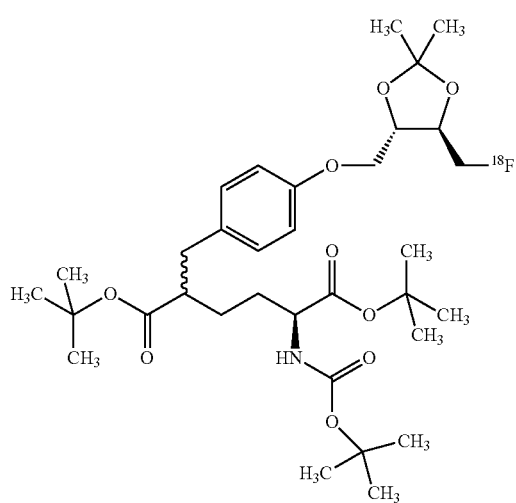 [SMILES: CC(C)(C)OC(=O)N[C@@H](CCC(Cc1ccc(OC[C@@H]2OC(C)(C)O[C@H]2C[18F])cc1)C(=O)OC(C)(C)C)C(=O)OC(C)(C)C]

Another more preferred compound of Formula II is di-tert-butyl (4S)—N-(tert-butoxycarbonyl)-4-({6-[2-($^{18}$F)fluoroethoxy]pyridin-3-yl}methyl)-L-glutamate:

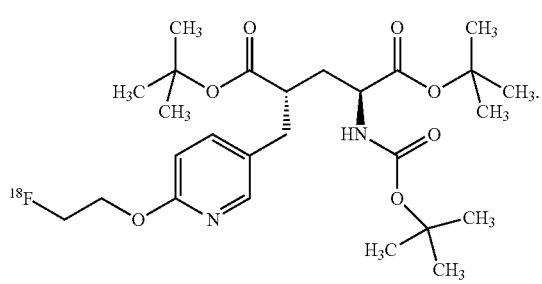 [SMILES: CC(C)(C)OC(=O)N[C@@H](C[C@H](Cc1ccc(OCC[18F])nc1)C(=O)OC(C)(C)C)C(=O)OC(C)(C)C]

Another more preferred compound of Formula II is di-tert-butyl (4S)—N-(tert-butoxycarbonyl)-4-[4-({(4S,5R)-5-[($^{18}$F)fluoromethyl]-2,2-dimethyl-1,3-dioxolan-4-yl}methoxy)benzyl]-L-glutamate:

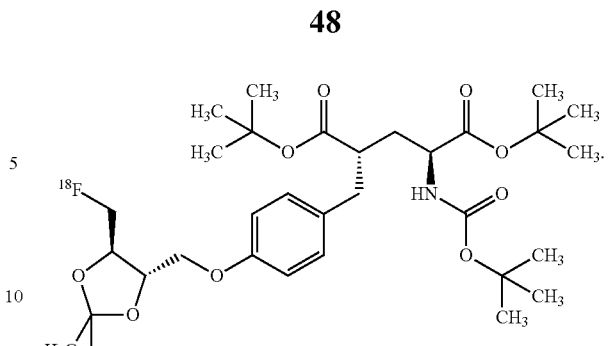

Another more preferred compound of Formula II is di-tert-butyl (4S)—N-(tert-butoxycarbonyl)-4-(4-{[1-($^{18}$F)fluoro-3-hydroxypropan-2-yl]oxy}benzyl)-L-glutamate:

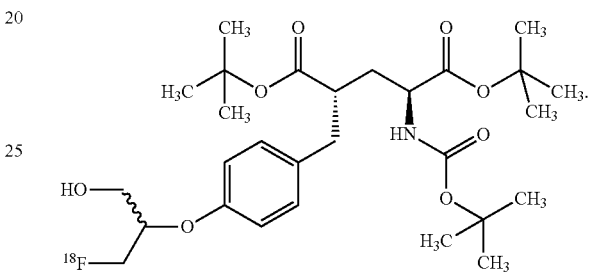

Another more preferred compound of Formula II is di-tert-butyl (4R)—N-(tert-butoxycarbonyl)-4-({1-[2-($^{18}$F)fluoroethyl]-1H-1,2,3-triazol-4-yl}methyl)-L-glutamate:

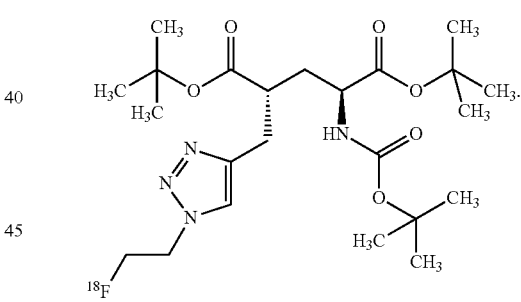

Another more preferred compound of Formula II is di-tert-butyl N-(tert-butoxycarbonyl)-4-{4-[($^{18}$F)fluoromethyl]benzyl}-L-glutamate:

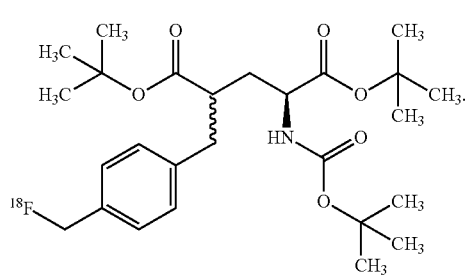 [SMILES: CC(C)(C)OC(=O)N[C@@H](CC(Cc1ccc(C[18F])cc1)C(=O)OC(C)(C)C)C(=O)OC(C)(C)C]

The fourth aspect of the present invention is directed to compounds of Formula VI:

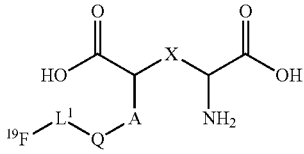

VI wherein,
X is selected from the group comprising
 a) $CH_2$,
 b) $CH_2$—$CH_2$,
 c) $CH_2$—$CH_2$—$CH_2$, and
 d) $CH_2$—$CH_2$—$CH_2$—$CH_2$.
A is alkylene.
Q is arylene or heteroarylene,
$L^1$ is selected from the group comprising:
 a) alkylene,
 b) alkylene-O*,
 c) alkylene-N*H,
 d) cycloalkylene-O*,
 e) monohydroxyalkylene,
 f) monohydroxyalkylene-O*,
 g) dihydroxyalkylene,
 h) dihydroxyalkylene-O*, and
 i) $(CH_2CH_2O)_n$—$CH_2CH_2$—O* with n=1, 2 or 3,
 * indicates the position of the bond to Q, and
single isomers, tautomers, diastereomers, enantiomers, stereoisomers, stereoisomeric mixtures or mixtures thereof.

In a further embodiment, the invention is directed to compounds of Formula VI:

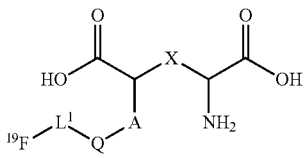

VI wherein,
X is selected from the group comprising
 a) $CH_2$,
 b) $CH_2$—$CH_2$, and
 c) $CH_2$—$CH_2$—$CH_2$,
A is alkylene,
Q is arylene or heteroarylene,
$L^1$ is selected from the group comprising:
 a) alkylene,
 b) alkylene-O*,
 c) alkylene-N*H,
 d) cycloalkylene-O*,
 e) monohydroxyalkylene,
 f) monohydroxyalkylene-O*,
 g) dihydroxyalkylene,
 h) dihydroxyalkylene-O*, and
 i) $(CH_2CH_2O)_n$—$CH_2CH_2$—O* with n=1, 2 or 3,
 * indicates the position of the bond to Q, and
single isomers, tautomers, diastereomers, enantiomers, stereoisomers, stereoisomeric mixtures or mixtures thereof.

In a further embodiment, the invention is directed to compounds of Formula VI:

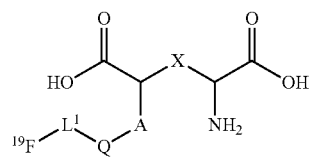

VI wherein,
X is selected from the group comprising
 a) $CH_2$, and
 b) $CH_2$—$CH_2$,
A is alkylene,
Q is arylene or heteroarylene,
$L^1$ is selected from the group comprising:
 a) alkylene,
 b) alkylene-O*,
 c) alkylene-N*H,
 d) cycloalkylene-O*,
 e) monohydroxyalkylene,
 f) monohydroxyalkylene-O*,
 g) dihydroxyalkylene,
 h) dihydroxyalkylene-O*, and
 i) $(CH_2CH_2O)_n$—$CH_2CH_2$—O* with n=1, 2 or 3,
 * indicates the position of the bond to Q, and
single isomers, tautomers, diastereomers, enantiomers, stereoisomers, stereoisomeric mixtures or mixtures thereof.
Preferred Features of Invention and Embodiments Thereof:
 Preferably, X is $CH_2$ or $CH_2$—$CH_2$.
 More preferably, X is $CH_2$.
 More preferably, X is $CH_2$—$CH_2$.
 Preferably, A is $C_1$-$C_6$ alkylene. More preferably, A is $C_1$-$C_3$ alkylene.
 Even more preferably, A is methylene.
 Even more preferably, A is ethylene.
 Even more preferably, A is propylene.
 Preferably, Q is phenylene, triazolylene or pyridylene.
 Preferably, Q is phenylene or pyridylene.
 More preferably, Q is phenylene.
 More preferably, Q is pyridylene or triazolylene.
 More preferably, Q is pyridylene.
 Even more preferably, Q is a pyridylene as defined below

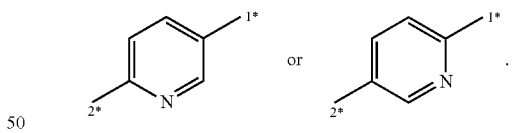

1* indicates the position of the bond to A and 2* indicates the position of the bond to $L^1$.
 Preferably, $L^1$ is selected from the group comprising:
 a) $C_2$-$C_6$ alkylene,
 b) $C_2$-$C_6$alkylene-O*,
 c) $C_2$-$C_6$alkylene-N*H,
 d) $C_3$-$C_6$cycloalkylene-O*,
 e) monohydroxy $C_2$-$C_6$alkylene,
 f) monohydroxy $C_3$-$C_6$alkylene-O*,
 g) dihydroxy $C_3$-$C_6$alkylene,
 h) dihydroxy $C_4$-$C_6$alkylene-O*, and
 i) $(CH_2CH_2O)_n$—$CH_2CH_2$—O* with n=1, 2 or 3.
* indicates the position of the bond to Q.
 More preferably, $L^1$ is selected from the group comprising:
 a) propylene,
 b) propylene-O*, c) ethylene-O*,
d) propylene-N*H,
e) cyclobutylene-O*, f)
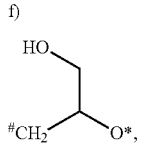

g)
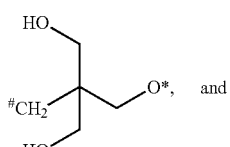 and h)
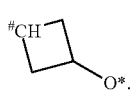

* indicates the position of the bond to Q and # indicates the position of the bond to F.

If $L^1$ is alkylene. $L^1$ is preferably linear or branched $C_2$-$C_6$ alkylene. More preferably, $L^1$ is $C_2$-$C_3$ alkylene selected from ethylene and propylene.

Preferably, $L^1$ is propylene.

Preferably, L is ethylene.

Preferably, L is methylene.

If $L^1$ is alkylene-O* $L^1$ is preferably $C_1$ alkylene-O* (methylene-O*) or linear or branched $C_2$-$C_6$ alkylene-O*. More preferably, $L^1$ is $C_2$-$C_3$ alkylene-O* is selected from ethylene-O* and propylene-O*.

Preferably, $L^1$ is propylene-O*.

Preferably, $L^1$ is ethylene-O*.

Preferably, L is methylene-O*.

If $L^1$ is alkylene-N*H $L^1$ is preferably $C_1$ alkylene-N*H or linear or branched $C_2$-$C_6$ alkylene-N*H. More preferably, $L^1$ is $C_2$-$C_3$ alkylene-N*H, selected from ethylene-N*H and propylene-N*H.

Preferably, $L^1$ is propylene-N*H.

Preferably, L is ethylene-N*H.

Preferably, L is methylene-N*H.

"Alkylene" represents a linear or branched saturated bivalent chain of carbon atoms having 1 to 6, preferably 1 to 3 or 4 to 6, carbon atoms, by way of example and by preference methylene, ethylene and propylene. Preferably, alkylene is $C_1$ alkylene or $C_2$-$C_6$ alkylene. More preferably, alkylene is $C_2$-$C_3$ alkylene or $C_4$-$C_6$ alkylene.

The same applies to $C_2$-$C_6$alkylene-O* and $C_2$-$C_6$alkylene-NH*.

"Cycloalkylene" represents an alicyclic bivalent group of carbon atoms having 3 to 8, preferably 4 to 6, carbon atoms, by way of example and by preference cyclopropylene, cyclobutylene, cyclopentylene and cyclohexylene.

If $L^1$ is cycloalkylene-O* $L^1$ is preferably $C_3$-$C_6$ cycloalkylene-O* such as cyclopropylene-O*, cyclobutylene-O*, cyclopentylene-O* or cyclohexylene-O*.

Preferably, $L^1$ is

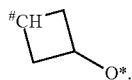

# indicates the position of the bond to F.

If $L^1$ is a monohydroxy $C_2$-$C_6$ alkylene, monohydroxy $C_3$-$C_6$alkylene-O*, dihydroxy $C_3$-$C_6$ alkylene, or dihydroxy $C_4$-$C_6$ alkylene-O*, $L^1$ is preferably an alkylene as defined above bearing one or two hydroxyl groups.

Preferably, $L^1$ is monohydroxy $C_3$-$C_6$alkylene-O* selected from

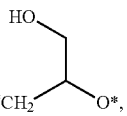

Preferably, $L^1$ is dihydroxy $C_4$-$C_6$alkylene-O* selected from

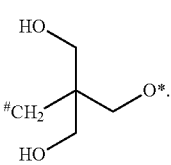

* indicates the position of the bond to Q, # indicates the position of the bond to F.

Compounds of Formula VI are defined by the general formula and/or the combination of the preferred features as defined above.

In a first embodiment, compounds of the formula VI are defined as compounds of Formula VI-1, See structure in table D.

In a second embodiment, compounds of the formula VI are defined as compounds of Formula VI-2, See structure in table D.

In a third embodiment, compounds of the formula VI are defined as compounds of Formula VI-3, See structure in table D.

In a fourth embodiment, compounds of the formula VI are defined as compounds of Formula VI-4, See structure in table D.

In a fifth embodiment, compounds of the formula VI are defined as encompassing single isomers or any mixture of at least two stereoisomers of Formula VI-1, Formula VI-2, Formula VI-3 and Formula VI-4 including racemates and diastereomeric mixtures.

Preferred features as disclosed above are incorporated herein for all embodiments.

TABLE D

Formula VI stereoisomers

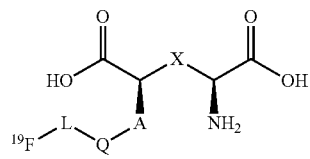

VI-1

TABLE D-continued

Formula VI stereoisomers

VI-2

HO-C(=O)-CH(-L-Q-A-19F)-X-CH(-NH2)-C(=O)-OH

VI-3

HO-C(=O)-CH(-L-Q-A-19F)-X-CH(-NH2)-C(=O)-OH

VI-4

HO-C(=O)-CH(-L-Q-A-19F)-X-CH(-NH2)-C(=O)-OH

The compounds of Formula VI-1, Formula VI-2, Formula VI-3, Formula VI-4 furthermore encompass pharmaceutically acceptable salts of an inorganic or organic acid or base thereof, hydrates, complexes, esters, amides, solvates and prodrugs thereof and optionally a pharmaceutically acceptable carrier, diluent, adjuvant or excipients.

The compounds of Formula VI may exist as zwitterions. All forms of the compounds, including free acid, free-base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

A preferred compound of Formula VI is 4-[4-(2-fluoroethoxy)benzyl]glutamic acid:

Another preferred compound of Formula VI is 4-[4-(3-fluoropropoxy)benzyl]glutamic acid:

Another preferred compound of Formula VI is 4-[4-(3-fluoropropyl)benzyl]glutamic acid:

Another preferred compound of Formula VI is 4-(4-{[3-fluoropropyl]amino}benzyl)-glutamic acid:

Another preferred compound of Formula VI is 4-(4-{[3-fluorocyclobutyl]oxy}benzyl)-glutamic acid:

Another preferred compound of Formula VI is 4-(3-{4-[2-fluoroethoxy]phenyl}propyl)-glutamic acid:

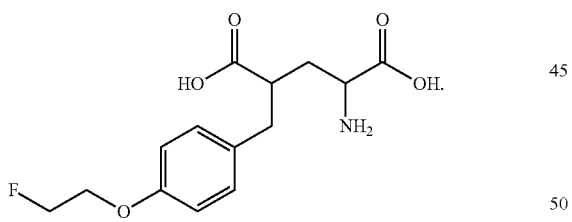

Another preferred compound of Formula VI is 4-{3-[4-(3-fluoropropyl)phenyl]propyl}glutamic acid:

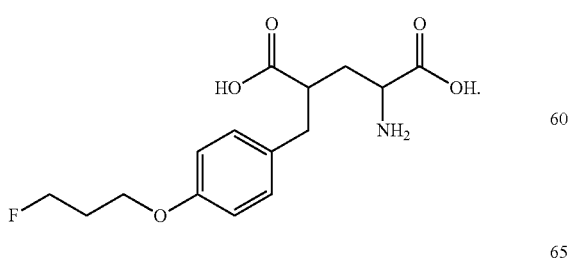

Another preferred compound of Formula VI is 2-amino-5-{4-[2-fluoroethoxy]benzyl}-hexanedioic acid:

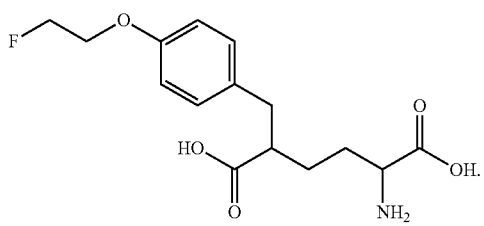

Another preferred compound of Formula VI is 4-{[5-(3-Fluoropropyl)pyridin-2-yl]methyl}-glutamic acid:

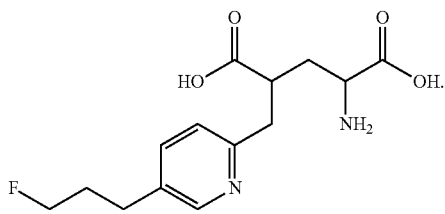 [SMILES: NC(CC(Cc1ccc(CCCF)cn1)C(=O)O)C(=O)O]

A more preferred compound of Formula VI is (4S)-4-[4-(2-fluoroethoxy)benzyl]-L-glutamic acid:

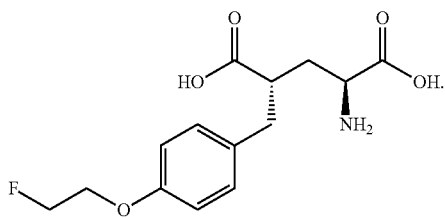 [SMILES: N[C@@H](C[C@H](Cc1ccc(OCCF)cc1)C(=O)O)C(=O)O]

Another more preferred compound of Formula VI is (4R)-4-[4-(2-fluoroethoxy)benzyl]-D-glutamic acid:

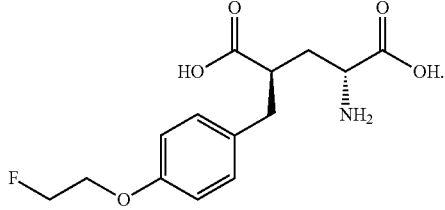 [SMILES: N[C@H](C[C@@H](Cc1ccc(OCCF)cc1)C(=O)O)C(=O)O]

Another more preferred compound of Formula VI is (4S)-4-[4-(3-fluoropropoxy)benzyl]-L-glutamic acid:

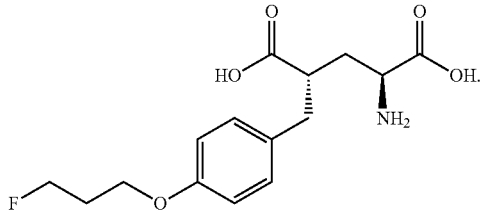 [SMILES: N[C@@H](C[C@H](Cc1ccc(OCCCF)cc1)C(=O)O)C(=O)O]

Another more preferred compound of Formula VI is (4R)-4-[4-(3-fluoropropoxy)benzyl]-D-glutamic acid:

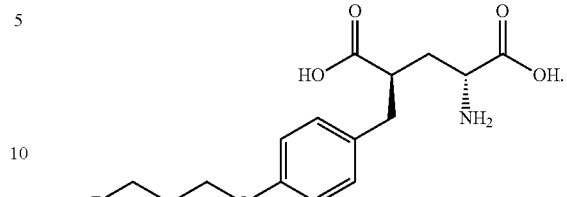

Another more preferred compound of Formula VI is 4-[4-(3-fluoropropyl)benzyl]-L-glutamic acid:

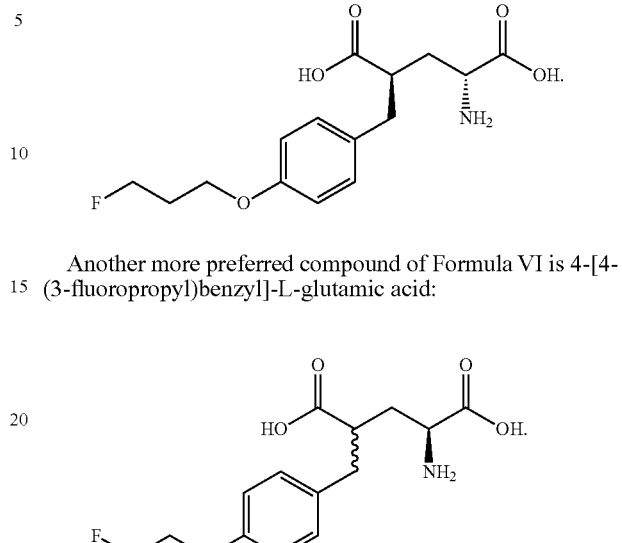

Another more preferred compound of Formula VI is (4S)-4-(4-{[3-fluoropropyl]amino}-benzyl)-L-glutamic acid:

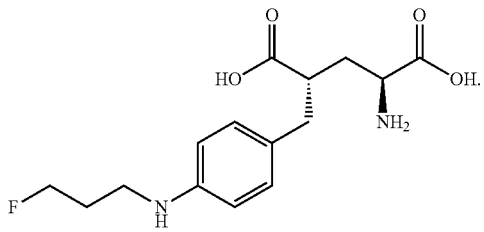 [SMILES: N[C@@H](C[C@H](Cc1ccc(NCCCF)cc1)C(=O)O)C(=O)O]

Another more preferred compound of Formula VI is (4S)-(4-{[cis-3-fluorocyclobutyl]-oxy}benzyl)-L-glutamic acid:

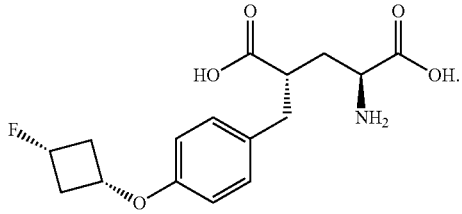 [SMILES: N[C@@H](C[C@H](Cc1ccc(O[C@H]2C[C@@H](F)C2)cc1)C(=O)O)C(=O)O]

Another more preferred compound of Formula VI is (4S)-4-(3-{4-[2-fluoroethoxy]-phenyl}propyl)-L-glutamic acid:

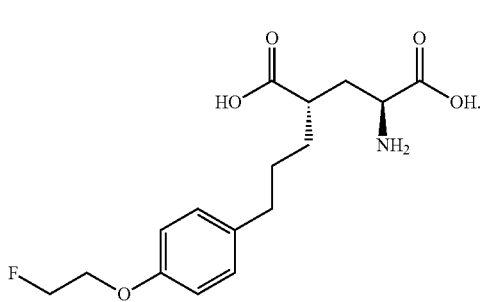 [SMILES: N[C@@H](C[C@H](CCCc1ccc(OCCF)cc1)C(=O)O)C(=O)O]

Another more preferred compound of Formula VI is (4S)-4-(3-{4-[2-fluoropropyl]-phenyl}propyl)-L-glutamic acid:

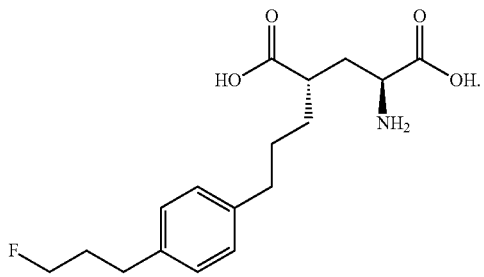 [SMILES: N[C@@H](C[C@H](CCCc1ccc(CCCF)cc1)C(=O)O)C(=O)O]

Another more preferred compound of Formula VI is (2S)-2-amino-5-[4-(2-fluoroethoxy)-benzyl]hexanedioic acid:

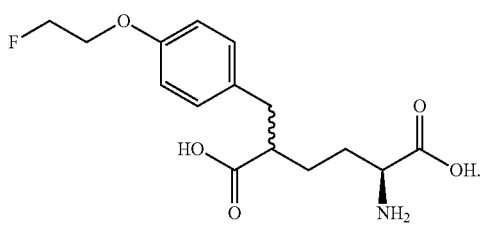

Another more preferred compound of Formula VI is (2R)-2-amino-5-[4-(2-fluoroethoxy)-benzyl]hexanedioic acid:

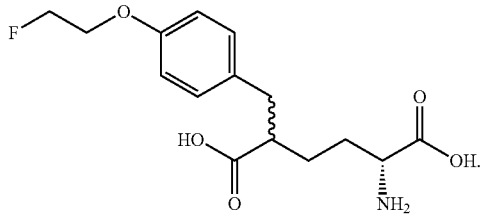 [SMILES: N[C@H](CCC(Cc1ccc(OCCF)cc1)C(=O)O)C(=O)O]

Another more preferred compound of Formula VI is (4R)-4-{[5-(3-Fluoropropyl)pyridin-2-yl]methyl}-L-glutamic acid:

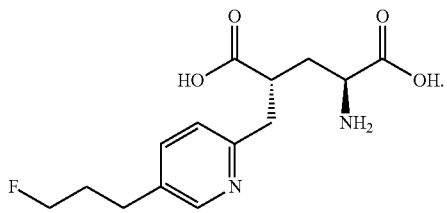 [SMILES: N[C@@H](C[C@H](Cc1ccc(CCCF)cn1)C(=O)O)C(=O)O]

Another more preferred compound of Formula VI is (4R)-(4-{[5-(2-fluoroethoxy)pyridin-2-yl]methyl}-L-glutamic acid:

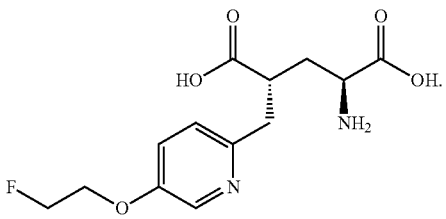

Another more preferred compound of Formula VI is (2S)-2-Amino-5-{[5-(2-fluoroethoxy)pyridin-2-yl]methyl}hexanedioic acid:

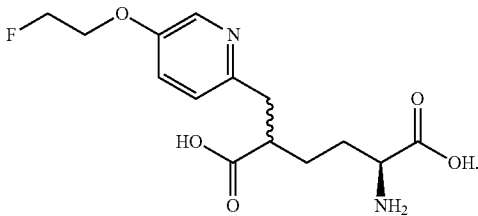

Another more preferred compound of Formula VI is (4R)-4-{[5-(2-fluoroethoxy)-1-oxidopyridin-2-yl]methyl}-L-glutamic acid:

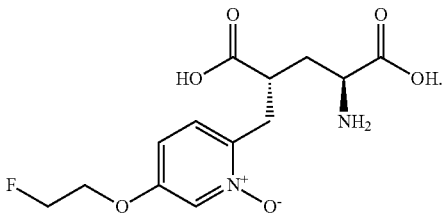

Another more preferred compound of Formula VI is (2S)-2-amino-5-{2-[4-(2-fluoroethoxy)phenyl]ethyl}hexanedioic acid:

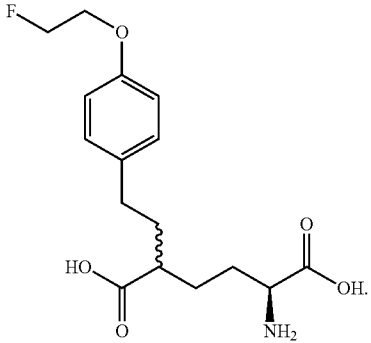 [SMILES: N[C@@H](CCC(CCc1ccc(OCCF)cc1)C(=O)O)C(=O)O]

Another more preferred compound of Formula VI is (2S)-2-amino-5-[4-(fluoromethoxy)benzyl]hexanedioic acid:

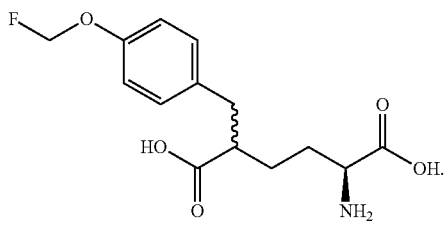 [SMILES: N[C@@H](CCC(Cc1ccc(OCF)cc1)C(=O)O)C(=O)O]

Another more preferred compound of Formula VI is (2S,5R)-2-amino-5-[4-(fluoromethoxy)benzyl]hexanedioic acid:

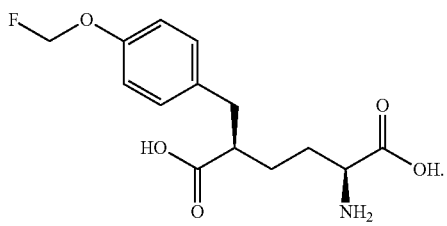 [SMILES: N[C@@H](CC[C@H](Cc1ccc(OCF)cc1)C(=O)O)C(=O)O]

Another more preferred compound of Formula VI is (2S,5S)-2-amino-5-[4-(fluoromethoxy)benzyl]hexanedioic acid:

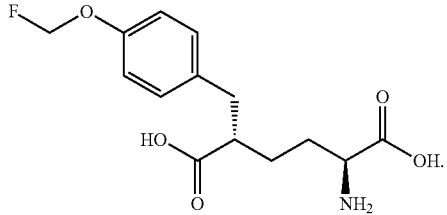

Another more preferred compound of Formula VI is (4S)-4-[4-(2-fluoroethoxy)-3-hydroxybenzyl]-L-glutamic acid:

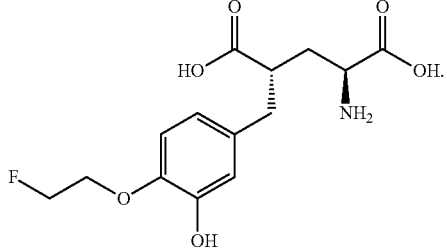 [SMILES: N[C@@H](C[C@H](Cc1ccc(OCCF)c(O)c1)C(=O)O)C(=O)O]

Another more preferred compound of Formula VI is (4S)-4-{4-[(fluoromethoxy]benzyl}-L-glutamic acid:

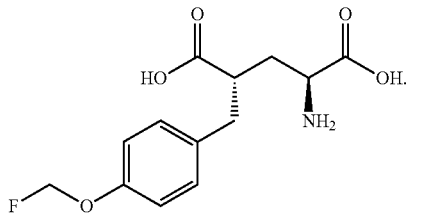 [SMILES: N[C@@H](C[C@H](Cc1ccc(OCF)cc1)C(=O)O)C(=O)O]

Another more preferred compound of Formula VI is (4R)-4-{4-[fluoromethoxy]benzyl}-L-glutamic acid:

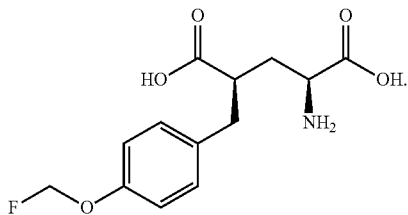 [SMILES: N[C@@H](C[C@@H](Cc1ccc(OCF)cc1)C(=O)O)C(=O)O]

Another more preferred compound of Formula VI is (2S)-2-amino-5-(4-{[2-fluoroethyl]amino}benzyl)hexanedioic acid:

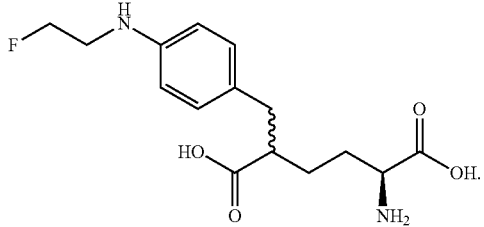 [SMILES: N[C@@H](CCC(Cc1ccc(NCCF)cc1)C(=O)O)C(=O)O]

Another more preferred compound of Formula VI is (2S)-2-amino-5-(4-{[(2S,3R)-4-fluoro-2,3-dihydroxybutyl]oxy}benzyl)hexanedioic acid:

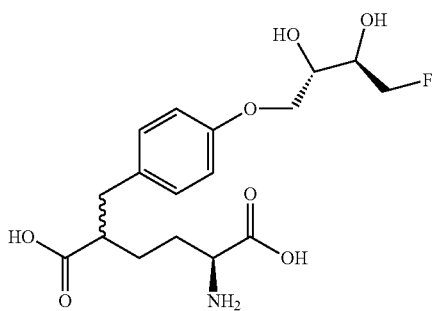 [SMILES: N[C@@H](CCC(Cc1ccc(OC[C@H](O)[C@@H](O)CF)cc1)C(=O)O)C(=O)O]

Another more preferred compound of Formula VI is (4S)-4-({6-[2-fluoroethoxy]pyridin-3-yl}methyl)-L-glutamic acid:

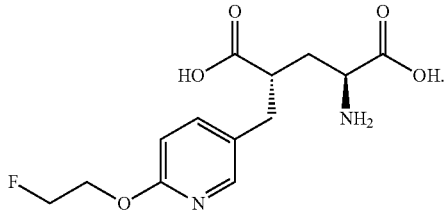

Another more preferred compound of Formula VI is (4S)-4-(4-{[(2S,3R)-4-fluoro-2,3-dihydroxybutyl]oxy}benzyl)-L-glutamic acid:

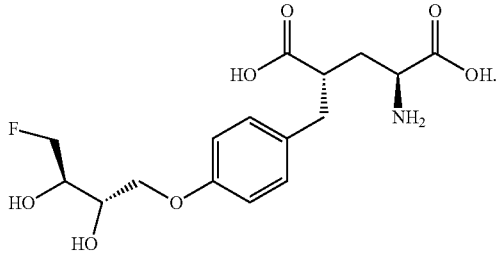 [SMILES: N[C@@H](C[C@H](Cc1ccc(OC[C@H](O)[C@@H](O)CF)cc1)C(=O)O)C(=O)O]

Another more preferred compound of Formula VI is (4S)-4-(4-{[1-fluoro-3-hydroxypropan-2-yl]oxy}benzyl)-L-glutamic acid:

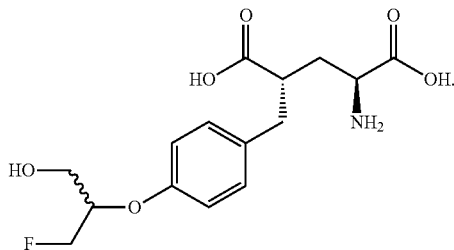

Another more preferred compound of Formula VI is 4-({1-[2-fluoroethyl]-1H-1,2,3-triazol-4-yl}methyl)-L-glutamic acid:

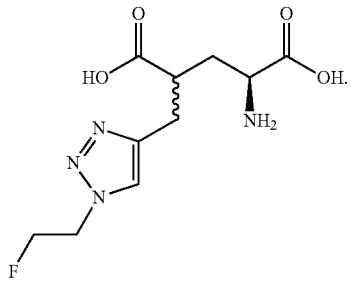 [SMILES: N[C@@H](CC(Cc1cn(CCF)nn1)C(=O)O)C(=O)O]

Another more preferred compound of Formula VI is (2S,5R)-2-amino-5-[4-(fluoroethoxy)benzyl]hexanedioic acid:

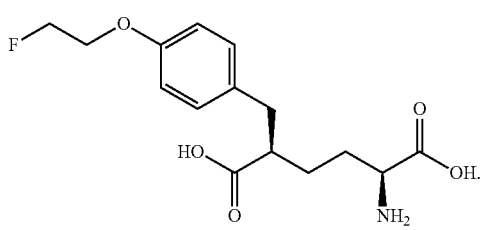

Another more preferred compound of Formula VI is (2S,5S)-2-amino-5-[4-(fluoroethoxy)benzyl]hexanedioic acid:

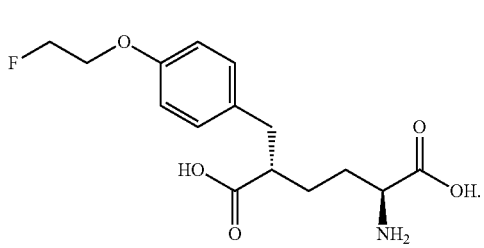

Another more preferred compound of Formula VI is (4S)-4-{4-fluoromethyl]benzyl}-L-glutamic acid:

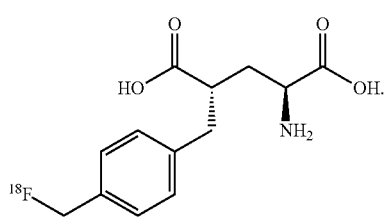 [SMILES: N[C@@H](C[C@H](Cc1ccc(C[18F])cc1)C(=O)O)C(=O)O]

The fifth aspect of the present invention is directed to compounds of Formula V:

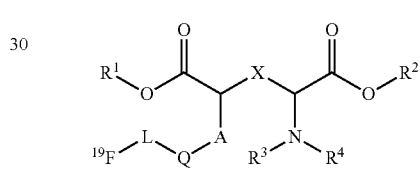

V wherein,
$R^1$ is hydrogen or a carboxyl protecting group,
$R^2$ is hydrogen or a carboxyl protecting group,
$R^3$ is hydrogen or an amine protecting group,
$R^4$ is hydrogen or an amine protecting group,
wherein at least one of $R^1$, $R^2$, $R^3$ and $R^4$ is not hydrogen,
X is selected from the group comprising:
  a) $CH_2$,
  b) $CH_2—CH_2$,
  c) $CH_2—CH_2—CH_2$, and
  d) $CH_2—CH_2—CH_2—CH_2—$,
A is alkylene.
Q is arylene or heteroarylene.
L is selected from the group comprising:
  a) alkylene,
  b) alkylene-O*,
  c) alkylene-N*H,
  d) cycloalkylene-O*,
  e) ($R^5$—O)-substituted alkylene,
  f) ($R^5$—O)-substituted alkylene-O*,
  g) ($R^6$—O), ($R^7$—O)-disubstituted alkylene,
  h) ($R^6$—O), ($R^7$—O)-disubstituted alkylene-O*, and
  i) $(CH_2CH_2O)_n—CH_2CH_2—O*$ with n=1, 2 or 3,
* indicates the position of the bond to Q.
$R^5$ is
  a) hydrogen or
  b) hydroxyl protecting group,
$R^6$ is
  a) hydrogen or
  b) hydroxyl protecting group, $R^7$ is
a) hydrogen or
b) hydroxyl protecting group, and
single isomers, tautomers, diastereomers, enantiomers, stereoisomers, stereoisomeric mixtures or mixtures thereof.

In a further embodiment, the invention is directed to compounds of Formula V:

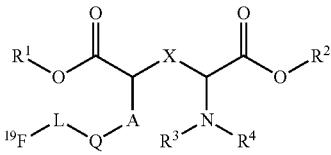

V wherein,
$R^1$ is hydrogen or a carboxyl protecting group.
$R^2$ is hydrogen or a carboxyl protecting group,
$R^3$ is hydrogen or an amine protecting group,
$R^4$ is hydrogen or an amine protecting group,
wherein at least one of $R^1$, $R^2$, $R^3$ and $R^4$ is not hydrogen,
X is selected from the group comprising:
a) $CH_2$,
b) $CH_2$—$CH_2$, and
c) $CH_2$—$CH_2$—$CH_2$,
A is alkylene.
Q is arylene or heteroarylene.
L is selected from the group comprising:
a) alkylene,
b) alkylene-O*,
c) alkylene-N*H,
d) cycloalkylene-O*,
e) ($R^5$—O)-substituted alkylene,
f) ($R^5$—O)-substituted alkylene-O*,
g) ($R^5$—O), ($R^7$—O)-disubstituted alkylene,
h) ($R^5$—O), ($R^7$—O)-disubstituted alkylene-O*, and
i) $(CH_2CH_2O)_n$—$CH_2CH_2$—O* with n=1, 2 or 3,
* indicates the position of the bond to Q,
$R^5$ is
a) hydrogen or
b) hydroxyl protecting group,
$R^6$ is
a) hydrogen or
b) hydroxyl protecting group,
$R^7$ is
a) hydrogen or
b) hydroxyl protecting group, and
single isomers, tautomers, diastereomers, enantiomers, stereoisomers, stereoisomeric mixtures or mixtures thereof.

In a further embodiment, the invention is directed to compounds of Formula V:

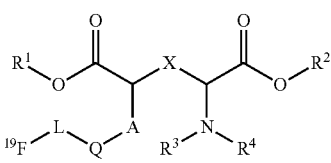

V wherein,
$R^1$ is hydrogen or a carboxyl protecting group,
$R^2$ is hydrogen or a carboxyl protecting group,
$R^3$ is hydrogen or an amine protecting group,
$R^4$ is hydrogen or an amine protecting group,
wherein at least one of $R^1$, $R^2$, $R^3$ and $R^4$ is not hydrogen,
X is selected from the group comprising:
a) $CH_2$, and
b) $CH_2$—$CH_2$.
A is alkylene.
Q is arylene or heteroarylene.
L is selected from the group comprising:
a) alkylene,
b) alkylene-O*,
c) alkylene-N*H,
d) cycloalkylene-O*,
e) ($R^5$—O)-substituted alkylene,
f) ($R^5$—O)-substituted alkylene-O*,
g) ($R^6$—O), ($R^7$—O)-disubstituted alkylene,
h) ($R^6$—O), ($R^7$—O)-disubstituted alkylene-O*, and
i) $(CH_2CH_2O)_n$—$CH_2CH_2$—O* with n=1, 2 or 3,
* indicates the position of the bond to Q.
$R^5$ is
a) hydrogen or
b) hydroxyl protecting group,
$R^6$ is
a) hydrogen or
b) hydroxyl protecting group,
$R^7$ is
a) hydrogen or
b) hydroxyl protecting group, and
single isomers, tautomers, diastereomers, enantiomers, stereoisomers, stereoisomeric mixtures or mixtures thereof.

Preferred Features of Invention and Embodiments Thereof:
Preferably, $R^1$ is a carboxyl-protecting group.
The carboxyl-protecting group is preferably selected from methyl, ethyl, propyl, butyl, tert-butyl, allyl, benzyl, 4-methoxybenzyl and 4-methoxyphenyl.
More preferably, $R^1$ is selected from the group comprising:
a) methyl,
b) ethyl, and
c) tert-butyl.
Even more preferably, $R^1$ is tert-butyl.
Preferably, $R^1$ is selected from the group comprising:
hydrogen, methyl, ethyl, propyl, butyl, tert-butyl, allyl, benzyl, 4-methoxybenzyl and 4-methoxyphenyl.
More preferably, $R^1$ is selected from the group comprising:
a) hydrogen,
b) methyl,
c) ethyl, and
d) tert-butyl.
Preferably, $R^2$ is a carboxyl-protecting group.
The carboxyl-protecting group is preferably selected from methyl, ethyl, propyl, butyl, tert-butyl, allyl, benzyl, 4-methoxybenzyl and 4-methoxyphenyl.
More preferably, $R^2$ is selected from the group comprising:
a) methyl,
b) ethyl, and
c) tert-butyl.
Even more preferably, $R^2$ is tert-butyl.
Preferably, $R^2$ is selected from the group comprising:
hydrogen, methyl, ethyl, propyl, butyl, tert-butyl, allyl, benzyl, 4-methoxybenzyl and 4-methoxyphenyl.
More preferably, $R^2$ is selected from the group comprising:
a) hydrogen,
b) methyl,
c) ethyl, and
d) tert-butyl.
Preferably, $R^1$ and $R^2$ are both a carboxyl protecting group.
Preferably, $R^3$ is hydrogen or an amine-protecting group.

The amine-protecting group is preferably carbobenzyloxy (Cbz), p-methoxybenzyl carbonyl (Moz or MeOZ), tert-butyloxycarbonyl (Boc), benzyl (Bn), p-methoxybenzyl (PMB), 3,4-dimethoxybenzyl (DMPM), p-methoxyphenyl (PMP), triphenylmethyl (Trityl) or methoxyphenyl diphenylmethyl (MMT).

Preferably $R^3$ is selected from the group comprising:
a) hydrogen,
b) tert-butyloxycarbonyl (Boc), and
c) triphenylmethyl (Trityl).

More preferably $R^3$ is selected from the group comprising:
a) tert-butyloxycarbonyl (Boc), and
b) triphenylmethyl (Trityl).

Preferably, $R^4$ is hydrogen or an amine-protecting group.

The amine-protecting group is preferably carbobenzyloxy (Cbz), p-methoxybenzyl carbonyl (Moz or MeOZ), tert-butyloxycarbonyl (Boc), benzyl (Bn), p-methoxybenzyl (PMB), 3,4-dimethoxybenzyl (DMPM), p-methoxyphenyl (PMP), triphenylmethyl (Trityl) or methoxyphenyl diphenylmethyl (MMT).

Preferably $R^4$ is selected from the group comprising:
a) hydrogen,
b) tert-butyloxycarbonyl (Boc), and
c) triphenylmethyl (Trityl).

More preferably $R^4$ is selected from the group comprising:
a) tert-butyloxycarbonyl (Boc) and
b) triphenylmethyl (Trityl).

Additionally, $R^3$ and $R^4$ optionally form an amine-protecting group, resulting in $NR^3R^4$ being 1,3-dioxo-1,3-dihydro-2H-isoindol-2-yl (phthalimido) or an azido group.

Preferably, $R^3$ is hydrogen and $R^4$ is an amine protecting group.

More preferably, $R^3$ is hydrogen and $R^4$ is tert-Butyloxycarbonyl (Boc).

More preferably, $R^3$ is hydrogen and $R^4$ is triphenylmethyl (Trityl).

Preferably, $R^3$ and $R^4$ are never Hydrogen at the same time.

Preferably, $R^1$ and $R^2$ are both a carboxyl protecting group, $R^3$ is hydrogen and $R^4$ is an amine protecting group.

Preferably, X is $CH_2$ or $CH_2$—$CH_2$.
More preferably, X is $CH_2$.
More preferably, X is $CH_2$—$CH_2$.

Preferably, A is $C_1$-$C_6$ alkylene. More preferably, A is $C_1$-$C_3$ alkylene.

Even more preferably, A is methylene.
Even more preferably, A is ethylene.
Even more preferably, A is propylene.
Preferably, Q is phenylene, triazolylene or pyridylene.
Preferably, Q is phenylene or pyridylene.
More preferably, Q is phenylene.
More preferably, Q is pyridylene or triazolylene.
More preferably, Q is pyridylene.
Even more preferably, Q is a pyridylene as defined below

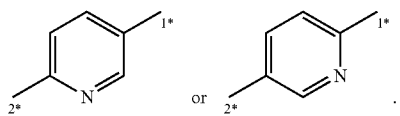

1* indicates the position of the bond to A and 2* indicates the position of the bond to L.

Preferably, L is selected from the group comprising:
a) $C_2$-$C_6$ alkylene,
b) $C_2$-$C_6$ alkylene-O*,
c) $C_2$-$C_6$ alkylene-N*H,
d) $C_3$-$C_6$ cycloalkylene-O*,
e) ($R^5$—O)-substituted $C_2$-$C_6$ alkylene,
f) ($R^5$—O)-substituted $C_3$-$C_6$ alkylene-O*,
g) ($R^6$—O), ($R^7$—O)-disubstituted $C_3$-$C_6$ alkylene,
h) ($R^6$—O), ($R^7$—O)-disubstituted $C_4$-$C_6$ alkylene-O*, and
i) $(CH_2CH_2O)_n$—$CH_2CH_2$—O* with n=1, 2 or 3.
* indicates the position of the bond to Q More preferably, L is selected from the group comprising:
a) propylene,
b) propylene-O*,
c) ethylene-O*,
d) propylene-N*H,
e) cyclobutylene-O*, f)
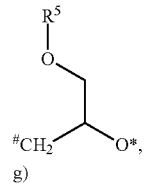

g)
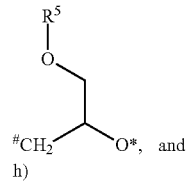
and h)
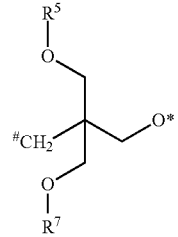

* indicates the position of the bond to Q and # indicates the position of the bond to F.

If L is alkylene. L is preferably linear or branched $C_2$-$C_6$ alkylene. More preferably, L is $C_2$-$C_3$ alkylene selected from ethylene and propylene.

Preferably, L is propylene.
Preferably, L is ethylene.
Preferably, L is methylene.

If L is alkylene-O* L is preferably $C_1$ alkylene-O* (methylene-O*) or linear or branched $C_2$-$C_6$ alkylene-O*. More preferably, L is $C_2$-$C_3$ alkylene-O* is selected from ethylene-O* and propylene-O*.

Preferably, L is propylene-O*.
Preferably, L is ethylene-O*.
Preferably, L is methylene-O*.

If L is alkylene-N*H L is preferably $C_1$ alkylene-N*H or linear or branched $C_2$-$C_6$ alkylene-N*H. More preferably, L is $C_2$-$C_3$ alkylene-N*H, selected from ethylene-N*H and propylene-N*H.

Preferably, L is propylene-N*H.
Preferably, L is ethylene-N*H.
Preferably, L is methylene-N*H.

"Alkylene" represents a linear or branched saturated bivalent chain of carbon atoms having 1 to 6, preferably 1 to 3 or 4 to 6, carbon atoms, by way of example and by preference methylene, ethylene and propylene. Preferably, alkylene is $C_1$ alkylene or $C_2$-$C_6$ alkylene. More preferably, alkylene is $C_2$-$C_3$ alkylene or $C_4$-$C_6$ alkylene.

The same applies to $C_2$-$C_6$alkylene-O* and $C_2$-$C_6$alkylene-NH*.

"Cycloalkylene" represents an alicyclic bivalent group of carbon atoms having 3 to 8, preferably 4 to 6, carbon atoms, by way of example and by preference cyclopropylene, cyclobutylene, cyclopentylene and cyclohexylene.

If L is cycloalkylene-O* L is preferably $C_3$-$C_6$ cycloalkylene-O* such as cyclopropylene-O*, cyclobutylene-O*, cyclopentylene-O* or cyclohexylene-O*.

Preferably, L is

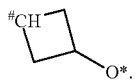

# indicates the position of the bond to F.

If L is ($R^5$—O)-substituted $C_2$-$C_6$ alkylene, ($R^5$—O)-substituted $C_3$-$C_6$ alkylene-O*, ($R^6$—O), ($R^7$—O)-disubstituted $C_3$-$C_6$alkylene, or ($R^6$—O), ($R^7$—O)-disubstituted $C_4$-$C_6$alkylene-O*, L is preferably an alkylene defined as above bearing one or two protected or unprotected hydroxyl groups.

Preferably, L is ($R^5$—O)-substituted $C_3$-$C_6$alkylene-O* selected from

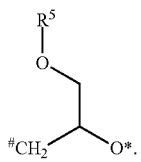

Preferably, L is ($R^6$—O), ($R^7$—O)-disubstituted $C_4$-$C_6$alkylene-O* selected from

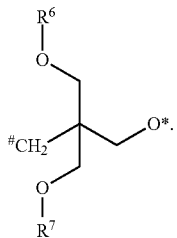

* indicates the position of the bond to Q, # indicates the position of the bond to F.

Preferably, $R^6$ is a hydroxyl protecting group.
Preferably, $R^6$ and $R^7$ are hydroxyl protecting groups.
Additionally, $R^6$ and $R^7$ optionally form together one-diol protecting group.

Compounds of Formula V are defined by the general formula and/or the combination of the preferred features as defined above.

In a first embodiment, compounds of the formula V are defined as compounds of Formula V-1, See structure in table E.

In a second embodiment, compounds of the formula V are defined as compounds of Formula V-2, See structure in table E.

In a third embodiment, compounds of the formula V are defined as compounds of Formula V-3, See structure in table E.

In a fourth embodiment, compounds of the formula V are defined as compounds of Formula V-4, See structure in table E.

In a fifth embodiment, compounds of the formula V are defined as encompassing single isomers or any mixture of at least two stereoisomers of Formula V-1, Formula V-2, Formula V-3 and Formula V-4 including racemates and diastereomeric mixtures.

Preferred features as disclosed above are incorporated herein for all embodiments.

TABLE E

Formula V stereoisomers

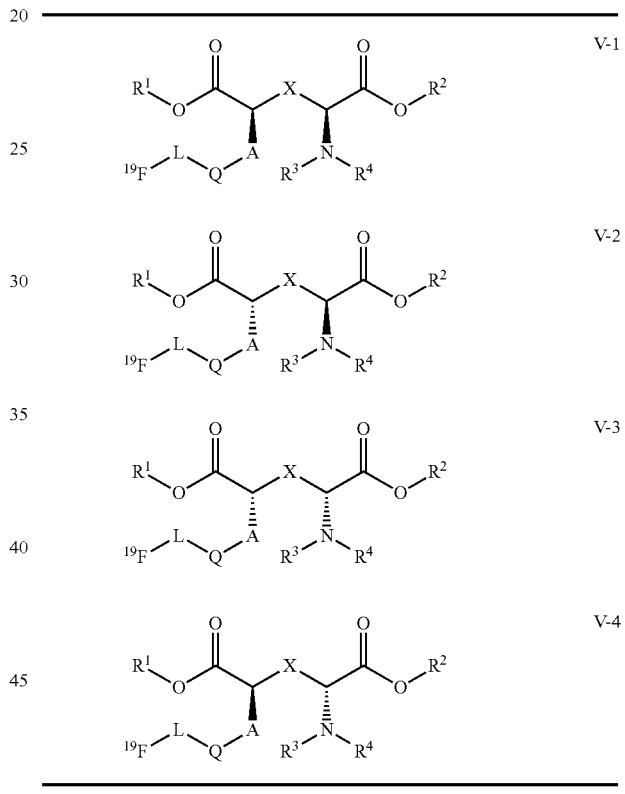

A preferred compound of Formula V is di-tert-butyl N-(tert-butoxycarbonyl)-4-{4-[2-fluoroethoxy]benzyl}glutamate:

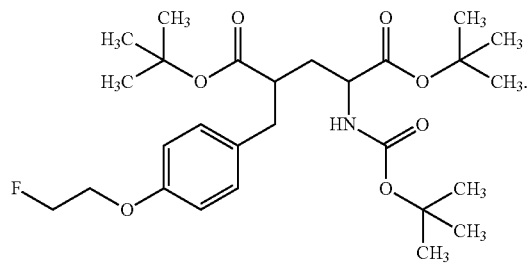

Another preferred compound of Formula V is di-tert-butyl N-(tert-butoxycarbonyl)-4-{4-[3-fluoropropoxy]benzyl}glutamate:

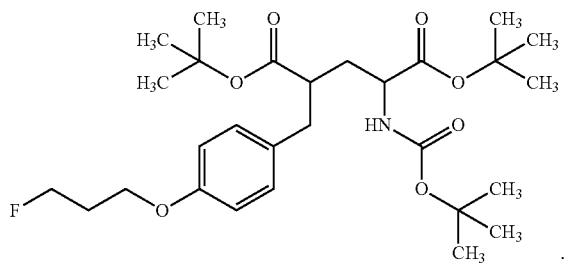 [SMILES: CC(C)(C)OC(=O)NC(CC(Cc1ccc(OCCCF)cc1)C(=O)OC(C)(C)C)C(=O)OC(C)(C)C]

Another preferred compound of Formula V is di-tert-butyl N-(tert-butoxycarbonyl)-4-{4-[3-fluoropropyl]benzyl}glutamate:

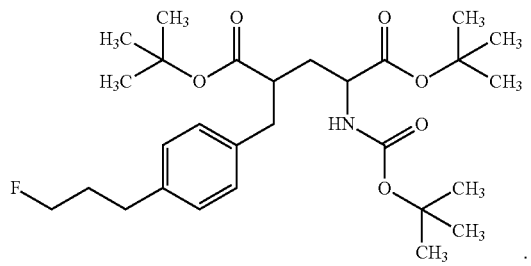 [SMILES: CC(C)(C)OC(=O)NC(CC(Cc1ccc(CCCF)cc1)C(=O)OC(C)(C)C)C(=O)OC(C)(C)C]

Another preferred compound of Formula V is di-tert-butyl N-(tert-butoxycarbonyl)-4-(4-{[3-fluoropropyl]amino}benzyl)glutamate:

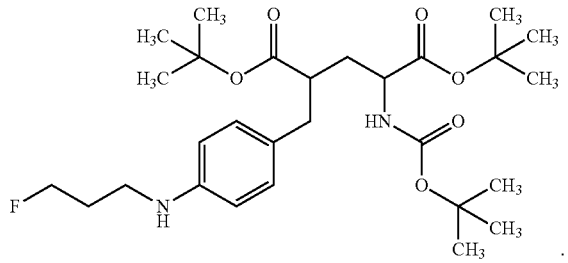 [SMILES: CC(C)(C)OC(=O)NC(CC(Cc1ccc(NCCCF)cc1)C(=O)OC(C)(C)C)C(=O)OC(C)(C)C]

Another preferred compound of Formula V is di-tert-butyl N-(tert-butoxycarbonyl)-4-(4-{[3-fluorocyclobutyl]oxy}benzyl)glutamate:

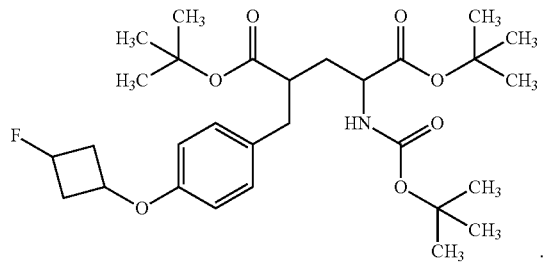 [SMILES: CC(C)(C)OC(=O)NC(CC(Cc1ccc(OC2CC(F)C2)cc1)C(=O)OC(C)(C)C)C(=O)OC(C)(C)C]

Another preferred compound of Formula V is di-tert-butyl N-(tert-butoxycarbonyl)-4-(3-{4-[2-fluoroethoxy]phenyl}propyl)glutamate:

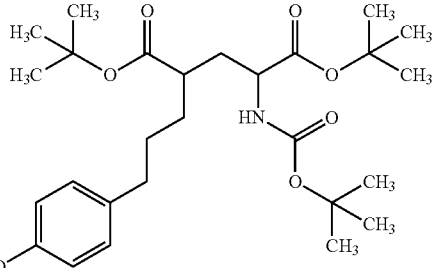

Another preferred compound of Formula V is di-tert-butyl N-(tert-butoxycarbonyl)-4-(3-{4-[2-fluoropropyl]phenyl}propyl)glutamate:

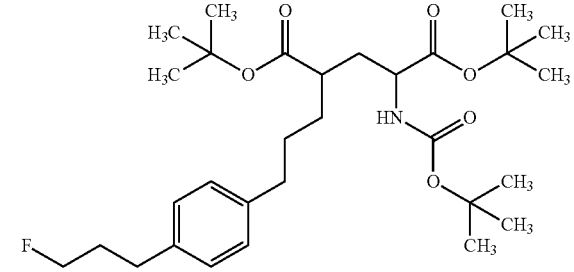

Another preferred compound of Formula V is di-tert-butyl 2-[(tert-butoxycarbonyl)amino]-5-{4-[2-fluoroethoxy]benzyl}hexanedioate:

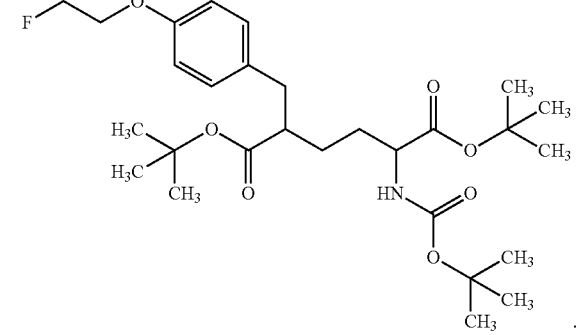

Another preferred compound of Formula V is di-tert-butyl N-(tert-butoxycarbonyl)-4-{[5-(2-fluoroethoxy)pyridin-2-yl]methyl}glutamate:

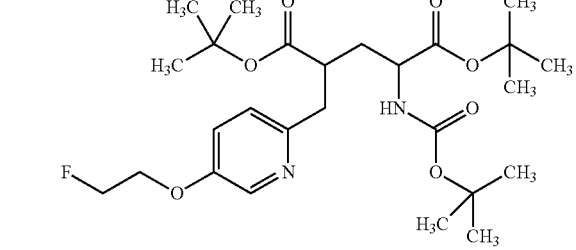

Another preferred compound of Formula V is di-tert-butyl N-(tert-butoxycarbonyl)-4-{[5-(3-fluoropropyl)pyridin-2-yl]methyl}-glutamate:

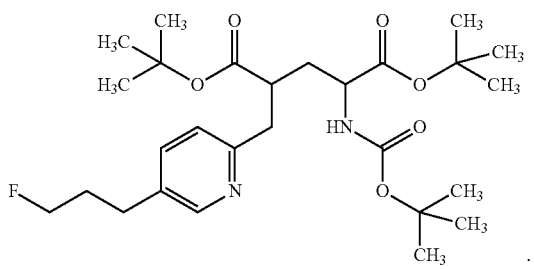 [SMILES: CC(C)(C)OC(=O)NC(CC(Cc1ccc(CCCF)cn1)C(=O)OC(C)(C)C)C(=O)OC(C)(C)C]

A more preferred compound of Formula V is di-tert-butyl (4S)—N-(tert-butoxycarbonyl)-4-[4-(2-fluoroethoxy)benzyl]-L-glutamate:

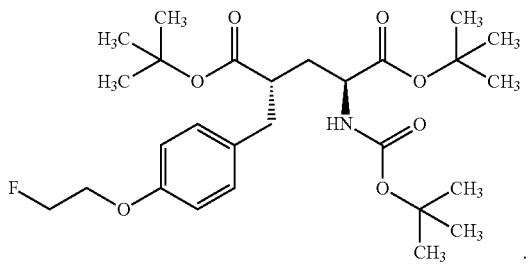 [SMILES: CC(C)(C)OC(=O)N[C@@H](C[C@H](Cc1ccc(OCCF)cc1)C(=O)OC(C)(C)C)C(=O)OC(C)(C)C]

Another more preferred compound of Formula V is di-tert-butyl (4R)—N-(tert-butoxycarbonyl)-4-[4-(2-fluoroethoxy)benzyl]-D-glutamate:

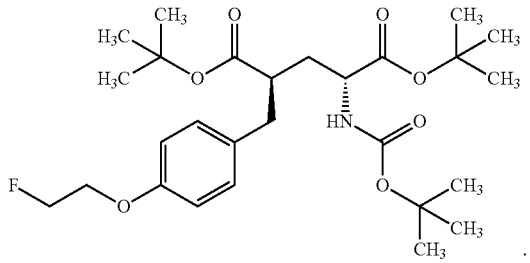 [SMILES: CC(C)(C)OC(=O)N[C@H](C[C@@H](Cc1ccc(OCCF)cc1)C(=O)OC(C)(C)C)C(=O)OC(C)(C)C]

Another more preferred compound of Formula V is di-tert-butyl (4S)—N-(tert-butoxycarbonyl)-4-{4-[3-fluoropropoxy]benzyl}-L-glutamate:

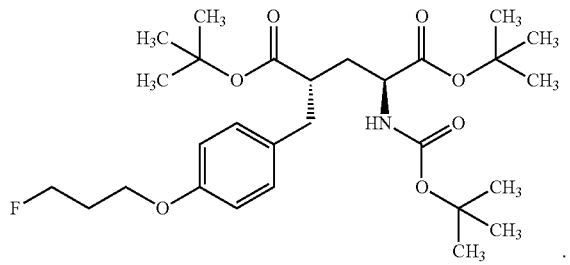 [SMILES: CC(C)(C)OC(=O)N[C@@H](C[C@H](Cc1ccc(OCCCF)cc1)C(=O)OC(C)(C)C)C(=O)OC(C)(C)C]

Another more preferred compound of Formula V is di-tert-butyl (4R)—N-(tert-butoxy-carbonyl)-4-{4-[3-fluoropropoxy]benzyl}-D-glutamate:

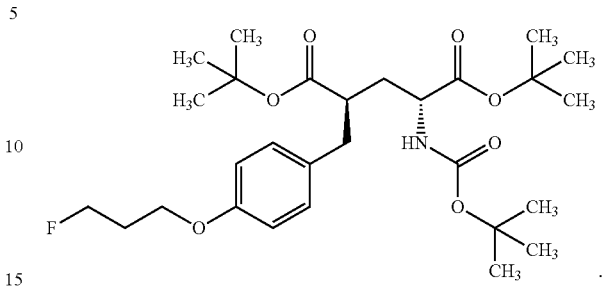

Another more preferred compound of Formula V is di-tert-butyl N-(tert-butoxycarbonyl)-4-{4-[3-fluoropropyl]benzyl}-L-glutamate:

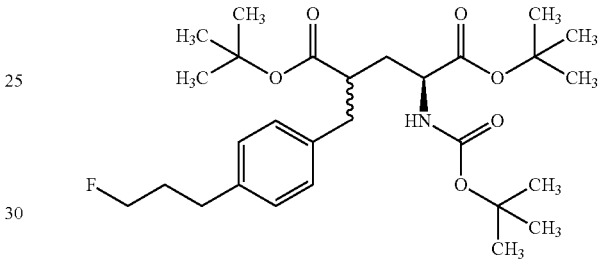

Another more preferred compound of Formula V is di-tert-butyl (4S)—N-(tert-butoxy-carbonyl)-4-(4-{[3-fluoropropyl]amino}benzyl)-L-glutamate:

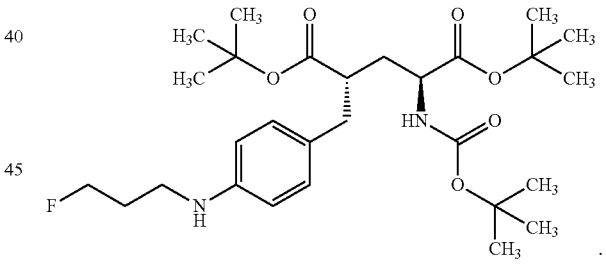

Another more preferred compound of Formula V is di-tert-butyl (4S)—N-(tert-butoxy(4S)-carbonyl)-4-(4-{[cis-3-fluorocyclobutyl]oxy}benzyl)-L-glutamate:

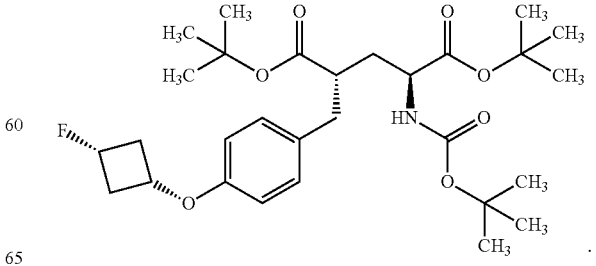

Another more preferred compound of Formula V is di-tert-butyl (4S)—N-(tert-butoxycarbonyl)-4-(3-{4-[2-fluoroethoxy]phenyl}propyl)-L-glutamate:

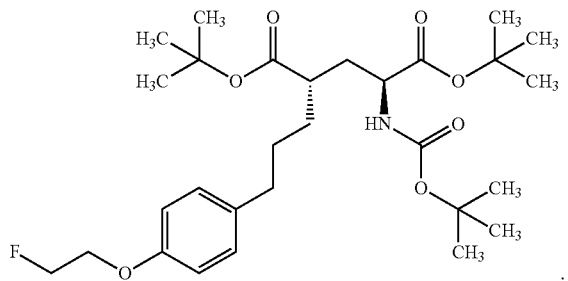

Another more preferred compound of Formula V is di-tert-butyl (2S)-2-[(tert-butoxycarbonyl)amino]-5-{4-[2-fluoroethoxy]benzyl}hexanedioate:

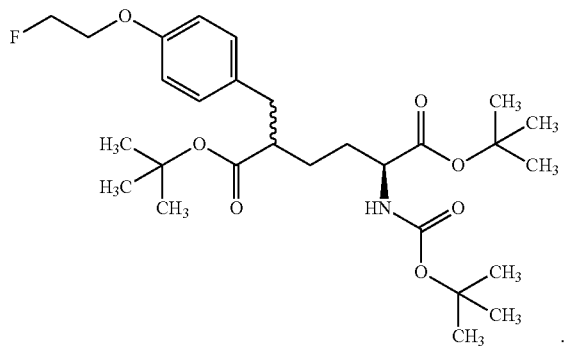 [SMILES: CC(C)(C)OC(=O)N[C@@H](CCC(Cc1ccc(OCCF)cc1)C(=O)OC(C)(C)C)C(=O)OC(C)(C)C]

Another more preferred compound of Formula V is di-tert-butyl (2R)-2-[(tert-butoxy-carbonyl)amino]-5-{4-[2-fluoroethoxy]benzyl}hexanedioate:

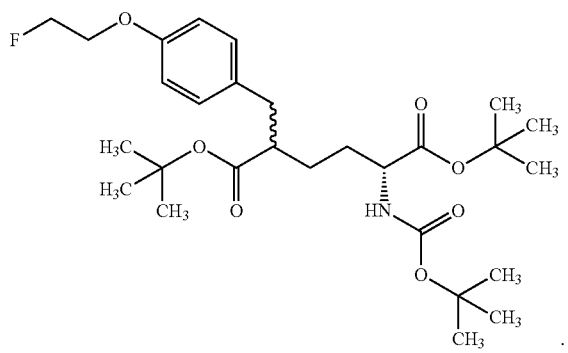

Another more preferred compound of Formula V is di-tert-butyl (4R)—N-(tert-butoxy-carbonyl)-4-{[5-(2-fluoroethoxy)pyridin-2-yl]methyl}-L-glutamate:

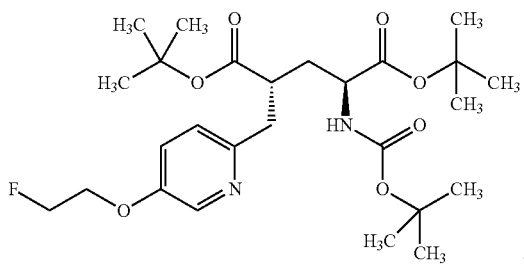

Another more preferred compound of Formula V is di-tert-butyl (4R)—N-(tert-butoxycarbonyl)-4-{[5-(3-fluoropropyl)pyridin-2-yl]methyl}-L-glutamate:

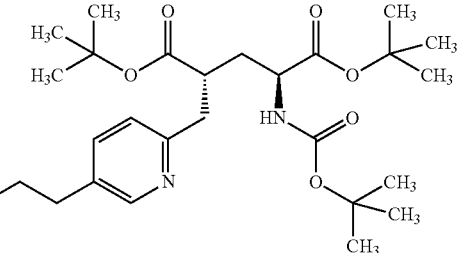

Another more preferred compound of Formula V is di-tert-butyl (4R)—N-(tert-butoxycarbonyl)-4-{[5-(2-fluoroethoxy)pyridin-2-yl]methyl}-L-glutamate:

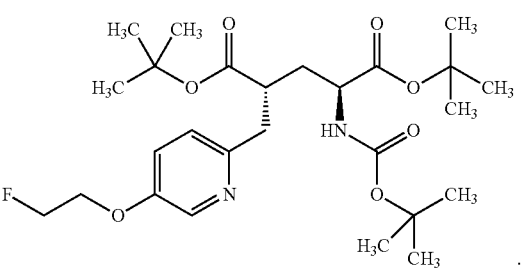 [SMILES: CC(C)(C)OC(=O)N[C@@H](C[C@H](Cc1ccc(OCCF)cn1)C(=O)OC(C)(C)C)C(=O)OC(C)(C)C]

Another more preferred compound of Formula V is di-tert-butyl (2S)-2-[(tert-butoxycarbonyl)amino]-5-{[5-(2-fluoroethoxy)pyridin-2-yl]methyl}hexanedioate:

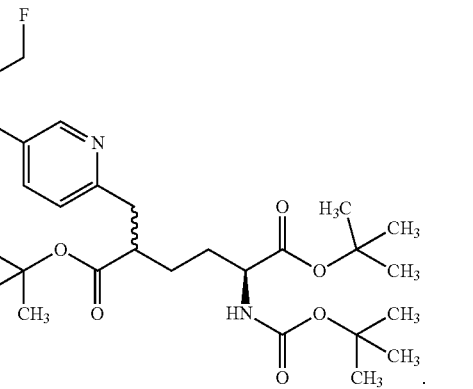

Another more preferred compound of Formula V is di-tert-butyl (4R) N-(tert-butoxycarbonyl)-4-{[5-(2-fluoroethoxy)-1-oxidopyridin-2-yl]methyl}-L-glutamate:

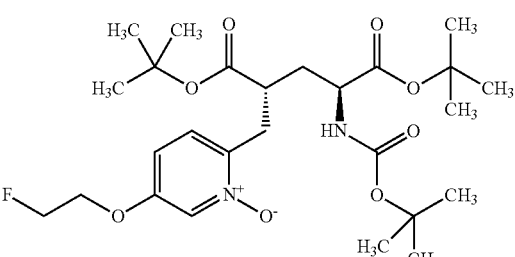

Another more preferred compound of Formula V is (2S)-2-tert-butoxycarbonylamino-5-{2-[4-(2-fluoro-ethoxy)-phenyl]-ethyl}-hexanedioic acid di-tert-butyl ester:

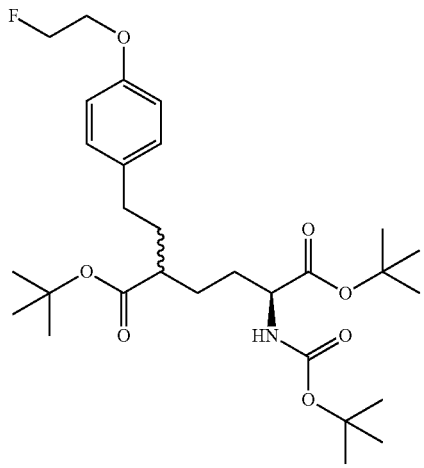

Another more preferred compound of Formula V is di-tert-butyl (4S)—N-(tert-butoxycarbonyl)-4-[3-tert-butoxy-4-(2-fluoroethoxy)benzyl]-glutamate:

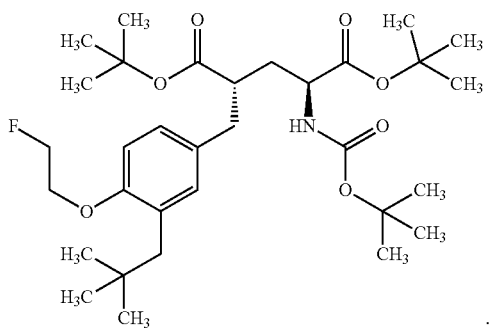 [SMILES: CC(C)(C)Cc1cc(C[C@@H](C[C@H](NC(=O)OC(C)(C)C)C(=O)OC(C)(C)C)C(=O)OC(C)(C)C)ccc1OCCF]

Another more preferred compound of Formula V is di-tert-butyl (2S)-2-[(tert-butoxycarbonyl)amino]-5-(4-{(tert-butoxycarbonyl)[2-fluoroethyl]amino}benzyl)hexanedioate:

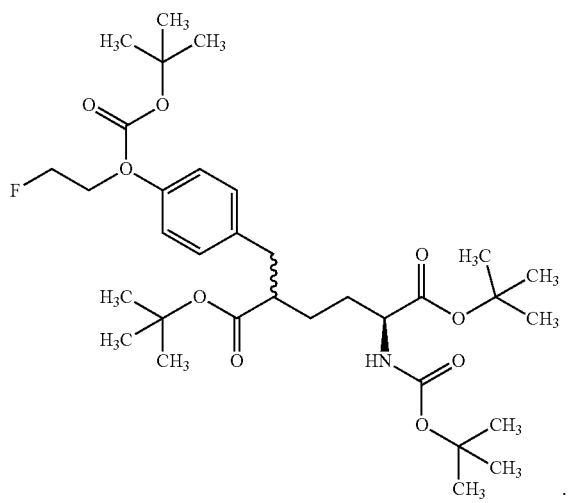

Another more preferred compound of Formula V is di-tert-butyl (2S)-2-[(tert-butoxycarbonyl)amino]-5-[4-({(4S,5R)-5-[fluoromethyl]-2,2-dimethyl-1,3-dioxolan-4-yl}methoxy)benzyl]hexanedioate:

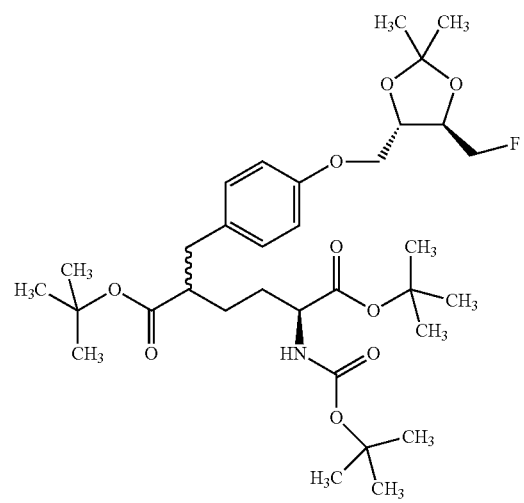 [SMILES: CC(C)(C)OC(=O)N[C@@H](CCC(Cc1ccc(OC[C@@H]2OC(C)(C)O[C@H]2CF)cc1)C(=O)OC(C)(C)C)C(=O)OC(C)(C)C]

Another more preferred compound of Formula V is di-tert-butyl (4S)—N-(tert-butoxycarbonyl)-4-({6-[2-fluoroethoxy]pyridin-3-yl}methyl)-L-glutamate:

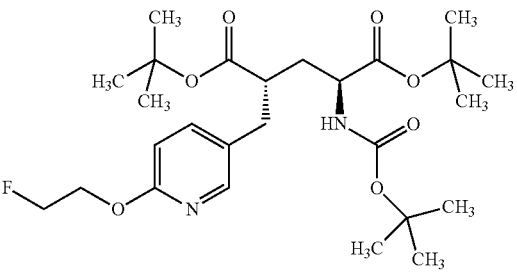

Another more preferred compound of Formula V is di-tert-butyl (4S)—N-(tert-butoxycarbonyl)-4-[4-({(4S,5R)-5-[fluoromethyl]-2,2-dimethyl-1,3-dioxolan-4-yl}methoxy)benzyl]-L-glutamate:

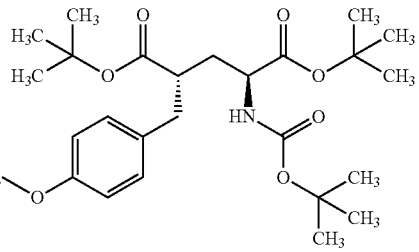

Another more preferred compound of Formula V is di-tert-butyl (4S)—N-(tert-butoxycarbonyl)-4-(4-{[1-fluoro-3-hydroxypropan-2-yl]oxy}benzyl)-L-glutamate:

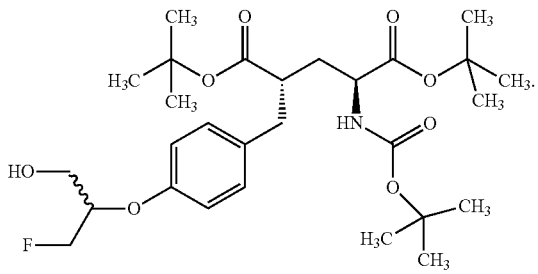 [SMILES: CC(C)(C)OC(=O)N[C@@H](C[C@H](Cc1ccc(OC(CO)CF)cc1)C(=O)OC(C)(C)C)C(=O)OC(C)(C)C]

Another more preferred compound of Formula V is di-tert-butyl (4R)—N-(tert-butoxycarbonyl)-4-({1-[2-fluoroethyl]-1H-1,2,3-triazol-4-yl}methyl)-L-glutamate:

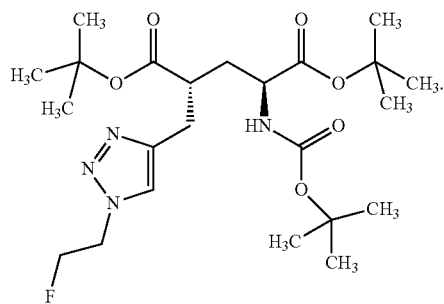 [SMILES: CC(C)(C)OC(=O)N[C@@H](C[C@H](Cc1cn(CCF)nn1)C(=O)OC(C)(C)C)C(=O)OC(C)(C)C]

Another more preferred compound of Formula V is di-tert-butyl (4S)—N-(tert-butoxycarbonyl)-4-[4-(fluoromethyl)benzyl]-L-glutamate:

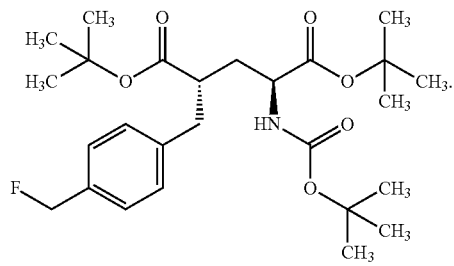 [SMILES: CC(C)(C)OC(=O)N[C@@H](C[C@H](Cc1ccc(CF)cc1)C(=O)OC(C)(C)C)C(=O)OC(C)(C)C]

The sixth aspect of the present invention is directed to compounds of Formula IV:

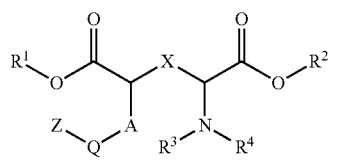

wherein
$R^1$ is hydrogen or a carboxyl protecting group.
$R^2$ is hydrogen or a carboxyl protecting group,
$R^3$ is hydrogen or an amine protecting group,
$R^4$ is hydrogen or an amine protecting group,
X is selected from the group comprising:
  a) $CH_2$,
  b) $CH_2$—$CH_2$,
  c) $CH_2$—$CH_2$—$CH_2$, and
  d) $CH_2$—$CH_2$—$CH_2$—$CH_2$—,
A is alkylene.
Q is arylene or heteroarylene.
Z is selected from the group comprising:
  a) HO-L*,
  b) OH,
  c) Halogen, and
  d) $NH_2$,
L is selected from the group comprising:
  a) alkylene,
  b) alkylene-O*,
  c) alkylene-N*H,
  d) cycloalkylene-O*,
  e) ($R^5$—O)-substituted alkylene,
  f) ($R^5$—O)-substituted alkylene-O*,
  g) ($R^6$—O), ($R^7$—O)-disubstituted alkylene,
  h) ($R^6$—O), ($R^7$—O)-disubstituted alkylene-O*, and
  i) $(CH_2CH_2O)_n$—$CH_2CH_2$—O* with n=1, 2 or 3,
* indicates the position of the bond to Q.
$R^5$ is
  a) hydrogen or
  b) hydroxyl protecting group,
$R^6$ is
  a) hydrogen or
  b) hydroxyl protecting group,
$R^7$ is
  a) hydrogen or
  b) hydroxyl protecting group, and
single isomers, tautomers, diastereomers, enantiomers, stereoisomers, stereoisomeric mixtures or mixtures thereof,
with the provisos, that:
Z is not Halogen if X is $CH_2$,
Z is not OH if X is $CH_2$, and Q is phenyl or
Z is not Halogen if X is $CH_2$—$CH_2$.

In a further embodiment, the invention is directed to compounds of Formula IV:

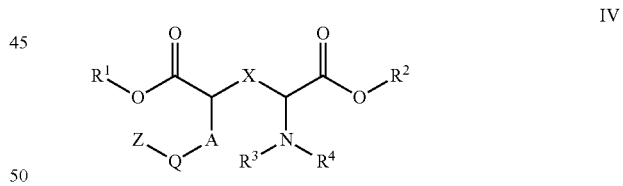

wherein
$R^1$ is hydrogen or a carboxyl protecting group.
$R^2$ is hydrogen or a carboxyl protecting group,
$R^3$ is hydrogen or an amine protecting group,
$R^4$ is hydrogen or an amine protecting group,
X is selected from the group comprising:
  a) $CH_2$,
  b) $CH_2$—$CH_2$, and
  c) $CH_2$—$CH_2$—$CH_2$,
A is alkylene.
Q is arylene or heteroarylene.
Z is selected from the group comprising:
  a) HO-L*,
  b) OH,
  c) Halogen, and
  d) $NH_2$, L is selected from the group comprising:
a) alkylene,
b) alkylene-O*,
c) alkylene-N*H,
d) cycloalkylene-O*,
e) ($R^5$—O)-substituted alkylene,
f) ($R^5$—O)-substituted alkylene-O*,
g) ($R^6$—O), ($R^7$—O)-disubstituted alkylene,
h) ($R^6$—O), ($R^7$—O)-disubstituted alkylene-O*, and
i) $(CH_2CH_2O)_n$—$CH_2CH_2$—O* with n=1, 2 or 3,
* indicates the position of the bond to Q.
$R^5$ is
a) hydrogen or
b) hydroxyl protecting group,
$R^6$ is
a. hydrogen or
b. hydroxyl protecting group,
$R^7$ is
a) hydrogen or
b) hydroxyl protecting group, and
single isomers, tautomers, diastereomers, enantiomers, stereoisomers, stereoisomeric mixtures or mixtures thereof,
with the provisos, that:
Z is not Halogen if X is $CH_2$.
Z is not OH if X is $CH_2$, and Q is phenyl or
Z is not Halogen if X is $CH_2$—$CH_2$.

In a further embodiment, the invention is directed to compounds of Formula IV:

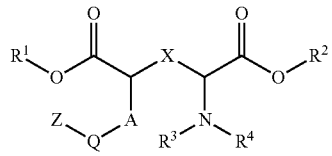

IV wherein
$R^1$ is hydrogen or a carboxyl protecting group.
$R^2$ is hydrogen or a carboxyl protecting group,
$R^3$ is hydrogen or an amine protecting group,
$R^4$ is hydrogen or an amine protecting group,
X is selected from the group comprising:
a) $CH_2$, and
b) $CH_2$—$CH_2$,
A is alkylene.
Q is arylene or heteroarylene,
Z is selected from the group comprising:
a) HO-L*,
b) OH,
c) Halogen, and
d) $NH_2$.
L is selected from the group comprising:
a) alkylene,
b) alkylene-O*,
c) alkylene-N*H,
d) cycloalkylene-O*,
e) ($R^5$—O)-substituted alkylene,
f) ($R^5$—O)-substituted alkylene-O*,
g) ($R^5$—O), ($R^7$—O)-disubstituted alkylene,
h) ($R^5$—O), ($R^7$—O)-disubstituted alkylene-O*, and
i) $(CH_2CH_2O)_n$—$CH_2CH_2$—O* with n=1, 2 or 3,
* indicates the position of the bond to Q.
$R^5$ is
a) hydrogen or
b) hydroxyl protecting group,
$R^6$ is
a. hydrogen or
b. hydroxyl protecting group,
$R^7$ is
a) hydrogen or
b) hydroxyl protecting group, and
single isomers, tautomers, diastereomers, enantiomers, stereoisomers, stereoisomeric mixtures or mixtures thereof,
with the provisos, that:
Z is not Halogen if X is $CH_2$,
Z is not OH if X is $CH_2$, and Q is phenyl or
Z is not Halogen if X is $CH_2$—$CH_2$.

In a further embodiment, the invention is directed to compounds of Formula IV:

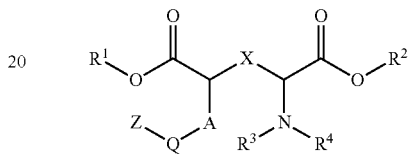

IV wherein
$R^1$ is hydrogen or a carboxyl protecting group.
$R^2$ is hydrogen or a carboxyl protecting group,
$R^3$ is hydrogen or an amine protecting group,
$R^4$ is hydrogen or an amine protecting group,
X is selected from the group comprising:
a) $CH_2$,
b) $CH_2$—$CH_2$, and
c) $CH_2$—$CH_2$—$CH_2$,
A is alkylene,
Q is arylene or heteroarylene.
Z is selected from the group comprising:
a) HO-L*,
b) OH,
c) Halogen, and
d) $NH_2$,
L is selected from the group comprising:
a) alkylene,
b) alkylene-O*,
c) alkylene-N*H,
d) cycloalkylene-O*,
e) ($R^5$—O)-substituted alkylene,
f) ($R^5$—O)-substituted alkylene-O*,
g) ($R^6$—O), ($R^7$—O)-disubstituted alkylene,
h) ($R^6$—O), ($R^7$—O)-disubstituted alkylene-O*, and
i) $(CH_2CH_2O)_n$—$CH_2CH_2$—O* with n=1, 2 or 3,
* indicates the position of the bond to Q,
$R^5$ is
a) hydrogen or
b) hydroxyl protecting group,
$R^6$ is
a) hydrogen or
b) hydroxyl protecting group,
$R^7$ is
a) hydrogen or
b) hydroxyl protecting group, and
single isomers, tautomers, diastereomers, enantiomers, stereoisomers, stereoisomeric mixtures or mixtures thereof,
Preferred Features of Invention and Embodiments Thereof:
Preferably, $R^1$ is a carboxyl-protecting group selected from methyl, ethyl, propyl, butyl, tert-butyl, allyl, benzyl, 4-methoxybenzyl and 4-methoxyphenyl.

More preferably, $R^1$ is selected from the group comprising:
a) methyl,
b) ethyl, and
c) tert-butyl.
Even more preferably, $R^1$ is tert-butyl.
Preferably, $R^1$ is hydrogen.
Preferably, $R^2$ is a carboxyl-protecting group selected from methyl, ethyl, propyl, butyl, tert-butyl, allyl, benzyl, 4-methoxybenzyl and 4-methoxyphenyl.
More preferably, $R^2$ is selected from the group comprising:
a) methyl,
b) ethyl, and
c) tert-butyl.
Even more preferably, $R^2$ is tert-butyl.
Preferably, $R^2$ is hydrogen.
Preferably, $R^1$ and $R^2$ are identical.
Preferably, $R^3$ is hydrogen or an amine-protecting group.
The amine-protecting group is preferably carbobenzyloxy (Cbz), p-methoxybenzyl carbonyl (Moz or MeOZ), tert-butyloxycarbonyl (Boc), benzyl (Bn), p-methoxybenzyl (PMB), 3,4-dimethoxybenzyl (DMPM), p-methoxyphenyl (PMP), triphenylmethyl (Trityl) or methoxyphenyl diphenylmethyl (MMT).
Preferably $R^3$ is selected from the group comprising:
a) Hydrogen,
b) tert-Butyloxycarbonyl (Boc), and
c) triphenylmethyl (Trityl).
More preferably $R^3$ is selected from the group comprising:
a) tert-butyloxycarbonyl (Boc), and
b) triphenylmethyl (Trityl).
Preferably, $R^4$ is hydrogen or an amine-protecting group.
The amine-protecting group is preferably carbobenzyloxy (Cbz), p-methoxybenzyl carbonyl (Moz or MeOZ), tert-butyloxycarbonyl (Boc), benzyl (Bn), p-methoxybenzyl (PMB), 3,4-dimethoxybenzyl (DMPM), p-methoxyphenyl (PMP), triphenylmethyl (Trityl) or methoxyphenyl diphenylmethyl (MMT).
Preferably $R^4$ is selected from the group comprising:
a) Hydrogen,
b) tert-Butyloxycarbonyl (Boc), and
c) triphenylmethyl (Trityl).
More preferably $R^4$ is selected from the group comprising:
a) tert-butyloxycarbonyl (Boc) and
b) triphenylmethyl (Trityl).
Additionally, $R^3$ and $R^4$ optionally form an amine-protecting group, resulting in $NR^3R^4$ being 1,3-dioxo-1,3-dihydro-2H-isoindol-2-yl (phthalimido) or an azido group.
Preferably, $R^3$ is hydrogen and $R^4$ is an amine protecting group.
More preferably, $R^3$ is hydrogen and $R^4$ is tert-Butyloxycarbonyl (Boc).
More preferably, $R^3$ is hydrogen and $R^4$ is triphenylmethyl (Trityl).
Preferably, $R^3$ and $R^4$ are never Hydrogen at the same time.
Preferably, $R^1$ and $R^2$ are both a carboxyl protecting group, $R^3$ is hydrogen and $R^4$ is an amine protecting group.
In another preferred embodiment, $R^1$, $R^2$, $R^3$ and $R^4$ are hydrogen.
Preferably, X is $CH_2$ or $CH_2$—$CH_2$.
More preferably, X is $CH_2$.
More preferably, X is $CH_2$—$CH_2$.
Preferably, A is $C_1$-$C_6$ alkylene. More preferably, A is $C_1$-$C_3$ alkylene.
Even more preferably, A is methylene.
Even more preferably, A is ethylene.
Even more preferably, A is propylene.
Preferably, Q is phenylene, triazolylene or pyridylene.

Preferably, Q is phenylene or pyridylene.
More preferably, Q is phenylene.
More preferably, Q is pyridylene or triazolylene.
More preferably, Q is pyridylene.
Even more preferably, Q is a pyridylene as defined below

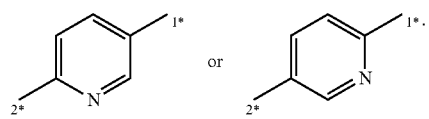

$^{1*}$ indicates the position of the bond to A and $^{2*}$ indicates the position of the bond to Z.
Preferably, Z is selected from the group comprising:
a) HO-L*,
b) OH,
c) $NH_2$.
* indicates the position of the bond to Q.
More preferably, Z is selected from the group comprising:
a) HO—($C_2$-$C_3$ alkylene),
b) HO—($C_2$-$C_3$ alkylene)-O*,
c) OH, and
d) $NH_2$,
More preferably, Z is selected from the group comprising:
a) HO-propylene-O* or OH-ethylene-O*,
b) HO-propylene,
c) OH, and
d) $NH_2$,
with the proviso, that:
Z is not OH if X is $CH_2$.
Preferably, Z is OH and X=$CH_2$—$CH_2$.
Preferably, L is selected from the group comprising:
a) $C_2$-$C_6$ alkylene,
b) $C_2$-$C_6$alkylene-O*,
c) $C_2$-$C_6$alkylene-N*H,
d) $C_3$-$C_6$cycloalkylene-O*,
e) ($R^5$—O)-substituted $C_2$-$C_6$ alkylene,
f) ($R^5$—O)-substituted $C_3$-$C_6$alkylene-O*,
g) ($R^6$—O), ($R^7$—O)-disubstituted $C_3$-$C_6$ alkylene,
h) ($R^6$—O), ($R^7$—O)-disubstituted $C_4$-$C_6$alkylene-O*, and
i) $(CH_2CH_2O)_n$—$CH_2CH_2$—O* with n=1, 2 or 3.
* indicates the position of the bond to Q
More preferably, L is selected from the group comprising:
a) propylene,
b) propylene-O*,
c) ethylene-O*,
d) propylene-N*H,
e) cyclobutylene-O*, f)

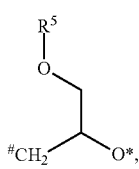

g) 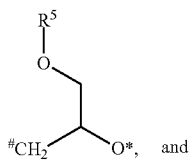

and h) 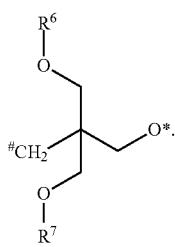

*indicates the position of the bond to Q and # indicates the position of the bond to OH.

If L is alkylene. L is preferably linear or branched $C_2$-$C_6$ alkylene. More preferably, L is $C_2$-$C_3$ alkylene selected from ethylene and propylene.

Preferably, L is propylene.

Preferably, L is ethylene.

Preferably, L is methylene.

If L is alkylene-O* L is preferably $C_1$ alkylene-O* (methylene-O*) or linear or branched $C_2$-$C_6$ alkylene-O*. More preferably, L is $C_2$-$C_3$ alkylene-O* is selected from ethylene-O* and propylene-O*.

Preferably, L is propylene-O*.

Preferably, L is ethylene-O*.

Preferably, L is methylene-O*.

If L is alkylene-N*H L is preferably $C_1$ alkylene-N*H or linear or branched $C_2$-$C_6$ alkylene-N*H. More preferably, L is $C_2$-$C_3$ alkylene-N*H, selected from ethylene-N*H and propylene-N*H.

Preferably, L is propylene-N*H.

Preferably, L is ethylene-N*H.

Preferably, L is methylene-N*H.

"Alkylene" represents a linear or branched saturated bivalent chain of carbon atoms having 1 to 6, preferably 1 to 3 or 4 to 6, carbon atoms, by way of example and by preference methylene, ethylene and propylene. Preferably, alkylene is $C_1$ alkylene or $C_2$-$C_6$ alkylene. More preferably, alkylene is $C_2$-$C_3$ alkylene or $C_4$-$C_6$ alkylene. The same applies to $C_2$-$C_6$alkylene-O* and $C_2$-$C_6$alkylene-NH*.

"Cycloalkylene" represents an alicyclic bivalent group of carbon atoms having 3 to 8, preferably 4 to 6, carbon atoms, by way of example and by preference cyclopropylene, cyclobutylene, cyclopentylene and cyclohexylene.

If L is cycloalkylene-O* L is preferably $C_3$-$C_6$ cycloalkylene-O* such as cyclopropylene-O*, cyclobutylene-O*, cyclopentylene-O* or cyclohexylene-O*.

Preferably, L is

# indicates the position of the bond to OH.

If L is ($R^5$—O)-substituted $C_2$-$C_6$ alkylene, ($R^5$—O)-substituted $C_3$-$C_6$ alkylene-O*, ($R^6$—O), ($R^7$—O)-disubstituted $C_3$-$C_6$ alkylene, or ($R^6$—O), ($R^7$—O)-disubstituted $C_4$-$C_6$alkylene-O*, L is preferably an alkylene defined as above bearing one or two protected or unprotected hydroxyl groups.

Preferably, L is ($R^5$—O)-substituted $C_3$-$C_6$alkylene-O* selected from

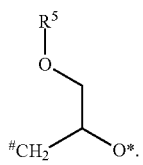

Preferably, L is ($R^6$—O), ($R^7$—O)-disubstituted $C_4$-$C_6$alkylene-O* selected from

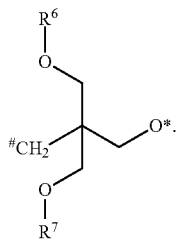

* indicates the position of the bond to Q, # indicates the position of the bond to OH.

Preferably, $R^5$ is a hydroxyl protecting group.

Preferably, $R^6$ and $R^7$ are hydroxyl protecting groups.

Additionally, $R^6$ and $R^7$ optionally form together optionally one-diol protecting group.

Compounds of Formula IV are defined by the general formula and/or the combination the preferred features as defined above.

In a first embodiment, compounds of the formula IV are defined as compounds of Formula IV-1, See structure in table F.

In a second embodiment, compounds of the formula IV are defined as compounds of Formula IV-2, See structure in table F.

In a third embodiment, compounds of the formula IV are defined as compounds of Formula IV-3, See structure in table F.

In a fourth embodiment, compounds of the formula IV are defined as compounds of Formula IV-4, See structure in table F.

In a fifth embodiment, compounds of the formula IV are defined as encompassing single isomers or any mixture of at least two stereoisomers of Formula IV-1, Formula IV-2, Formula IV-3 and Formula IV-4 including racemates and diastereomeric mixtures.

Preferred features as disclosed above are incorporated herein for all embodiments.

TABLE F

Formula IV stereoisomers

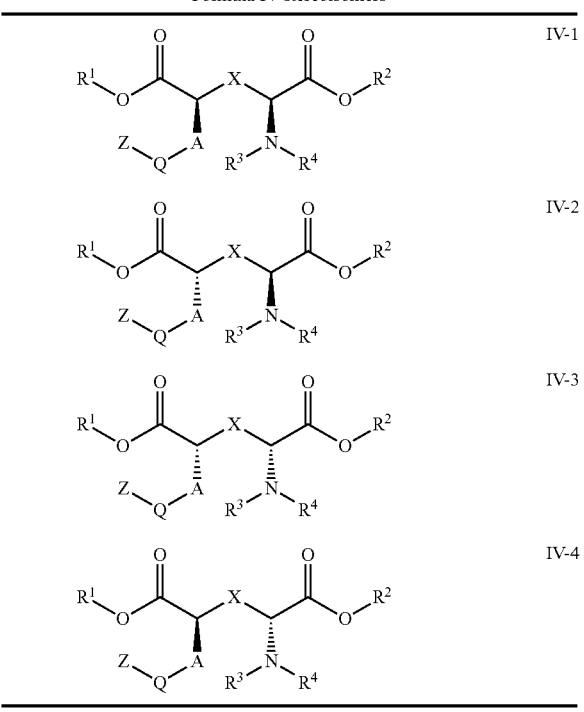

IV-1

IV-2

IV-3

IV-4

The compounds of Formula IV-1, Formula IV-2, Formula IV-3, Formula IV-4 furthermore encompass pharmaceutically acceptable salts of an inorganic or organic acid or base thereof, hydrates, complexes, esters, amides, and solvates thereof and optionally a pharmaceutically acceptable carrier, diluent, adjuvant or excipients.

A preferred compound of Formula IV is di-tert-butyl N-(tert-butoxycarbonyl)-4-(4-hydroxybenzyl)glutamate.

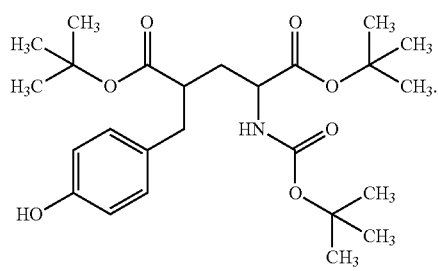 [SMILES: CC(C)(C)OC(=O)NC(CC(Cc1ccc(O)cc1)C(=O)OC(C)(C)C)C(=O)OC(C)(C)C]

Another preferred compound of Formula IV is di-tert-butyl 4-(4-aminobenzyl)-N-(tert-butoxycarbonyl)glutamate:

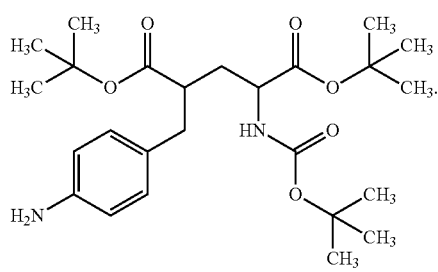 [SMILES: CC(C)(C)OC(=O)NC(CC(Cc1ccc(N)cc1)C(=O)OC(C)(C)C)C(=O)OC(C)(C)C]

Another preferred compound of Formula IV is di-tert-butyl N-(tert-butoxycarbonyl)-4-[4-(3-hydroxypropyl)benzyl]glutamate:

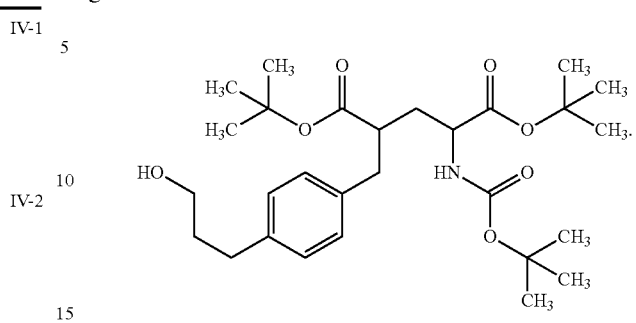

Another preferred compound of Formula IV is di-tert-butyl N-(tert-butoxycarbonyl)-4-[3-(4-hydroxyphenyl)propyl]glutamate:

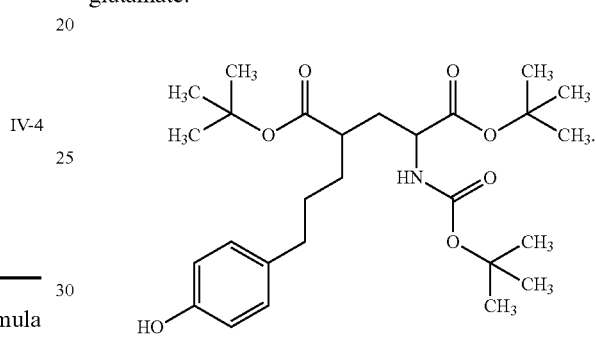

Another preferred compound of Formula IV is di-tert-butyl 2-[(tert-butoxycarbonyl)-amino]-5-(4-hydroxybenzyl)hexanedioate:

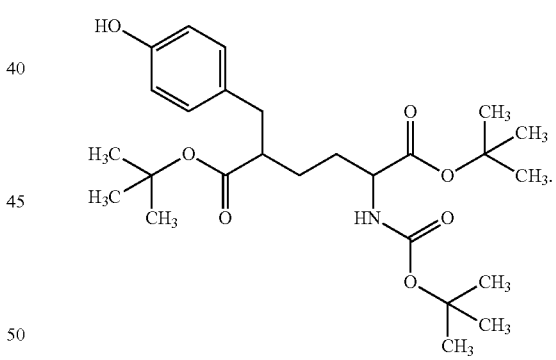

Another preferred compound of Formula IV is di-tert-butyl N-(tert-butoxycarbonyl)-4-[(5-hydroxypyridin-2-yl)methyl]glutamate

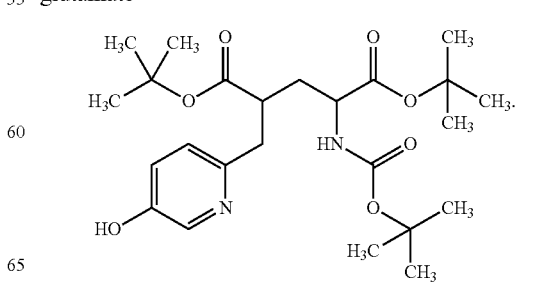

Another more preferred compound of Formula IV is di-tert-butyl (4S)-4-(4-aminobenzyl)-N-(tert-butoxycarbonyl)-L-glutamate:

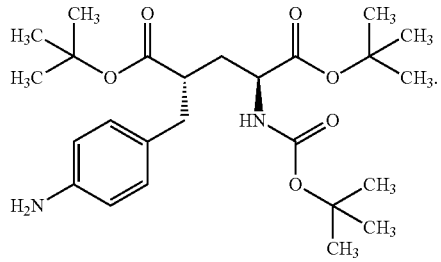 [SMILES: CC(C)(C)OC(=O)N[C@@H](C[C@H](Cc1ccc(N)cc1)C(=O)OC(C)(C)C)C(=O)OC(C)(C)C]

Another more preferred compound of Formula IV is di-tert-butyl (4S)—N-(tert-butoxy-carbonyl)-4-[4-(3-hydroxypropyl)benzyl]-L-glutamate:

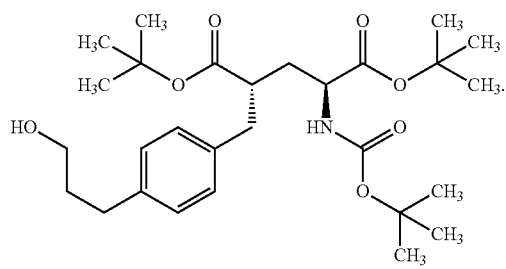 [SMILES: CC(C)(C)OC(=O)N[C@@H](C[C@H](Cc1ccc(CCCO)cc1)C(=O)OC(C)(C)C)C(=O)OC(C)(C)C]

Another more preferred compound of Formula IV is di-tert-butyl (4S)—N-(tert-butoxy-carbonyl)-4-[3-(4-hydroxyphenyl)propyl]-L-glutamate:

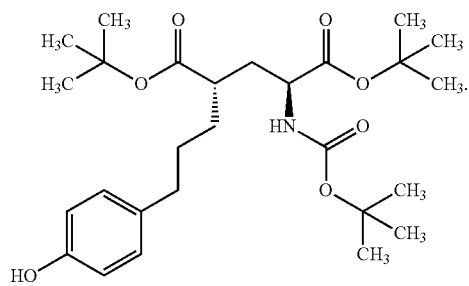 [SMILES: CC(C)(C)OC(=O)N[C@@H](C[C@H](CCCc1ccc(O)cc1)C(=O)OC(C)(C)C)C(=O)OC(C)(C)C]

Another more preferred compound of Formula IV is di-tert-butyl (2S)-2-[(tert-butoxy-carbonyl)amino]-5-(4-hydroxybenzyl)hexanedioate:

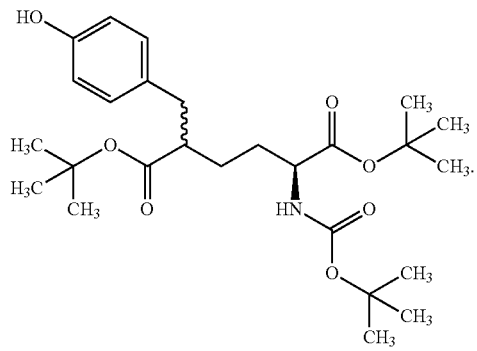 [SMILES: CC(C)(C)OC(=O)N[C@@H](CCC(Cc1ccc(O)cc1)C(=O)OC(C)(C)C)C(=O)OC(C)(C)C]

Another more preferred compound of Formula IV is di-tert-butyl (2R)-2-[(tert-butoxy-carbonyl)amino]-5-(4-hydroxybenzyl)hexanedioate:

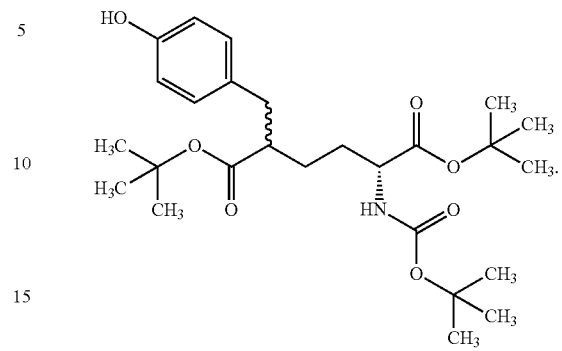

Another more preferred compound of Formula IV is di-tert-butyl (4R)—N-(tert-butoxycarbonyl)-4-[(5-hydroxypyridin-2-yl)methyl]-L-glutamate

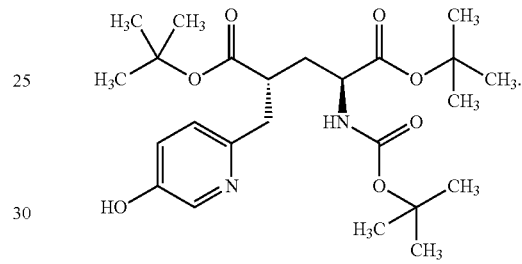

Another more preferred compound of Formula IV is di-tert-butyl (2S)-2-[(tert-butoxycarbonyl)amino]-5-[(5-hydroxypyridin-2-yl)methyl]hexanedioate:

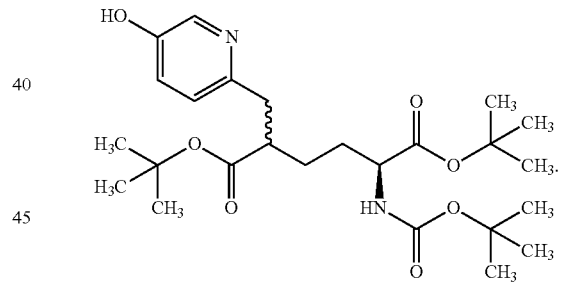

Another more preferred compound of Formula IV is di-tert-butyl (2S)-2-[(tert-butoxycarbonyl)amino]-5-[2-(4-hydroxyphenyl)ethyl]hexanedioate:

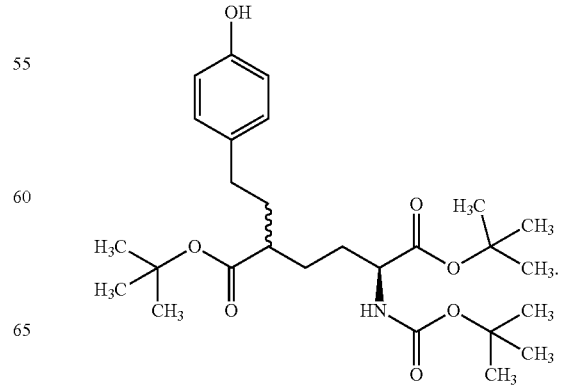

Another more preferred compound of Formula IV is (2S)-2-tert.-Butoxycarbonylamino-5-(4-hydroxy-benzyl)-hexanedioic acid di-tert.-butyl ester:

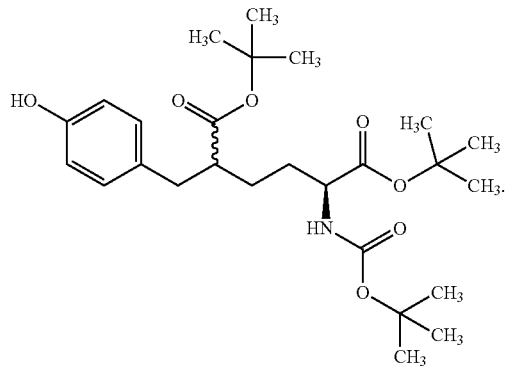 [SMILES: CC(C)(C)OC(=O)N[C@@H](CCC(Cc1ccc(O)cc1)C(=O)OC(C)(C)C)C(=O)OC(C)(C)C]

Another more preferred compound of Formula IV is (2S)-2-amino-5-(4-hydroxybenzyl)hexanedioic acid:

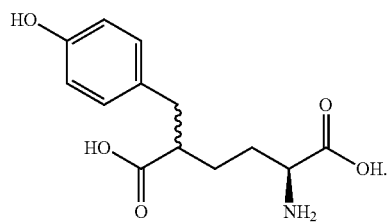 [SMILES: N[C@@H](CCC(Cc1ccc(O)cc1)C(=O)O)C(=O)O]

Another more preferred compound of Formula IV is (2S, 5R)-2-amino-5-(4-hydroxybenzyl)hexanedioic acid:

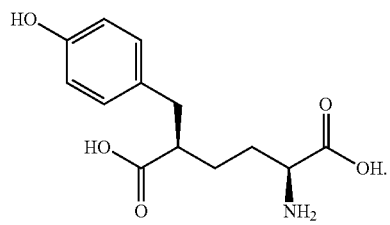 [SMILES: N[C@@H](CC[C@H](Cc1ccc(O)cc1)C(=O)O)C(=O)O]

Another more preferred compound of Formula IV is (2S, 5S)-2-amino-5-(4-hydroxybenzyl)hexanedioic acid:

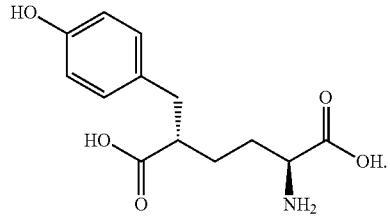 [SMILES: N[C@@H](CC[C@@H](Cc1ccc(O)cc1)C(=O)O)C(=O)O]

Another more preferred compound of Formula IV is dimethyl (2S)-2-amino-5-(4-hydroxybenzyl)hexanedioate:

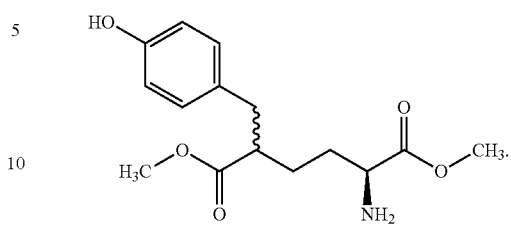

Another more preferred compound of Formula IV is di-tert-butyl (4S)—N-(tert-butoxycarbonyl)-4-[3-tert-butoxy-4-(2-hydroxyethoxy)benzyl]-L-glutarnate:

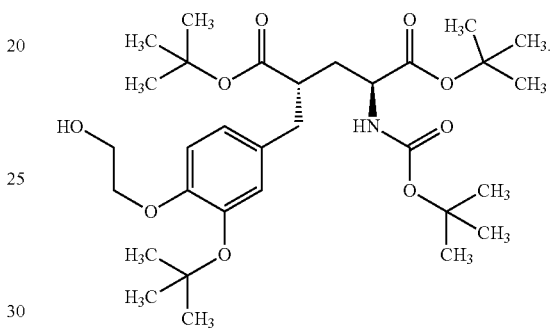

Another more preferred compound of Formula IV is di-tert-butyl (5S)-2-(4-aminobenzyl)-5-[(tert-butoxycarbonyl)amino]hexanedioate:

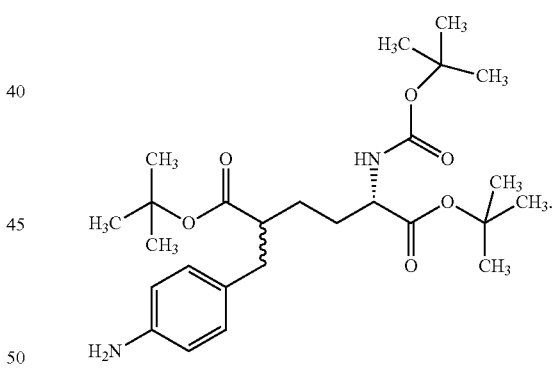

The seventh aspect of the present invention is directed to methods for preparation of compound of Formula III (Radiopharmaceutical)

In a first embodiment, the invention is directed to a method for preparation of compound of Formula III comprising the steps of:
  $^{18}$F-radiofluorination of compound of Formula I to obtain compound of Formula II, and
  Cleavage of protecting groups from compound of Formula II to obtain compound of Formula III.

Optionally the method is followed by the purification of compound of Formula III by solid-phase-extraction. Preferably solid-phase-extraction cartridges or column is used.

The preferred features and embodiments disclosed for compounds of general formula I, II and III are herein incorporated.

Methods for $^{18}$F-fluorination are well known to the person skilled in the art. For example, the $^{18}$F-Fluorination agent can be K$^{18}$F, H$^{18}$F, Rb$^{18}$F, Cs$^{18}$F, Na$^{18}$F.

Optionally, the $^{18}$F-Fluorination agent comprises a chelating agent such as a cryptand (e.g.: 4,7,13,16,21,24-Hexaoxa-1,10-diazabicyclo[8.8.8]-hexacosane—Kryptofix®) or a crown ether (e.g.: 18-crown-6).

The $^{18}$F-Fluorination agent can also be a tetraalkylammonium salt of $^{18}$F$^{-}$ or a tetraalkylphosphonium salt of $^{18}$F$^{-}$, known to those skilled in the art, e.g.: tetrabutylammonium [$^{18}$F]fluoride, tetrabutylphosphonium [$^{18}$F]fluoride.

Preferably, the $^{18}$F-Fluorination agent is Cs$^{18}$F, K$^{18}$F, tetrabutylammonium [$^{18}$F]fluoride.

The reagents, solvents and conditions which can be used for this fluorination are common and well-known to the skilled person in the field. See, e.g., *J. Fluorine Chem.*, 27 (1985):177-191; Coenen, Fluorine-18 Labeling Methods: Features and Possibilities of Basic Reactions, (2006), in: Schubiger P. A., Friebe M., Lehmann L. (ads), PET-Chemistry—The Driving Force in Molecular Imaging. Springer, Berlin Heidelberg, pp. 15-50). Preferably, the solvents used in the present method are DMF. DMSO, acetonitrile, DMA, or mixtures thereof, preferably the solvent is acetonitrile. DMSO.

In a second embodiment, the invention is directed to a method for preparation of compounds of Formula III, wherein L$^{1}$ is alkylene-O, alkylene-NH or cycloalkylene-O, comprising the steps of:

Reacting of a compound of Formula IV, wherein Z is OH or NH$_{2}$, with an $^{18}$F labeled building block VII, and Optionally, cleaving of protecting groups to obtain a compound of Formula III.

Optionally the method is followed by the purification of compound of Formula III by solid-phase-extraction. Preferably solid-phase-extraction cartridges or column is used.

[$^{18}$F]Fluorine containing building block is a compound of formula VII $$^{18}\text{F-L'-LG} \qquad \text{VII}$$

wherein
LG is defined as above, and
L' is alkylene or cycloalkylene as defined above.

The preferred features and embodiments disclosed for compounds of general formula III and IV are herein incorporated.

In a more preferred embodiment, a compound of Formula IV, wherein Z is OH and R$^{1}$ is H and R$^{2}$ is H and R$^{3}$ is H and R$^{4}$ is H is reacted with a building block selected from $^{18}$F—CH$_{2}$-LG and $^{18}$F—CH$_{2}$—CH$_{2}$-LG.

The eighth aspect of the present invention is directed to methods for preparation of compound of Formula VI (cold standard).

In a first embodiment, the invention is directed to a method for preparation of compound of Formula VI comprising the steps of:

Fluorination of compound of Formula I to obtain compounds of Formula V, and

Cleavage of protecting groups from compound of Formula V to obtain compound of Formula VI.

Optionally the method is followed by the purification of compound of Formula VI. Suitable purification methods are chromatography methods (e.g. HPLC, flash-chromatography).

The preferred features and embodiments disclosed for compounds of general formula I, V and VI are herein incorporated.

In a second embodiment, the invention is directed to a method for preparation of compound of Formula VI comprising the steps of Reacting of compound of Formula IV with a fluorine containing building block VIII or with a fluorinating reagent and Optionally, cleaving of protecting groups to obtain compound of Formula VI.

Optionally the method is followed by the purification of compound of Formula VI. Suitable purification methods are chromatography methods (e.g. HPLC, flash-chromatography).

Fluorine containing building block is a compound of formula VIII $$\text{F-L'-LG} \qquad \text{VIII}$$

wherein
LG is defined as above, and
L' is alkylene or cycloalkylene as defined above.

The fluorinating reagent is a suitable reagent for the reaction and is exemplified by but not limited to DAST or nonafluorobutylsulfonyl fluoride.

F is a Cold Fluorine Isotope [$^{19}$F].

The preferred features and embodiments disclosed for compounds of general formula IV and VI are herein incorporated.

The ninth aspect of the present invention is directed to methods for preparation of Formula I (precursor).

In a first embodiment, the invention is directed to a method for preparation of compound of Formula I comprising the steps of:

Introducing a leaving group to compounds of Formula IV wherein Z is OH-L.

Optionally the method is followed by the purification of compound of Formula I. Suitable purification methods are chromatography methods (e.g. HPLC, flash-chromatography).

The preferred features and embodiments disclosed for compounds of general formula I and IV are herein incorporated.

In a second embodiment, the invention is directed to a method for preparation of compound of Formula I, wherein L is alkylene-O, alkylene-NH or cycloalkylene-O, comprising the steps of:

Reacting of compound of Formula IV, wherein Z is OH or NH$_{2}$ with a building block of formula IX
wherein compound of formula IX is $$\text{LG-L'-LG'} \qquad \text{IX}$$

LG is described above and LG' is a leaving group selected from the group of
a) Sulfonate leaving group, and
b) Halogen, and
L' is alkylene or cycloalkylene.

Optionally the method is followed by the purification of compound of Formula I. Suitable purification methods are chromatography methods (e.g. HPLC, flash-chromatography).

The preferred features and embodiments disclosed for compounds of general formula IV and I are herein incorporated.

In a tenth aspect of the present invention compounds of Formula III are provided as medicament or pharmaceutical.

The invention relates also to the use of compound of Formula III for the manufacture of medicament or pharmaceutical for treatment.

In a eleventh aspect of the invention, compounds according to Formula III for the manufacture of an imaging tracer or radiopharmaceutical agent for imaging proliferative diseases. The imaging agent or radiopharmaceutical agent is preferably suitable as imaging agent for PET applications.

In other words, the invention is directed to compound of general formula III as imaging tracer or radiopharmaceutical agent.

The invention is directed to compound of general formula III for use in the imaging of proliferative diseases.

The invention is also directed to a method for imaging or diagnosing of proliferative diseases comprising the steps:
- Administering to a mammal an effective amount of a compound comprising compound of formula III,
- Obtaining images of the mammal and
- Assessing images.

In a more preferred embodiment the use concerns the imaging of proliferative diseases. Proliferative diseases in oncology are characterized by the presence of tumor and/or metastases. Preferably tumors include but are not limited to malignomas of the gastrointestinal or colorectal tract, liver carcinoma, pancreas carcinoma, kidney carcinoma, bladder carcinoma, thyroid carcinoma, prostate carcinoma, endometrial carcinoma, ovary carcinoma, testes carcinoma, melanoma, small-cell and non-small-cell lung carcinoma, dysplastic oral mucosa carcinoma, invasive oral cancer; breast cancer, including hormone-dependent and hormone-independent breast cancer, squamous cell carcinoma, neurological cancer disorders including neuroblastoma, glioma, astrocytoma, osteosarcoma, meningioma, soft tissue sarcoma, haemangioma and endocrine tumors, including pituitary adenoma, chromocytoma, paraganglioma, haematological tumor disorders including lymphoma and leukaemias. Preferably, metastases are metastases of one of the tumors mentioned above.

The present invention is also directed to a method of imaging comprising the step of introducing into a patient a detectable quantity of an $^{18}F$ labeled compound of Formula III and imaging said patient.

Another aspect of the invention is the use of a compound of Formula III as described above and herein for diagnosing and/or treating oncology disease in a patient, in particular in a mammal, such as a human.

Preferably, the use of a compound of the invention in the diagnosis is performed using positron emission tomography (PET).

Another aspect of the invention is directed to a method of imaging tumors. Such a method comprises a) administering to a mammal a compound as described above and herein containing a detectable label, and b) detecting the signal stemming from the compound that is specifically taken up by a tumor.

In a further aspect, the invention is directed to a method of diagnosing a patient with oncology disease. This method comprises a) administering to a human in need of such diagnosis a compound of the invention with a detectable label for detecting the compound in the human as described above and herein, and b) measuring the signal from the detectable label arising from the administration of the compound to the human, preferably by positron emission tomography (PET).

Methods of diagnosing and use for PET imaging of proliferative diseases involve administration of one of the preferred compounds listed below:

(4S)-4-[4-(2-[$^{18}F$]Fluoroethoxy)benzyl]-L-glutamic acid

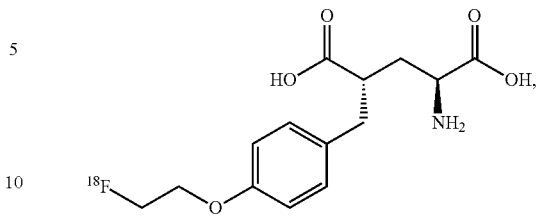

(4S)-4-[4-(3-[$^{18}F$]Fluoropropoxy)benzyl]-L-glutamic acid

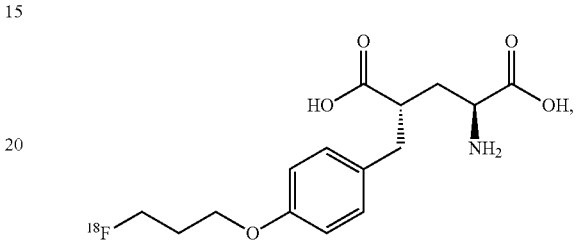

4-{4-[(3-[$^{18}F$]Fluoropropyl)amino]benzyl}-L-glutamic acid

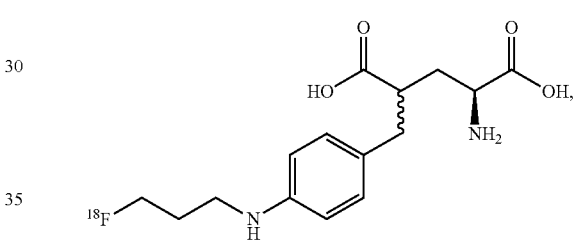

or
(2S)-2-Amino-5-[4-(2-[$^{18}F$]fluoroethoxy)benzyl]hexanedioic acid

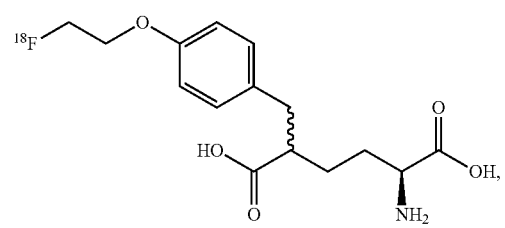

and stereoisomers and mixtures thereof.

In a twelfth aspect, the invention is directed to a kit comprising one vial or more than one vial comprising a predetermined quantity of:
a) compounds of Formula I or Formula IV, or
b) compounds of Formula VI.

Further, according to this aspect of the present invention the kit comprises a compound having general chemical Formula as disclosed above along with an acceptable carrier, diluent, excipient or adjuvant or mixture thereof.

Preferably, the Kit comprises physiologically acceptable vehicle or carrier and optional adjuvants and preservatives, reagents suitable to perform the herein disclosed reactions and/or to generate the [$^{18}F$] labeling reagents. Furthermore, the kit may contain instructions for its use.

In a thirteenth aspect, the invention is directed to the use of compounds of general formula III or VI for conducting biological assays and chromatographic identification.

More preferably, the use relates to compounds of general formula VI.

Compounds of general formula VI are useful as references and/or measurement agents.

The compounds of general formula III and VI are herein defined as above and encompass all embodiments and preferred features.

In a fourteenth aspect, the invention is directed to a composition comprising compounds of formula I, II, III, IV, V or VI as defined in the above aspects and included embodiments.

In a first embodiment, the invention is directed to a composition comprising compound of formula III and pharmaceutically suitable adjuvants. These adjuvants include, inter alia, carriers, solvents, or stabilizers.

The person skilled in the art is familiar with adjuvants which are suitable for the desired pharmaceutical formulations, preparations or compositions on account of his/her expert knowledge.

The administration of the compounds, pharmaceutical compositions or combinations according to the invention is performed in any of the generally accepted modes of administration available in the art. Intravenous deliveries are preferred.

Preferably, the compositions according to the invention are administered such that the dose of the active compound for imaging is in the range of 37 MBq (1 mCi) to 740 MBq (20 mCi). In particular, a dose in the range from 100 MBq to 400 MBq will be used.

Preferably, the composition comprises one of the compounds disclosed below (4S)-4-[4-(2-[$^{18}$F]Fluoroethoxy)benzyl]-L-glutamic acid

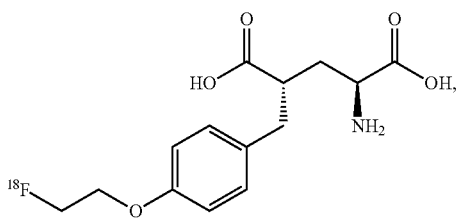

(4S)-4-[4-(3-[$^{18}$F]Fluoropropoxy)benzyl]-L-glutamic acid

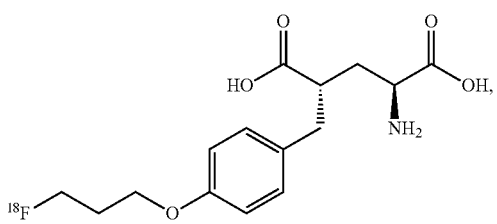

4-{4-[(3-[$^{18}$F]Fluoropropyl)amino]benzyl}-L-glutamic acid

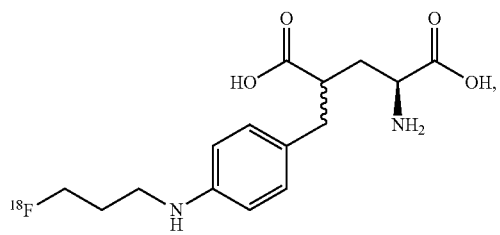 [SMILES: N[C@@H](CC(Cc1ccc(NCCC[18F])cc1)C(=O)O)C(=O)O]

or (2S)-2-Amino-5-[4-(2-[$^{18}$F]fluoroethoxy)benzyl]hexanedioic acid

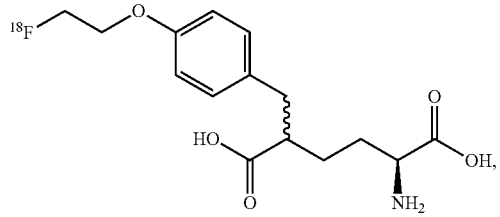

and stereoisomers and mixtures thereof, and suitable salts thereof, and pharmaceutically acceptable carriers or diluents as described above.

In a second embodiment, the invention is directed to a composition comprising compound of formula VI. Such composition can be used for analytical purposes. Preferably, the composition comprises one of the compounds disclosed below (4S)-4-[4-(2-Fluoroethoxy)benzyl]-L-glutamic acid

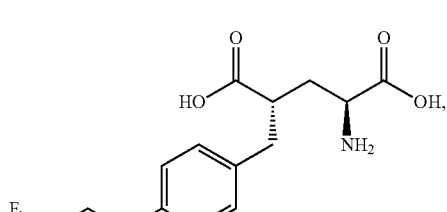

(4S)-4-[4-(3-Fluoropropoxy)benzyl]-L-glutamic acid

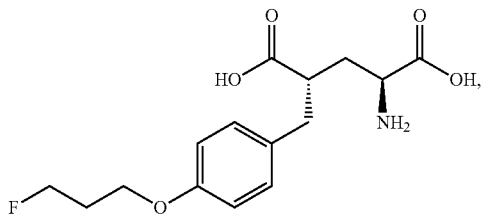 [SMILES: N[C@@H](C[C@H](Cc1ccc(OCCCF)cc1)C(=O)O)C(=O)O]

4-{4-[(3-Fluoropropyl)amino]benzyl}-L-glutamic acid

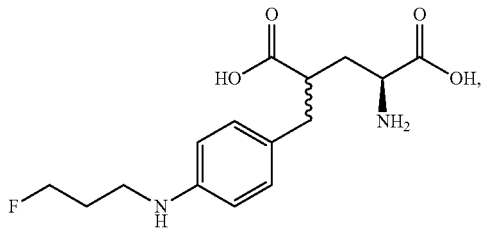 [SMILES: N[C@@H](CC(Cc1ccc(NCCCF)cc1)C(=O)O)C(=O)O]

or
(2S)-2-Amino-5-[4-(2-fluoroethoxy)benzyl]hexanedioic acid

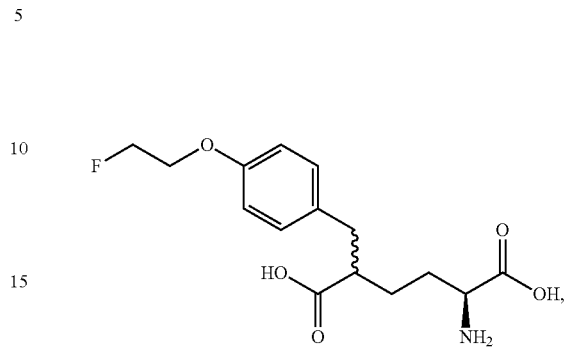

and stereoisomers and mixtures thereof.

In a third embodiment, the invention is directed to a composition comprising compound of formula I or IV. Such composition can be used for manufacturing of compound of formula III (radiopharmaceutical) and/or VI (cold standard).

Preferably, the composition comprises one of the compounds disclosed below:

di-tert-butyl (4S)—N-(tert-butoxycarbonyl)-4-{4-[2-(tosyloxy)ethoxy]benzyl}-L-glutamate:

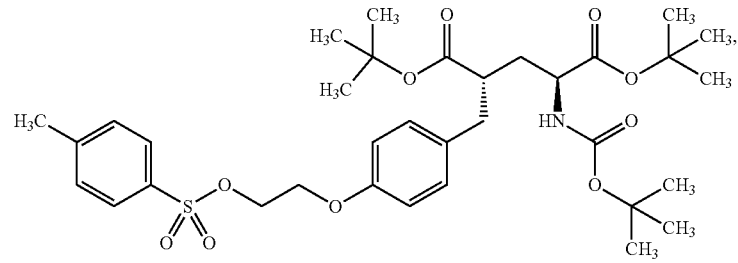 [SMILES: Cc1ccc(S(=O)(=O)OCCOc2ccc(C[C@@H](C[C@H](NC(=O)OC(C)(C)C)C(=O)OC(C)(C)C)C(=O)OC(C)(C)C)cc2)cc1]

di-tert-butyl (4S)—N-(tert-butoxycarbonyl)-4-{4-[3-(tosyloxy)propoxy]benzyl}-L-glutamate:

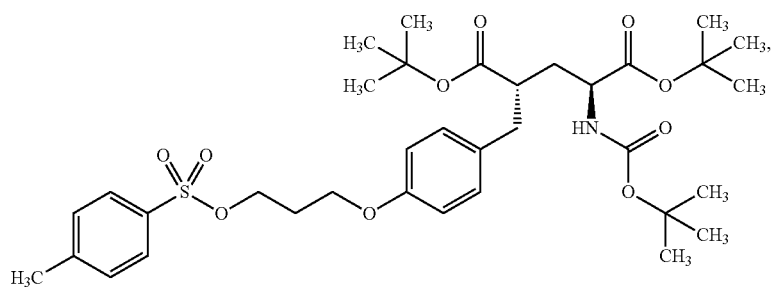 [SMILES: Cc1ccc(S(=O)(=O)OCCCOc2ccc(C[C@@H](C[C@H](NC(=O)OC(C)(C)C)C(=O)OC(C)(C)C)C(=O)OC(C)(C)C)cc2)cc1]

di-tert-butyl (4S)—N-(tert-butoxycarbonyl)-4-(4-{[3-(tosyloxy)propyl]amino}benzyl)-L-glutamate:

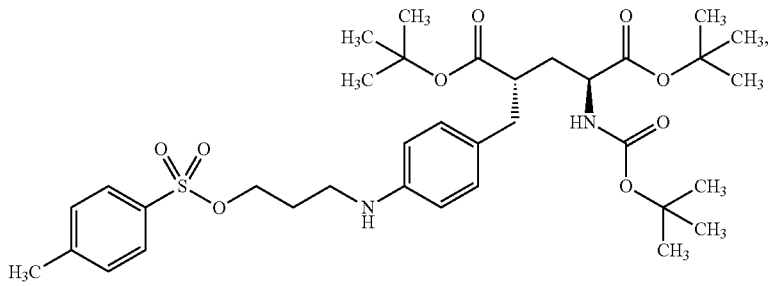 [SMILES: Cc1ccc(S(=O)(=O)OCCCNc2ccc(C[C@@H](C[C@H](NC(=O)OC(C)(C)C)C(=O)OC(C)(C)C)C(=O)OC(C)(C)C)cc2)cc1]

di-tert-butyl (2S)-2-[(tert-butoxycarbonyl)amino]-5-{4-[2-(tosyloxy)ethoxy]benzyl}-hexanedioate:

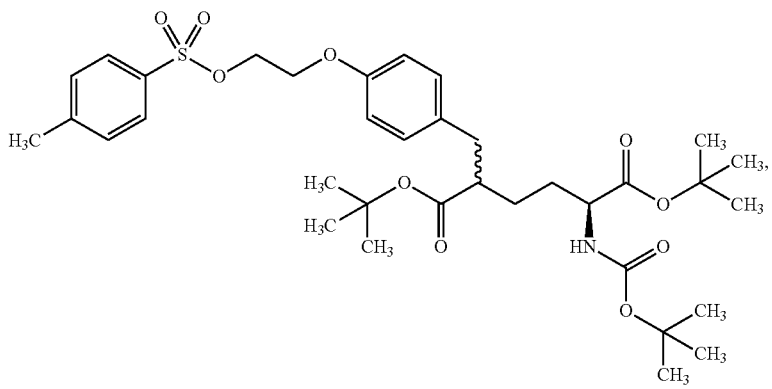 [SMILES: Cc1ccc(S(=O)(=O)OCCOc2ccc(CC(CC[C@H](NC(=O)OC(C)(C)C)C(=O)OC(C)(C)C)C(=O)OC(C)(C)C)cc2)cc1]

and stereoisomers thereof.

DEFINITIONS

The following terms describe generic and specific structural elements of the chemical scaffold of the compounds of the present invention, as well as functional groups and substituents attached thereto. They can be combined in a way resulting in structures in line with the chemical valency rules and of suitable chemical stability, that is, compounds that are sufficiently robust to survive isolation to a useful degree of purity from a reaction mixture, and for their intended use, such as formulation into a pharmaceutical composition.

For the purposes of the present invention, the terms have the following meaning, unless otherwise specified:

"Alkyl" per se and "alk" and "alkyl" in alkoxy, alkylcarbonyl, alkylamino, alkylaminocarbonyl, alkoxycarbonyl, alkoxycarbonylamino and alkylcarbonylamino represent a linear or branched alkyl radical having, as a rule, 1 to 6, preferably 1 to 4, especially preferably 1 to 3, carbon atoms, by way of example and by preference methyl, ethyl, n-propyl, iso-propyl, tert-butyl, n-pentyl and n-hexyl.

As used herein, the term "alkylene" refers to linear or branched saturated bivalent chain of carbon atoms having, as a rule, 1 to 6, preferably 1 to 4, especially preferably 1 to 3, carbon atoms, by way of example and including but not limited to methylene, ethylene, propylene, butylene, pentylene, hexylene, iso-propylene, iso-butylene, sec-butylene, tert-butylene, iso-pentylene, 2-methylbutylene, 1-methylbutylene, 1-ethylpropylene, 1,2-dimethylpropylene, neo-pentylene, 1,1-dimethylpropylene, 4-methylpentylene, 3-methylpentylene, 2-methylpentylene, 1-methylpentylene, 2-ethylbutylene, 1-ethylbutylene, 3,3-dimethylbutylene, 2,2-dimethylbutylene, 1,1-dimethylbutylene, 2,3-dimethylbutylene, 1,3-dimethylbutyene, 1,2-dimethylbutylene and by preference methylene, ethylene and propylene.

"Cycloalkylene" represents an alicyclic bivalent group of carbon atoms having 3 to 8, preferably 5 to 7, carbon atoms, by way of example and by preference cyclopropylene, cyclobutylene, cyclopentylene and cyclohexylene.

"Arylene" represents a mono- or bicyclic aromatic, carbocyclic bivalent radical having, as a rule, 6 to 10 carbon atoms, optionally substituted by one or two "substituents"; by way of example and by preference phenylene.

"Heteroarylene" represents an aromatic, mono- or bicyclic bivalent radical having, as a rule, 5 to 10, preferably 5 to 6, ring atoms and up to 3, preferably 1, hetero atoms from the series consisting of S, O and N; by way of example and including but not limited to thienylene, furylene, pyrrolylene, thiazolylene, oxazolylene, imidazolylene, pyridylene, pyrimidylene, pyridazinylene, indolylene, indazolylene, benzofuranylene, benzothiophenylene, quinolinylene, isoquinolinylene, triazolylene. Wherein said "heteroarylene" is optionally substituted by one or two "substituents". Preferably, "heteroarylene" is pyridylene or triazolylene.

"Substituent" as used herein represents alkyl, trifluormethyl, fluoro, chloro, cyano, nitro, hydroxyl, protected hydroxyl, alkoxy; preferably methoxy, ethoxy, hydroxyl, protected hydroxyl.

"Halogen" represents fluorine, chlorine, bromine and iodine.

The term "amine-protecting group" as employed herein by itself or as part of another group is known or obvious to someone skilled in the art, which is chosen from but not limited to a class of protecting groups namely carbamates, amides, imides, N-alkyl amines, N-aryl amines, imines, enamines, boranes, N—P protecting groups, N-sulfenyl, N-sulfonyl and N-silyl, and which is chosen from but not limited to those described in the textbook Greene and Wuts, Protecting groups in Organic Synthesis, third edition, page 494-653, included herewith by reference. The "amine-protecting group" is preferably carbobenzyloxy (Cbz), p-methoxybenzyl carbonyl (Moz or MeOZ), tert-butyloxycarbonyl (BOC), 9-fluorenylmethyloxycarbonyl (FMOC), benzyl (Bn), p-methoxybenzyl (PMB), 3,4-dimethoxybenzyl (DMPM), p-methoxyphenyl (PMP), triphenylmethyl (Trityl), methoxyphenyl diphenylmethyl (MMT) or the protected amino group is a 1,3-dioxo-1,3-dihydro-2H-isoindol-2-yl (phthalimido) or an azido group.

"Carboxyl-protecting group" as employed herein by itself or as part of another group is known or obvious to someone skilled in the art, which is chosen from but not limited to a class of protecting groups namely esters, amides and hydrazides, and which is chosen from but not limited to those described in the textbook Greene and Wuts, Protecting groups in Organic Synthesis, third edition, page 369-453, included herewith by reference. The "carboxyl-protecting group" is preferably methyl, ethyl, propyl, butyl, tert-butyl, allyl, benzyl, 4-methoxybenzyl or 4-methoxyphenyl.

"Hydroxyl-protecting group" as employed herein by itself or as part of another group is known or obvious to someone skilled in the art, which is chosen from but not limited to a class of protecting groups namely ethers, esters, and which is chosen from but not limited to those described in the textbook Greene and Wuts, Protecting groups in Organic Synthesis, third edition, page 17-200, included herewith by reference. Hydroxyl protecting group which is chosen from but not limited to a class of protecting groups namely ethers, esters such as t-butyl, benzyl, p-methoxybenzyl, p-nitrobenzyl, allyl, trityl, methoxymethyl, methoxyethoxymethyl, ethoxyethyl, 1-methyl-1-methoxyethyl, tetrahydropyranyl, trialkylsilyl; benzoyl, acetyl, and phenylacetyl.

Additionally, for the protection of 1,2- and 1,3-diols, one or two "hydroxyl-protecting groups" as employed herein by itself or as part of another group for is known or obvious to someone skilled in the art, which is chosen from but not limited to a class of protecting groups namely cyclic acetals, cyclic ketals, cyclic ortho esters, silyl derivatives, cyclic carbonates and cyclic boronates such as methylene, ethylidene, benzylidene, isopropylidene, cyclohexylidene, cyclopentylidene, and di-t-butylsilylene, and which is chosen from but not limited to those described in the textbook Greene and Wuts, Protecting groups in Organic Synthesis, third edition, page 201-245, included herewith by reference.

The term "leaving group" as employed herein by itself or as part of another group is known or obvious to someone skilled in the art, and means that an atom or group of atoms is detachable from a chemical substance by a nucleophilic agent. Examples are given e.g. in Synthesis (1982), p. 85-125, table 2 (p. 86; (the last entry of this table 2 needs to be corrected: "n-$C_4F_9S(O)_2$—O— nonaflat" instead of "n-$C_4H_9S(O)_2$—O— nonaflat"), Carey and Sundberg, Organische Synthese, (1995), page 279-281, table 5.8; or Netscher, Recent Res. Dev. Org. Chem., 2003, 7, 71-83, scheme 1, 2, 10 and 15 and others). (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50, explicitly: scheme 4 pp. 25, scheme 5 pp 28, table 4 pp 30, FIG. 7 pp 33).

Preferably, the "leaving group" is Br, I or a sulfonate leaving group including but not limited to methylsulfonyloxy, (4-methylphenyl)sulfonyloxy, trifluormethylsulfonyloxy, nonafluorobutylsulfonyloxy, (4-bromo-phenyl)sulfonyloxy, (4-nitro-phenyl)sulfonyloxy, (2-nitro-phenyl)sulfonyloxy, (4-isopropyl-phenyl)sulfonyloxy, (2,4,6-tri-isopropyl-phenyl)sulfonyloxy, (2,4,6-trimethyl-phenyl)sulfonyloxy, (4-tertbutyl-phenyl)sulfonyloxy, (4-methoxy-phenyl)sulfonyloxy, etc.

If chiral centers or other forms of isomeric centers are not otherwise defined in a compound according to the present invention, all forms of such stereoisomers, including enantiomers and diastereoisomers, are intended to be covered herein. Compounds containing chiral centres may be used as racemic mixture or as an enantiomerically enriched mixture or as a diastereomeric mixture or as a diastereomerically enriched mixture, or these isomeric mixtures may be separated using well-known techniques, and an individual stereoisomer may be used alone. In cases wherein compounds may exist in tautomeric forms, each tautomeric form is contemplated as being included within this invention whether existing in equilibrium or predominantly in one form.

Suitable salts of the compounds according to the invention include salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalene disulfonic acid, acetic acid, trifluoroacetic acid, propionic acid, lactic acid, tartaric acid, malic acid, citric acid, fumaric acid, maleic acid and benzoic acid.

Suitable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine. N-methylmorpholine, arginine, lysine, ethylenediamine and N-methylpiperidine.

The term "purification" as employed herein has the objective to eliminate the excess of side product such as $^{18}$F-Fluoride and to concentrate and trap the reaction product. Purification is carried out by any method known to those in the art, suitable for radiotracer e.g. chromatography. HPLC, solid-phase-extraction cartridges or column.

ABBREVIATIONS

| | |
|---|---|
| Boc | tert-butyloxycarbonyl |
| br | broad signal (in NMR data) |
| d.c. | corrected for decay |

ABBREVIATIONS

| | |
|---|---|
| Cbz | carboxybenzoyl |
| CI | chemical ionisation |
| d | doublet |
| DAD | diode array detector |
| dd | doublet of doublet |
| Ddd | doublet of doublet of doublet |
| DIPEA | N,N-diisopropylethylamine |
| dt | doublet of triplet |
| DMF | N,N-dimethylformamide |
| DMSO | dimethylsulfoxide |
| EI | electron ionisation |
| ELSD | evaporative light scattering detector |
| ESI | electrospray ionisation |
| EtOAc | ethyl acetate |
| FDG | fluorodeoxyglucose |
| Fmoc | fluorenylmethyloxycarbonyl |
| HPLC | high performance liquid chromatography |
| GBq | Giga Bequerel |
| $K_{222}$ | 4, 7, 13, 16, 21, 24-hexaoxa-1,10-diazabicyclo[8.8.8]-hexacosane (Kryptofix 222) |
| LiHMDS | lithium bis(trimethylsilyl)amide |
| MBq | Mega Bequerel |
| MRI | Magnetic Resonance Imaging, |
| MS | mass spectrometry |
| MeCN | acetonitrile |
| MTB | methyl tert-butyl ether |
| m | multiplet |
| mc | centred multiplet |
| n.d.c. | not decay corrected |
| NMR | nuclear magnetic resonance spectroscopy: chemical shifts (δ) are given in ppm. |
| PET | Positron-Emmision-Tomography |
| PMB | para-methoxybenzyl |
| q | quadruplett (quartet) |
| RT | room temperature |
| s | singulet |
| t | triplet |
| TBDMS | tert-butyldimethylsilyl |
| Trt | trityl (=triphenylmethyl) |
| THF | tetrahydrofuran |
| THP | tetrahydropyran |
| TLC | thin layer chromatography |
| Ts | tosyl, 4-methylphenyl)sulfonyl |
| TsO | tosyloxy, 4-methylphenyl)sulfonyloxy |
| UPLC | Ultra Performance Liquid Chromatography |

General Synthesis

A. Alkylation of Glutamate Backbone

Compounds of the invention in which X stands for $CH_2$ can be approached by alkylation of glutamate derivatives A-1 as shown in Scheme 1.

Scheme 1

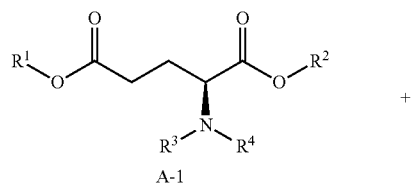

A-1

+

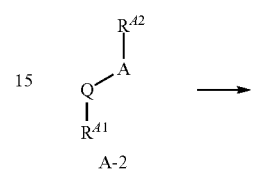

A-2

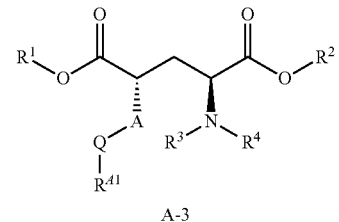

A-3

+

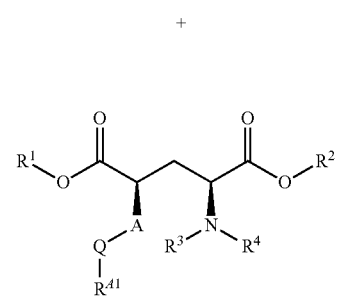

A-4

Alkylation of glutamate backbone ($R^1$, $R^2$, $R^3$, $R^3$, $R^4$, A, Q, Z, L are described above, $R^{42}$ is a leaving group, $R^{41}$ is Z or L, a derivative of Z or L or can be subsequently transformed to Z or L or a derivative of Z or L)

$R^{42}$ acts as a leaving group (for example Br, I, sulfonate) and $R^{41}$ is Z or L, a derivative of Z or L or can be subsequently transformed to Z or L or a derivative of Z or L.

The alkylation of glutamate derivatives is described in the literature, e.g.: M. A. Brimble et al., *Bioorg. Med. Chem.* 2005, 13, 519-523; S. Hanessian et al., *J. Org. Chem.* 2005, 70, 5070-5085; S. Hanessian et al., *Org. Lett.* 2004, 6, 4683-4686; J. Zhang at al., *Tetrahedron Lett.* 2003, 44, 1413-1415. It is well known, that the alkylation affords selectively compounds A-3 if $R^3$ is hydrogen and $R^4$ is a carbamate-type protecting group (e.g. Boo). Mixtures of A-3 and A-4 can be obtained and separated by chromatography methods if other combinations of $R^3$ and $R^4$ are used (e.g. $R^3$=hydrogen and $R^4$=Trityl).

Corresponding D-glutamate derivatives can be obtained if D-glutamate building blocks A-5 are used (Scheme 2).

Scheme 2

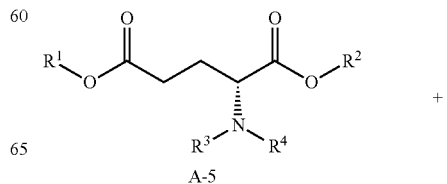

A-5

+

-continued

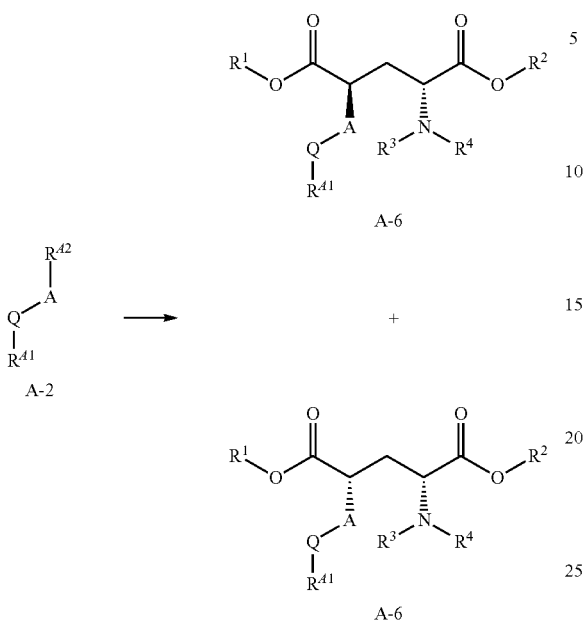

A-6

(Alkylation of D-glutamate backbone (R$^1$, R$^2$, R$^3$, R$^3$, R$^4$, A, Q, Z, L are described above, R$^{A2}$ is a leaving group, R$^{41}$ is Z or L, a derivative of Z or L or can be subsequently transformed to Z or L or a derivative of Z or L)

Compounds wherein X stands for —CH$_2$— and A stands for propyl can be obtained by alkylation of compounds A-1 or A-5 using allyl bromide (as described in the literature cited above) and subsequent cross-coupling with aryl/heteroaryl halides or sulfonates, followed by hydrogenation.

B. Synthesis of Homoglutamate derivatives

Compounds of the invention in which X stands for CH$_2$—CH$_2$ can be approached as shown in Scheme 3. The synthesis commences with the alkylation of phosphonoacetates B-1 with appropriately substituted arenes or heteroarenes B-2 to give phosphonate intermediates B-3. Compounds of the formula B-2 are often known to the person skilled in the art and commercially available in some cases. Multiple syntheses of compounds of the formula B-2, and of useful intermediates for their preparation are described in the scientific literature, see e.g. *Helv. Chem. Acta* 2002, 85, 3422, *J. Med. Chem.* 1977, 20, 1258, *Coll. Czechoslovak Chem. Comm.* 1948, 13, 289, *J. Am. Chem. Soc.* 1958, 80, 2217, EP 379928.

Subsequently, compounds of formula B-3 are, following deprotonation with an appropriate base, reacted with aldehydes B-4 to give olefins B-5a and B-5b, typically as mixture of double bond isomers. Aldehydes B-4 are available from the corresponding homo-serine derivatives, which are known to the person skilled in the art, by standard oxidation reaction, e.g. by hypervalent iodine based reagents such as Dess-Martin's periodinane.

The double bond present in B-5a and B-5b is then saturated e.g. by catalytic hydrogenation, and Z' is transferred into Z by removal of the corresponding protecting group. This can be accomplished in one single step if said protecting group is amenable for hydrogenolytic cleavage. This leads to compounds B-6 which are equivalent to compounds of the formula IV with the proviso that X stands for an ethylene group.

Scheme 3

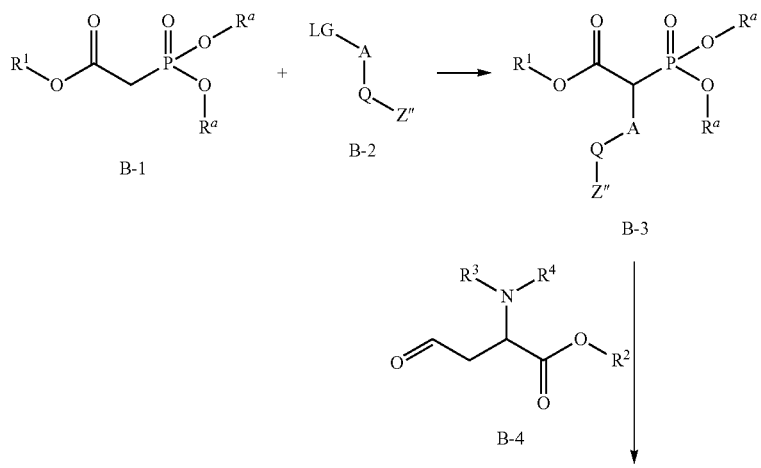

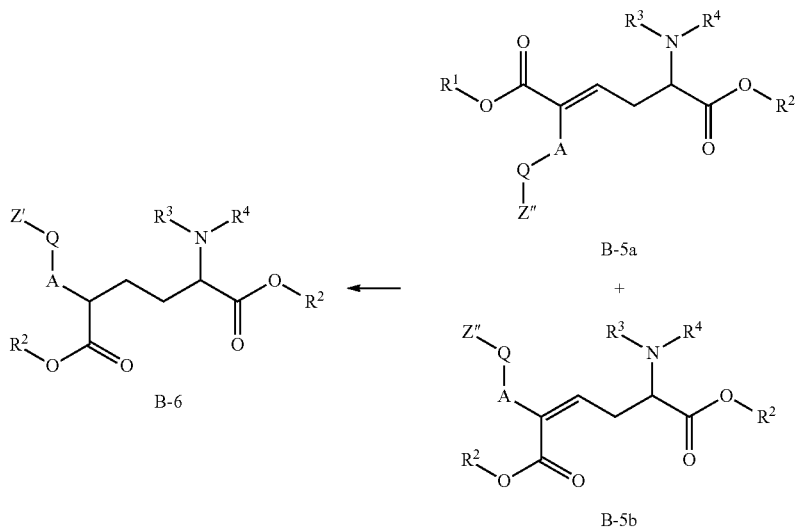

B-5a

+

B-6

B-5b

Preparation of compounds of the formula B-6, wherein $R^1$, $R^2$, $R^3$, $R^4$, A, and Q are defined as in the claims and description of this invention, and wherein $R^a$ is a $C_1$-$C_6$ alkyl group, and Z' stands for Z as defined as in the claims and description of this invention with the proviso that Z' is not a halogen, and Z" stands for a protected form of Z', wherein the hydroxyl group contained in Z' is protected by a suitable hydroxyl-protecting group known to the person skilled in the art and as described in the definitions and in the literature cited herein, furthermore Z" can be nitro as a protected synthon if Z' $NH_2$.

Alternatively, compounds of the formula B-6 can be prepared starting from orthogonally protected malonic esters B-7 which can be sequentially alkylated by reactive homo-serine derivatives B-8, followed by alkylation of the resulting product B-9 with compounds of the formula B-2 to give B-10. Subsequently, Rb is selectively cleaved in the presence of the other carboxylate protecting groups to yield the corresponding monocarboxylic acid, which is then decarboxylated to give compounds of the formula B-6. In addition, Z" is converted into Z'; most advantageously, the protecting group present in Z" is chosen suitably to enable simultaneous cleavage with Rb, for example by hydrogenolysis. The person skilled in the art will readily recognize the advantage of this synthetic route for the introduction of a diverse set of Z"-Q-A- groups. It could be shown that stereochemical information present in the homo-serine derivative B-8 can be retained over both malonate alkylation steps. In addition, the chiral HPLC methods used herein offer the possibility to isolate and characterize single stereoisomers.

Scheme 4

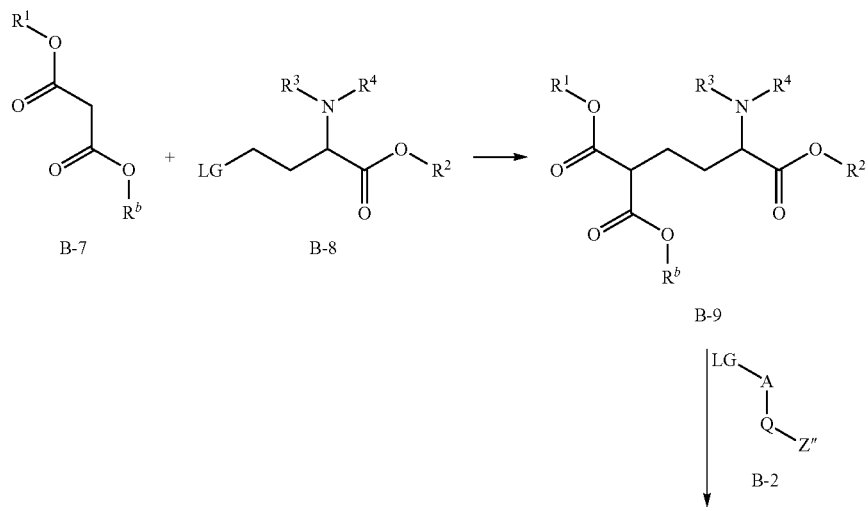

-continued

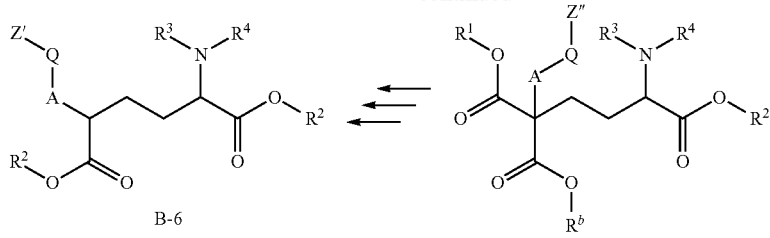

Alternative Preparation of compounds of the formula B-6, wherein $R^1$, $R^2$, $R^3$, $R^4$, A, and Q are defined as in the claims and description of this invention, and wherein Z' stands for Z as defined in the claims and description of this invention with the proviso that Z' is not a halogen, and Z" stands for a protected form of Z', wherein the hydroxyl group contained in Z' is protected by a suitable hydroxyl-protecting group known to the person skilled in the art and as described in the definitions and in the literature cited herein. $R^b$ is a group which can be removed in the presence of other protecting groups present in intermediate B-10, e.g. other carboxyl- and amine-protecting groups, which can be exemplified by but is not limited to an optionally substituted benzylic group.

Subsequently, compounds of the formula B-6, constituting a sub-set of compounds of formula IV, can be elaborated into compounds of the formula I as outlined in the following paragraph (if Z' stands for OH), or, if Z' stands for HO-L, by conversion of the terminal hydroxyl group into a leaving group. If said leaving group is a sulfonate, this can be accomplished by standard sulfonylation procedures well known to the person skilled in the art, such as treatment of the respective hydroxyl compound with a sulfonyl halide (such as tosyl chloride) or a sulfonyl anhydride in the presence of a suitable base, such as pyridine, 2,6-lutidine, or triethylamine. If said leaving group is Br or I, conversion can be performed by reacting the respective hydroxyl compound e.g. with a triaryl phosphine and the respective N-halo succinimide (see examples section) or carbon tetrahalide. To facilitate work-up and product purification, the triaryl phosphine may also be used as a polymer bound reagent.

Using the methods described above compounds of compounds of the formula B-6' and B-6" can be synthesized by a sequence starting by reacting compounds of formula B-8' and B-8" with of formula B-7 (Scheme 4-B).

Scheme 4-B

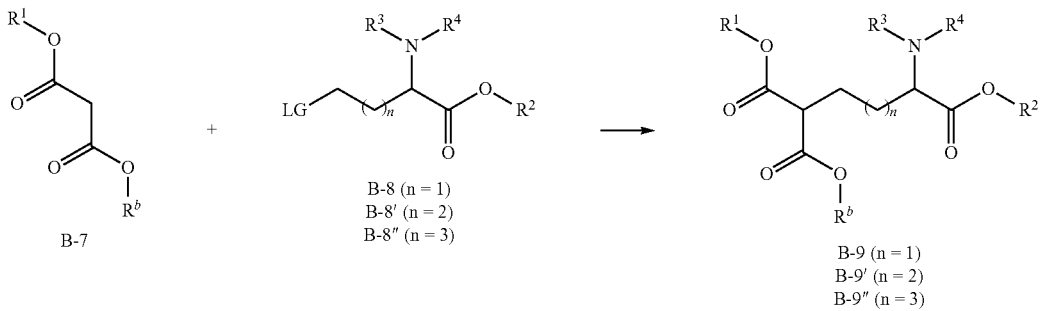

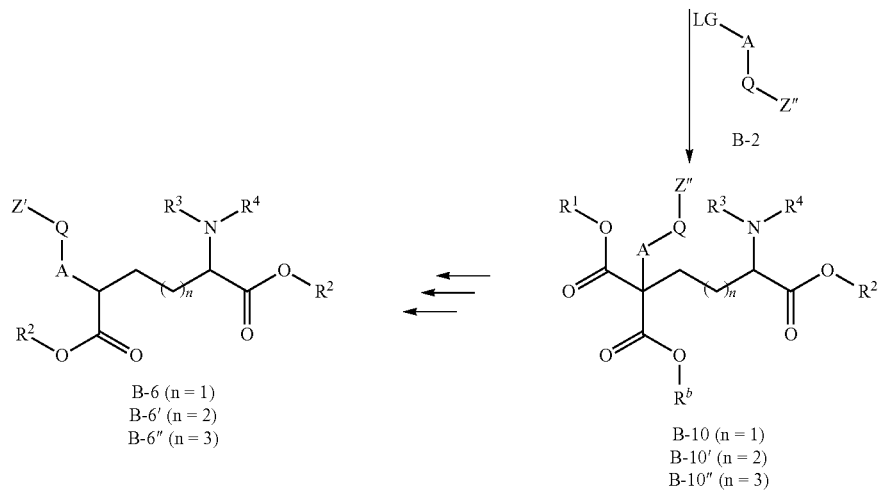

Preparation of compounds of the formula B-6' and B", wherein $R^1, R^2, R^3, R^4$, A, and Q are defined as in the claims and description of this invention, and wherein Z' stands for Z as defined as in the claims and description of this invention with the proviso that Z' is not a halgen, and Z" stands for a protected form of Z', wherein the hydroxyl group contained in Z' is protected by a suitable hydroxyl-protecting group known to the person skilled in the art and as described in the definitions and in the literature cited herein. $R^b$ is a group which can be removed in the presence of other protecting groups present in intermediate B-10, e.g. other carboxyl- and amine-protecting groups, which can be exemplified by but is not limited to an optionally substituted benzylic group.

C. Alkylation of Aryl/Heteroaryl-OH

Numerous methods and variations for the transformation of hydroxyl substituted aryl or heteroaryl derivatives into their corresponding alkyl aryl ethers or alkyl heteroaryl ethers have been reported (for an overview see for example: R. C. Larock, in "Comprehensive Organic Transformations," 2nd ed., John Wiley & Sons, Inc., New York (1999), p 889). Hence, compounds of this invention, wherein L stands for alkylene-O can be obtained by conversion of hydroxyl substituted aryl- or heteroaryl derivatives C-1 according to Scheme 5. Compounds of formula C-7 can serve as intermediates for the synthesis of compounds of formula I and compounds of formula V. For example, $R^{C1}$ can be deprotected and the resulting free hydroxyl group can be further converted either into a leaving group (applying methods described above) to give compounds of formula I, or into a fluoride (applying methods described above) to give compounds of formula V.

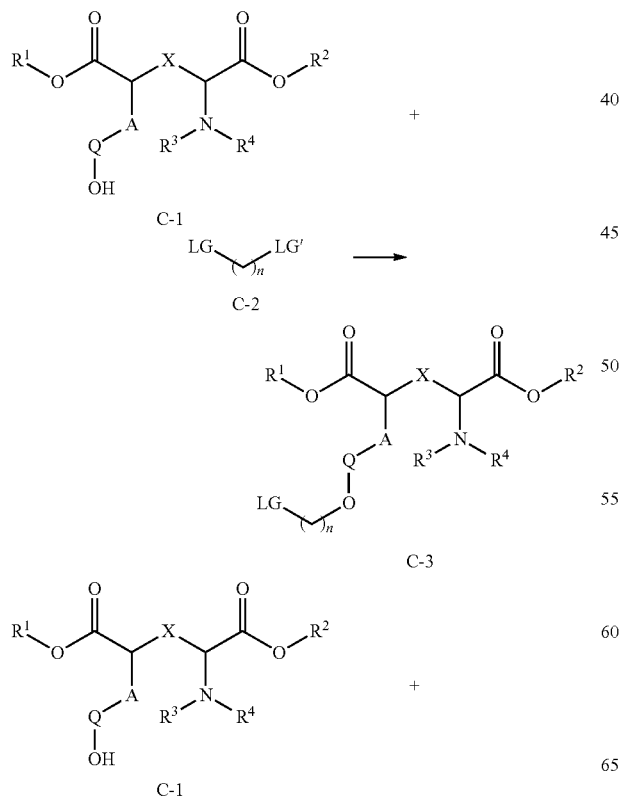

Scheme 5

Alkylation of hydroxyl-substituted aryl or heteroaryl derivatives ($R^1, R^2, R^3, R^4$, LG, LG', A, Q, X are described above, $R^{c1}$ is an optionally protected hydroxyl group, L' is optionally substituted alkylene or cycloalkylene, L" stands for L as defined in the claims and description of this invention with the proviso that L" contains at least one oxygen atom and the bond between Q and L" is a bond between Q and one oxygen atom of L' and n is 1-4')

Alternatively, certain compounds of formula C-7, can be obtained by reactions of compounds of formula C-1 with compounds of formula C-8 (Scheme 6) under conditions known to the person skilled in the art (*Bull. Chem. Soc. Jon.* 1967, 40, 4235; *Chem. Lett* 2001, 2, 94; *J. Org. Chem.* 1998, 63, 8554).

Scheme 6

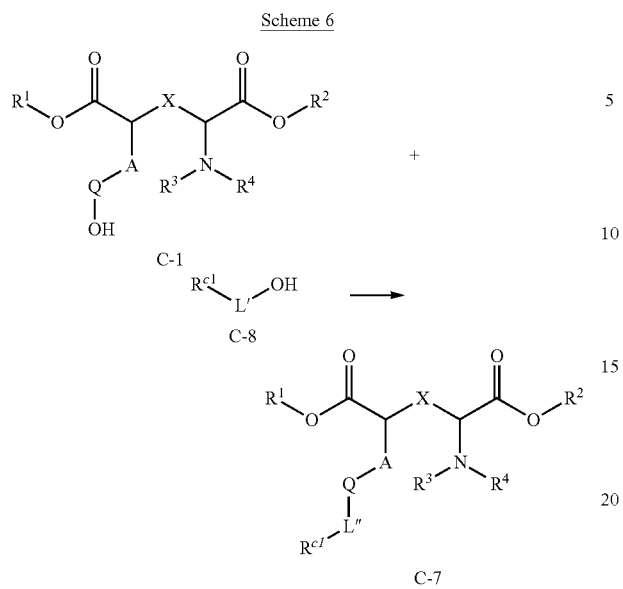

Reaction of hydroxyl substituted aryl or heteroaryl derivatives C-1 with alcohols according to formula C-8 ($R^1$, $R^2$, $R^3$, $R^4$, A, Q, X are described above, L' is optionally substituted alkylene or cycloalkylene, L" stands for L as defined in the claims and description of this invention with the proviso that L" contains at least one oxygen atom and the bond between Q and L" is a bond between Q and one oxygen atom of L", $R^{c1}$ is an optionally protected hydroxyl group).

Alternatively, compounds of formula C-7 can be obtained by reactions of compounds of formula C-9 with compounds of formula C-8 (Scheme 7) under conditions known to the person skilled in the art (For examples, see: *J. Am. Chem. Soc.* 2005, 127, 8146; *J. Org. Chem.* 2009, 74, 5075; *J. Am. Chem. Soc.* 2001, 123, 10770; *Tetrahedron Lett.* 2006, 47, 5333; *J. Med. Chem.* 1996, 39, 3837; *Tetrahedron Lett.* 2007, 48, 4293)

Scheme 7

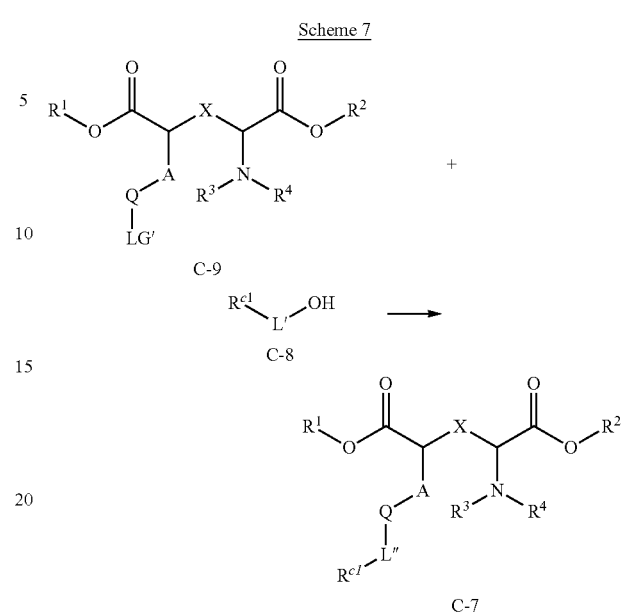

Reaction of aryl or heteroaryl derivatives C-9 with alcohols according to formula C-8 ($R^1$, $R^2$, $R^3$, $R^4$, A, Q, X are described above, L' is optionally substituted alkylene or cycloalkylene, L" stands for L as defined in the claims and description of this invention with the proviso that L" contains at least one oxygen atom and the bond between Q and L" is a bond between Q and one oxygen atom of L", LG' is halogen, $R^{c1}$ is an optionally protected hydroxyl group)

D. Alkylation of aryl/heteroaryl-NH$_2$

Compounds, wherein L stands for alkylene-NH can be obtained by conversion of aniline derivatives D-1 (Scheme 8) as known to the person skilled in the art, e.g. by alkylation using compounds C-2 or C-4, or by reductive amination using compounds D-4.

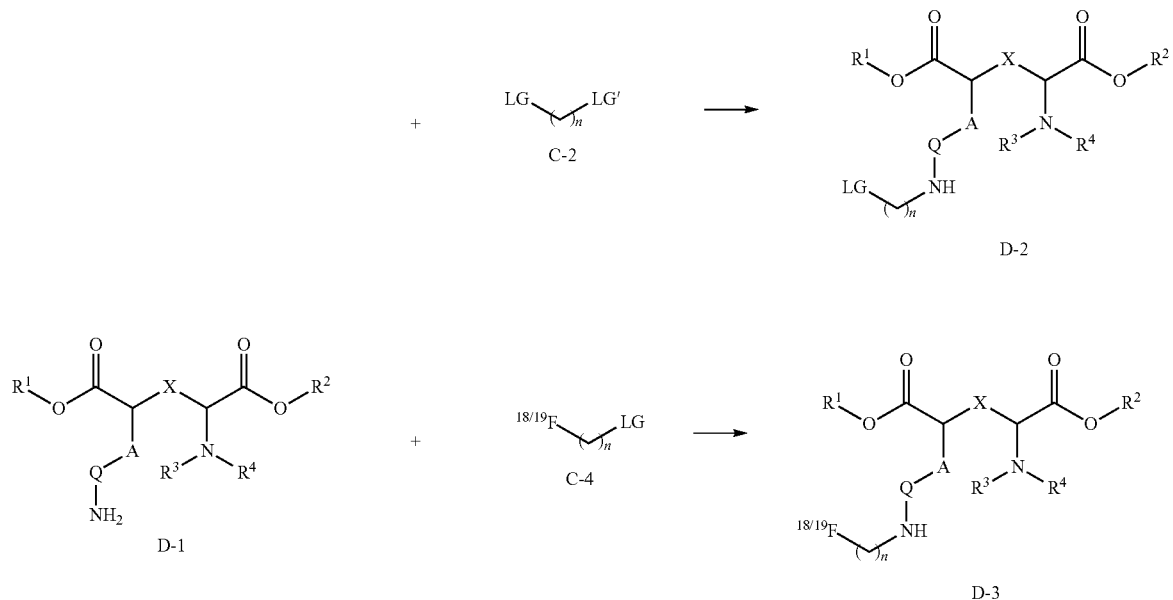

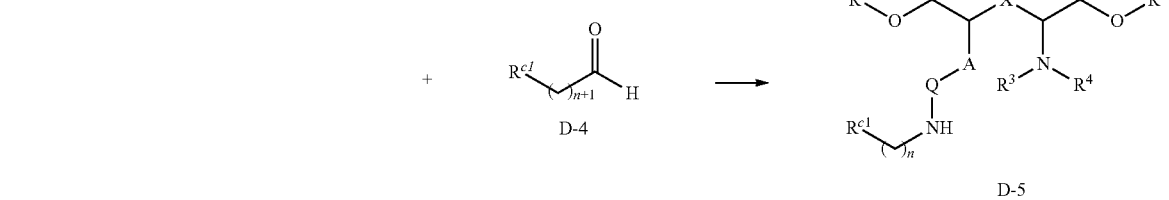

D-4

D-5

Alkylation of aniline derivatives ($R^1$, $R^2$, $R^3$, $R^3$, $R^4$, LG, LG′, A, Q, X are described above)

E. Synthesis of Alkylaryl Derivatives and Building Blocks

Compounds of this invention, where L stands for alkylene or substituted alkylene, can be synthesized according to Scheme 9 by reacting compounds of formula C-9 with suitable alkenes of formula E-1 (see for example *Synthesis* 2005, 20, 3589), alkynes of formula E-3 (see for example *Organic Lett.* 2002, 4, 1411; *J. Org. Chem.* 2003, 68, 3327), alkenyl metal species of formula E-5 (see for example *Collect. Czech. Chem. Commun.* 2000, 65, 434; *Organic Lett.* 2000, 2, 565; *SYNLETT* 2002, 7, 1137; *Tetrahedron Lett.* 1992, 33, 6139; *Tetrahedron Lett.* 2002, 43, 4935), or alkyl metal species of formula E-6 (see for example *Tetrahedron Lett.* 1994, 35, 1177; *Liebigs Ann. Chem.* 1991, 3, 295; *Bull. Chem. Soc. Jon.* 1997, 70, 437; *Tetrahedron* 1998, 54, 197; *Tetrahedron Lett.* 1999, 40, 197; *Tetrahedron Lett.* 2004, 45, 2467) under conditions described in the literature and known to the person skilled in the art (wherein metal includes, but is not limited to Sn, Si, Mg, Zn, and B in their appropriate oxidation states and further substituted by suitable ligands in order to facilitate the cross coupling reactions described in Scheme 9 and in the literature cited above). Compounds of formulas E-2, E-4 and E-7 can further be elaborated into compounds of formula I and compounds of formula V by methods known to the person skilled in the art. In case of compounds of formula E-2 and E-4, the non-aromatic double bonds and triple bonds can be saturated e.g. by hydrogenolysis. This may also deprotect the $R^{C1}$ hydroxyl group, if the protecting group is chosen accordingly (e.g. benzyl protecting group), which might otherwise be deprotected before or subsequently by other means (e.g. using TBAF in case of silicon based protecting groups). Deprotection of the $R^{C1}$ hydroxyl group of E-7 can be achieved similarly. In some cases, the corresponding building blocks comprising unprotected hydroxyl groups may also be used. The so-derived free hydroxyl groups of compounds of formula E-7 can be transformed by methods described above into suitable leaving groups to give compounds of formula I, or into fluoride to give compounds of formula V.

Scheme 9

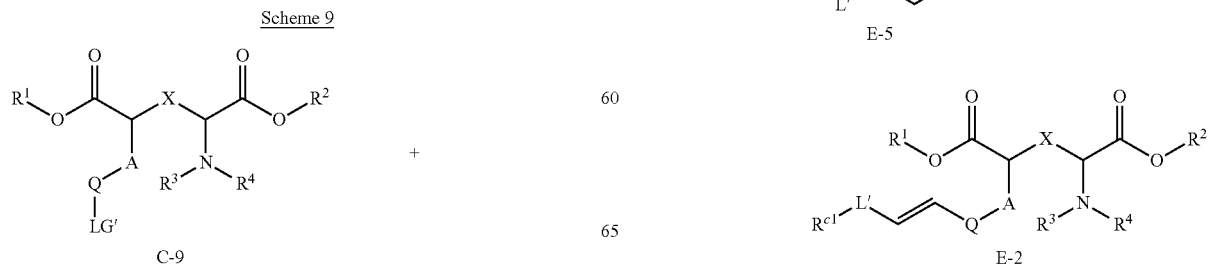

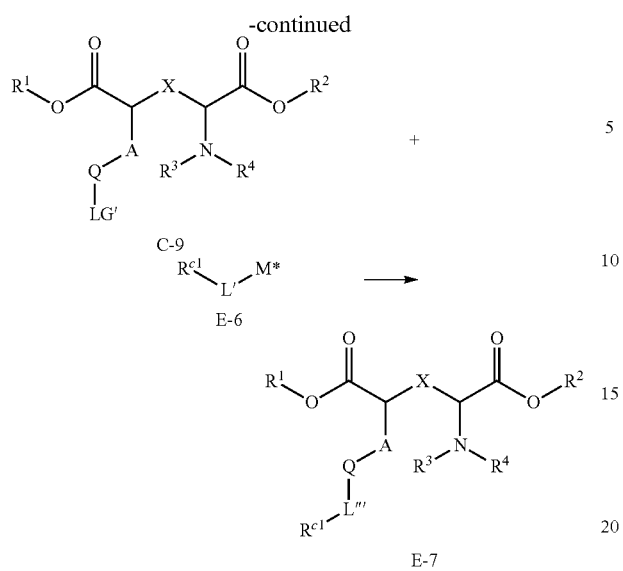

Reactions of aryl or heteroaryl derivatives of C-9 with alkenes, alkynes, alkenyl metal derivatives, and alkyl metal derivativs ($R^1$, $R^2$, $R^3$, $R^4$, A, Q, X, LG', are described above, L' is optionally substituted alkylene or cycloalkylene, L''' stands for L as defined as in the claims and description of this invention with the proviso that the bond between Q and L''' Q is a bond between Q and one carbon atom of L''', $R^{cl}$ is an optionally protected hydroxyl group, M* is a metal atom in an appropriate oxidation state and may be further substituted by suitabel ligands)

Alternatively, compounds of formula E-1, E-3, E-5, and E-6 can be used in the same manner as described for reactions with compounds of formula C-9 for reactions with compounds of formula E-8 (Scheme 10). Non aromatic double bonds and triple bonds can be saturated e.g. by hydrogenolysis. A' can be transformed into A-$R^{A2}$. For example, if A' is optionally protected hydroxyalkyl, deprotection of the hydroxyl group and subsequent conversion into a halide or sulfonate leads to compounds of formula E-10 or E-13, which can be used in the same manner as compounds of formulas A-2 and B-2 in the respective examples.

Scheme 10

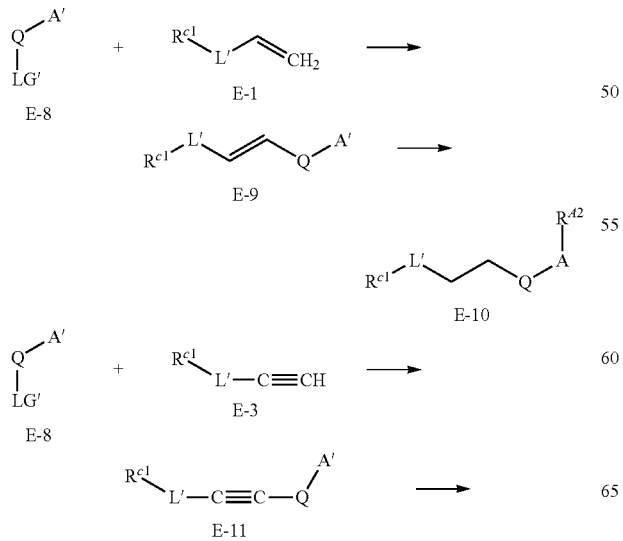

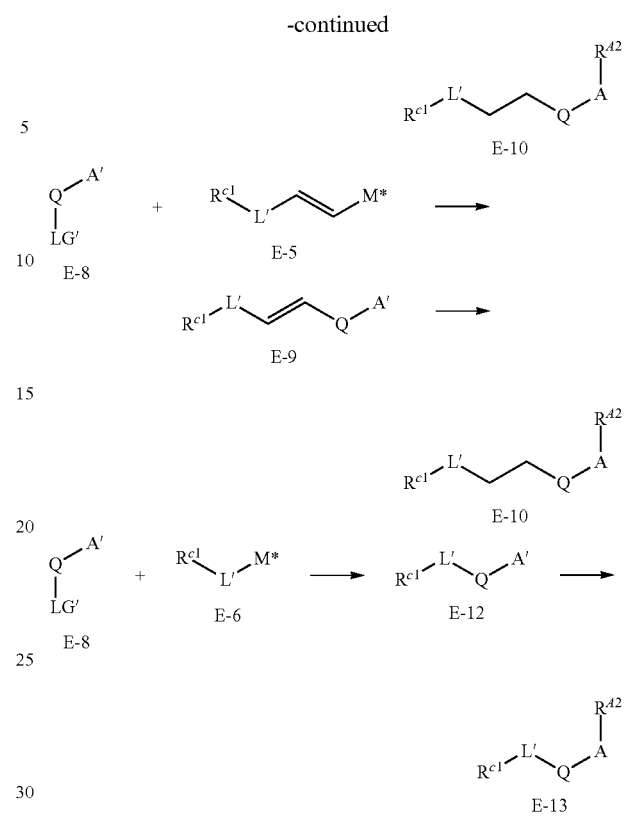

Reaction of aryl or heteroaryl derivatives E-8 with alkenes, alkynes, alkenyl metal derivatives, and alkyl metal derivatives (A, Q, LG', L', $R^{cl}$, $R^{A2}$, M* are described above, A' is a residue which can be transformed into A—$R^{A2}$ by methods known to the person skilled in the art).

F. Synthesis of Sulfonates

Precursors for $^{18}$F-alkyl compounds of general Formula I are e.g. tosylates, brosylates, nosylates, mesylates, triflates, nonaflates etc. which can be synthesized from the respective hydroxyl compounds according to methods known in the art (J. March, Advanced Organic Chemistry, 4th ed. 1992, John Wiley & Sons, pp 352ff). An additional method is described in Examples 5 and 7 and comprises the synthesis by suitable bis(tosylates) and the like, e.g. TsO—$(CH_2)_n$—OTs.

Other precursors for $^{18}$F-alkyl compounds of general Formula I are e.g. iodides and bromides and the like whose conversion to the respective fluorides is also known in the art (J. March, see above).

G. $^{18}$F Fluorination

The radiosynthesis of the $^{18}$F labeled compounds of the invention can be accomplished in multiple ways using known methods described in the literature and databases in reach of the person skilled in the art.

More specifically, compounds of the invention according to the general Formulae II and III can be synthesized starting from I as outlined in Scheme 11. Such nucleophilic fluorinations are known to the person skilled in the art and also described in the literature, for reviews and cited references within see e.g. Cai et al., *Eur. J. Org. Chem.*, 2008, 2853; Ametamey et al., *Chem. Rev.*, 2008, 108, 1501, Miller et al., *Angew. Chem. Int. Ed.* 2008, 47, 8998.

Scheme 11

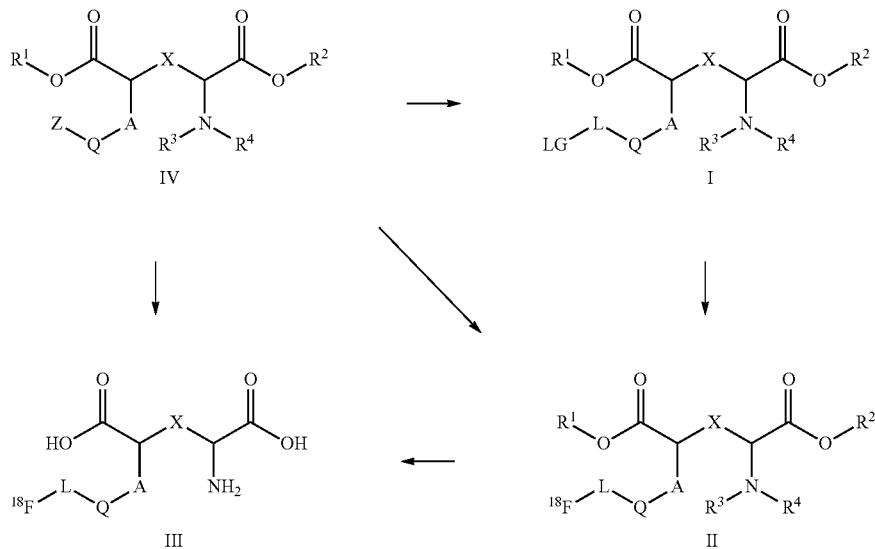

Synthesis of $^{18}$F-labeled compounds of Formula III ($R^1$, $R^2$, $R^3$, $R^3$, $R^4$, LG, A, Q, X, Z) are describe above)

Additionally, compounds of the invention according to the general Formulae II and III wherein L is "alkylene-O" or "alkylene-NH" can be obtained by conversion of compounds of Formula IV, wherein Z is OH or $NH_2$ with a $^{18}$F labeled building block (e.g. $^{18}$F-alkylene-LG). Such $^{18}$F labeled building block can be bromo-[$^{18}$F]fluoromethane ($^{18}$F—$CH_2$—Br). $^{18}$F—$CH_2$—Br can be synthesized by reacting di-bromo-methane with a [$^{18}$F] fluoride source.

H. $^{19}$F Fluorination

In a similar way, as described for $^{18}$F labeled compounds of Formulae II and III, $^{19}$F-derivatives of Formula V can be obtained by nucleophilc fluorination of molecules of Formula I with subsequential removal of protecting groups in one or more steps affording $^{19}$F compounds of Formula VI (Scheme 12).

Alternatively, $^{19}$F substituted compounds of the invention according to the general formulae V and VI can be approached starting from intermediates H-1 by fluorination of the hydroxyl group by methods known to the person skilled in the art to compounds of Formula V.

Additionally, compounds of the invention according to the general Formulae V and VI wherein L is "alkylene-O" or "alkylene-NH" can be obtained by conversion of compounds of Formula IV, wherein Z is OH or $NH_2$ with a F containing building block (e.g. F-alkylene-LG).

Scheme 12

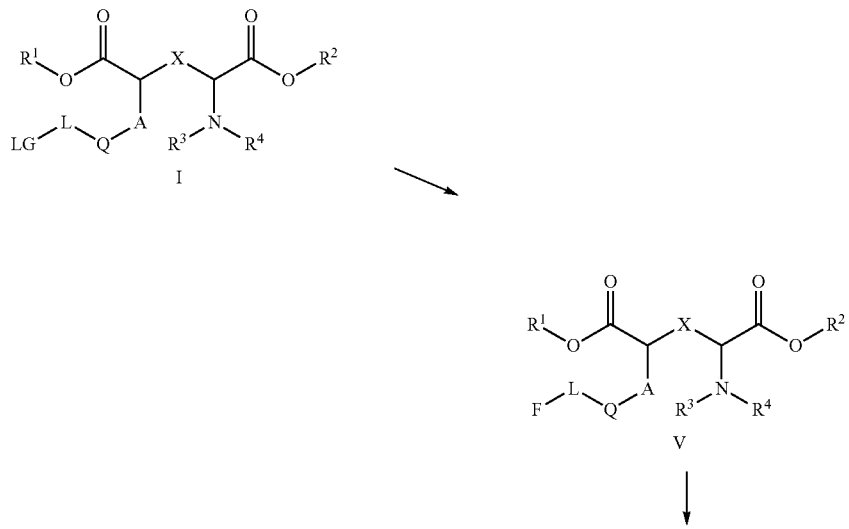

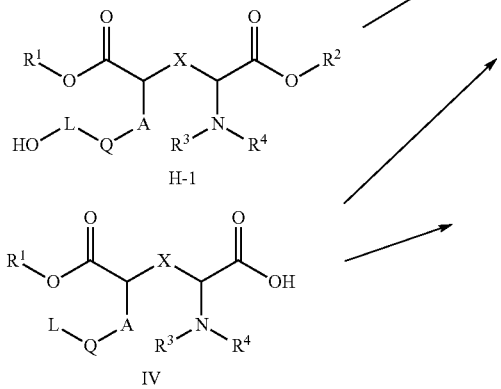

Synthesis of $^{19}$F-derivatives of Formula V and VI ($R^1$, $R^2$, $R^3$, $R^3$, $R^4$, LG, A, Q, X, Z) are describe above)

It is obvious to the person skilled in the art, that starting form different building blocks (such as L- or D-amino acid derivatives or L/D mixtures) a variety of different stereoisomers can be synthesized following the general description above and in the examples.

HPLC Methods

Preparative HPLC, if not stated otherwise, was performed on HPLC devices comprising a Labomatic HD-3000 HPLC gradient pump, a 125×30 mm Chromatorex C-18 column, a standard UV detector, and Labomatic Labocol Vario-2000 fraction collector. Flow rate was typically 150 nL/minute, and total gradient time in the range of 7 minutes.

Method A:
  Column: Chromatorex C-18 10 µm, 125×30 mm
  Eluents: A: 0.1% HCOOH in water, B: MeCN,
  Gradient: A 35%/B 65%→B 100%

Method B:
  Column: Chromatorex C-18 10 µm, 125×30 mm
  Eluents: A: 0.1% HCOOH in water, B: MeCN,
  Gradient: A 90%/B 10%→A 50%/B 50%

Method C:
  Column: Chromatorex C-18 10 µm, 125×30 mm
  Eluents: A: 0.1% HCOOH in water, B: MeCN,
  Gradient: A 70%/B 30%→A 30%/B 70%

Method D:
  Column: Chromatorex C-18 10 µm, 125×30 mm
  Eluents: A: 0.1% HCOOH in water, B: MeCN,
  Gradient: A60%/B 40%→A20%/B 80%

Method E:
  Column: Chromatorex C-18 10 µm, 125×30 mm
  Eluents: A: 0.1% HCOOH in water, B: MeCN,
  Gradient: A 75%/B 25%→A 99%/B 1%

Analytical HPLC Methods

Analytical HPLC was used for determination of radiochemical purity of the $^{18}$F labeled derivatives. The corresponding $^{19}$F derivatives were used for confirmation of the identity.

Analytical HPLC System 1:
  HPLC pump: Agilent 1200, Bin Pump SL G1315B
  UV detector: Agilent 1200, DAD SL G131C
  Radioactivity detector: Raytest Gabi Analytical HPLC System 2:
  HPLC pump: Agilent 1100, Bin Pump G1312A
  UV detector: Agilent 1100, DAD G1315B
  Radioactivity detector: Raytest Gabi Analytical HPLC Method C:
  Column: ACE 3 C18, 4.6×50 mm, 3 µm, 100 A
  Eluents: A: water+0.1% TFA; B: acetonitrile+0.1% TFA
  Flow: 2 mL/min
  Gradient: 0:00-01:00 min 5% B, 01:00-04:00 min 5-95% B, 04:00-04:20 min 95-100% B, 04:20-05:50 min 100% B, 05:00-06:00 min 100-5% B, 06:00-07:00 min 5% B.

Analytical HPLC Method D:
  Column: Chromolith SpeedROD, 50*4.6 mm, RP-18e, Merck
  Eluents: A: 0.01M $Na_2HPO_4$ (pH 7.4); B: acetonitrile
  Flow: 2 mL/min
  Gradient: 00:00-02:00 min 0% B, 02:00-07:00 min 0-95% B, 07:00-07:20 min 95-100% B, 07:20-08:50 min 100% B, 08:50-09:00 min 100-0% B, 09:00-10:50 min 0% B Analytical HPLC Method E:
  Column: ACE 3 C18, 4.6×50 mm, 3 µm, 100 A
  Eluents: A: water+0.1% TFA; B: acetonitrile+0.1% TFA
  Flow: 2 mL/min
  Gradient: 00:00-02:00 min 5% B, 02:00-07:00 min 5-95% B, 07:00-07:20 min 95-100% B, 07:20-08:50 min 100% B, 08:50-09:00 min 100-5% B, 09:00-10:50 min 5% B Analytical HPLC Method F:
  Column: Hypercarb, 100×4.6 mm, 7 µm, Thermo Scientific
  Eluents: A: water+0.1% TFA; B: acetonitrile+0.1% TFA
  Flow: 2 mL/min
  Gradient: 00:00-07:00 min 5-95% B, 07:00-07:20 min 95-100% B, 07:20-08:50 min 100% B, 08:50-09:00 min 100-5% B, 09:00-12:00 min 5% B Analytical HPLC Method G Pre-Column Derivatization Method:
  Column: Luna 5µ C18, 250×4.6 mm, 5 µm, Phenomenex
  Eluents: A $Na_2HPO_4$-buffer 0.04 M pH 7.8; B: acetonitrile/methanol/water 45/45/10

Flow: 1.5 mL/min

Gradient: 00:00-30:00 min 10-50% B, 30:00-31:00 min 50-100% B, 31:00-34:00 min 100% B, 34:00-35:00 min 100-10% B, 35:00-37:00 min 10% B Pre-column derivatization: 20 μL sample+20 μL borate buffer (Agilent)+20 μL OPA-reagent (Agilent)

Analytical HPLC Method H:
  Column: ACE 3 C18, 4.6×50 mm, 3 μm, 100 A
  Eluents: A: water+0.1% TFA; B: acetonitrile+0.1% TFA
  Flow: 2 mL/min
  Gradient: 00:00-10:00 min 5-30% B, 10:00-10:50 min 30-100% B, 10:50-12:00 min 100% B, 12:00-12:50 min 100-5% B, 12:50-14:00 min 5% B Analytical HPLC Method I:
  Column: ACE 3 C18, 4.6×50 mm, 3 μm, 100 A
  Eluents: A: water+0.1% TFA; B: acetonitrile+0.1% TFA
  Flow: 2 mL/min
  Gradient: 00:00-07:00 min 5-95% B, 07:00-08:00 min 95-100% B, 08:00-08:80 min 100% B, 08:80-09:00 min 100-5% B, 09:00-11:00 min 5% B Chiral Analytical HPLC Methods If not stated otherwise, chiral analytical HPLC was performed at a flow rate of 1.0 mL/min and with the column at room temperature. Analyte loading typically is 5 μL of a 1.0 mg/mL solution in a suitable solvent. For further details, the reader is referred to the individual methods.

Chiral HPLC Method c1:
  System: Waters: Alliance 2695, DAD 996, ESA: Corona
  Column: Chiralpak AD-H 5 μm 150×4.6 mm
  Eluent: hexane/ethanol 90:10 isocratic
  Detection: DAD 210 nm Chiral HPLC Method c2:
  System: Waters: Alliance 2695, DAD 996, ESA: Corona
  Column: Chiralpak IA 5 μm 150×4.6 mm
  Eluent: hexane/ethanol 95:5 isocratic
  Detection: DAD 210 nm Chiral HPLC Method c3:
  System: Dionex: Pump 680, ASI 100, Knauer: UV-Detector K-2501
  Column: Chiralpak AD-H 5 μm 150×4.6 mm
  Eluent: hexane/isopropanol 80:20+0.1% HCOOH isocratic
  Detection: UV 210 nm Chiral HPLC Method c4:
  System: Dionex: Pump 680, ASI 100, Waters: UV-Detector 2487
  Column: Chiralpak AD-H 5 μm 150×4.6 mm
  Eluent: hexane/isopropanol 85:15+0.1% diethylamine isocratic
  Detection: DAD 220 nm Chiral HPLC Method c5:
  System: Dionex: Pump 680, ASI 100, Waters: UV-Detector 2487
  Column: Chiralpak AD-H 5 μm 150×4.6 mm
  Eluent: hexane/isopropanol 80:20+0.1% diethylamine isocratic
  Detection: DAD 220 nm The phrase "Water (pH 2)" as used in the examples below, is refering to a diluted hydrochloric acid of pH 2.

EXAMPLES

Chemistry Examples

Example 1

(4S)-4-[4-(2-Fluoroethoxy)benzyl]-L-glutamic acid

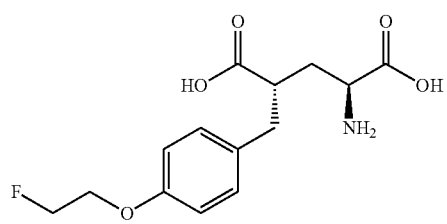

a) Di-tert-butyl (4S)-4-[4-(benzyloxy)benzyl]-Nert-butoxycarbonyl)-L-glutamate

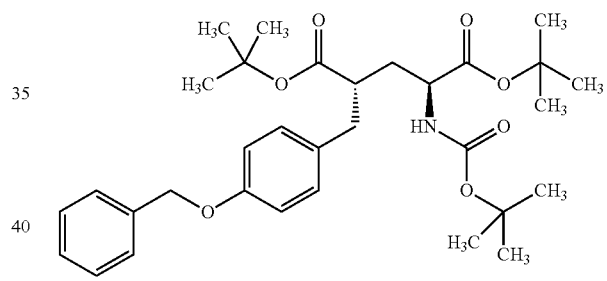

6.0 g (16.7 mmol) of di-tert-butyl Boc-glutamate (Journal of Peptide Research (2001), 58, 338) were dissolved in 50 mL of tetrahydrofuran and cooled to −70° C. 36.7 mL (36.7 mmol) of a 1M solution of lithium bis(trimethylsilyl)amide in tetrahydrofuran were added dropwise over a period of 90 min at this temperature and the mixture was stirred at −70° C. for another 2 hours. 13.88 g (50 mmol) of 4-(benzyloxy)benzyl bromide (Helvetica Chimica Acta, 2002, 85, 3422) in 40 mL of tetrahydrofuran were than added dropwise, and after 2 h at this temperature, the cooling bath was removed and 90 mL of 2N aqueous hydrochloric acid and 500 mL of dichloromethane were added. The organic phase was separated off, washed with water until neutral, dried over sodium sulfate and filtered, and the filtrate was concentrated. The crude product obtained in this manner was chromatographed on silica gel using a hexane/ethyl acetate gradient, and the appropriate fractions were combined and concentrated.

Yield: 3.44 g (37.1%)

$^1$H-NMR (400 MHz, CHLOROFORM-d): δ [ppm]==1.31 (s, 9H), 1.44-1.57 (m, 18H), 1.87 (t, 2H), 2.61 (m, 1H), 2.78-2.81 (m, 2H), 4.14-4.20 (m, 1H), 4.89 (d, 1H), 5.04 (s, 2H), 6.87 (d, 2H), 7.08 (d, 2H), 7.37-7.44 (m, 5H).

ESI+ m/z 556 (M+H).

b) Di-tert-butyl (4S)—N-(tert-butoxycarbonyl)-4-(4-hydroxybenzyl)-L-glutamate

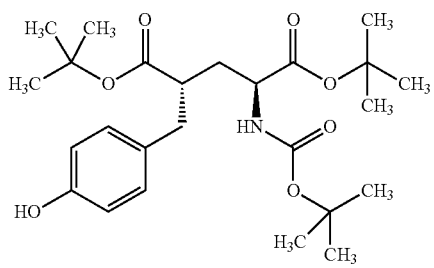 [SMILES: CC(C)(C)OC(=O)N[C@@H](C[C@H](Cc1ccc(O)cc1)C(=O)OC(C)(C)C)C(=O)OC(C)(C)C]

3.3 g (5.94 mmol) of di-tert-butyl (4S)-4-[4-(benzyloxy)benzyl]-Nert-butoxycarbonyl)-L-glutamate were dissolved in 200 mL of methanol and under argon atmosphere palladium (10% on charcoal) was added and the suspension hydrogenated overnight at room temperature. The reaction mixture was filtered, the solvent evaporated and the residue was chromatographed on silica gel using a hexane/ethyl acetate gradient, and the appropriate fractions were combined and concentrated.

Yield: 2.07 g (74.9%)

$^1$H-NMR (600 MHz, CHLOROFORM-d): δ [ppm]=1.33 (s, 9H), 1.44 (m, 18H), 1.88 (t, 2H), 2.61 (m, 1H), 2.74-2.83 (m, 2H), 4.15-4.21 (m, 1H), 4.89 (d, 1H), 5.08 (s, 1H), 6.72 (d, 2H), 7.03 (d, 2H).

ESI+ m/z 466 (M+H).

c) (4S)-4-[4-(2-Fluoroethoxy)benzyl]-L-glutamic acid

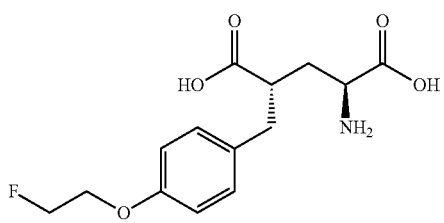

To 315 mg (0.68 mmol) of di-tert-butyl (4S)—N-(tert-butoxycarbonyl)-4-(4-hydroxy-benzyl)-L-glutamate in 30 mL N,N-dimethylformamide were added 206 mg (1.5 mmol) of powdered potassium carbonate and 104 mg (0.81 mmol) of 1-bromo-2-fluoroethane and the resulting suspension was stirred for 5 h at 60° C. and overnight at room temperature. The reaction mixture was then filtered, the solvent evaporated and the residue was taken up in ethyl acetate and water. The organic phase was separated off, washed with water until neutral, dried over sodium sulfate and filtered, and the filtrate was concentrated in vacuo. Di-tert-butyl (4S)—N-(tert-butoxycarbonyl)-4-[4-(2-fluoroethoxy)benzyl]-L-glutamate was obtained as crude product (110 mg, 32.6%) and deprotected without further purification: 3 mL of trifluoro acetic acid were added to the oily residue and the solution was stirred for 2 days at room temperature. The excess of trifluoro acetic acid was evaporated and the residue was taken up three times in tetrahydrofuran and than evaporated. The resulting oil was chromatographed on C-18 reversed phase silica gel using a water/acetonitrile gradient, the appropriate fractions were combined and concentrated.

Yield: 25 mg (41.8%)

$^1$H-NMR (400 MHz, DIMETHYLFORMAMIDE-d7): δ [ppm]=1.90-1.94 (m, 2H), 2.54-2.56 (m, 1H), 3.00-3.03 (m, 2H), 3.82-3.87 (m, 1H), 4.22-4.31 (m, 2H), 4.80 (dt, 2H), 6.90 (d, 2H), 7.17 (d, 2H).

ESI+ m/z 300 (M+H).

Example 2

Di-tert-butyl (4S)—N-(tert-butoxycarbonyl)-4-{4-[2-(tosyloxy)ethoxy]benzyl}-L-glutamate

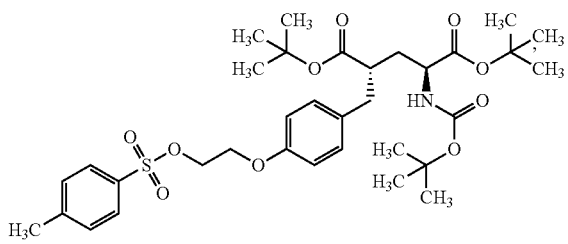 [SMILES: Cc1ccc(S(=O)(=O)OCCOc2ccc(C[C@@H](C[C@H](NC(=O)OC(C)(C)C)C(=O)OC(C)(C)C)C(=O)OC(C)(C)C)cc2)cc1]

Di-tert-butyl (4S)—N-(tert-butoxycarbonyl)-4-(4-hydroxybenzyl)-L-glutamate (90 mg, 0.19 mmol), 1,2-ethanediol-bis(4-methylbenzenesulfonate) (358 mg, 0.97 mmol), and caesium carbonate (189 mg, 0.580 mmol) were dissolved in 9 mL N,N-dimethylformamide and the solution was stirred at room temperature for 16 h. Another 200 mg of caesium carbonate were added and the mixture stirred for additional 4 h. The reaction was then poured into 1 N aqueous hydrochloric acid (50 mL) and extracted with dichloromethane (3×75 mL). The combined organic phases were dried over magnesium sulfate and concentrated in vacuo. The crude product was purified on silica gel using a hexane/ethyl acetate gradient, and the appropriate fractions were combined and concentrated.

Yield: 90 mg (70.1%)

$^1$H-NMR (400 MHz, CHLOROFORM-d): δ [ppm]=1.31 (s, 9H), 1.42-1.43 (m, 9H), 1.43 (s, 9H), 1.85 (t, 2H), 2.44 (s, 3H), 2.59 (quin, 1H), 2.70-2.85 (m, 2H), 4.06-4.12 (m, 3H), 4.29-4.37 (m, 2H), 4.88 (d, 1H), 6.63-6.71 (m, 2H), 7.01-7.08 (m, 2H), 7.30-7.37 (m, 2H), 7.77-7.84 (m, 2H).

ESI+ m/z 664.6 (M+H).

Example 3

4-[4-(2-[$^{18}$F]Fluoroethoxy)benzyl]-L-glutamic acid

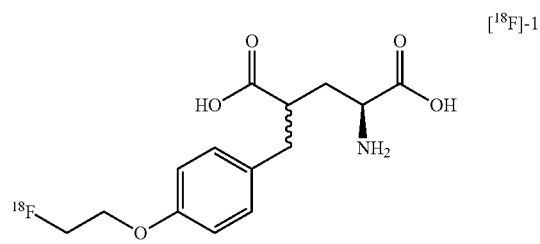 [SMILES: N[C@@H](CC(Cc1ccc(OCC[18F])cc1)C(=O)O)C(=O)O]

[<sup>18</sup>F]Fluoride (3138 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of di-tert-butyl (4S)—N-(tert-butoxycarbonyl)-4-{4-[2-(tosyloxy)ethoxy]benzyl}-L-glutamate in 1 mL acetonitrile were added to the dried residue. The resulting mixture was stirred at 100° C. for 10 min. After cooling for 5 min at rt, 2M HCl (1 mL) was added and the mixture was stirred at 120° C. for 13 min. The crude product was diluted with water (pH 2) up to 30 mL and passed through two preconditioned Strata-X-C cartridges (Phenomenex). The cartridges were washed with 50 mL water (pH 2) and 50 mL ethanol. 782 MBq (43% d.c.) 4-[4-(2-[$^{18}$F]Fluoroethoxy)benzyl]-L-glutamic acid ([$^{18}$F]-1) were eluted with 5 mL phosphate buffer (7 g Na$_2$HPO$_4$.2H$_2$O; 6 g NaCl in 1 L water). Radiochemical purity was determined to be >95% ($t_R$=3.5 min, analytical HPLC method D).

Example 4

(4S)-4-[4-(3-Fluoropropoxy)benzyl]-L-glutamic acid

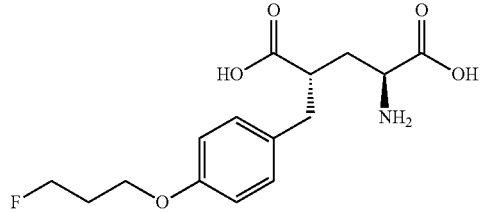

a) Di-tert-butyl (4S)—N-(tert-butoxycarbonyl)-4-[4-(3-fluoropropoxy)benzyl]-L-glutamate

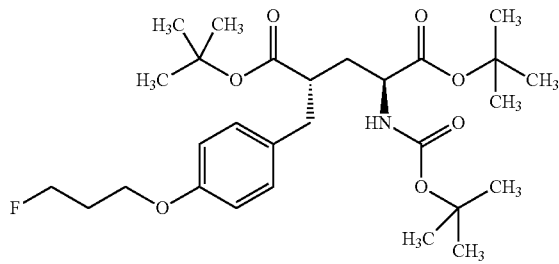 [SMILES: CC(C)(C)OC(=O)N[C@@H](C[C@H](Cc1ccc(OCCCF)cc1)C(=O)OC(C)(C)C)C(=O)OC(C)(C)C]

To 93 mg (0.20 mmol) of di-tert-butyl (4S)—N-(tert-butoxycarbonyl)-4-(4-hydroxybenzyl)-L-glutamate (Example 1b) in 9 mL N,N-dimethylformamide were added 60.7 mg (0.44 mmol) of powdered potassium carbonate and 45 mg (0.24 mmol) of 1-iodo-3-fluoropropane (ABCR GmbH, Germany) and the resulting suspension was stirred for 5 h at 60° C. and overnight at room temperature. The reaction mixture was than filtered, the solvent evaporated and the residue was taken up in ethyl acetate and water. The organic phase was separated off, washed with water until neutral, dried over sodium sulfate and filtered, and the filtrate was concentrated in vacuo. The crude product obtained in this manner was chromatographed on silica gel using a dichloromethane/methanol gradient, and the appropriate fractions were combined and concentrated.

Yield: 96 mg (91.4%)

$^1$H-NMR (500 MHz, CHLOROFORM-d): δ [ppm]=1.33 (s, 9H), 1.44 (s, 18H), 1.87 (m, 2H), 2.09-2.22 (m, 2H), 2.56-2.66 (m, 1H), 2.80 (d, 2H), 4.06 (t, 2H), 4.18 (m, 1H), 4.64 (m, 2H), 4.87 (d, 1H), 6.80 (d, 2H), 7.08 (d, 2H).

ESI+ m/z 526 (M+H).

b) (4S)-4-[4-(3-Fluoropropoxy)benzyl]-L-glutamic acid

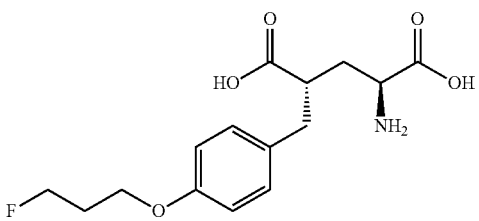

60 mg (0.11 mmol) of di-tert-butyl (4S)—N-(tert-butoxycarbonyl)-4-[4-(3-fluoropropoxy)-benzyl]-L-glutamate were taken up in 2 mL of trifluoro acetic acid and 1 mL of methoxybenzene and stirred overnight at room temperature. The excess of trifluoro acetic acid was evaporated and the residue was taken up three times in tetrahydrofuran and then evaporated. The resulting oil was chromatographed on C-18 reversed phase silica gel using a water/acetonitrile gradient, the appropriate fractions were combined and concentrated.

Yield: 15 mg (40.7%)

$^1$H-NMR (500 MHz, DMSO-d6): δ [ppm]=1.56-1.71 (m, 2H), 2.01-2.15 (m, 2H), 2.44-2.49 (m, 2H), 2.66-2.75 (m, 2H), 2.90 (m, 2H), 3.32-3.38 (m, 1H), 4.02 (t, 2H), 4.59 (m, 2H), 6.83 (d, 2H), 7.08 (d, 2H).

ESI+ m/z 314 (M+H).

Example 5

Di-tert-butyl (4S)—N-(tert-butoxycarbonyl)-4-{4-[3-(tosyloxy)propoxy]benzyl}-L-glutamate

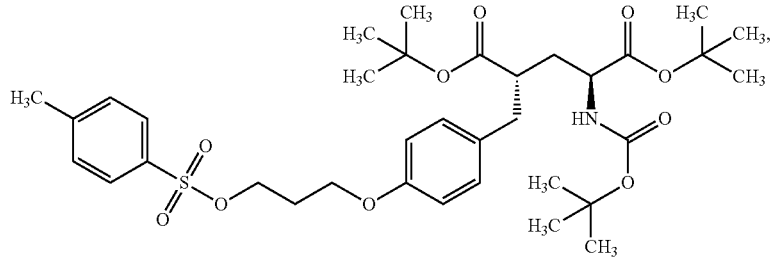 [SMILES: Cc1ccc(S(=O)(=O)OCCCOc2ccc(C[C@@H](C[C@H](NC(=O)OC(C)(C)C)C(=O)OC(C)(C)C)C(=O)OC(C)(C)C)cc2)cc1]

To 100 mg (0.22 mmol) of di-tert-butyl (4S)—N-(tert-butoxycarbonyl)-4-(4-hydroxy-benzyl)-L-glutamate (Example 1b) in 10 mL N,N-dimethylformamide were added 210 mg (0.64 mmol) of cesium carbonate and 413 mg (1.07 mmol) of 1,3-propanediol di-p-toluenesulfonate (Aldrich) and the resulting suspension was stirred overnight at room temperature. The reaction mixture was then filtered, the solvent evaporated and the residue was taken up in dichloromethane and 1 M hydrochloric acid. The organic phase was separated off, washed with water until neutral, dried over sodium sulfate and filtered, and the filtrate was concentrated in vacuo. The crude product obtained in this manner was chromatographed on silica gel using a hexane/ethyl acetate gradient, and the appropriate fractions were combined and concentrated.

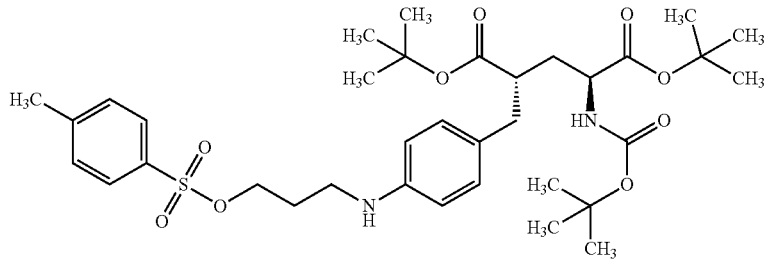 [SMILES: Cc1ccc(S(=O)(=O)OCCCNc2ccc(C[C@@H](C[C@H](NC(=O)OC(C)(C)C)C(=O)OC(C)(C)C)C(=O)OC(C)(C)C)cc2)cc1]

Yield: 87 mg (56.8%)
$^1$H-NMR (500 MHz, CHLOROFORM-d): δ [ppm]=1.33 (s, 9H), 1.44 (d, 18H), 1.87 (t, 2H), 2.10 (m, 2H), 2.40 (s, 3H), 2.57-2.65 (m, 1H), 2.74-2.84 (m, 2H), 3.92 (t, 2H), 4.15-4.26 (m, 3H), 4.88 (d, 1H), 6.67 (d, 2H), 7.05 (d, 2H), 7.27 (d, 2H), 7.76 (d, 2H).
ESI+ m/z 678 (M+H).

Example 6

4-[4-(3-[$^{18}$F]Fluoropropoxy)benzyl]-L-glutamic acid

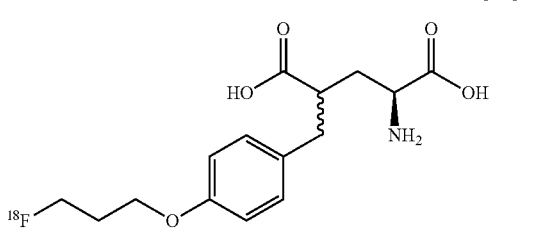

[$^{18}$F]Fluoride (3055 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of di-tert-butyl (4S)—N-(tert-butoxycarbonyl)-4-{4-[3-(tosyloxy)propoxy]benzyl}-L-glutamate in 1 mL acetonitrile were added to the dried residue. The resulting mixture was stirred at 100° C. for 10 min. After cooling for 5 min at rt, 2M HCl (1 mL) was added and the mixture was stirred at 120° C. for 10 min. The crude product was diluted with water (pH 2) up to 30 mL and passed a preconditioned Strata-X-C cartridge (Phenomenex). The cartridge was washed with 30 mL water (pH 2) and 40 mL ethanol. 1216 MBq (63% d.c.) 4-[4-(3-[$^{18}$F]fluoropropoxy)benzyl]-L-glutamic acid ([$^{18}$F]-4) were eluted with 5 mL phosphate buffer (7 g Na$_2$HPO$_4$.2H$_2$O; 6 g NaCl in 1 L water). Radiochemical purity was determined to be >95% (t$_R$=3.9 min, analytical HPLC method D).

Example 7

Di-tert-butyl (4S)—N-(tert-butoxycarbonyl)-4-(4-{[3-(tosyloxy)propyl]amino}benzyl)-L-glutamate a) Di-tert-butyl (4S)—N-(tert-butoxycarbonyl)-4-(4-nitrobenzyl)-L-glutamate

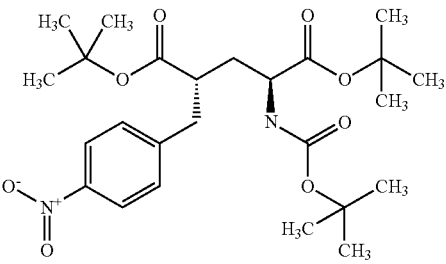 [SMILES: CC(C)(C)OC(=O)N[C@@H](C[C@H](Cc1ccc([N+](=O)[O-])cc1)C(=O)OC(C)(C)C)C(=O)OC(C)(C)C]

5.0 g (13.9 mmol) of di-tert-butyl Boc-glutamate (Journal of Peptide Research (2001), 58, 338) were dissolved in 30 mL of tetrahydrofuran and cooled to −70° C. 30.6 mL (30.6 mmol) of a 1M solution of lithium bis(trimethylsilyl)amide in tetrahydrofuran were added dropwise over a period of 85 min at this temperature and the mixture was stirred at −70° C. for another 2 hours. 9.0 g (41.7 mmol) of 4-nitrobenzyl bromide in 30 mL of tetrahydrofuran were than added dropwise, and after 1.5 h at this temperature, the cooling bath was removed and 100 mL of 2N aqueous hydrochloric acid and 450 mL of dichloromethane were added. The organic phase was separated off, washed with water (3×150 mL), dried over sodium sulfate and filtered, and the filtrate was concentrated. The crude product obtained in this manner was chromatographed on silica gel using a hexane/ethyl acetate gradient, and the appropriate fractions were combined and concentrated.
Yield: 2.56 g (33.5%)
$^1$H-NMR (400 MHz, CHLOROFORM-d): δ [ppm]=1.29 (s, 9H), 1.43-1.52 (m, 18H), 1.87-1.97 (m, 2H), 2.60-2.71 (m, 1H), 2.86-2.97 (m, 1H), 3.04-3.15 (m, 1H), 4.24-4.33 (m, 1H), 4.96 (d, 1H), 7.39 (d, 2H), 8.14 (d, 2H).
ESI+ m/z 495 (M+H).

b) Di-tert-butyl (4S)-4-(4-aminobenzyl)-N-(tert-butoxycarbonyl)-L-glutamate

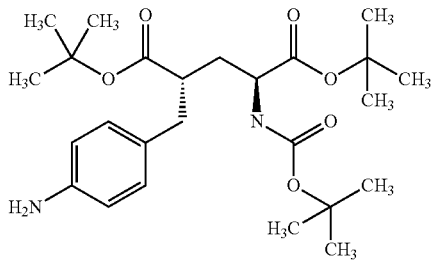 [SMILES: CC(C)(C)OC(=O)N[C@@H](C[C@H](Cc1ccc(N)cc1)C(=O)OC(C)(C)C)C(=O)OC(C)(C)C]

To 2.35 g (4.3 mmol) di-tert-butyl (4S)—N-(tert-butoxycarbonyl)-4-(4-nitrobenzyl)-L-glutamate in 50 mL methanol and under argon atmosphere palladium (10% on charcoal) was added and the suspension hydrogenated overnight at room temperature. The reaction mixture was filtered, the solvent evaporated and the residue was chromatographed on silica gel using a hexane/ethyl acetate gradient, and the appropriate fractions were combined and concentrated.

Yield: 1.84 g (90.8%)

$^1$H-NMR (400 MHz, CHLOROFORM-d): δ [ppm]=1.34 (s, 9H), 1.39-1.49 (m, 18H), 1.80-1.91 (m, 2H), 2.55-2.64 (m, 1H), 2.69-2.78 (m, H), 3.57 (br. s, 2H), 4.11-4.21 (m, 1H), 4.86 (d, 1H), 6.58 (d, 2H), 6.96 (d, 2H).

ESI+ m/z 465 (M+H).

c) Di-tert-butyl (4S)—N-(tert-butoxycarbonyl)-4-(4-{[3-(tosyloxy)propyl]amino}-benzyl)-L-glutamate

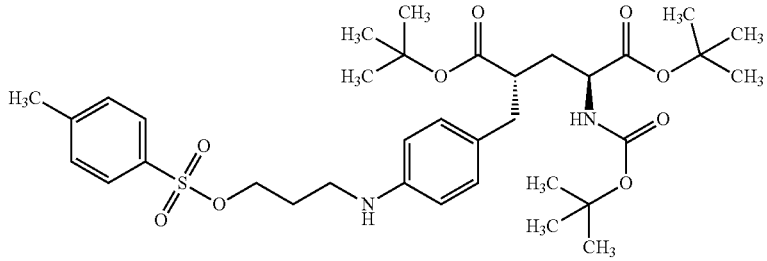 [SMILES: Cc1ccc(S(=O)(=O)OCCCNc2ccc(C[C@@H](C[C@H](NC(=O)OC(C)(C)C)C(=O)OC(C)(C)C)C(=O)OC(C)(C)C)cc2)cc1]

To 230 mg (0.5 mmol) of di-tert-butyl (4S)-4-(4-aminobenzyl)-N-(tert-butoxycarbonyl)-L-glutamate in 12 mL N,N-dimethylformamide were added 138 mg (1.0 mmol) of potassium carbonate and 385 mg (1.0 mmol) of 1,3-propanediol di-p-toluenesulfonate (Aldrich) and the resulting suspension was heated for 1 h at 100° C. in a microwave oven. The reaction mixture was then filtered, the solvent evaporated and the residue was taken up in dichloromethane. The crude product obtained in this manner was chromatographed on a Biotage® SNAP cartridge KP-NH using a hexane/ethyl acetate gradient, and the appropriate fractions were combined and concentrated.

Yield: 6 mg (1.8%)

$^1$H-NMR (500 MHz, CHLOROFORM-d): δ [ppm]=1.34 (s, 9H), 1.44 (s, 18H), 1.83-1.94 (m, 5H), 2.45 (s, 3H), 2.57- 2.60 (m, 1H), 2.72-2.75 (m, 2H), 3.16-3.20 (m, 2H), 4.12-4.16 (m, 3H), 4.86 (d, 1H), 6.43 (d, 2H), 6.95 (d, 2H), 7.33 (d, 2H), 7.80 (d, 2H).

ESI+ m/z 677 (M+H).

Example 8

4-{4-[(3-[$^{18}$F]Fluoropropyl)amino]benzyl}-L-glutamic acid

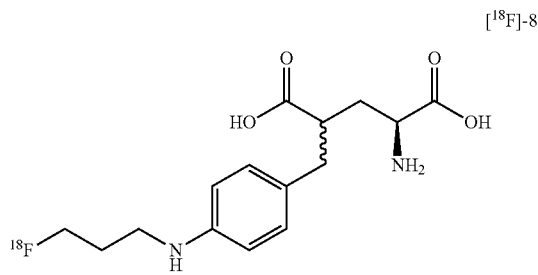 [SMILES: N[C@@H](CC(Cc1ccc(NCCC[18F])cc1)C(=O)O)C(=O)O]

[$^{18}$F]-8

[$^{18}$F]Fluoride (2900 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of di-tert-butyl (4S)—N-(tert-butoxycarbonyl)-4-(4-{[3-(tosyloxy)propyl]amino}benzyl)-L-glutamate in 1 mL acetonitrile were added to the dried residue. The resulting mixture was stirred at 100° C. for 10 min. After cooling for 5 min at rt, 2M HCl (1 mL) was added and the mixture was stirred at 120° C. for 10 min. The crude product was diluted with water up to 5 mL and purified by semi-preparative HPLC (ACE 5 C18, 250×10 mm; 5-30% acetonitrile in water+0.1% TFA over 20 min). The product fraction at ≈10:50 min was collected, diluted up to 20 mL with water pH2 and passed trough a SCX cartridge (Strata-X-C 200 mg by Phenomenex). The cartridge was washed with ethanol (20 mL) and the product was eluted with 5 mL phosphate buffer (7 g Na$_2$HPO$_4$.2H$_2$O; 6 g NaCl in 1 l H$_2$O). 67 MBq (4% d.c.) 4-{4-[(3-[$^{18}$F]fluoropropyl)amino]benzyl}-L-glutamic acid ([$^{18}$F]-8) were obtained. Radiochemical purity was determined to be >95% ($t_R$=1.7 min, analytical HPLC method C).

Example 9

4-[4-(3-Fluoropropyl)benzyl]-L-glutamic acid

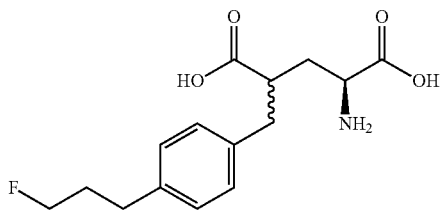

a) 3-(4-Bromophenyl)propan-1-ol

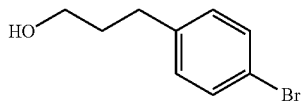

3-(4-bromophenyl)propionic acid (Aldrich) (12.25 g, 53.48 mmol) was dissolved in tetrahydrofuran (100 mL) and the solution was slowly added to lithium aluminum hydride (1.22 g, 32.09 mmol) in tetrahydrofuran (100 mL). The reaction was stirred for 3 h, then 150 mL 1 N aqueous sodium hydrogen carbonate was added, the mixture was extracted with ethyl acetate (3×150 mL) and the organic phases were dried over magnesium sulphate and concentrated in vacuo. The crude product was used without purification.

Yield: 5.77 g (50.2%)

$^1$H-NMR (300 MHz, CHLOROFORM-d): δ [ppm]=1.59 (br. s., 1H), 1.79-1.96 (m, 2H), 2.57-2.74 (m, 2H), 3.67 (t, 2H), 7.02-7.15 (m, 2H), 7.36-7.47 (m, 2H).

b) Benzyl 3-(4-bromophenyl)propyl ether

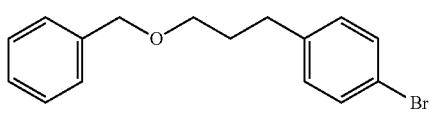 [SMILES: Brc1ccc(CCCOCc2ccccc2)cc1]

3-(4-bromophenyl)propan-1-d (5.77 g, 26.83 mmol) was mixed with dichloromethane (30 mL) and water (30 mL), and benzyl bromide (6.88 g, 40.24 mmol), tetra-n-butylammonium hydrogen sulfate (0.46 g, 1.34 mmol), and sodium hydroxide (5.37 g, 134.17 mmol) were added subsequently. The mixture was stirred overnight, extracted several times with dichloromethane and the combined organic phases were dried over magnesium sulfate and concentrated in vacuo. The crude product was purified on silica gel using a hexane/ethyl acetate gradient, and the appropriate fractions were combined and concentrated.

Yield: 3.59 g (43.9%)

$^1$H-NMR (300 MHz, CHLOROFORM-d): δ [ppm]=1.80-2.04 (m, 2H), 2.69 (t, 2H), 3.48 (t, 2H), 4.51 (s, 2H), 7.06 (d, 2H), 7.32-7.47 (m, 7H).

c) 4-[3-(Benzyloxy)propyl]benzaldehyde

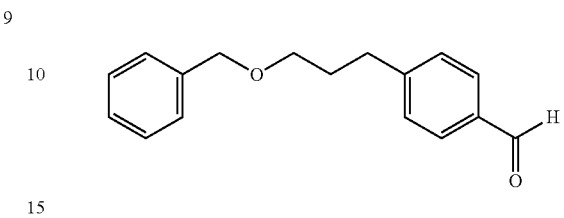

To a solution of benzyl 3-(4-bromophenyl)propyl ether (3.59 g, 11.77 mmol) in tetrahydrofuran (32 mL) at −75° C. under an argon atmosphere was added n-butyllithium (1.6 M in hexane, 8.83 mL). The solution was stirred for 15 min, and N,N-dimethylformamide (1.09 mL, 14.13 mmol) was added dropwise. The reaction was stirred for another 30 min and than warmed to room temperature, quenched with aqueous ammonium chloride solution, extracted with tert-butyl methyl ether and concentrated in vacuo. The crude product was purified on silica gel using a hexane/ethyl acetate gradient, and the appropriate fractions were combined and concentrated.

Yield: 1.86 g (62.1%)

$^1$H-NMR (400 MHz, CHLOROFORM-d): δ [ppm]=1.89-2.04 (m, 2H), 2.75-2.90 (m, 2H), 3.50 (t, 2H), 4.52 (s, 2H), 7.29-7.43 (m, 7H), 7.80 (d, 2H), 9.98 (s, 1H).

d) 4-[3-(Benzyloxy)propyl]benzyl alcohol

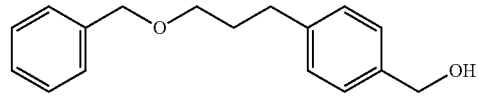 [SMILES: OCc1ccc(CCCOCc2ccccc2)cc1]

To a solution of 4-[3-(benzyloxy)propyl]benzaldehyde (1.86 g, 7.31 mmol) in ethanol (28 mL), sodium borohydride (83 mg, 2.19 mmol) was slowly added at room temperature. The mixture was stirred for 1 h. Water (50 mL) was added, and the mixture was extracted with ethyl acetate (3×50 mL), dried over magnesium sulfate and concentrated in vacuo. The crude product was used without purification.

Yield: 2.12 g (113.2%)

$^1$H-NMR (400 MHz, CHLOROFORM-d): δ [ppm]=1.67 (br. s, 1H), 1.87-2.02 (m, 2H), 2.66-2.81 (m, 2H), 3.50 (t, 2H), 4.52 (s, 2H), 4.67 (s, 2H), 7.13-7.23 (m, 2H), 7.27-7.34 (m, 3H), 7.34-7.42 (m, 4H).

e) Benzyl 3-[4-(bromomethyl)phenyl]propyl ether

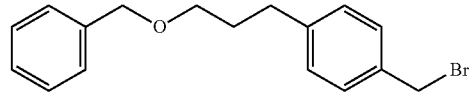 [SMILES: BrCc1ccc(CCCOCc2ccccc2)cc1]

{4-[3-(benzyloxy)propyl]benzyl alcohol (1.86 g, 7.31 mmol) was dissolved in 82 mL dichloromethane. The solution was cooled to 0° C. 3.25 g (12.41 mmol) triphenyl phosphine and 4.11 g (12.41 mmol) carbon tetrabromide were added to the solution. The ice bath was removed and the reaction was stirred for 1 h. The solution was concentrated in vacuo, to the residue was added tert-butyl methyl ether (100 mL) and the mixture was stirred at −20° C. for 30 min. The mixture was filtrated and the filtrate was concentrated in vacuo. The crude product was purified on silica gel using a hexane/ethyl acetate gradient, and the appropriate fractions were combined and concentrated.

Yield: 1.75 g (75%)

$^1$H-NMR (400 MHz, CHLOROFORM-d): δ [ppm]=1.86-2.01 (m, 2H), 2.73 (t, 2H), 3.50 (t, 2H), 4.50 (s, 2H), 4.52 (s, 2H), 7.16 (d, 2H), 7.28-7.42 (m, 7H).

f) Di-tert-butyl (4S)-4-{4-[3-(benzyloxy)propyl]benzyl}-N-(tert-butoxycarbonyl)-L-glutamate

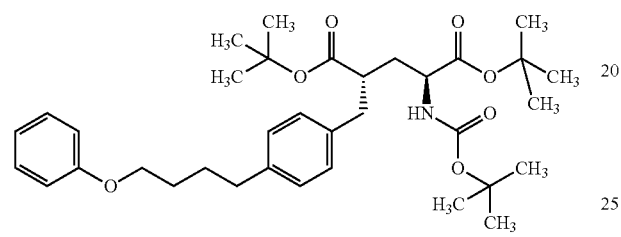

To a solution of 1.08 g (3.38 mmol) di-tert-butyl N-(tert-butoxycarbonyl)-L-glutamate in tetrahydrofuran (18 mL) at −78° C., lithium 1,1,1,3,3,3-hexamethyldisilazan-2-ide (1.0 M in tetrahydrofuran, 6.20 mL) was added dropwise. The solution was stirred for 2 h, then 1-[3-(benzyloxy)propyl]-4-(bromomethyl)benzene (1.01 g, 2.82 mmol) dissolved in 5 mL tetrahydrofuran were added slowly. The reaction was stirred for additional 2 h and then quenched by the addition of 10 mL of 2 N aqueous hydrogen chloride. The mixture was warmed to room temperature poured into 10 mL 1 N aqueous hydrogen chloride and extracted with dichloromethane (3×30 mL). The organic phases were dried over magnesium sulfate and concentrated in vacuo. The crude product was purified on silica gel using a hexane/ethyl acetate gradient, and the appropriate fractions were combined and concentrated.

Yield: 1.36 g (67.3%)

$^1$H-NMR (300 MHz, CHLOROFORM-d): δ [ppm]=1.31 (s, 9H), 1.44 (s, 9H), 1.45 (s, 9H), 1.82-1.98 (m, 4H), 2.60-2.75 (m, 3H), 2.77-2.89 (m, 2H), 3.49 (t, 2H), 4.07-4.27 (m, 1H), 4.51 (s, 2H), 4.89 (d, 1H), 7.08 (s, 4H), 7.28-7.45 (m, 5H).

ESI+ m/z 598.5 (M+H).

g) Di-tert-butyl (4S)—N-(tert-butoxycarbonyl)-4-[4-(3-hydroxypropyl)benzyl]-L-glutamate

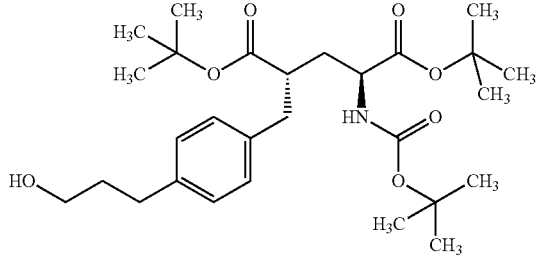 [SMILES: CC(C)(C)OC(=O)N[C@@H](C[C@H](Cc1ccc(CCCO)cc1)C(=O)OC(C)(C)C)C(=O)OC(C)(C)C]

To a solution of 690 mg (1.15 mmol) di-tert-butyl (4S)-4-{4-[3-(benzyloxy)propyl]benzyl}-N-(tert-butoxycarbonyl)-L-glutamate in 17 mL of methanol, palladium (10% on charcoal) was added and the suspension was stirred overnight at room temperature under a hydrogen atmosphere. The mixture was filtered over celite, and the solvent was evaporated. The remaining material was used without purification.

Yield: 563 mg (96.1%)

$^1$H-NMR (400 MHz, CHLOROFORM-d): δ [ppm]=1.31 (s, 9H), 1.44 (s, 9H), 1.45 (s, 9H), 1.81-1.95 (m, 4H), 2.62-2.73 (m, 3H), 2.83 (dd, 2H), 3.67 (t, 2H), 4.04-4.28 (m, 1H), 4.89 (d, 1H), 7.09 (s, 4H).

ESI+ m/z 508.4 (M+H).

h) Di-tert-butyl N-(tert-butoxycarbonyl)-4-[4-(3-fluoropropyl)benzyl]-L-glutamate

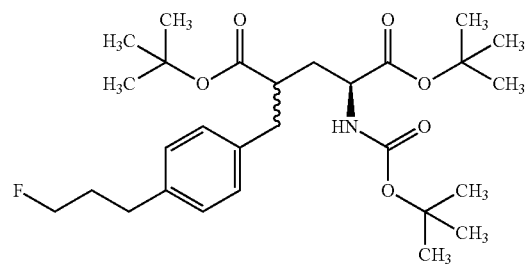 [SMILES: CC(C)(C)OC(=O)N[C@@H](CC(Cc1ccc(CCCF)cc1)C(=O)OC(C)(C)C)C(=O)OC(C)(C)C]

Di-tert-butyl (4S)—N-(tert-butoxycarbonyl)-4-{4-[3-(tosyloxy)propyl]benzyl}-L-glutamate (see Example 10) (100 mg, 0.15 mmol) was dissolved in 1 ml acetonitrile, and tetra-n-butylammonium tetra-(tert-butyl alcohol)-coordinated fluoride (*Angew. Chem.* 2008, 120, 8532-8534) (169 mg, 0.30 mmol) were added. The mixture was stirred at 70° C. for 2 h. Another 169 mg of the fluoride source was added and the reaction stirred for further 1.5 h at 70° C. After cooling to room temperature, the mixture was poured into water (10 ml) and extracted with tert-butyl methyl ether (3×10 ml). The organic phases were dried over magnesium sulfate and concentrated in vacuo. The residue was purified on a reversed phase (RP-18) column with an acetonitrile/water gradient. The appropriate fractions were collected, the acetonitrile evaporated under reduced pressure and the remaining aqueous solution was lyophilized.

Yield 50 mg (64.9%) (mixture of diastereomers)

ESI+ m/z 510.6 (M+H)

i) 4-[4-(3-Fluoropropyl)benzyl]-L-glutamic acid

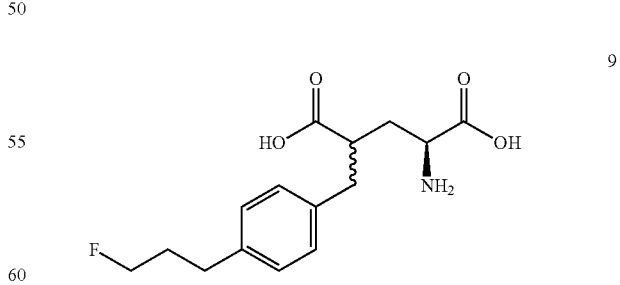

Di-tert-butyl N-(tert-butoxycarbonyl)-4-[4-(3-fluoropropyl)benzyl]glutamate (50 mg, 0.10 mmol) was dissolved in 3 ml trifluoroacetic acid and stirred at room temperature for 1 d. Then, 5 ml toluene were added and the solution was concentrated in vacuo. The product was purified by preparative HPLC. The appropriate fractions were collected, the acetonitrile evaporated under reduced pressure and the remaining aqueous solution was lyophilized.

Yield: 9.8 mg (32.3%) (mixture of diastereomers)

$^1$H-NMR (400 MHz, DMSO-d$_6$): δ [ppm]=1.64-1.83 (m, 1.66H), 1.84-2.00 (m, 2H), 2.03-2.12 (m, 0.31H), 2.54-2.07 (m, 2.61H), 2.77-2.96 (m, 2.36H), 3.57 (dd, 0.8H), 3.61-3.68 (m, 0.4H), 4.44 (dt, 2H, J (H, F)=47.4 Hz), 7.00-7.25 (m, 4H).

ESI+ m/z 298.4 (M+H).

Example 10

Di-tert-butyl (4S)—N-(tert-butoxycarbonyl)-4-{4-[3-(tosyloxy)propyl]benzyl}-L-glutamate

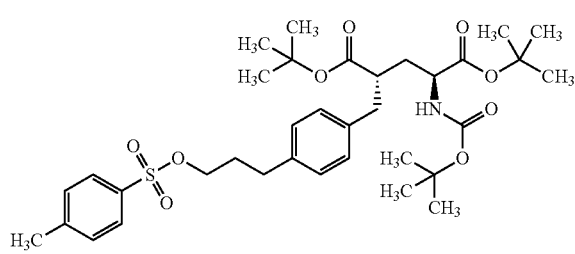 [SMILES: Cc1ccc(S(=O)(=O)OCCCc2ccc(C[C@@H](C[C@H](NC(=O)OC(C)(C)C)C(=O)OC(C)(C)C)C(=O)OC(C)(C)C)cc2)cc1]

Di-tert-butyl (4S)—N-(tert-butoxycarbonyl)-4-[4-(3-hydroxypropyl)benzyl]-L-glutamate (514 mg, 1.01 mmol) was dissolved in pyridine (25 mL) and p-toluenesulfonic anhydride (Aldrich) (661 mg, 2.03 mmol) was slowly added at 0° C. The reaction was stirred for 2 h, than poured into 25 mL 1 N aqueous hydrogen chloride. The mixture was extracted with tert-butyl methyl ether (3×50 mL), the organic phases washed with saturated aqueous sodium hydrogen carbonate, dried over sodium sulfate and concentrated in vacuo. The crude product was chromatographed on silica gel using a hexane/ethyl acetate gradient, and the appropriate fractions were combined and concentrated. The product was repurified on a reversed phase (RP-18) HPLC column with an acetonitrile/water gradient. The appropriate fractions were collected, the acetonitrile evaporated under reduced pressure and the remaining aqueous solution was lyophilized.

Yield: 179 mg (26.7%)

$^1$H-NMR (400 MHz, CHLOROFORM-d): δ [ppm]=1.30 (s, 9H), 1.44 (s, 9H), 1.45 (s, 9H), 1.81-1.99 (m, 4H), 2.47 (s, 3H), 2.56-2.69 (m, 3H), 2.73-2.91 (m, 2H), 4.03 (t, 2H), 4.11-4.32 (m, 1H), 4.89 (d, 1H), 6.97 (d, 2H), 7.05 (d, 2H), 7.36 (d, 2H), 7.80 (d, 2H).

ESI+ m/z 662.6 (M+H).

Example 11

4-[4-(3-[$^{18}$F]Fluoropropyl)benzyl]-L-glutamic acid

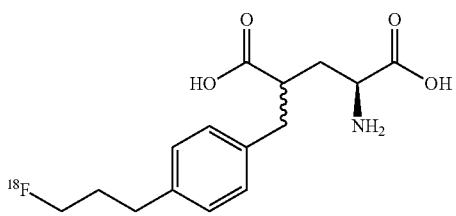

[$^{18}$F]-9

[$^{18}$F]Fluoride (2837 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of tosylate di-tert-butyl (4S)—N-(tert-butoxycarbonyl)-4-{4-[3-(tosyloxy)propyl]benzyl}-L-glutamate in 1 mL acetonitrile were added to the dried residue. The resulting mixture was stirred at 100° C. for 10 min. After cooling for 5 min at rt, 2M HCl (1 mL) was added and the mixture was stirred at 120° C. for 10 min. The crude product was diluted with water (pH 2) up to 30 mL and passed a preconditioned Strata-X-C cartridge (Phenomenex). The cartridge was washed with 30 mL water (pH 2) and 40 mL ethanol. 940 MBq (50% d.c.) 4-[4-(3-[$^{18}$F]fluoropropyl)benzyl]-L-glutamic acid ([$^{18}$F]-9) were eluted with 5 mL phosphate buffer (7 g Na$_2$HPO$_4$.2H$_2$O; 6 g NaCl in 1 L water). Radiochemical purity was determined to be >95% (t$_R$=2.9 min, analytical HPLC method E).

Example 12

(2S)-2-Amino-5-[4-(2-fluoroethoxy)benzyl]hexanedioic acid

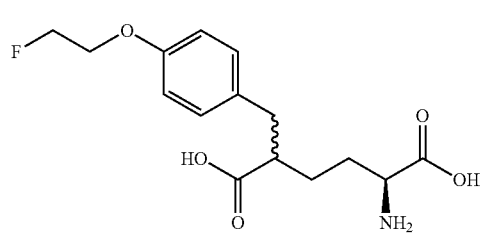

12 a) tert-Butyl (2S)-2-[(tert-butoxycarbonyl)amino]-4-oxobutanoate

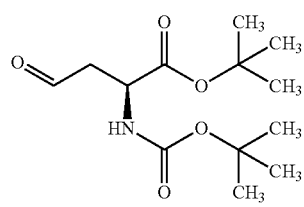

12a

To a solution of 1.10 g (4.0 mmol) tert-butyl N-(tert-butoxycarbonyl)-L-homoserinate (prepared according to *J. Org. Chem.* 1988, 53, 1900-1903) in dichloromethane (50 mL) was added pyridine (0.97 mL, 12.0 mmol), followed by 2.55 g Dess Martin periodinane (6.0 mmol), at room temperature. The mixture was stirred 90 min at room temperature prior to being diluted with ethyl acetate (40 mL). The mixture was washed with 10% aqueous sodium thiosulfate, saturated aqueous sodium bicarbonate and brine. The organic layer was dried over sodium sulfate and then evaporated. The crude product (1.09 g, quantitative yield) was used immediately without further purification.

¹H-NMR (300 MHz, CHLOROFORM-d): δ [ppm]=1.45 (abr. 9H), 1.46 (s, 9H), 2.88-3.10 (m, 2H), 4.42-4.55 (m, 1H), 5.27-5.46 (m, 1H), 9.74 (s, 1H).

b) tert-Butyl 3-[4-(benzyloxy)phenyl]-2-(dimethoxy-phosphoryl)propanoate

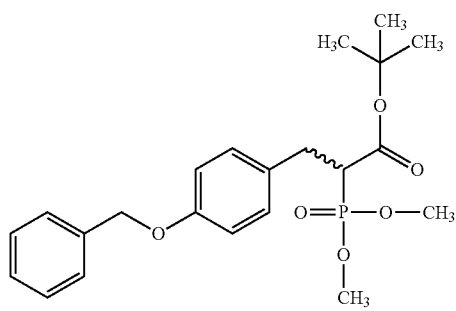

To a suspension of 1.71 g sodium hydride (50% in oil, 35.7 mmol) in anhydrous tetrahydrofuran (100 mL) was added a solution of 8.0 g tert-butyl P,P-dimethylphosphonoacetate (35.7 mmol) in anhydrous tetrahydrofuran (25 mL) at room temperature, and the resulting mixture was stirred for 1 h at room temperature. Subsequently, a solution of 4.95 g 4-benzyloxybenzyl bromide (17.8 mmol; prepared according to Helv. Chim. Acta, 2002, 85, 3422) in tetrahydrofuran (25 mL) was added, and the mixture was stirred at room temperature overnight. Saturated aqueous ammonium chloride (50 mL) was then added, the mixture was stirred for another 20 minutes at room temperature, and extracted with ethyl acetate. The organic layer was dried over magnesium sulfate and evaporated. Column chromatography over silica gel (2.5→50% ethyl acetate in hexane) gave 1.48 g (20% yield based on 4-benzyloxybenzyl bromide) of the target compound.

¹H-NMR (400 MHz, CHLOROFORM-d): δ [ppm]=1.34 (s, 9H), 3.06-3.22 (m, 3H), 3.81 (s br, 3H), 3.83 (s br, 3H), 5.05 (s, 2H), 6.89 (d, 2H), 7.13 (d, 2H), 7.29-7.45 (m, 5H).

ESI+ m/z 365 (M+H—C₄H₈, m/z (M+H) 421, m/z (M+NH₄) 438.

c) Di-tert-butyl (E)-(S)-2-[4-(benzyloxy)benzyl]-5-[(tert-butoxycarbonyl)amino]hex-2-enedioate, and Di-tert-butyl (Z)—(S)-2-[4-(benzyloxy)benzyl]-5-[(tert-butoxy-carbonyl)amino]hex-2-enedioate

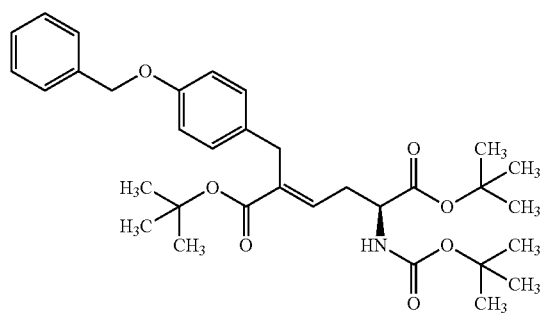

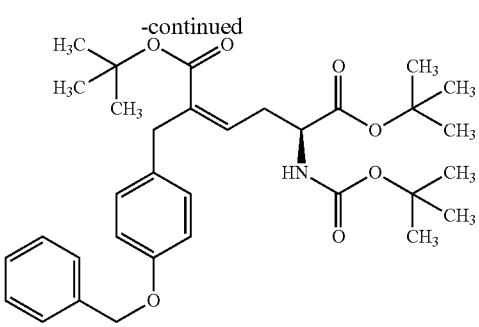

To a suspension of 169 mg of sodium hydride (60% in oil, 4.22 mmol) in anhydrous tetrahydrofuran (30 mL) was added a solution of 1.48 g of tert-butyl 3-[4-(benzyloxy)phenyl]-2-(dimethoxyphosphoryl)propanoate (3.52 mmol) in anhydrous tetrahydrofuran (20 mL) at a temperature of 0° C. The mixture was stirred for 15 minutes at 0° C., followed by the dropwise addition of a solution of 1.06 g of tert-butyl (2S)-2-[(bent-butoxycarbonyl)amino]-4-oxobutanoate (3.87 mmol) in anhydrous tetrahydrofuran (10 mL), also at a temperature of 0° C. The mixture was stirred for another 90 minutes at 0° C. before the reaction was stopped by the addition of saturated aqueous sodium bicarbonate. The mixture was extracted with ethyl acetate (3×), the combined organic layers were dried over sodium sulfate and then evaporated. The residue was purified by column chromatography on silica gel (2.5→35% ethyl acetate in hexane) to give 1.60 g of the target compound (80% yield) as a mixture of double bond isomers.

¹H-NMR (300 MHz, CHLOROFORM-d): δ [ppm]=1.34-1.54 (m, 27H), 2.56-2.90 (m, 2H), 3.43-3.66 (m, 2H), 4.22 (q br, 1H, minor isomer), 4.35 (q br, 1H, major isomer), 5.03 (s, 2H, minor isomer), 5.05 (s, 2H, major isomer), 5.13 (d br, 1H, major isomer), 5.37 (d br, 1H, minor isomer), 5.71-5.80 (m, 1H, minor isomer), 6.67-6.77 (m, 1H, major isomer), 6.84-6.93 (m, 2H), 7.03-7.12 (m, 2H), 7.28-7.47 (m, 5H).

ESI+ m/z 568 (M+H).

d) Di-tert-butyl (2S)-2-[(tert-butoxycarbonyl)amino]-5-(4-hydroxybenzyl)hexanedioate

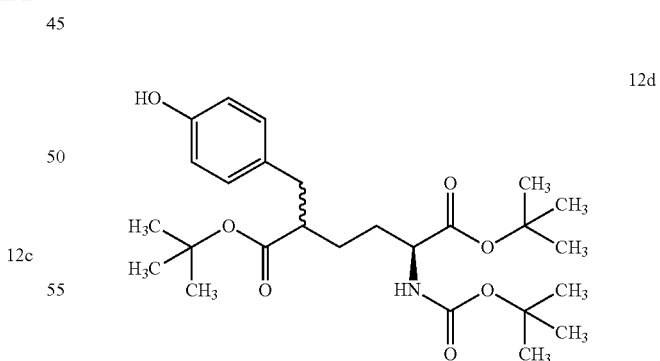

To a solution of 1.50 g of di-tert-butyl (E)-(S)-2-[4-(benzyloxy)benzyl]-5-[(tert-butoxycarbonyl)amino]hex-2-enedioate and di-tert-butyl (Z)—(S)-2-[4-(benzyloxy)benzyl]-5-[(tert-butoxycarbonyl)amino]hex-2-enedioate (mixture of double bond isomers, 2.64 mmol) in methanol (50 mL) was added 750 mg of a 10% palladium on carbon catalyst, and the mixture was stirred under an atmosphere of hydrogen for 1.5 hours. The catalyst was filtered off, and the filtrate was evaporated. Column chromatography of the residue on silica gel (2.5→35% ethyl acetate in hexane) gave 920 mg of the target compound (73% yield).

¹H-NMR (300 MHz, CHLOROFORM-d): δ [ppm]=1.35 (s, 9H, minor diastereomer), 1.36 (s, 9H, major diastereomer), 1.41-1.48 (m, 18H), 1.52-1.68 (m, 3H), 1.72-1.86 (m, 1H), 2.41-2.07 (m, 2H), 2.74-2.86 (m, 1H), 4.12-4.25 (m, 1H), 5.06 (t br, 1H), 5.29-5.38 (s br, 1H), 6.72 (d, 2H), 6.98-7.07 (m, 2H), ESI+ m/z 480 (M+H).

chiral HPLC (method c5): $t_R$=4.2 and 5.2 minutes (two peaks, baseline separation of C-5 epimers).

The compound synthesized in Example 12d was also prepared via an alternative procedure. It was shown by chiral HPLC that the stereocenter stemming from the L-homoserine synthon used is being retained during the sequence (see also examples 15a-15d which were prepared starting from the corresponding D-homoserine synthon).

e) tert-Butyl (S)-4-bromo-2-[(tert-butoxycarbonyl) amino]butanoate

12e

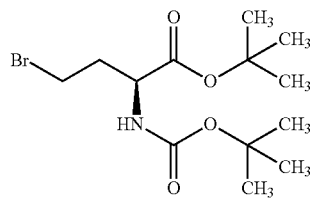

A mixture of 5.00 g (18.2 mmol) tert-butyl N-(tert-butoxycarbonyl)-L-homoserinate (prepared according to *J. Org. Chem.* 1988, 53, 1900-1903), 3.23 g N-bromo succinimide (18.2 mmol), and 6.16 g polymer bound triphenylphosphine (loading approx. 3 mmol/g, approx. 18.5 mmol) in dichloromethane (60 mL) was stirred overnight at room temperature. All solids were removed by filtration, and the filtrate was concentrated in vacuo. The residue was purified by column chromatography on silica gel (2.5→25% ethyl acetate in hexane) to give 2.56 g of the title compound (38% yield).

¹H-NMR (300 MHz, CHLOROFORM-d): δ [ppm]=1.46 (s, 9H), 1.49 (s, 9H); 2.10-2.26 (m app sext, 1H), 2.30-2.46 (m, 1H), 3.36-3.50 (m, 2H), 4.21-4.34 (m, 1H), 5.10 (s br, 1H).

ESI+ m/z 338, 340 (M+H, Br isotopes well reflected).

f) Di-tert-butyl (5S)-2-(benzyloxycarbonyl)-5-[(tert-butoxycarbonyl)amino]hexanedioate 12f

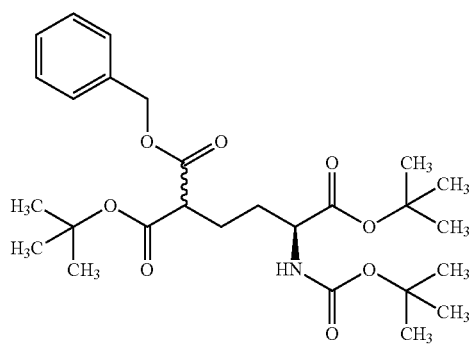

To a suspension of 296 mg sodium hydride (60% in oil, 7.39 mmol) in N,N-dimethyl formamide (40 mL) was added a solution of 2.04 g benzyl tert-butyl malonate (commercial, 8.13 mmol) in N,N-dimethylformamide (20 mL) at room temperature. The mixture was stirred for one hour at room temperature before a solution of 2.50 g tert-butyl (2S)-4-bromo-2-[(bent-butoxycarbonyl)amino]butanoate (7.39 mmol) in N,N-dimethylformamide (20 mL) was added. The mixture was stirred overnight at room temperature and was then evaporated in vacuo. The residue was purified by column chromatography on silica gel (2.5→20% ethyl acetate in hexane) to give the title compound in approx. 90% purity (2.56 g, 61% purity adjusted yield).

¹H-NMR (300 MHz, CHLOROFORM-d): δ [ppm]=1.39+1.40 (2 s, 9H, diastereomers), 1.44 (s, 9H), 1.46+1.47 (2 s, 9H, diastereomers), 1.59-2.00 (m, 4H), 3.27-3.37 (m, 1H), 4.19 (s br, 1H), 5.05 (s br, 1H), 5.14 (app. d, 1H), 5.21 (app. dd, 1H), 7.31-7.40 (m, 5H).

ESI+ m/z 508 (M+H).

chiral HPLC (method c1): $t_R$=8.5 minutes (broad peak with shoulder, C-1 epimers not fully resolved). The (4R)-analogue prepared from the respective D-homoserine synthon shows separate C-1 epimers at 4.1 and 4.8 minutes (see example 15b).

g) Di-tert-butyl (5S)-2-[4-(benzyloxy)benzyl]-2-(benzyloxycarbonyl)-5-[(tert-butoxy-carbonyl) amino]hexanedioate 12g

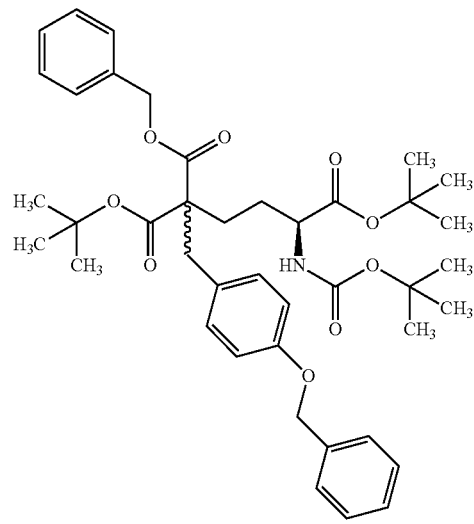

To a solution of 1.00 g di-tert-butyl (5S)-2-(benzyloxycarbonyl)-5-[(tert-butoxycarbonyl)-amino]hexanedioate (1.97 mmol) in NA-dimethyl formamide (20 mL) was added under argon atmosphere 71 mg of sodium hydride (60% in oil, 1.77 mmol). The resulting mixture was stirred at room temperature for 30 minutes. A solution of 546 mg 4-benzyloxybenzyl bromide (1.97 mmol; prepared according to *Helv. Chim. Acta*, 2002, 85, 3422) in N,N-dimethylformamide (10 mL) was added, and the mixture was stirred at 60° C. for one hour. After cooling to room temperature, the mixture was concentrated in vacuo and partitioned between water and ethyl acetate. The organic layer was washed with brine, dried over sodium sulfate and evaporated. The residue was purified by column chromatography on silica gel (2.5→20% ethyl acetate in hexane) to give 1.22 g of the title compound (88% yield).

¹H-NMR (500 MHz, CHLOROFORM-d): δ [ppm]=1.34 (s, 9H, minor diastereomer), 1.35 (s, 9H, major diastereomer), 1.41 (s, 9H, minor diastereomer), 1.42 (s, 9H, major diastereomer), 1.44 (s, 9H, minor diastereomer), 1.45 (s, 9H, major diastereomer), 1.60-1.91 (m, 4H), 3.08 (dd, 1H), 3.19 (dd, 1H), 4.15-4.21 (m, 1H), 4.99-5.07 (m, 3H), 5.09-5.19 (m, 2H), 6.79-6.85 (m, 2H), 6.93-6.99 (m, 2H), 7.31-7.45 (m, 10H).

ESI+ m/z 704 (M+H).

chiral HPLC (method c2): $t_R$=6.1 minutes single peak, C-4 epimers not resolved). The (1R)-analogue prepared from the respective D-homoserine synthon shows separate C-4 epimers at 4.0 and 4.7 minutes (see example 15c).

h) (5S)-2-(tert-Butoxycarbonyl)-5-[(tert-butoxycarbonyl)amino]-2-(4-hydroxybenzyl)hexanedioic acid 6-tert-butyl ester

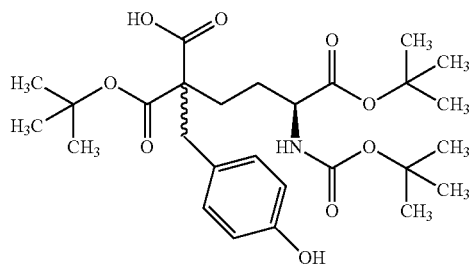

12h

To a solution of 1.07 g di-tert-butyl (5S)-2-[4-(benzyloxy)benzyl]-2-(benzyloxycarbonyl)-5-[(tert-butoxycarbonyl)amino]hexanedioate (1.52 mmol) in methanol (20 mL) was added a 10% palladium on carbon hydrogenation catalyst (100 mg) at room temperature. The suspension was stirred overnight at room temperature under an atmosphere of hydrogen. The catalyst was removed by filtration and all volatiles were removed in vacuo. The crude product (800 mg, quantitative yield) was used in the next step without further purification.

¹H-NMR (300 MHz, CHLOROFORM-d): δ [ppm]=1.41-1.53 (m, 27H), 1.60-2.06 (m, 4H), 3.03 (dd, 1H), 3.26 (d br, 1H), 4.07-4.27 (m, 1H), 5.15 (app dd, 1H), 6.68-6.76 (m, 2H), 6.96-7.05 (m, 2H).

ESI+ m/z 524 (M+H).

chiral HPLC (method c3): $t_R$=4.8 minutes, C-2 epimers are not resolved. The (5R)-analogue prepared from the respective D-homo-serine synthon shows separate C-2 epimers at 3.0 and 3.7 minutes (see example 15d).

i) Di-tert-butyl (2S)-2-[(tert-butoxycarbonyl)amino]-5-(4-hydroxybenzyl)hexanedioate

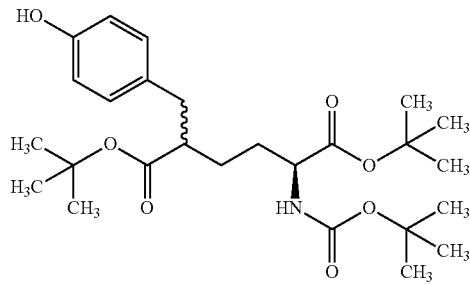

12i (identical with 12d)

A solution of 730 mg (5S)-2-(tert-butoxycarbonyl)-5-[(tert-butoxycarbonyl)amino]-2-(4-hydroxybenzyl)hexanedioic acid 6-tert-butyl ester (1.39 mmol) and 290 mg 4-N,N-dimethylaminopyridine (2.37 mmol) in tetrahydrofuran (10 mL) was heated under reflux for 18 hours. Since the turnover was only approx. 75% then, and to drive the reaction to completion, the mixture was evaporated, the residue dissolved in 1,4-dioxane, and heated under reflux for another 2 hours after which turnover was complete. The mixture was evaporated and the residue was purified by column chromatography on silica gel (2.5→35% ethyl acetate in hexane), to give 590 mg (88% yield) of the target compound featuring an HNMR spectrum in line with the HNMR data for example 12d.

¹H-NMR (500 MHz, CHLOROFORM-d): δ [ppm]=1.35 (s, 9H, minor diastereomer), 1.36 (s, 9H, major diastereomer), 1.42-1.47 (m, 18H), 1.51-1.67 (m, 3H), 1.75-1.84 (m, 1H), 2.43-2.51 (m, 1H, major diastereomer), 2.51-2.59 (m, 1H, minor diastereomer), 2.59-2.66 (m, 1H), 2.76-2.85 (m, 1H), 4.14-4.23 (m, 1H), 4.92-4.97 (m, 1H), 5.04 (app t br, 1H), 6.73 (d, 2H), 6.99-7.05 (m, 2H).

ESI+ m/z 480 (M+H).

chiral HPLC (method c4): $t_R$=6.4 and 8.5 minutes (two peaks, baseline separation of C-5 epimers). The (2R)-analogue prepared from the respective D-homoserine synthon shows baseline separated C-5 epimers at 4.7 and 7.9 minutes (see example 15e).

j) Di-tert-butyl (2S)-2-[(tert-butoxycarbonyl)amino]-5-[4-(2-fluoroethoxy)benzyl]-hexanedioate

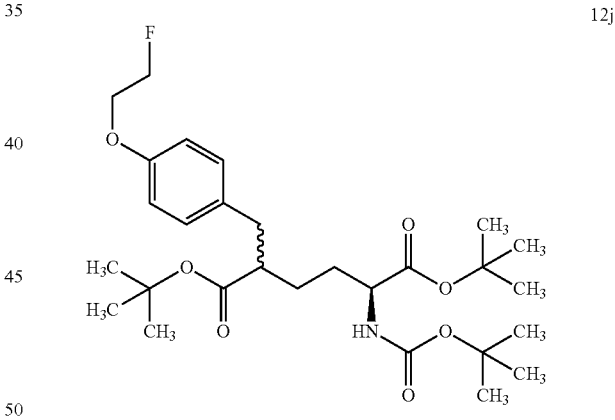

12j

To a solution of 54 mg 1-fluoro-2-iodoethane (0.31 mmol) in N,N-dimethylformamide (10 mL) was subsequently added 101 mg potassium carbonate (0.73 mmol), followed by 100 mg di-tert-butyl (2S)-2-[(tert-butoxycarbonyl)amino]-5-(4-hydroxybenzyl)-hexanedioate (from example 12d; 0.21 mmol), and the resulting mixture was stirred for 4 h at room temperature. The mixture was then partitioned between water and ethyl acetate, the aqueous layer was than extracted with ethyl acetate again. The combined organic layers were washed with brine, dried over sodium sulfate, and evaporated. The residue was purified by preparative HPLC, method A to give 85 mg (62% purity adjusted yield) of the target compound in approx. 80% purity.

¹H-NMR (400 MHz, CHLOROFORM-d): δ [ppm]=1.35 (s, 9H, minor diastereomer), 1.36 (s, 9H, major diastereomer), 1.41-1.47 (m, 18H), 1.52-1.67 (m, 3H), 1.73-1.85 (m, 1H), 2.43-2.68 (m, 2H), 2.78-2.88 (m, 1H), 4.12-4.26 (m, 3H), 4.67-4.84 (m, 2H), 4.98-5.09 (m, 1H), 6.83 (d, 2H), 7.06-7.13 (m, 2H).

ESI+ m/z 526 (M+H).

k) (2S)-2-Amino-5-[4-(2-fluoroethoxy)benzyl]hexanedioic acid

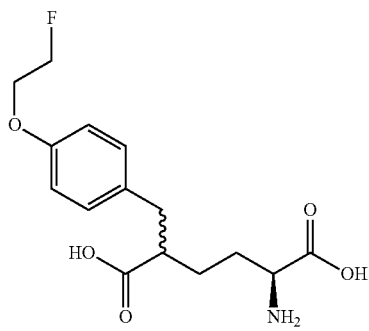

12

To a solution of 80 mg of di-tert-butyl (2S)-2-[(tert-butoxycarbonyl)amino]-5-[4-(2-fluoroethoxy)benzyl]hexanedioate (0.15 mmol) in anisol (1.0 mL) was added trifluoroacetic acid (2.0 mL), and the resulting mixture was stirred overnight at room temperature. All volatiles were removed in vacuo and the residue was purified by preparative HPLC, method B, to give 30 mg of the target compound as white lyophilisate (62% yield).

$^1$H-NMR (400 MHz, d$_6$-DMSO): δ [ppm]=1.25-1.91 (m, 4H), 2.26-2.38 (m, 1H), 2.53-2.78 (m, 2H), 3.04-3.19 (m, 1H), 4.12-4.25 (m, 2H), 4.63-4.80 (m, 2H), 6.83-6.88 (m, 2H), 7.06-7.13 (m, 2H). OH and NH signals not considered due to proton exchange/overlap with broad water signal.

ESI+ m/z 314 (M+H).

Example 13

Di-tert-butyl (2S)-2-[(tert-butoxycarbonyl)amino]-5-{4-[2-(tosyloxy)ethoxy]benzyl}-hexanedioate

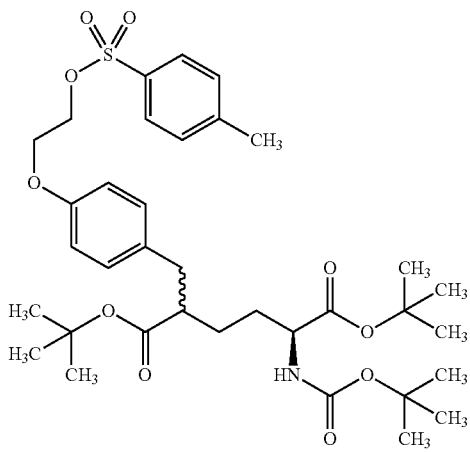 [SMILES: Cc1ccc(S(=O)(=O)OCCOc2ccc(CC(CC[C@H](NC(=O)OC(C)(C)C)C(=O)OC(C)(C)C)C(=O)OC(C)(C)C)cc2)cc1]

To a solution of 541 mg 1,2-ethanediol di-p-toluenesulfonate (1.46 mmol) in N,N-dimethylformamide (10 mL) was subsequently added 238 mg cesium carbonate (0.73 mmol), followed by 100 mg di-tert-butyl (2S)-2-[(tert-butoxycarbonyl)amino]-5-(4-hydroxybenzyl)hexanedioate (from example 12d; 0.21 mmol), and the resulting mixture was stirred overnight at room temperature. The mixture was then concentrated in vacuo and partitioned between water and dichloromethane. The organic layer was washed with brine, dried over sodium sulfate, and evaporated. Combined purification by column chromatography over silica gel (10→80% ethyl acetate in hexane) and prep. HPLC (Method A) gave 71 mg (49% yield) of the desired tosylate in very high purity.

$^1$H-NMR (300 MHz, CHLOROFORM-d): δ [ppm]=1.34 (s, 9H, minor diastereomer), 1.36 (s, 9H, major diastereomer), 1.41-1.49 (m, 18H), 1.51-1.68 (m, 3H), 1.72-1.87 (m, 1H), 2.40-2.68 (m, 2H), 2.46 (s, 3H), 2.74-2.87 (m, 1H), 4.08-4.24 (m, 3H), 4.32-4.40 (m, 2H), 5.03 (t br, 1H), 6.69 (d, 2H), 7.00-7.10 (m, 2H), 7.35 (d, 2H), 7.83 (d, 2H).

ESI+ m/z 622 (M+H—C$_4$H$_8$, m/z (M+H) 678.

Example 14

(2S)-2-Amino-5-[4-(2-[$^{18}$F]fluoroethoxy)benzyl]hexanedioic acid

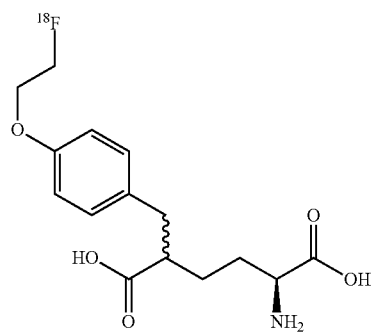

[$^{18}$F]-12

[$^{18}$F]Fluoride (3728 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of tosylate di-tert-butyl (2S)-2-[(tert-butoxycarbonyl)amino]-5-{4-[2-(tosyloxy)ethoxy]benzyl}hexanedioate in 1 mL acetonitrile were added to the dried residue. The resulting mixture was stirred at 100° C. for 10 min. After cooling for 5 min at rt, 2M HCl (1 mL) was added and the mixture was stirred at 120° C. for 10 min. The crude product was diluted with water (pH 2) up to 30 mL and passed through a preconditioned Strata-X-C cartridge (Phenomenex). The cartridge was washed with 30 mL water (pH 2) and 45 mL ethanol. 1704 MBq (50% d.c.) (2S)-2-Amino-5-[4-(2-[$^{18}$F]fluoroethoxy)benzyl]hexanedioic acid ([$^{18}$F]-12) were eluted with 5 mL phosphate buffer (7 g Na$_2$HPO$_4$.2H$_2$O; 6 g NaCl in 1 L water). Radiochemical purity was determined to be >95% (t$_R$=3.0 min, analytical HPLC method E).

Example 15

Di-tert-butyl (2R)-2-[(tert-butoxycarbonyl)amino]-5-{4-[2-(tosyloxy)ethoxy]benzyl}-hexanedioate

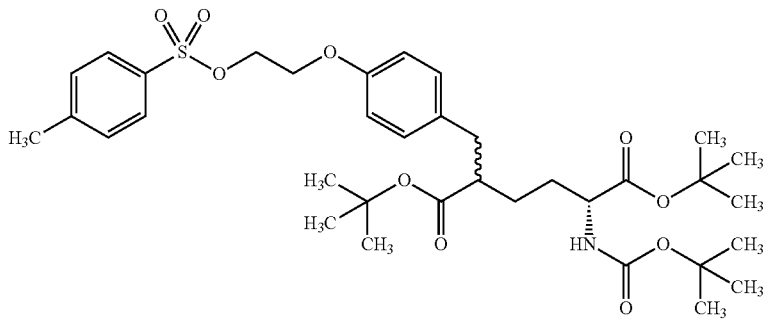 [SMILES: Cc1ccc(S(=O)(=O)OCCOc2ccc(CC(CC[C@@H](NC(=O)OC(C)(C)C)C(=O)OC(C)(C)C)C(=O)OC(C)(C)C)cc2)cc1]

a) tert-Butyl (2R)-4-bromo-2-[(tert-butoxycarbonyl)amino]butanoate

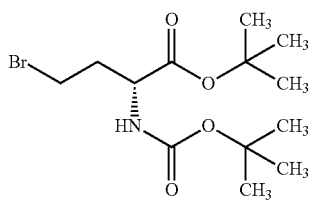 [SMILES: CC(C)(C)OC(=O)N[C@H](CCBr)C(=O)OC(C)(C)C]

A mixture of 1.39 g (5.05 mmol) tert-butyl N-(tert-butoxycarbonyl)-D-homoserinate (prepared according to *J. Org. Chem.* 1988, 53, 1900-1903), 899 mg N-bromo succinimide (5.05 mmol), and 1.68 g polymer bound triphenylphosphine (loading approx. 3 mmol/g, approx. 5.0 mmol) in dichloromethane (17 mL) was stirred overnight at room temperature. All solids were removed by filtration, and the filtrate was concentrated in vacuo. The residue was purified by column chromatography on silica gel (2.5→25% ethyl acetate in hexane) to give 580 mg of the title compound (34% yield).

¹H-NMR (400 MHz, CHLOROFORM-d): δ [ppm]=1.46 (s, 9H), 1.49 (s, 9H); 2.11-2.24 (m app sext, 1H), 2.31-2.45 (m, 1H), 3.37-3.49 (m, 2H), 4.21-4.33 (m, 1H), 5.10 (s br, 1H).

b) Di-tert-butyl (5R)-2-(benzyloxycarbonyl)-5-[(tert-butoxycarbonyl)amino]hexanedioate

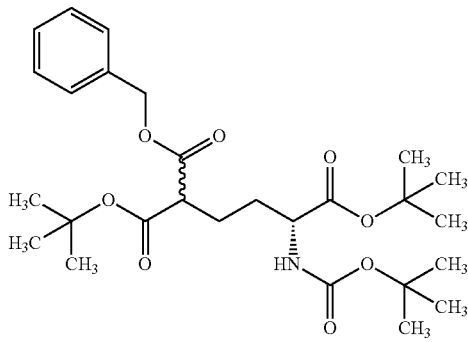 [SMILES: CC(C)(C)OC(=O)N[C@H](CCC(C(=O)OCc1ccccc1)C(=O)OC(C)(C)C)C(=O)OC(C)(C)C]

To a suspension of 66 mg sodium hydride (60% in oil, 1.66 mmol) in N,N-dimethyl-formamide (10 mL) was added a solution of 456 mg benzyl tert-butyl malonate (commercial, 1.82 mmol) in N,N-dimethylformamide (5 mL) at room temperature. The mixture was stirred for one hour at room temperature before a solution of 560 mg tert-butyl (2R)-4-bromo-2-[(tert-butoxycarbonyl)amino]butanoate (1.66 mmol) in N,N-dimethylformamide (5 mL) was added. The mixture was stirred for 60 hours at room temperature and was then evaporated in vacuo. The residue was purified by column chromatography on silica gel (1.5→20% ethyl acetate in hexane) to give the title compound (390 mg, 46% yield).

¹H-NMR (300 MHz, CHLOROFORM-d): δ [ppm]=1.39+1.40 (2 s, 9H, diastereomers), 1.42-1.49 (m, 18H), 1.59-2.00 (m, 4H), 3.26-3.37 (m, 1H), 4.19 (s br, 1H), 5.05 (s br, 1H), 5.14 (app. d, 1H), 5.21 (app. dd, 1H), 7.31-7.41 (m, 5H).

ESI+ m/z 508 (M+H).

chiral HPLC (method c1): $t_R$=4.1 and 4.8 minutes (two peaks, baseline separation of C-1 epimers). The (4S)-analogue prepared from the respective L-homo-serine synthon shows the C-1 epimers as one broad peak at 8.5 minutes (see example 12f).

c) Di-tert-butyl (5R)-2-[4-(benzyloxy)benzyl]-2-(benzyloxycarbonyl)-5-[(tert-butoxycarbonyl)amino]hexanedioate

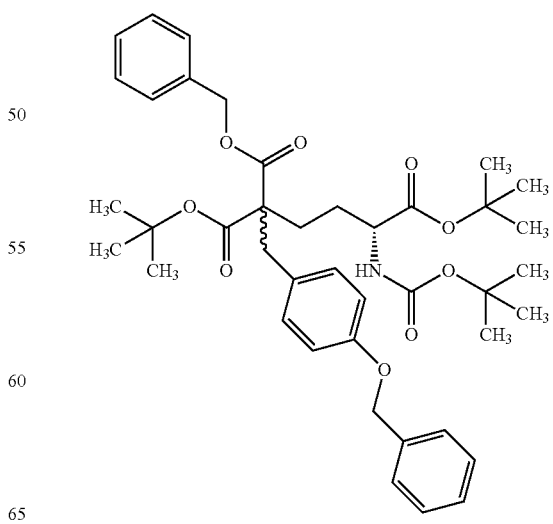

To a solution of 340 mg di-tert-butyl (5R)-2-[4-(benzyloxy)benzyl]-2-(benzyloxycarbonyl)-5-[(tert-butoxycarbonyl)amino]hexanedioate (0.67 mmol) in N,N-dimethylformamide (7 mL) was added under argon atmosphere 24 mg of sodium hydride (60% in oil, 0.60 mmol). The resulting mixture was stirred at room temperature for 60 minutes. A solution of 186 mg 4-benzyloxybenzyl bromide (0.67 mmol; prepared according to Helv. Chim. Acta, 2002, 85, 3422) in N,N-dimethylformamide (3 mL) was added, and the mixture was stirred at 60° C. for one hour. After cooling to room temperature, the mixture was concentrated in vacuo and partitioned between water and ethyl acetate. The organic layer was washed with brine, dried over sodium sulfate and evaporated. The residue was purified by column chromatography on silica gel using an ethyl acetate/hexane gradient to give 470 mg of the title compound (quantitative yield).

$^1$H-NMR (500 MHz, CHLOROFORM-d): δ [ppm]=1.34 (s, 9H, minor diastereomer), 1.35 (s, 9H, major diastereomer), 1.41 (s, 9H, minor diastereomer), 1.42 (s, 9H, major diastereomer), 1.44 (s, 9H, minor diastereomer), 1.45 (s, 9H, major diastereomer), 1.60-1.91 (m, 4H), 3.08 (dd, 1H), 3.19 (dd, 1H), 4.15-4.21 (m, 1H), 4.99-5.07 (m, 3H), 5.09-5.19 (m, 2H), 6.79-6.85 (m, 2H), 6.93-6.99 (m, 2H), 7.31-7.45 (m, 10H).

ESI+ m/z 704 (M+H).

chiral HPLC (method c2): $t_R$=4.0 and 4.7 minutes, two peaks, baseline separation of C-4 epimers). The (1S)-analogue prepared from the respective L-homo-serine synthon shows unresolved C-4 epimers at 6.1 minutes (see example 12g).

d) (5R)-6-tert-Butoxy-2-(tert-butoxycarbonyl)-5-[(tert-butoxycarbonyl)amino]-2-(4-hydroxybenzyl)-6-oxohexanoic acid

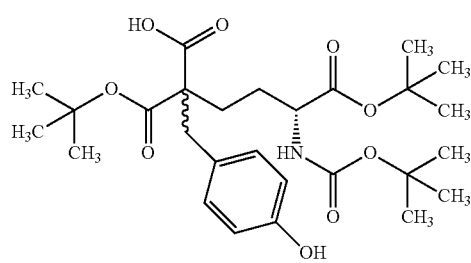 [SMILES: CC(C)(C)OC(=O)N[C@H](CCC(Cc1ccc(O)cc1)(C(=O)O)C(=O)OC(C)(C)C)C(=O)OC(C)(C)C]

To a solution of 370 mg di-tert-butyl (5R)-2-[4-(benzyloxy)benzyl]-2-(benzyloxycarbonyl)-5-[(tert-butoxycarbonyl)amino]hexanedioate (0.53 mmol) in methanol (10 mL) was added a 10% palladium on carbon hydrogenation catalyst (50 mg) at room temperature. The suspension was stirred for 2.5 hours at room temperature under an atmosphere of hydrogen. The catalyst was removed by filtration and all volatiles were removed in vacuo. The crude product (273 mg, 99% yield) was used in the next step without further purification.

$^1$H-NMR (400 MHz, CHLOROFORM-d): δ [ppm]=1.43-1.52 (m, 27H), 1.58-2.14 (m, 4H), 3.03 (dd, 1H), 3.25 (d br, 1H), 4.07-4.27 (m, 1H), 5.12 (app d br, 1 H, minor diastereomer), 5.19 (app d br, 1H, major diastereomer), 6.68-6.75 (m, 2H), 6.96-7.04 (m, 2H).

ESI+ m/z 524 (M+H).

chiral HPLC (method c3): $t_R$=3.0 and 3.7 minutes, two peaks, baseline separation of C-2 epimers). The (5S)-analogue prepared from the respective L-homoserine synthon shows unresolved C-2 epimers at 4.8 minutes (see example 12 h).

e) Di-tert-butyl (2R)-2-[(tert-butoxycarbonyl)amino]-5-(4-hydroxybenzyl)hexanedioate

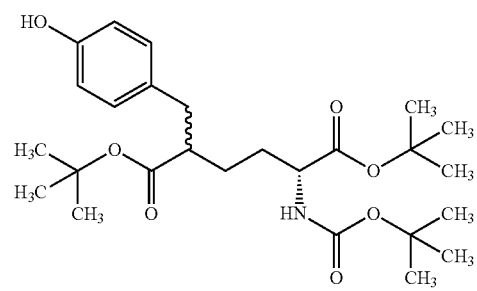 [SMILES: CC(C)(C)OC(=O)N[C@H](CCC(Cc1ccc(O)cc1)C(=O)OC(C)(C)C)C(=O)OC(C)(C)C]

A solution of 237 mg (5R)-6-tert-butoxy-2-(tert-butoxycarbonyl)-5-[(tert-butoxycarbonyl)-amino]-2-(4-hydroxybenzyl)-6-oxohexanoic acid (0.45 mmol) and 94 mg 4-N,N-dimethylaminopyridine (0.77 mmol) in 1,4-dioxane (5 mL) was heated under reflux for 2 hours. The residue was purified by column chromatography on silica gel using an ethyl acetate/hexane gradient to give 141 mg of the title compound (65% yield).

$^1$H-NMR (500 MHz, CHLOROFORM-d): δ [ppm]=1.35 (s, 9H, minor diastereomer), 1.36 (s, 9H, major diastereomer), 1.42-1.47 (m, 18H), 1.51-1.67 (m, 3H), 1.74-1.84 (m, 1H), 2.43-2.51 (m, 1H, major diastereomer), 2.51-2.59 (m, 1H, minor diastereomer), 2.59-2.66 (m, 1H), 2.76-2.84 (m, 1H), 4.14-4.23 (m, 1H), 4.96-5.00 (m, 1H), 5.04 (app t br, 1H), 6.73 (d, 2H), 6.99-7.05 (m, 2H).

ESI+ m/z 480 (M+H).

chiral HPLC (method c4): $t_R$=4.7 and 7.9 minutes (two peaks, baseline separation of C-5 epimers). The (2S)-analogue prepared from the respective L-homoserine synthon shows baseline separated C-5 epimers at 6.4 and 8.5 minutes (see example 12i).

f) Di-tert-butyl (2R)-2-[(tert-butoxycarbonyl)amino]-5-{4-[2-(tosyloxy)ethoxy]-benzyl}hexanedioate

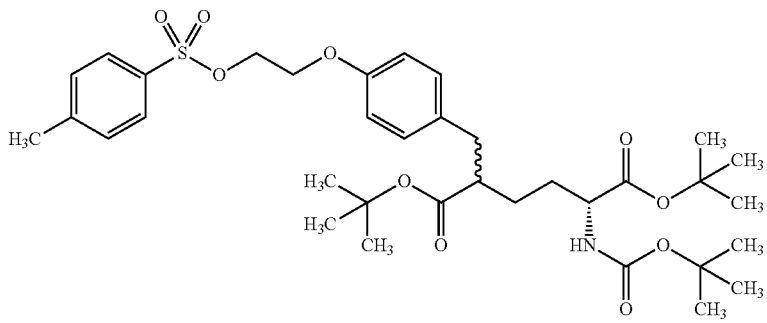 [SMILES: Cc1ccc(S(=O)(=O)OCCOc2ccc(CC(CC[C@@H](NC(=O)OC(C)(C)C)C(=O)OC(C)(C)C)C(=O)OC(C)(C)C)cc2)cc1]

To a solution of 351 mg 1,2-ethanediol di-p-toluenesulfonate (0.95 mmol) in N,N-dimethylformamide (6.5 mL) was subsequently added 155 mg cesium carbonate (0.47 mmol), followed by 65 mg di-tert-butyl (2R)-2-[(tert-butoxycarbonyl)amino]-5-(4-hydroxybenzyl)hexanedioate (0.136 mmol), and the resulting mixture was stirred for 2.5 hours at room temperature. The mixture was then concentrated in vacuo and purified by prep. HPLC (Method A) to give 80 mg (87% yield) of the desired tosylate.

$^1$H-NMR (300 MHz, CHLOROFORM-d): δ [ppm]=1.34 (s, 9H, minor diastereomer), 1.36 (s, 9H, major diastereomer), 1.40-1.48 (m, 18H), 1.50-1.69 (m, 3H), 1.72-1.86 (m, 1H), 2.46 (s, 3H), 2.42-2.67 (m, 2H), 2.76-2.87 (m, 1H), 4.07-4.24 (m, 3H), 4.32-4.39 (m, 2H), 4.97-5.08 (m, 1H), 6.69 (d, 2H), 7.00-7.10 (m, 2H), 7.35 (d, 2H), 7.83 (d, 2H).
ESI+ m/z 678 (M+H).

Example 16

(2R)-2-Amino-5-[4-(2-[$^{18}$F]fluoroethoxy)benzyl]hexanedioic acid

[$^{18}$F]-16

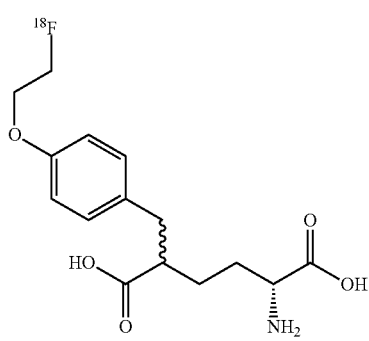

[$^{18}$F]Fluoride (570 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of tosylate di-tert-butyl (2R)-2-[(tert-butoxycarbonyl)amino]-5-{4-[2-(tosyloxy)ethoxy]benzyl}hexanedioate in 1 mL acetonitrile were added to the dried residue. The resulting mixture was stirred at 100° C. for 10 min. After cooling for 5 min at rt, 2M HCl (1 mL) was added and the mixture was stirred at 120° C. for 10 min. The crude product was diluted with water (pH 2) up to 30 mL and passed through a preconditioned Strata-X-C cartridge (Phenomenex). The cartridge was washed with 20 mL water (pH 2) and 20 mL ethanol. 207 MBq (58% d.c.) (2R)-2-Amino-5-[4-(2-[$^{18}$F]fluoroethoxy)benzyl]hexanedioic acid ([$^{18}$F]-16) were eluted with 5 mL phosphate buffer (7 g Na$_2$HPO$_4$.2H$_2$O; 6 g NaCl in 1 L water). Radiochemical purity was determined to be >98% ($t_R$=2.8 min, analytical HPLC method C).

Example 17

Di-tert-butyl (4R)—N-(tert-butoxycarbonyl)-4-{[5-(2-fluoroethoxy)pyridin-2-yl]methyl}-L-glutamate

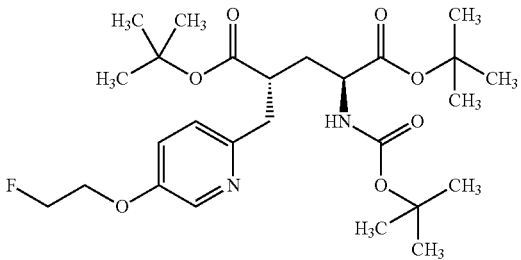 [SMILES: CC(C)(C)OC(=O)N[C@@H](C[C@H](Cc1ccc(OCCF)cn1)C(=O)OC(C)(C)C)C(=O)OC(C)(C)C]

a) 5-(Benzyloxy)-2-(bromomethyl)pyridine

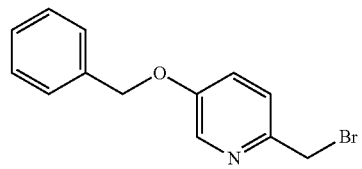 [SMILES: BrCc1ccc(OCc2ccccc2)cn1]

A mixture of 540 mg (2.51 mmol) 5-benzyloxy-2-pyridinemethanol (prepared according to J. Med. Chem. 1977, 20, 1258-1262), 536 mg N-bromo succinimide (3.01 mmol), and 1.2 g polymer bound triphenylphosphine (loading approx. 3 mmol/g, approx. 3.3 mmol) in dichloromethane (40 mL) was stirred overnight at room temperature. All solids were removed by filtration, and the filtrate was washed with aqueous sodium bicarbonate and water, and than concentrated in vacuo. The crude product (540 mg of a slightly pink solid, 79% crude yield) was used without further purification.

¹H-NMR (300 MHz, CHLOROFORM-d): δ [ppm]=4.55 (s, 2H), 5.12 (s, 2H), 7.24 (dd, 1H), 7.31-7.47 (m, 6H), 8.35 (d, 1H).

ESI+ m/z 278, 280 (M+H, Br isotopes well reflected).

b) Di-tert-butyl (4R)-4-{[5-(benzyloxy)pyridin-2-yl]methyl}-N-(tert-butoxycarbonyl)-L-glutamate

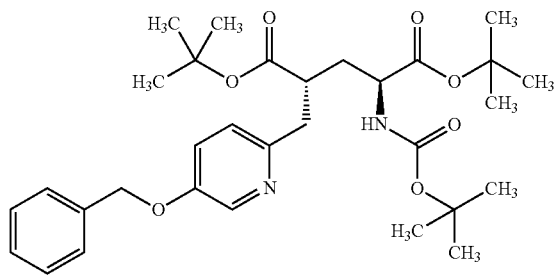 [SMILES: CC(C)(C)OC(=O)N[C@@H](C[C@H](Cc1ccc(OCc2ccccc2)cn1)C(=O)OC(C)(C)C)C(=O)OC(C)(C)C]

540 mg (1.50 mmol) of di-tert-butyl Boc-glutamate (prepared according to *J. Peptide Res.* 2001, 58, 338) were dissolved in 6 mL of tetrahydrofuran and cooled to −75° C. 3.45 mL (3.45 mmol) of a 1M solution of lithium bis(trimethylsilyl)amide in tetrahydrofuran were added dropwise and the mixture was stirred at −75° C. for another 60 minutes. 460 mg (1.65 mmol) of 5-(benzyloxy)-2-(bromomethyl)pyridine in 5 mL of tetrahydrofuran were then added dropwise, and after stirring 2 hours at −75° C., 3.45 mL of 2N aqueous hydrochloric acid were added, and after stirring another 30 minutes at −75° C., the cooling bath was removed and the mixture was allowed to warm up to room temperature. The mixture was partitioned between dichloromethane and aqueous sodium bicarbonate, and the organic layer was dried over magnesium sulfate and evaporated. The crude residue was purified by column chromatography on silica gel (ethyl acetate in hexane 0%→100%) to give 610 mg of the desired compound as yellowish oil (66% yield).

¹H-NMR (300 MHz, CHLOROFORM-d): δ [ppm]=1.36 (s, 9H), 1.43 (s, 9H), 1.54 (s, 9H), 1.79-2.05 (m, 2H), 2.81-3.09 (m, 3H), 4.12-4.22 (m, 1H), 5.05 (app d br), 5.09 (s, 2H), 7.06 (d, 1H), 7.17 (dd, 1H), 7.30-7.46 (m, 5H), 8.29 (d, 1H).

ESI+ m/z 557 (M+H)

c) Di-tert-butyl (4R)—N-(tert-butoxycarbonyl)-4-[(5-hydroxypyridin-2-yl)methyl]-L-glutamate

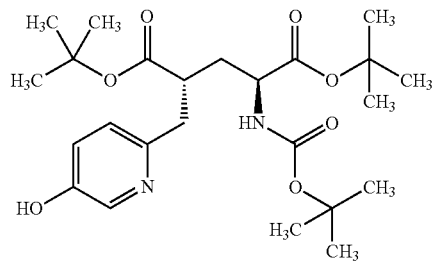 [SMILES: CC(C)(C)OC(=O)N[C@@H](C[C@H](Cc1ccc(O)cn1)C(=O)OC(C)(C)C)C(=O)OC(C)(C)C]

To a solution of 610 mg (1.10 mmol) of di-tert-butyl (4R)-4-{[5-(benzyloxy)pyridin-2-yl]methyl}-N-(tert-butoxycarbonyl)-L-glutamate in methanol (35 mL) was added a 10% palladium on charcoal catalyst (29 mg), and the resulting suspension was stirred overnight under an atmosphere of hydrogen at room temperature. The catalyst was removed by filtration, and the filtrate was evaporated to give 500 mg of the pure target compound as colorless foam (98% yield).

¹H-NMR (300 MHz, CHLOROFORM-d): δ [ppm]=1.35 (s, 9H), 1.43 (s, 9H), 1.44 (s, 9H), 1.82-2.08 (m, 2H), 2.78-3.07 (m, 3H), 4.08-4.19 (m, 1H), 5.13 (d br, 1H), 5.33 (s br, OH, weak signal likely due to H/D exchange), 7.06 (d, 1H), 7.18 (dd, 1H), 8.19 (d, 1H).

ESI+ m/z 467 (M+H)

d) Di-tert-butyl (4R)—N-(tert-butoxycarbonyl)-4-{[5-(2-fluoroethoxy)pyridin-2-yl]methyl}-L-glutamate

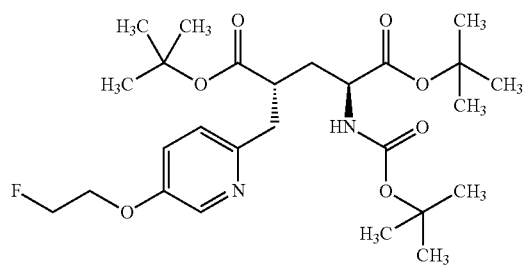 [SMILES: CC(C)(C)OC(=O)N[C@@H](C[C@H](Cc1ccc(OCCF)cn1)C(=O)OC(C)(C)C)C(=O)OC(C)(C)C]

To a solution of 196 mg 1-fluoro-2-iodoethane (1.13 mmol) in N,N-dimethylformamide (25 mL) was subsequently added 363 mg potassium carbonate (2.63 mmol), followed by 350 mg di-tert-butyl (4R)—N-(tert-butoxycarbonyl)-4-[(5-hydroxypyridin-2-yl)methyl]-L-glutamate 0.75 mmol), and the resulting mixture was stirred for 4 h at room temperature. The mixture was than partitioned between water and dichloromethane, and the organic layer was washed with brine, dried over magnesium sulfate, and evaporated. Purification of the crude product by preparative HPLC (method A) gave 313 mg of the target compound (81% yield).

¹H-NMR (600 MHz, CHLOROFORM-d): δ [ppm]=1.37 (s, 9H), 1.42 (s, 9H), 1.44 (s, 9H), 1.85-1.89 (m, 1H), 1.98 (dt, 1H), 2.87-2.96 (m, 2H), 3.01-3.04 (m, 1H), 4.13-4.17 (m, 1H), 4.21-4.22 (m, 1H), 4.25-4.27 (m, 1H), 4.71-4.80 (m, 2H), 5.05 (d, 1H), 7.08 (d, 1H), 7.15 (dd, 1H), 8.24 (d, 1H).

ESI+ m/z 513 (M+H)

Example 17-e (4R)-4-{[5-(2-fluoroethoxy)pyridin-2-yl]methyl}-L-glutamic acid

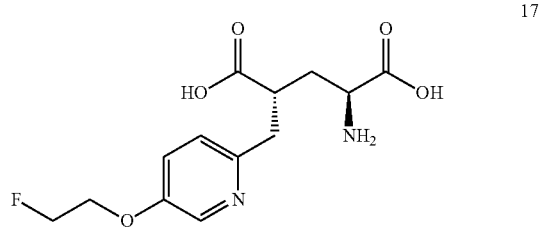 [SMILES: N[C@@H](C[C@H](Cc1ccc(OCCF)cn1)C(=O)O)C(=O)O]

(4R)-4-{[5-(2-fluoroethoxy)pyridin-2-yl]methyl}-L-glutamic acid (17) can be synthesized by deprotection of di-tert-butyl (4R)—N-(tert-butoxycarbonyl)-4-{[5-(2-fluoroethoxy)pyridin-2-yl]methyl}-L-glutamate (e.g. by treatment with TFA).

Example 18

Di-tert-butyl (4S)—N-(tert-butoxycarbonyl)-4-[4-({2-phenyl-5-[(tosyloxy)methyl]-1,3-dioxan-5-yl}methoxy)benzyl]-L-glutamate

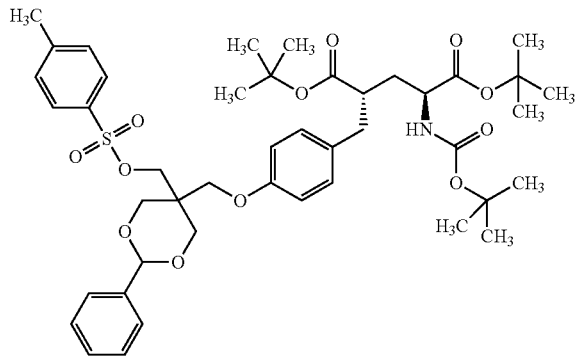 [SMILES: Cc1ccc(S(=O)(=O)OCC2(COc3ccc(C[C@@H](C[C@H](NC(=O)OC(C)(C)C)C(=O)OC(C)(C)C)C(=O)OC(C)(C)C)cc3)COC(c3ccccc3)OC2)cc1]

To 466 mg (1.0 mmol) of di-tert-butyl (4S)—N-(tert-butoxycarbonyl)-4-(4-hydroxybenzyl)-L-glutamate in 12 mL N,N-dimethylformamide were added 138 mg (1.0 mmol) of potassium carbonate and 533 mg (1.0 mmol) of (2-phenyl-1,3-dioxane-5,5-diyl)bis(methylene) bis(4-methylbenzenesulfonate) (Heterocycles 34. (1992), 739), and the resulting suspension was heated for 2 h at 100° C. in a microwave oven. The reaction mixture was then filtered, the solvent evaporated and the residue was taken up in ethyl acetate and water. The organic phase was separated off, washed with water until neutral, dried over sodium sulfate and filtered, and the filtrate was concentrated in vacuo. The residue was chromatographed on silica gel using a dichloromethane/ethyl acetate gradient, and the appropriate fractions were combined and concentrated.

Yield: 23 mg (28%)

$^1$H-NMR (400 MHz, CHLOROFORM-d): δ [ppm]=7.77 (d, 2H), 7.28-7.38 (m, 5H), 7.24 (d, 2H), 7.08 (d, 2H), 6.69 (d, 2H), 5.40 (s, 1H), 4.90 (br. d, 1H), 4.49 (s, 2H), 4.14-4.26 (m), 4.14 (d, 2H), 3.93 (d, 2H), 3.71 (s, 2H), 2.82 (br. d, 2H), 2.56-2.67 (m, 1H), 2.38 (s, 3H), 1.88 (t, 2H), 1.46 (s, 9H), 1.45 (s, 9H), 1.36 (s, 9H).

ESI+ m/z 826 (M$^+$).

Example 19

4-{3-[4-(3-Fluoropropyl)phenyl]propyl}-L-glutamic acid

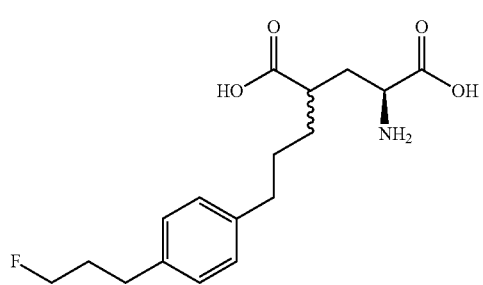

a) Di-tert-butyl (4S)-4-allyl-N-(tert-butoxycarbonyl)-L-glutamate

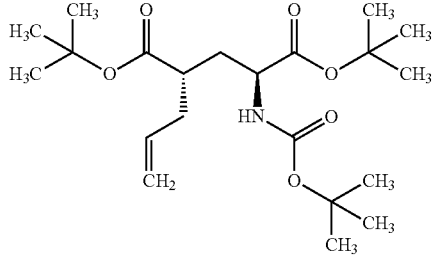 [SMILES: C=CC[C@@H](C[C@H](NC(=O)OC(C)(C)C)C(=O)OC(C)(C)C)C(=O)OC(C)(C)C]

To a solution of 719 mg (2.00 mmol) di-tert-butyl N-(tert-butoxycarbonyl)-L-glutamate in tetrahydrofuran (12 mL) at −78° C., lithium 1,1,1,3,3,3-hexamethyldisilazan-2-ide (1.0 M in tetrahydrofuran, 4.40 mL) was added dropwise. The solution was stirred for 30 min, then allyl bromide (0.52 mL, 6.00 mmol) was added dropwise. The reaction was stirred at −78° C. overnight and then quenched at −10° C. by the addition of 10 mL of 2 N aqueous hydrogen chloride. The mixture was warmed to room temperature poured into 10 mL 1 N aqueous hydrogen chloride and extracted with dichloromethane (3×30 mL). The organic phases were dried over magnesium sulfate and concentrated in vacuo. The crude product was purified on silica gel using a hexane/ethyl acetate gradient, and the appropriate fractions were combined and concentrated.

Yield: 673 mg (84.2%)

$^1$H NMR (300 MHz, CHLOROFORM-d) δ ppm 1.32-1.58 (m, 27H) 1.81-1.92 (m, 2H) 2.25-2.39 (m, 2H) 2.40-2.48 (m, 1H), 4.10-4.18 (m, 1H) 4.85-4.92 (d, 1H) 5.02-5.11 (m, 2H) 5.68-5.77 (m, 1H)

ESI+ m/z 400.2 (M+H).

b) 3-(4-Iodophenyl)propan-1-ol

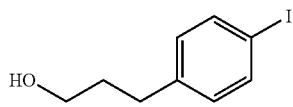 [SMILES: OCCCc1ccc(I)cc1]

3-(4-iodophenyl)propanoic acid (Atlantic Research Chemicals Ltd.) (2.76 g, 10.00 mmol) were dissolved in tetrahydrofuran (100 mL) and added slowly to a suspension of lithium aluminium hydride (0.23 g, 6.00 mmol) in 100 mL tetrahydrofuran. The reaction was stirred for 3 h, then 1 N aqueous sodium hydrogen carbonate (150 mL) were added slowly and the resulting mixture was extracted with ethyl acetate (3×400 mL), the organic extracts were dried over magnesium sulfate and concentrated in vacuo. The crude product was purified on silica gel using a hexane/ethyl acetate gradient, and the appropriate fractions were combined and concentrated.

Yield: 1.30 g (49.8%)

$^1$H-NMR (300 MHz, CHLOROFORM-d): δ [ppm]=1.88 (m, 2H), 2.62-2.72 (m, 2H), 3.64-3.70 (m, 2H), 6.97 (d, 2H), 7.61 (d, 2H).

ESI+ m/z 263.2 (M+H).

c) Di-tert-butyl (4S)—N-(tert-butoxycarbonyl)-4-{(E)-3-[4-(3-hydroxypropyl)phenyl]-prop-2-en-1-yl}-L-glutamate

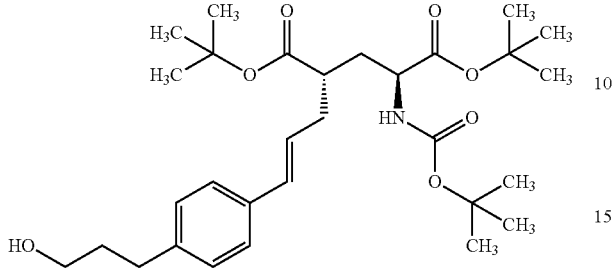

To a solution of di-tert-butyl (4S)-4-allyl-N-(tert-butoxycarbonyl)-L-glutamate (940 mg, 2.53 mmol) in 5 mL acetonitrile under an argon atmosphere was added 3-(4-iodophenyl)propan-1-ol (740 mg, 2.82 mmol), triethylamine (394 µl, 2.82 mmol), and palladium(II) acetate (106 mg, 0.47 mmol). The mixture was stirred in a pressure tube at 80° C. for 2 h. After cooling to room temperature, the solvent was removed under reduced pressure and the crude material was purified on silica gel using a hexane/ethyl acetate gradient, and the appropriate fractions were combined and concentrated.

Yield: 316 mg (25.2%)

$^1$H-NMR (300 MHz, CHLOROFORM-d): δ [ppm]=1.43-1.47 (m, 27H), 1.82-1.97 (m, 4H), 2.49 (m, 3H), 2.69 (m, 2H), 3.69 (m, 2H), 4.10-4.29 (m, 1H), 4.90 (d, 1H), 6.00-6.16 (m, 1H), 6.40 (d, 1H), 7.13 (d, 2H), 7.24 (d, 2H, partially overlayed by chloroform signal).

ESI+ m/z 534.5 (M+H).

d) Di-tert-butyl (4S)—N-(tert-butoxycarbonyl)-4-{3-[4-(3-hydroxypropyl)phenyl]-propyl}-L-glutamate

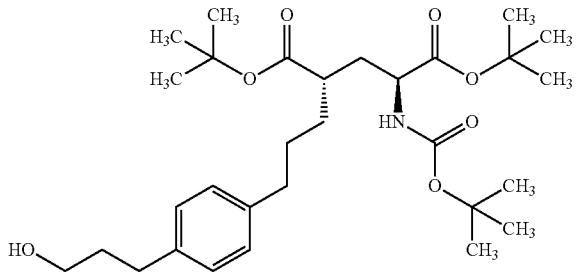 [SMILES: CC(C)(C)OC(=O)N[C@@H](C[C@H](CCCc1ccc(CCCO)cc1)C(=O)OC(C)(C)C)C(=O)OC(C)(C)C]

To a solution of 316 mg (0.59 mmol) di-tert-butyl (4S)—N-(tert-butoxycarbonyl)-4-{(E)-3-[4-(3-hydroxypropyl)phenyl]prop-2-en-1-yl}-L-glutamate in 29 mL of methanol, palladium (10% on charcoal, 126 mg) was added and the suspension was stirred overnight at room temperature under a hydrogen atmosphere. The mixture was filtered over celite, and the solvent was evaporated. The remaining material was used without purification.

Yield: 163 mg (51.4%)

ESI+ m/z 536.3 (M+H).

e) Di-tert-butyl N-(tert-butoxycarbonyl)-4-{3-[4-(3-fluoropropyl)phenyl]propyl}-L-glutamate

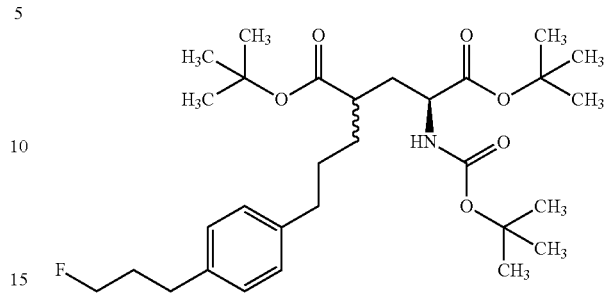

Di-tert-butyl (4S)—N-(tert-butoxycarbonyl)-4-(3-{4-[3-(tosyloxy)propyl]phenyl}propyl)-L-glutamate (see Example 20) (79 mg, 0.12 mmol) was dissolved in 1 ml acetonitrile, and tetra-n-butylammonium tetra-(tert-butyl alcohol)-coordinated fluoride (*Angew. Chem.* 2008, 120, 8532-8534) (128 mg, 0.23 mmol) were added. The mixture was stirred at 70° C. for 1.5 h. After cooling to room temperature, the mixture was poured into water (10 ml) and extracted with tert-butylmethyl ether (3×10 ml). The organic phases were dried over magnesium sulfate and concentrated in vacuo. The crude material was used in the next step without purification.

Yield: 40 mg (65.0%)

ESI+ m/z 538.6 (M+H)

f) 4-{3-[4-(3-Fluoropropyl)phenyl]propyl}-L-glutamic acid

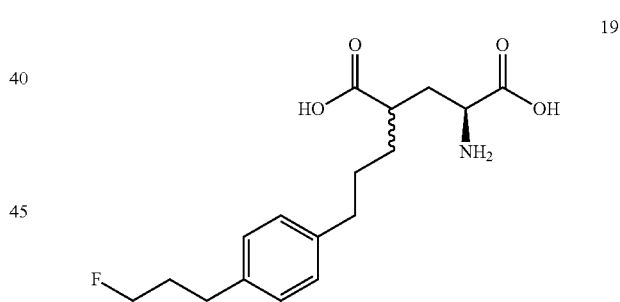

Di-tert-butyl N-(tert-butoxycarbonyl)-4-{3-[4-(3-fluoropropyl)phenyl]propyl}-L-glutamate (40 mg, 0.07 mmol) was dissolved in 3 ml trifluoroacetic acid and stirred at room temperature for 1d. Then, 5 ml toluene were added and the solution was concentrated in vacuo. The product was purified by preparative HPLC. The appropriate fractions were collected, the acetonitrile evaporated under reduced pressure and the remaining aqueous solution was lyophilized.

Yield: 21.4 mg (84.9%) (mixture of diastereomers)

$^1$H-NMR (400 MHz, DMSO-d$_6$): δ [ppm]=1.12-1.20 (m, 1H), 1.35-1.64 (m, 3.6H), 1.66-1.82 (m, 1H), 1.82-1.99 (m, 3H), 2.07-2.16 (m, 0.4H), 2.52-2.67 (m, 4H), 3.63 (dd, 0.6H), 3.67-3.73 (m, 0.4H), 4.34-4.43 (m, 1H), 4.43-4.53 (m, 1H), 7.02-7.20 (m, 4H).

ESI+ m/z 326.4 (M+H).

ESI+ m/z 626 (M+H).

Example 20

Di-tert-butyl (4S)—N-(tert-butoxycarbonyl)-4-(3-{4-[3-(tosyloxy)propyl]phenyl}-propyl)-L-glutamate

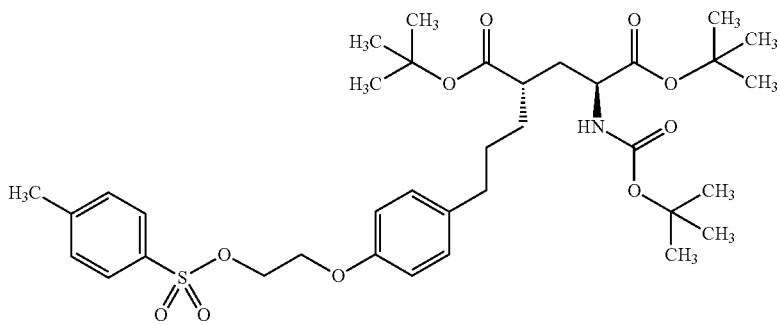 [SMILES: Cc1ccc(S(=O)(=O)OCCOc2ccc(CCC[C@@H](C[C@H](NC(=O)OC(C)(C)C)C(=O)OC(C)(C)C)C(=O)OC(C)(C)C)cc2)cc1]

Di-tert-butyl (4S)—N-(tert-butoxycarbonyl)-4-{3-[4-(3-hydroxypropyl)phenyl]propyl}-L-glutamate (163 mg, 0.30 mmol) was dissolved in pyridine (7 mL) and p-toluenesulfonic anhydride (Aldrich) (199 mg, 0.61 mmol) was slowly added at 0° C. The reaction was stirred for 2 h, then poured into 25 mL 1 N aqueous hydrogen chloride. The mixture was extracted with tert-butylmethyl ether (3×50 mL), the organic phases washed with saturated aqueous sodium hydrogen carbonate, dried over sodium sulfate and concentrated in vacuo. The crude product was chromatographed on silica gel using a hexane/ethyl acetate gradient, and the appropriate fractions were combined and concentrated.

Yield: 147 mg (70.0%)

$^1$H-NMR (400 MHz, CHLOROFORM-d): δ [ppm]=1.18-1.31 (m, 1H), 1.42-1.48 (m, 27H), 1.57-1.64 (m, 3H), 1.79-1.99 (m, 4H), 2.29-2.44 (m, 1H), 2.47 (s, 3H), 2.53-2.65 (m, 4H), 4.04 (t, 2H), 4.07-4.19 (m, 1H), 4.86 (d, 1H), 6.96-7.07 (m, 4H), 7.36 (d, 2H), 7.80 (d, 2H).

ESI+ m/z 690.5 (M+H).

Example 21

Di-tert-butyl (4S)—N-(tert-butoxycarbonyl)-4-(4-{trans-[3-(tosyloxy)cyclobutyl]oxy}-benzyl)-L-glutamate

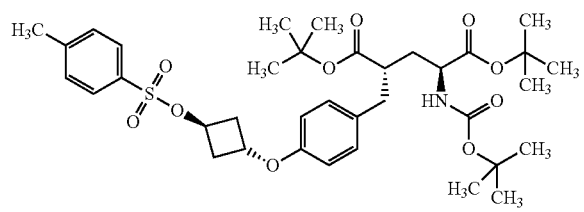 [SMILES: Cc1ccc(S(=O)(=O)O[C@H]2C[C@H](Oc3ccc(C[C@@H](C[C@H](NC(=O)OC(C)(C)C)C(=O)OC(C)(C)C)C(=O)OC(C)(C)C)cc3)C2)cc1]

a) Di-tert-butyl (4S)-4-(4-{trans-[3-(benzyloxy)cyclobutyl]oxy}benzyl)-N-(tert-butoxycarbonyl)-L-glutamate

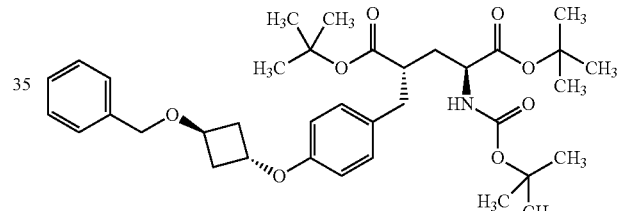

To 349 mg (0.75 mmol) of di-tert-butyl (4S)—N-(tert-butoxycarbonyl)-4-(4-hydroxy-benzyl)-L-glutamate (Example 1 b) in 15 mL NA-dimethylformamide were added 138 mg (1.0 mmol) of potassium carbonate and 332 mg (1.0 mmol) of 2-phenyl-1,3-dioxan-5-yl 4-methylbenzenesulfonate (Studii si Cercetari de Chimie (1960), 8, 187-99.) and the resulting suspension was heated for 2 h at 100° C. in a microwave oven. The reaction mixture was then filtered, the solvent evaporated and the residue was taken up in DMSO. The crude product obtained in this manner was chromatographed on a PrepCon® C-18 reversed phase column using a water/acetonitrile gradient (35/65 to 0/100), and the appropriate fractions were combined and concentrated.

Yield: 43 mg (9.2%)

$^1$H-NMR (300 MHz, CHLOROFORM-d): δ [ppm]=1.31-1.44 (m, 27H), 1.58 (s, 1H), 1.87 (t, 2H), 2.39-2.52 (m, 4H), 2.58-2.63 (m, 1H), 2.77-2.80 (m, 2H), 4.16-4.19 (m, 1H), 4.31-4.35 (m, 1H), 4.44 (s, 2H), 4.80-4.88 (m, 2H), 6.68 (d, 2H), 7.06 (d, 2H), 7.34-7.35 (m, 5H).

b)) Di-tert-butyl (4S)-4-{4-[trans-(3-hydroxycyclobutyl)oxy]benzyl}-N-(tert-butoxy-carbonyl)-L-glutamate

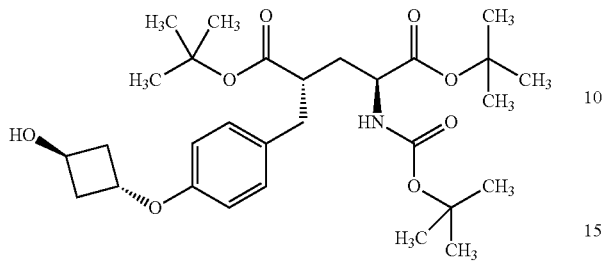

43 mg (0.07 mmol) of di-tert-butyl (4S)-4-(4-{trans-[3-(benzyloxy)cyclobutyl]oxy}benzyl)-N-(tert-butoxycarbonyl)-L-glutamate were dissolved in 10 mL of methanol and under argon atmosphere palladium (10% on charcoal) was added and the suspension hydrogenated overnight at room temperature. The reaction mixture was filtered, the solvent evaporated and the residue was chromatographed on silica gel using a hexane/ethyl acetate gradient, and the appropriate fractions were combined and concentrated.

Yield: 35 mg (95.1%)

$^1$H-NMR (300 MHz, CHLOROFORM-d): δ [ppm]=1.33 (s, 9H), 1.44 (m, 18H), 1.88 (m, 2H), 2.39-2.63 (m, 5H), 2.77-2.79 (m, 2H), 4.16-4.18 (m, 1H), 4.84-4.86 (m, 2H), 6.68 (d, 2H), 7.06 (d, 2H).

ESI+ m/z 536 (M+H).

c) Di-tert-butyl (4S)—N-(tert-butoxycarbonyl)-4-(4-{trans-[3-(tosyloxy)cyclobutyl]-oxy}benzyl)-L-glutamate

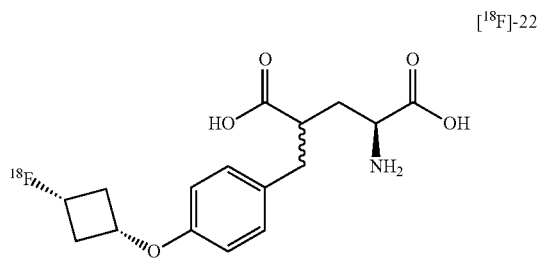 [SMILES: N[C@@H](CC(Cc1ccc(O[C@H]2C[C@@H]([18F])C2)cc1)C(=O)O)C(=O)O]

0.233 g (0.50 mmol) Di-tert-butyl (4S)-4-{4-[trans-(3-hydroxycyclobutyl)oxy]benzyl}-N-(tert-butoxycarbonyl)-L-glutamate, 0.14 g (1 mmol) potassium carbonate and 0.198 g (0.50 mmol) cis-cyclobutane-1,3-diyl bis(4-methylbenzenesulfonate) in 5 ml dimethylformamide were heated for 3.5 h at 100° C. in a microwave. The reaction mixture was diluted with water and extracted with dichloromethane. The organic layer was dried over sodium sulfate, filtrated, the solvent was evaporated and the residue was chromatographed on silica gel using a hexane/ethyl acetate gradient, and the appropriate fractions were combined and concentrated.

Yield: 24 mg (7%)

$^1$H NMR (CHLOROFORM-d, 300 MHz): δ (ppm) 7.79 (d, 2H), 7.35 (d, 2H), 7.04 (d, 2H), 6.61 (d, 2H), 4.9-5.11 (m, 1H), 4.87 (br. d, 1H), 4.73-4.83 (m, 1H), 4.09-4.25 (m, 1H), 2.69-2.85 (m, 2H), 2.54-2.68 (m, 3H), 2.47-2.53 (m, 2H), 2.45 (s, 3H), 1.86 (t, 2H), 1.44 (s, 9H), 1.43 (s, 9H), 1.31 (s, 9H).

ESI+ m/z 712 (M+Na).

Example 22

4-{4-[(cis-3-[$^{18}$F]Fluorocyclobutyl)oxy]benzyl}-L-glutamic acid

[$^{18}$F]-22

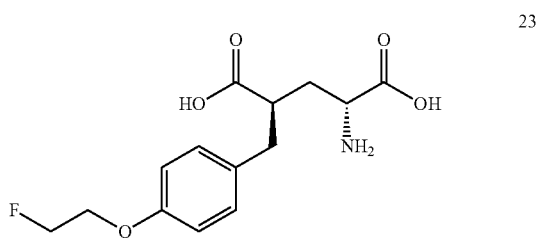 [SMILES: N[C@H](C[C@@H](Cc1ccc(OCCF)cc1)C(=O)O)C(=O)O]

[$^{18}$F]Fluoride (3028 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of di-tert-butyl (4S)—N-(bent-butoxycarbonyl)-4-{4-[(3-{[(4-methylphenyl)sulfonyl]oxy}cyclobutyl)oxy]benzyl}-L-glutamate in 1 mL acetonitrile were added to the dried residue. The resulting mixture was stirred at 140° C. for 10 min. After cooling for 5 min at rt, 2M HCl (1 mL) was added and the mixture was stirred at 120° C. for 10 min. The crude product was diluted with water up to 20 mL and passed through a preconditioned Strata-X-C cartridge (Phenomenex). The cartridge was washed with 10 mL water (pH 2) and 10 mL ethanol. 319 MBq (17% d.c.) 4-{4-[(cis-3-[$^{18}$F]fluorocyclobutyl)oxy]benzyl}-L-glutamic acid ([$^{18}$F]-22) were eluted with 5 mL phosphate buffer (7 g Na$_2$HPO$_4$.2H$_2$O; 6 g NaCl in 1 L water). Radiochemical purity was determined to be >98% ($t_R$=2.9 min, analytical HPLC method C).

Example 23

(4R)-4-[4-(2-Fluoroethoxy)benzyl]-D-glutamic acid

23 a) Di-tert-butyl (4R)-4-[4-(benzyloxy)benzyl]-Nert-butoxycarbonyl)-D-glutamate

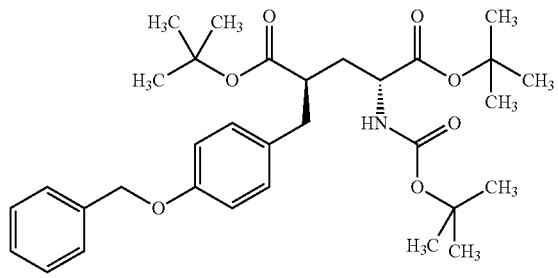 [SMILES: CC(C)(C)OC(=O)N[C@H](C[C@@H](Cc1ccc(OCc2ccccc2)cc1)C(=O)OC(C)(C)C)C(=O)OC(C)(C)C]

1.26 g (3.5 mmol) of di-tert-butyl Boc-D-glutamate (prepared in analogy to Journal of Peptide Research (2001), 58, 338 from di-tert-butyl D-glutamate) were dissolved in 15 mL of tetrahydrofuran and cooled to −70° C. 7.7 mL (7.7 mmol) of a 1M solution of lithium bis(trimethylsilyl)amide in tetrahydrofuran were added dropwise over a period of 30 min at this temperature and the mixture was stirred at −70° C. for another 2 hours. 1.11 g (4 mmol) of 4-benzyloxybenzyl bromide (Helvetica Chimica Acta, 2002, 85, 3422) in 5 mL of tetrahydrofuran were then added dropwise, and after 2 h at this temperature, the cooling bath was removed and 17.5 mL of 2N aqueous hydrochloric acid and 100 mL of dichloromethane were added. The organic phase was separated off, washed with water until neutral, dried over sodium sulfate and filtered, and the filtrate was concentrated. The crude product obtained in this manner was chromatographed on silica gel using a hexane/ethyl acetate gradient, and the appropriate fractions were combined and concentrated.

Yield: 1.0 g (36.0%)

¹H-NMR (400 MHz, CHLOROFORM-d): δ [ppm]=1.31 (s, 9H), 1.44-1.57 (m, 18H), 1.87 (t, 2H), 2.61 (m, 1H), 2.78-2.81 (m, 2H), 4.14-4.20 (m, 1H), 4.89 (d, 1H), 5.04 (s, 2H), 6.87 (d, 2H), 7.08 (d, 2H), 7.37-7.44 (m, 5H).

ESI+ m/z 556 (M+H).

b) Di-tert-butyl (4R)—N-(tert-butoxycarbonyl)-4-(4-hydroxybenzyl)-D-glutamate

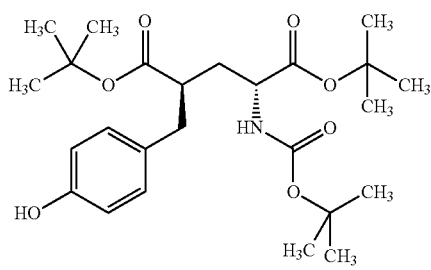 [SMILES: CC(C)(C)OC(=O)N[C@H](C[C@@H](Cc1ccc(O)cc1)C(=O)OC(C)(C)C)C(=O)OC(C)(C)C]

1.0 g (1.8 mmol) of di-tert-butyl (4R)-4-[4-(benzyloxy) benzyl]-Nert-butoxycarbonyl)-D-glutamate were dissolved in 35 mL of methanol and under argon atmosphere palladium (10% on charcoal) was added and the suspension hydrogenated overnight at room temperature. The reaction mixture was filtered, the solvent evaporated and the residue was chromatographed on silica gel using a hexane/ethyl acetate gradient, and the appropriate fractions were combined and concentrated.

Yield: 0.40 g (63.6%)

¹H-NMR (400 MHz, CHLOROFORM-d): δ [ppm]==1.33 (s, 9H), 1.44 (m, 18H), 1.88 (t, 2H), 2.61 (m, 1H), 2.74-2.83 (m, 2H), 4.15-4.21 (m, 1H), 4.90 (d, 1H), 5.26 (s, 1H), 6.72 (d, 2H), 7.02 (d, 2H).

ESI+ m/z 465.6 (M+H).

c) (4R)-4-[4-(2-Fluoroethoxy)benzyl]-D-glutamic acid

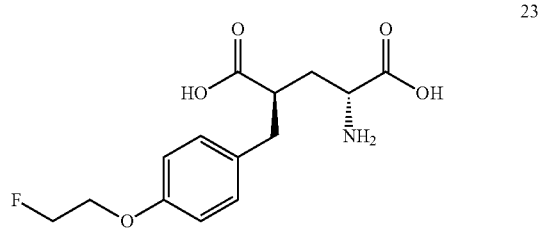 [SMILES: N[C@H](C[C@@H](Cc1ccc(OCCF)cc1)C(=O)O)C(=O)O]

23

To 93 mg (0.2 mmol) of di-tert-butyl (4R)—N-(tert-butoxycarbonyl)-4-(4-hydroxybenzyl)-D-glutamate in 4 mL N,N-dimethylformamide were added 56 mg (0.4 mmol) of powdered potassium carbonate and 69.6 mg (0.40 mmol) of 1-iodo-2-fluoroethane and the resulting suspension was heated for 1 h at 100° C. in a microwave oven. The reaction mixture was then filtered, the solvent evaporated and the residue was taken up in ethyl acetate and water. The organic phase was separated off, washed with water until neutral, dried over sodium sulfate and filtered, and the filtrate was concentrated in vacuo. Di-tert-butyl (4R)—N-(tert-butoxycarbonyl)-4-[4-(2-fluoroethoxy)benzyl]-D-glutamate was obtained as crude product (40 mg, 39.1%) and deprotected without further purification: 2 mL of trifluoro acetic acid were added to the oily residue and the solution was stirred for 2 d at room temperature. The excess of trifluoro acetic acid was evaporated and the residue was taken up three times in tetrahydrofuran and then evaporated. The resulting oil was chromatographed on C-18 reversed phase silica gel using a water/ acetonitrile gradient, the appropriate fractions were combined and concentrated.

Yield: 13 mg (55.6%)

¹H-NMR (400 MHz, DMSO-d6): δ [ppm]=1.60-1.74 (m, 2H), 2.76-2.96 (m, 2H), 3.46 (m, 1H), 4.12-4.25 (m, 2H), 4.63-4.80 (m, 2H), 6.86 (d, 2H), 7.10 (d, 2H).

ESI+ m/z 300 (M+H).

Example 24

(4R)-4-[4-(3-Fluoropropoxy)benzyl]-D-glutamic acid

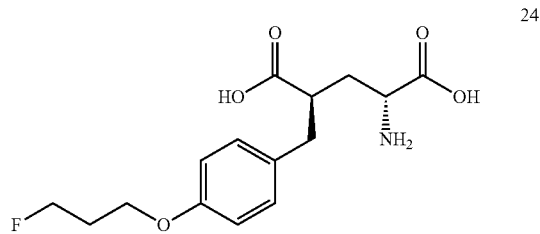 [SMILES: N[C@H](C[C@@H](Cc1ccc(OCCCF)cc1)C(=O)O)C(=O)O]

24 a) Di-tert-butyl (4R)—N-(tert-butoxycarbonyl)-4-[4-(3-fluoropropoxy)benzyl]-D-glutamate

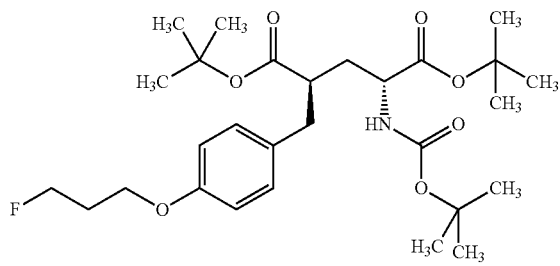 [SMILES: CC(C)(C)OC(=O)N[C@H](C[C@@H](Cc1ccc(OCCCF)cc1)C(=O)OC(C)(C)C)C(=O)OC(C)(C)C]

To 140 mg (0.30 mmol) of di-tert-butyl (4R)—N-(tert-butoxycarbonyl)-4-(4-hydroxy-benzyl)-D-glutamate in 5 mL N,N-dimethylformamide were added 42 mg (0.3 mmol) of powdered potassium carbonate and 56 mg (0.30 mmol) of 1-iodo-3-fluoropropane (ABCR GmbH, Germany) and the resulting suspension was heated for 2 h at 100° C. in a microwave oven. The reaction mixture was then filtered, the solvent evaporated and the residue was taken up in ethyl acetate and water. The organic phase was separated off, washed with water until neutral, dried over sodium sulfate and filtered, and the filtrate was concentrated in vacuo. The crude product obtained in this manner was chromatographed on silica gel using a dichloromethane/methanol gradient, and the appropriate fractions were combined and concentrated.

Yield: 60 mg (38.1%)

$^1$H-NMR (300 MHz, CHLOROFORM-d): δ [ppm]=1.33 (s, 9H), 1.44 (s, 18H), 1.87 (t, 2H), 2.09-2.22 (m, 2H), 2.61 (t, 1H), 2.80 (d, 2H), 4.06 (t, 2H), 4.18 (m, 1H), 4.54-4.58 (m, 1H), 4.70-4.74 (m, 1H), 4.87 (d, 1H), 6.80 (d, 2H), 7.08 (d, 2H).

ESI+ m/z 526 (M+H).

b) (4R)-4-[4-(3-Fluoropropoxy)benzyl]-D-glutamic acid

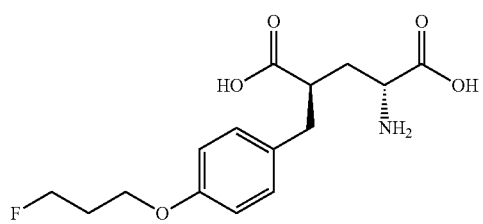

60 mg (0.11 mmol) of di-tert-butyl (4R)—N-(tert-butoxycarbonyl)-4-[4-(3-fluoropropoxy)-benzyl]-D-glutamate were taken up in 3 mL of trifluoro acetic acid and stirred overnight at room temperature. The excess of trifluoro acetic acid was evaporated and the residue was taken up three times in tetrahydrofuran and then evaporated. The resulting oil was chromatographed on C-18 reversed phase silica gel using a water/acetonitrile gradient, the appropriate fractions were combined and concentrated.

Yield: 18 mg (50.3%)

$^1$H-NMR (400 MHz, DMSO-d6): δ [ppm]=1.60-1.74 (m, 2H), 2.01-210 (m, 2H), 2.43-2.49 (m, 2H), 2.77-2.94 (m, 2H), 3.47 (m, 1H), 4.02 (t, 2H), 4.50-4.69 (m, 2H), 6.84 (d, 2H), 7.09 (d, 2H).

ESI+ m/z 313.8 (M+H).

Example 25

(4S)-4-{3-[4-(2-Fluoroethoxy)phenyl]propyl}-L-glutamic acid

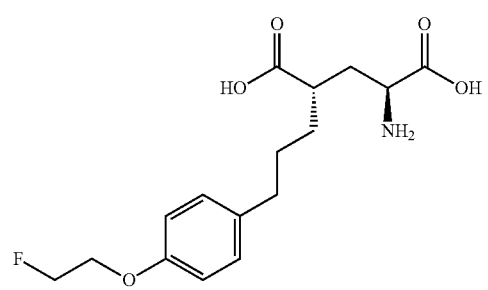

a) Di-tert-butyl (4S)-4-{(E)-3-[4-(benzyloxy)phenyl]prop-2-en-1-yl}-N-(tert-butoxycarbonyl)-L-glutamate

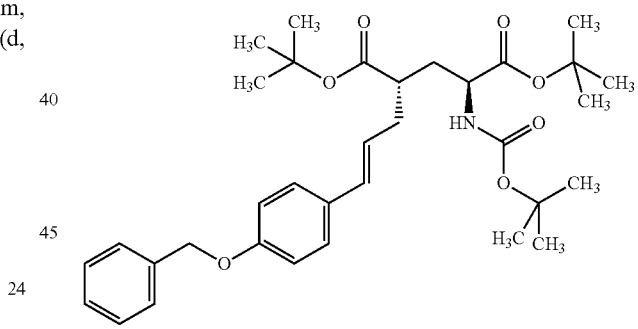

To a stirred solution of di-tert-butyl (4S)-4-allyl-N-(tert-butoxycarbonyl)-L-glutamate (345 mg, 0.86 mmol) in acetonitrile (5 ml) at room temperature was slowly added 1-(benzyloxy)-4-iodobenzene (ABCR GmbH & CO. KG) (321 mg, 1.04 mmol) in 3 ml acetonitrile, triethylamine (144 µl, 1.04 mmol) in 3 ml acetonitrile, and palladium(II) acetate (Aldrich) (39 mg, 0.17 mmol). The mixture was heated in a pressure tube at 80° C. for 2 h. After cooling to room temperature, the mixture was filtered and the filtrate was concentrated in vacuo. The crude material was chromatographed on silica gel using a hexane/ethyl acetate gradient, and the appropriate fractions were combined and concentrated.

Yield: 110 mg (21.9%)

ESI+ m/z 582.5 (M+H).

b) Di-tert-butyl (4S)—N-(tert-butoxycarbonyl)-4-[3-(4-hydroxyphenyl)propyl]-L-glutamate

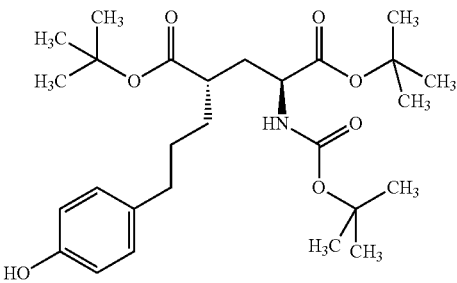 [SMILES: CC(C)(C)OC(=O)N[C@@H](C[C@H](CCCc1ccc(O)cc1)C(=O)OC(C)(C)C)C(=O)OC(C)(C)C]

To a solution of 110 mg (0.19 mmol) di-tert-butyl (4S)-4-{4-[3-(benzyloxy)propyl]benzyl}-N-(tert-butoxycarbonyl)-L-glutamate in 5 ml of methanol, palladium (10% on charcoal, 60 mg) was added and the suspension was stirred overnight at room temperature under a hydrogen atmosphere. The mixture was filtered over celite, and the solvent was evaporated. The remaining material was chromatographed on silica gel using a hexane/ethyl acetate gradient, and the appropriate fractions were combined and concentrated.

Yield: 65 mg (69.6%)

¹H-NMR (400 MHz, CHLOROFORM-d): δ [ppm]=1.45 (m, 27H), 1.52-1.69 (m, 4H), 1.75-1.96 (m, 2H), 2.28-2.43 (m, 1H), 2.45-2.63 (m, 2H), 4.07-4.19 (m, 1H), 4.88 (d, 1H), 6.75 (d, 2H), 7.01 (d, 2H).

ESI+ m/z 494.2 (M+H).

c) Di-tert-butyl (4S)—N-(tert-butoxycarbonyl)-4-{3-[4-(2-fluoroethoxy)phenyl]-propyl}-L-glutamate

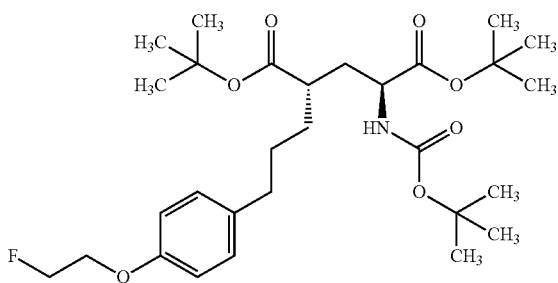 [SMILES: CC(C)(C)OC(=O)N[C@@H](C[C@H](CCCc1ccc(OCCF)cc1)C(=O)OC(C)(C)C)C(=O)OC(C)(C)C]

Di-tert-butyl (4S)—N-(tert-butoxycarbonyl)-4-[3-(4-hydroxyphenyl)propyl]-L-glutamate (80 mg, 0.16 mmol), 1-bromo-2-fluoroethane (103 mg, 0.81 mmol), and caesium carbonate (158 mg, 0.49 mmol) were dissolved in 8 ml N,N-dimethylformamide and the solution was stirred at 60° C. for 4 h. The reaction was then poured into 1 N aqueous hydrochloric acid (50 ml) and extracted with dichloromethane (3×75 ml). The combined organic phases were dried over magnesium sulfate and concentrated in vacuo. The crude product was purified by pHPLC on a reversed phase (RP-18) column with an acetonitrile/water gradient. The appropriate fractions were collected, the acetonitrile evaporated under reduced pressure and the remaining aqueous solution was lyophilized.

Yield: 31 mg (35.4%)

ESI+ m/z 540.6 (M+H)

d) (4S)-4-{3-[4-(2-Fluoroethoxy)phenyl]propyl}-L-glutamic acid

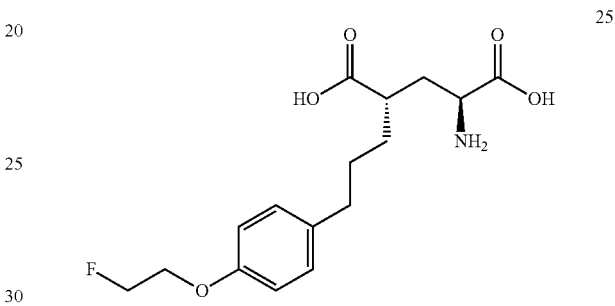

Di-tert-butyl (4S)—N-(tert-butoxycarbonyl)-4-{3-[4-(2-fluoroethoxy)phenyl]propyl}-L-glutamate (31 mg, 0.06 mmol) was dissolved in 3 ml trifluoroacetic acid and stirred at room temperature for 1d. Then, 5 ml toluene were added and the solution was concentrated in vacuo. The product was purified by preparative HPLC. The appropriate fractions were collected, the acetonitrile evaporated under reduced pressure and the remaining aqueous solution was lyophilized.

Yield: 4.5 mg (23.9%)

¹H-NMR (400 MHz, DMSO-de): δ [ppm]=1.32-1.62 (m, 4H), 1.69-1.94 (m, 2H), 2.53-2.64 (m, 1H), 3.63 (dd, 1H), 4.19 (m, 2H J (H, F)=30.4 Hz), 4.72 (m, 2H, J (H, F)=47.7 Hz), 6.82-6.92 (m, 2H), 7.05-7.14 (m, 2H). Two hydrogen signals are apparently hidden under the DMSO solvent peak.

ESI+ m/z 328.4 (M+H).

Example 26

Di-tert-butyl (4S)—N-(tert-butoxycarbonyl)-4-(3-{4-[2-(tosyloxy)ethoxy]phenyl}-propyl)-L-glutamate

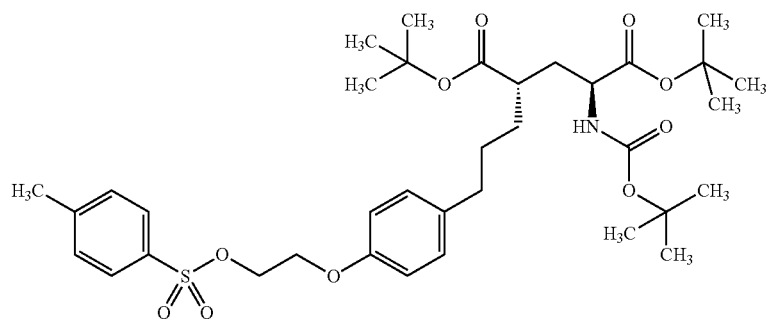 [SMILES: Cc1ccc(S(=O)(=O)OCCOc2ccc(CCC[C@@H](C[C@H](NC(=O)OC(C)(C)C)C(=O)OC(C)(C)C)C(=O)OC(C)(C)C)cc2)cc1]

Di-tert-butyl (4S)—N-(tert-butoxycarbonyl)-4-[3-(4-hydroxyphenyl)propyl]-L-glutamate (240 mg, 0.49 mmol), 1,2-ethanediol-bis(4-methylbenzenesulfonate) (901 mg, 2.43 mmol), and caesium carbonate (475 mg, 1.46 mmol) were dissolved in 10 ml N,N-dimethylformamide and the solution was stirred at 60° C. for 4 h. The reaction was then poured into 1 N aqueous hydrochloric acid (50 ml) and extracted with dichloromethane (3×75 ml). The combined organic phases were dried over magnesium sulfate and concentrated in vacuo. The crude product was pre-purified by pHPLC on a reversed phase (RP-18) column with an acetonitrile/water gradient. The appropriate fractions were collected, the acetonitrile evaporated under reduced pressure and the remaining aqueous solution was lyophilized. The pre-purified product was purified on silica gel using a hexane/ethyl acetate gradient, and the appropriate fractions were combined and concentrated.

Yield: 54 mg (15.7%)

$^1$H-NMR (300 MHz, CHLOROFORM-d): δ [ppm]=1.42-1.49 (m, 27H), 1.58 (m, 4H), 1.72-1.96 (m, 2H), 2.29-2.42 (m, 1H), 2.46 (s, 3H), 2.54 (m, 2H), 4.05-4.19 (m, 3H), 4.30-4.43 (m, 2H), 4.86 (d, 1H), 6.62-6.77 (m, 2H), 6.96-7.09 (m, 2H), 7.31-7.41 (m, 2H), 7.77-7.88 (m, 2H).

ESI+ m/z 692.6 (M+H).

Example 27

(4S)-4-{3-[4-(2-[$^{18}$F]Fluoroethoxy)phenyl]propyl}-L-glutamic acid

[$^{18}$F]-25

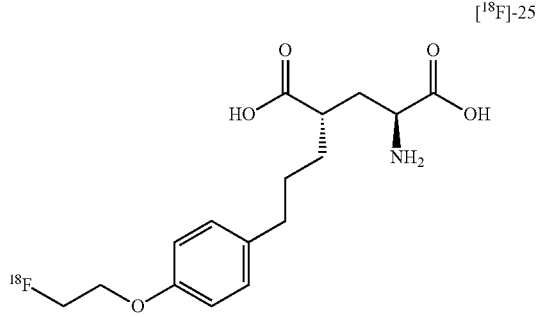 [SMILES: N[C@@H](C[C@H](CCCc1ccc(OCC[18F])cc1)C(=O)O)C(=O)O]

[$^{18}$F]Fluoride (1353 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of di-tert-butyl (4S)—N-(tert-butoxycarbonyl)-4-(3-{4-[2-(tosyloxy)ethoxy]phenyl}propyl)-L-glutamate in 1 mL acetonitrile were added to the dried residue. The resulting mixture was stirred at 100° C. for 10 min. After cooling for 5 min at rt, 2M HCl (1 mL) was added and the mixture was stirred at 120° C. for 10 min. The crude product was diluted with water (pH 2) up to 30 mL and passed through a preconditioned Strata-X-C cartridge (Phenomenex). The cartridge was washed with 30 mL water (pH 2) and 45 mL ethanol. 128 MBq (14% d.c.) (4S)-4-{3-[4-(2-[$^{18}$F]fluoroethoxy)phenyl]propyl}-L-glutamic acid ([$^{18}$F]-25) were eluted with 5 mL phosphate buffer (7 g Na$_2$HPO$_4$.2H$_2$O; 6 g NaCl in 1 L water). Radiochemical purity was determined to be >95% (t$_R$=3.1 min, analytical HPLC method C).

Example 28

(4R)-4-{[5-(3-Fluoropropyl)pyridin-2-yl]methyl}-L-glutamic acid

28

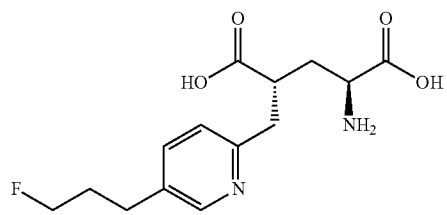

a) Di-tert-butyl (4R)-4-[(5-bromopyridin-2-yl)methyl]-Nert-butoxycarbonyl)-L-glutamate

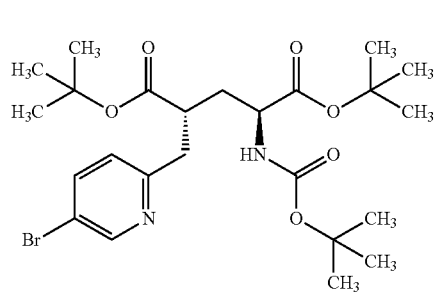 [SMILES: CC(C)(C)OC(=O)N[C@@H](C[C@H](Cc1ccc(Br)cn1)C(=O)OC(C)(C)C)C(=O)OC(C)(C)C]

To a solution of 575 mg (1.60 mmol) di-tert-butyl N-(tert-butoxycarbonyl)-L-glutamate in tetrahydrofuran (4 ml) at −78° C., lithium 1,1,1,3,3,3-hexamethyldisilazan-2-ide (1.0 M in tetrahydrofuran, 3.52 ml) was added dropwise. The solution was stirred for 2 h, then 5-bromo-2-(bromomethyl)pyridine (for synthesis see for example *Bioorg. Med. Chem.* 2008, 16, 1992-2010) (1.08 g, 3.38 mmol) dissolved in 4 ml tetrahydrofuran were added slowly. The reaction was stirred for additional 3 h and than quenched by the addition of 5 ml of 2 N aqueous hydrogen chloride. The mixture was warmed to room temperature poured into 10 ml 1 N aqueous hydrogen chloride and extracted with dichloromethane (3×20 ml). The organic phases were washed with 1 N aqueous sodium hydrogen carbonate solution (2×20 ml) and brine (20 ml), dried over sodium sulfate and concentrated in vacuo. The crude product was purified on silica gel using a hexane/ethyl acetate gradient, and the appropriate fractions were combined and concentrated.

Yield: 233 mg (27.5%)

$^1$H-NMR (300 MHz, CHLOROFORM-d): δ [ppm]=1.37 (s, 9H), 1.44 (s, 9H), 1.46 (s, 9H), 1.82-2.05 (m, 2H), 2.85-3.12 (m, 3H), 4.10-4.32 (m, 1H), 5.01 (d, 1H), 7.07 (d, 1H), 7.70 (dd, 1H), 8.50-8.65 (m, 1H).

ESI+ m/z 529.3 (M+H).

b) Di-tert-butyl (4R)—N-(tert-butoxycarbonyl)-4-({5-[(E)-3-{[tert-butyl(dimethyl)silyl]oxy}prop-1-en-1-yl]pyridin-2-yl}methyl)-L-glutamate

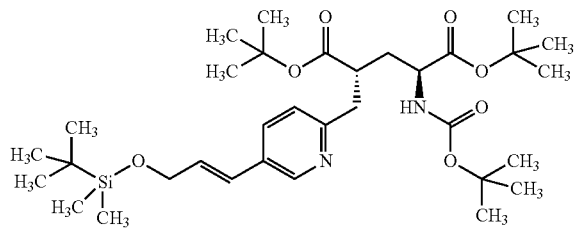 [SMILES: CC(C)(C)OC(=O)N[C@@H](C[C@H](Cc1ccc(/C=C/CO[Si](C)(C)C(C)(C)C)cn1)C(=O)OC(C)(C)C)C(=O)OC(C)(C)C]

Di-tert-butyl (4R)-4-[(5-bromopyridin-2-yl)methyl]-Nert-butoxycarbonyl)-L-glutamate (233 mg, 0.44 mmol) was dissolved in 1,2-dimethoxyethane (2 ml). Tert-butyl(dimethyl){[(E)-3-(4,4,5,5-tetramethyl-1,3,2-dioxaborolan-2-yl)prop-2-en-1-yl]oxy}silane (197 mg, 0.66 mmol), palladium(II) acetate (10 mg, 0.04 mmol), triphenylphosphine (46 mg, 0.18 mmol), and potassium carbonate (182 mg, 18.68 mmol) were added, and nitrogen was bubbled through the solution for 10 min. Then, 40 µl water were added and nitrogen was bubbled through the solution for additional 20 min. The solution was stirred at 80° C. for 16 h. After cooling to room temperature, the mixture was filtered, the filtrate was concentrated and purified on silica gel using a hexane/ethyl acetate gradient. The appropriate fractions were combined and concentrated.

Yield: 140 mg (51.2%)

ESI+ m/z 621.3 (M+H).

c) Di-tert-butyl (4R)—N-(tert-butoxycarbonyl)-4-{[5-(3-{[tert-butyl(dimethyl)silyl]-oxy}propyl)pyridin-2-yl]methyl}-L-glutamate

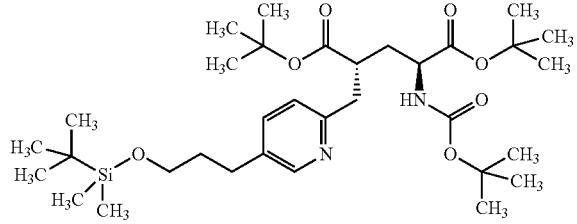 [SMILES: CC(C)(C)OC(=O)N[C@@H](C[C@H](Cc1ccc(CCCO[Si](C)(C)C(C)(C)C)cn1)C(=O)OC(C)(C)C)C(=O)OC(C)(C)C]

To a solution of 140 mg (0.23 mmol) di-tert-butyl (4R)—N-(tert-butoxycarbonyl)-4-({5-[(E)-3-{[tert-butyl(dimethyl)silyl]oxy}prop-1-en-1-yl]pyridin-2-yl}methyl)-L-glutamate in 8 ml of methanol, palladium (10% on charcoal, 7 mg) was added and the suspension was stirred for 3 h at room temperature under a hydrogen atmosphere. The mixture was filtered over celite, and the solvent was evaporated. The crude material was used without further purification.

Yield: 140 mg (99.7%)

ESI+ m/z 623.5 (M+H).

d) Di-tert-butyl (4R)—N-(tert-butoxycarbonyl)-4-{[5-(3-hydroxypropyl)pyridin-2-yl]methyl}-L-glutamate

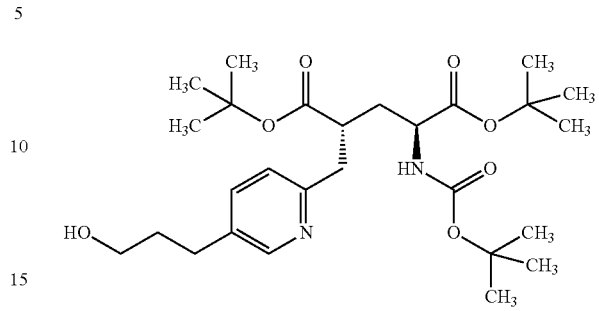

To a solution of di-tert-butyl (4R)—N-(tert-butoxycarbonyl)-4-{[5-(3-{[tert-butyl(dimethyl)silyl]oxy}propyl)pyridin-2-yl]methyl}-L-glutamate (140 mg, 0.23 mmol) in tetrahydrofuran (7 ml) was added acetic acid (80 µl, 1.40 mmol). The solution was cooled to 0° C., and tetra-n-butylammonium fluoride (1M in tetrahydrofuran, 674 µl) was added dropwise. The cooling bath was removed and the reaction was stirred overnight, then mixed with 1 N aqueous sodium hydrogen carbonate solution (20 ml), and extracted with dichloromethane (3×20 ml). The organic phases were washed with brine (10 ml), dried over sodium sulfate and concentrated in vacuo. The crude material was used without further purification.

Yield: 122 mg (106.7% crude)

ESI+ m/z 509.2 (M+H).

e) Di-tert-butyl (4R)—N-(tert-butoxycarbonyl)-4-{[5-(3-fluoropropyl)pyridin-2-yl]-methyl}-L-glutamate

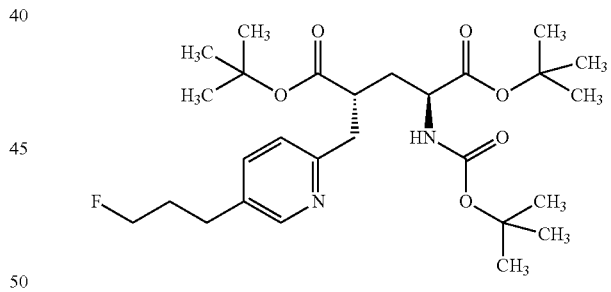

Di-tert-butyl (4R)—N-(tert-butoxycarbonyl)-4-{[5-(3-hydroxypropyl)pyridin-2-yl]methyl}-L-glutamate (68 mg, 0.13 mmol) was dissolved in 2 ml tetrahydrofuran, and cooled to 0° C. Triethylamine (280 µl, 2.01 mmol), 1,1,2,2,3,3,4,4,4-nonafluorobutane-1-sulfonyl fluoride (162 mg, 0.53 mmol), and triethylamine trihydrofluoride (86 mg, 0.53 mmol) were added, and the reaction was stirred at room temperature for 24 h. The same amounts of triethylamine, 1,1,2,2,3,3,4,4,4-nonafluorobutane-1-sulfonyl fluoride and triethylamine trihydrofluoride were added again and the reaction was continued for 1 h. Water (10 ml) was added, and the mixture was extracted with dichloromethane (3×10 ml). The organic phases were dried over magnesium sulfate and concentrated. The so derived material was used without further purification.

Yield 72 mg (105.5% crude)

ESI+ m/z 511.2 (M+H).

f) (4R)-4-{[5-(3-Fluoropropyl)pyridin-2-yl]methyl}-L-glutamic acid

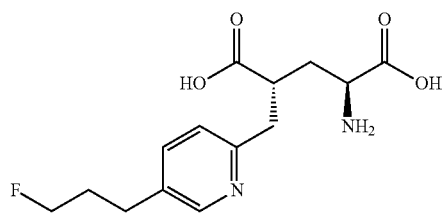

Di-tert-butyl (4R)—N-(tert-butoxycarbonyl)-4-{[5-(3-fluoropropyl)pyridin-2-yl]methyl}-L-glutamate (68 mg, 0.13 mmol) was solved in 3 ml trifluoroacetic acid and stirred for 24 h. To the mixture was added toluene (10 ml) and the resulting solution was concentrated in vacuo. The crude product was purified by HPLC. The appropriate fractions were collected, the acetonitrile evaporated under reduced pressure and the remaining aqueous solution was lyophilized.

Yield: 18 mg (45.3%)

$^1$H-NMR (400 MHz, DMSO-$d_6$): δ [ppm]=1.76-1.87 (m, 1H), 1.88-2.09 (m, 3H), 2.95-3.05 (m, 1H), 3.05-3.14 (m, 4H), 3.82-3.92 (m, 1H), 4.40 (t, 1H), 4.52 (t, 1H), 7.34 (d, 1H), 7.73-7.81 (m, 1H), 8.42-8.45 (m, 1H).

ESI+ m/z 299.3 (M+H).

Example 29

Di-tert-butyl (4R)—N-(tert-butoxycarbonyl)-4-({5-[3-(tosyloxy)propyl]pyridin-2-yl}-methyl)-L-glutamate

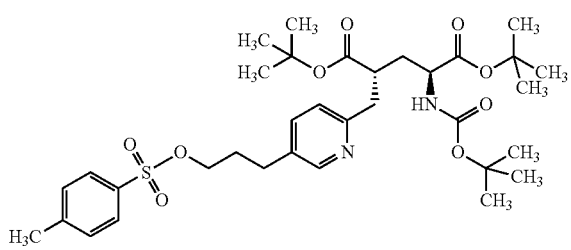 [SMILES: Cc1ccc(S(=O)(=O)OCCCc2ccc(C[C@@H](C[C@H](NC(=O)OC(C)(C)C)C(=O)OC(C)(C)C)C(=O)OC(C)(C)C)nc2)cc1]

Di-tert-butyl (4R)—N-(tert-butoxycarbonyl)-4-{[5-(3-hydroxypropyl)pyridin-2-yl]methyl}-L-glutamate (25 mg, 0.05 mmol) was dissolved in dichloromethane (0.5 ml), and p-toluenesulfonic anhydride (Aldrich) (27 mg, 0.08 mmol), triethylamine (13 µl, 0.09 mmol) and 4-(dimethylamino)pyridine (0.3 mg, 2 µmol) were added at room temperature. The reaction was stirred for 2 h, then poured into 5 ml water. The mixture was extracted with dichloromethane (3×5 ml). The organic phases were concentrated in vacuo, and the crude product was chromatographed on silica gel using a hexane/ethyl acetate gradient, and the appropriate fractions were combined and concentrated.

Yield: 15 mg (44.8%)

$^1$H-NMR (600 MHz, CHLOROFORM-d): δ [ppm]=1.35 (s, 9H), 1.43 (s, 9H), 1.44 (s, 9H), 1.90-2.02 (m, 4H), 2.47 (s, 3H), 2.63 (t, 2H), 2.88-2.98 (m, 2H), 2.99-3.08 (m, 1H), 4.05 (t, 2H), 4.11-4.18 (m, 1H), 5.06 (d, 1H), 7.04 (d, 1H), 7.30-7.34 (m, 1H), 7.34-7.38 (m, 2H), 7.77-7.83 (m, 2H), 8.28 (s, 1H).

ESI+ m/z 663.3 (M+H).

Example 30

Di-tert-butyl (4R)—N-(tert-butoxycarbonyl)-4-{[5-(2-{[(4-methylphenyl)sulfonyl]oxy}ethoxy)pyridin-2-yl]methyl}-L-glutamate

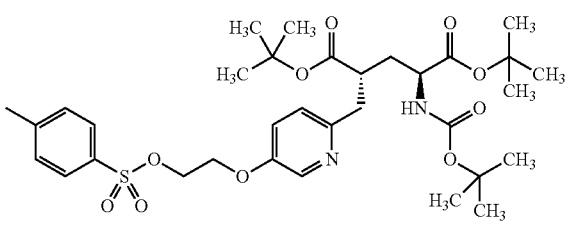 [SMILES: Cc1ccc(S(=O)(=O)OCCOc2ccc(C[C@@H](C[C@H](NC(=O)OC(C)(C)C)C(=O)OC(C)(C)C)C(=O)OC(C)(C)C)nc2)cc1]

To a solution of 150 mg di-tert-butyl (4R)—N-(tert-butoxycarbonyl)-4-[(5-hydroxypyridin-2-yl)methyl]-L-glutamate (0.32 mmol) in N,N-dimethylformamide (8 mL) was added 126 mg of cesium carbonate (0.39 mmol), followed by 143 mg of 1,2-ethanediol di-p-toluenesulfonate (0.39 mmol). The mixture was stirred for 5 h at room temperature. Water was added, the mixture was extracted with dichloromethane, and the organic layer was washed with brine, dried over magnesium sulfate, and evaporated. The crude product was purified by preparative HPLC (method A) to give 86 mg (40% yield) of the title compound.

$^1$H-NMR (300 MHz, CHLOROFORM-d): δ [ppm]=1.37 (s, 9H), 1.43 (s, 9H), 1.45 (s, 9H), 1.79-2.05 (m, 2H), 2.46 (s, 3H), 2.79-3.09 (m, 3H), 4.09-4.22 (m, 3H), 4.34-4.43 (m, 2H), 5.04 (br. d, 1H), 6.98-7.09 (m, 2H), 7.36 (d, 2H), 7.82 (d, 2H), 8.10 (br. s, 1H).

ESI+ m/z 665 (M+H)

Example 31

(4-{[5-(2-[$^{18}$F]fluoroethoxy)pyridin-2-yl]methyl}-L-glutamic acid

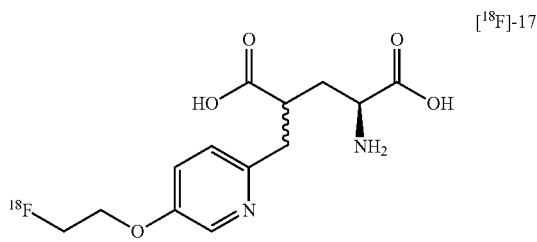 [SMILES: N[C@@H](CC(Cc1ccc(OCC[18F])cn1)C(=O)O)C(=O)O]

[$^{18}$F]Fluoride (2120 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of di-tert-butyl (4R)—N-(tart-butoxycarbonyl)-4-{[5-(2-{[(4-methylphenyl)sulfonyl]oxy}ethoxy)pyridin-2-yl]methyl}-L-glutamate in 1 mL acetonitrile were added to the dried residue. The resulting mixture was stirred at 120° C. for 10 min. After cooling to rt, 2M HCl (1 mL) was added and the mixture was stirred at 120° C. for 4 min. The crude product was diluted with water (pH 2) up to 30 mL and passed through a preconditioned Strata-X-C cartridge (200 mg, Phenomenex). The cartridge was washed with 30 mL water (pH 2) and 20 mL ethanol. The cartridge was eluted with 5 mL phosphate buffer (7 g $Na_2HPO_4.2H_2O$; 6 g NaCl in 1 L water) yielding 520 MBq (42% d.c.) (4-{[5-(2-fluoroethoxy)pyridin-2-yl]methyl}-L-glutamic acid ([$^{18}$F]-17) in a fraction of 1 ml buffer. Radiochemical purity was determined to be >95% ($t_R$=2.7 min, analytical HPLC method F).

Example 32

(2S)-2-Amino-5-{[5-(2-fluoroethoxy)pyridin-2-yl]methyl}hexanedioic acid

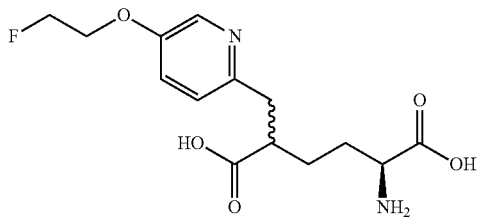

a) 4-Benzyl 1,4-di-tert-butyl (1S)-5-[5-(benzyloxy)pyridin-2-yl]-1-[(tert-butoxycarbonyl)amino]pentane-1,4,4-tricarboxylate

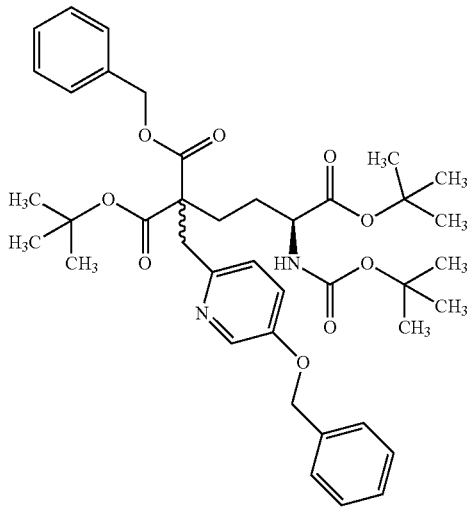 [SMILES: CC(C)(C)OC(=O)N[C@@H](CCC(Cc1ccc(OCc2ccccc2)cn1)(C(=O)OCc1ccccc1)C(=O)OC(C)(C)C)C(=O)OC(C)(C)C]

To a solution of 360 mg of di-tert-butyl (5S)-2-(benzyloxycarbonyl)-5-[(tert-butoxy-carbonyl)amino]hexanedioate (0.71 mmol; see example 12f) in N,N-dimethyl formamide (10 mL) was added under argon atmosphere 26 mg of sodium hydride (60% in oil, 0.64 mmol). The resulting mixture was stirred at room temperature for 30 minutes. A solution of 197 mg 5-(benzyloxy)-2-(bromomethyl)pyridine (prepared according to example 17a; 0.71 mmol) in N,N-dimethylformamide (5 mL) was added, and the mixture was stirred at 60° C. for one hour. After cooling to room temperature, the mixture was concentrated in vacuo and the residue was purified by preparative HPLC (method A) to give 327 mg of the title compound (65% yield).

$^1$H-NMR (400 MHz, CHLOROFORM-d): δ [ppm]=1.35 (s, 9H, major diastereomer), 1.36 (s, 9H, minor diastereomer), 1.40-1.50 (m, 18H), 1.68-2.00 (m, 4H), 3.24-3.37 (m, 2H), 4.01-4.12 (m, 1H), 5.03-5.23 (m, 4H), 5.97 (br. d, minor diastereomer, 1H), 6.14 (br. d, major diastereomer, 1H), 6.82-6.92 (m, 1H), 7.02-7.09 (m, 1H), 7.31-7.44 (m, 10H), 8.32-8.38 (m, 1H).

ESI+ m/z 705 (M+H).

b) (5S)-6-tert-Butoxy-2-(tert-butoxycarbonyl)-5-[(tert-butoxycarbonyl)amino]-2-[(5-hydroxypyridin-2-yl)methyl]-6-oxohexanoic acid

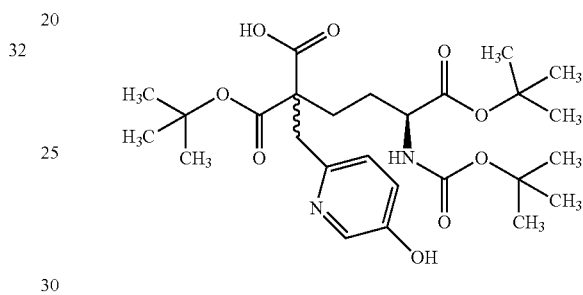

To a solution of 310 mg of 4-benzyl 1,4-di-tert-butyl (1S)-5-[5-(benzyloxy)pyridin-2-yl]-1-[(tert-butoxycarbonyl)amino]pentane-1,4,4-tricarboxylate (0.44 mmol) in methanol (10 mL) was added a 10% palladium on carbon hydrogenation catalyst (15 mg) at room temperature. The suspension was stirred for 3 h at room temperature under an atmosphere of hydrogen. The catalyst was removed by filtration and all volatiles were removed in vacuo. The crude product (234 mg, quantitative yield) was used in the next step without further purification.

$^1$H-NMR $^1$H-NMR (400 MHz, CHLOROFORM-d): δ [ppm]=1.27 (s, minor diastereomer, 9H), 1.28 (s, major diastereomer, 9H), 1.43-1.52 (m, 18H), 1.68-2.23 (m, 4H), 2.91-3.06 (m, 1H), 3.43-3.56 (m, 1H), 4.10-4.23 (m, 1H), 5.15-5.27 (m, 1H), 7.24-7.31 (m, 1H, overlaps with solvent signal), 7.50-7.60 (m, 1H), 8.24 (d, major diastereomer, 1H), 8.27 (d, minor, diastereomer, 1H).

ESI+ m/z 525 (M+H).

c) Di-tert-butyl (2S)-2-[(tert-butoxycarbonyl)amino]-5-[(5-hydroxypyridin-2-yl)methyl]hexanedioate

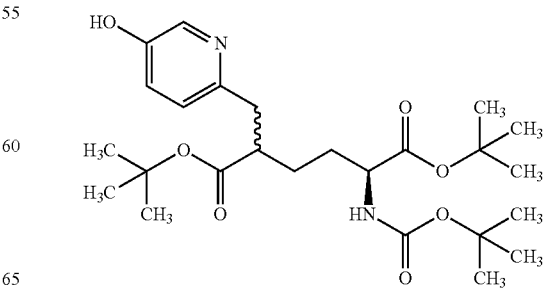

A solution of 220 mg of (5S)-6-tert-butoxy-2-(tert-butoxy-carbonyl)-5-[(tert-butoxycarbonyl)amino]-2-[(5-hydroxy-pyridin-2-yl)methyl]-6-oxohexanoic acid (0.42 mmol) and 100 mg 4-N,N-dimethylaminopyridine (0.84 mmol) in 1,4-dioxan (10 mL) was heated under reflux for 2 hours. The mixture was evaporated and the residue was purified by column preparative HPLC (method C) to give two batches (107+49 mg; 78% combined yield) of the target compound.

$^1$H-NMR (taken from main batch; 400 MHz, CHLOROFORM-d): δ [ppm]=1.36 (s, 9H), 1.41-1.50 (m, 18H), 1.58-1.75 (m, 3H), 1.78-1.91 (m, 1H), 2.70-2.84 (m, 1H), 2.90 (dd, 1H), 3.05 (dd, 1H), 4.11-4.23 (m, 1H), 5.10-5.21 (m, 1H), 5.99 (br. s, 1H), 7.12-7.21 (m, 1H), 7.28-7.35 (m, 1H), 8.32-8.39 (m, 1H).

ESI+ m/z 481 (M+H).

d) Di-tert-butyl (2S)-2-[(tert-butoxycarbonyl)amino]-5-{[5-(2-fluoroethoxy)pyridin-2-yl]methyl}hexanedioate

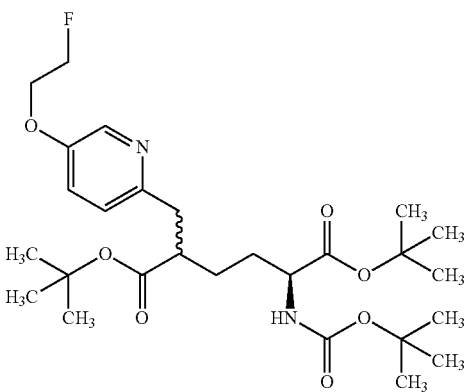 [SMILES: CC(C)(C)OC(=O)N[C@@H](CCC(Cc1ccc(OCCF)cn1)C(=O)OC(C)(C)C)C(=O)OC(C)(C)C]

To a solution of 54 mg 1-fluoro-2-iodoethane (0.31 mmol) in N,N-dimethylformamide (10 mL) was subsequently added 101 mg potassium carbonate (0.73 mmol), followed by 100 mg of di-tert-butyl (2S)-2-[(tert-butoxycarbonyl)amino]-5-[(5-hydroxypyridin-2-yl)methyl]hexanedioate (0.21 mmol), and the resulting mixture was stirred for 20 h at room temperature. The mixture was then partitioned between water and ethyl acetate, the aqueous layer was then extracted with ethyl acetate again. The combined organic layers were washed with brine, dried over sodium sulfate, and evaporated. The residue was purified by preparative HPLC, method A to give 56 mg (approx. 90% purity, 46% purity adjusted yield) of the target compound.

$^1$H-NMR $^1$H-NMR (300 MHz, CHLOROFORM-d): δ [ppm]=1.37 (s, 9H), 1.45 (s, 18H), 1.55-1.91 (m, 4H), 2.71-2.88 (m, 2H), 2.96-3.10 (m, 1H), 4.10-4.33 (m, 3H), 4.65-4.89 (m, 2H), 5.05-5.17 (m, 1H), 7.03-7.20 (m, 2H), 8.23-8.29 (m, 1H).

ESI+ m/z 527 (M+H).

e) (2S)-2-Amino-5-{[5-(2-fluoroethoxy)pyridin-2-yl]methyl}hexanedioic acid

32

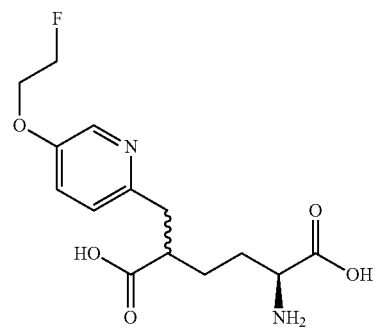

To a solution of 56 mg of di-tert-butyl (2S)-2-[(tert-butoxycarbonyl)amino]-5-{[5-(2-fluoroethoxy)pyridin-2-yl]methyl}hexanedioate (0.1 mmol) in anisol (0.7 mL) was added trifluoroacetic acid (1.5 mL), and the resulting mixture was stirred for 3 h at room temperature. Trifluoroacetic acid was removed under reduced pressure, water (approx. 2 mL) was added and separating anisol (which was expected to encumber preparative HPLC if present in large excess) was removed. The remaining aqueous solution of the crude product was directly loaded onto a preparative HPLC, method B, to give 14 mg of the target compound as white, hygroscopic lyophilisate (approx. 40% yield).

$^1$H-NMR (300 MHz, DEUTERIUM OXIDE): δ [ppm]=1.50-1.97 (m, 4H), 2.70-2.82 (m, 1H), 3.10-3.20 (m, 2H), 3.68-3.81 (m, 1H), 4.39-4.57 (m, 2H), 4.76-4.97 (m, 2H, overlaps with solvent signal), 7.71-7.80 (m, 1H), 8.00-8.10 (m, 1H), 8.31-8.39 (m, 1H).

ESI+ m/z 315 (M+H).

Example 33

Di-tert-butyl (2S)-2-[(tert-butoxycarbonyl)amino]-5-{[5-(2-{[(4-methylphenyl)-sulfonyl]oxy}ethoxy)pyridin-2-yl]methyl}hexanedioate

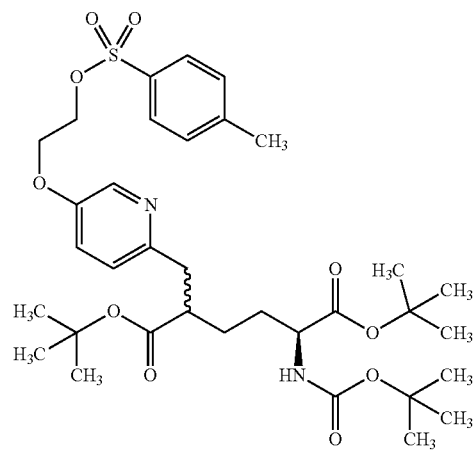 [SMILES: Cc1ccc(S(=O)(=O)OCCOc2ccc(CC(CC[C@H](NC(=O)OC(C)(C)C)C(=O)OC(C)(C)C)C(=O)OC(C)(C)C)nc2)cc1]

To a solution of 69 mg 1,2-ethanediol di-p-toluenesulfonate (0.19 mmol) in N,N-dimethylformamide (4.5 mL) was subsequently added 61 mg cesium carbonate (0.19 mmol), followed by 45 mg of di-tert-butyl (2S)-2-[(tert-butoxycarbonyl)amino]-5-[(5-hydroxypyridin-2-yl)methyl] hexanedioate (0.09 mmol), and the resulting mixture was stirred for 20 h at room temperature. The mixture was then concentrated in vacuo and partitioned between water and dichloromethane. The organic layer was washed with brine, dried over sodium sulfate, and evaporated. Purification by preparative HPLC (Method A) gave 37 mg (58% purity adjusted yield) of the desired tosylate in approx. 90% purity.

$^1$H-NMR (300 MHz, CHLOROFORM-d): δ [ppm]=1.34-1.39 (m, 9H), 1.41-1.48 (m, 18H), 1.54-1.90 (m, 4H), 2.46 (s, 3H), 2.70-3.07 (m, 3H), 4.10-4.21 (m, 3H), 4.34-4.42 (m, 2H), 5.05-5.15 (m, 1H), 6.99-7.08 (m, 2H), 7.36 (d, 2H), 7.83 (d, 2H), 8.08-8.13 (m, 1H).

ESI+ m/z 679 (M+H).

Example 34

(2S)-2-Amino-5-{[5-(2-[$^{18}$F]fluoroethoxy)pyridin-2-yl]methyl}hexanedioic acid

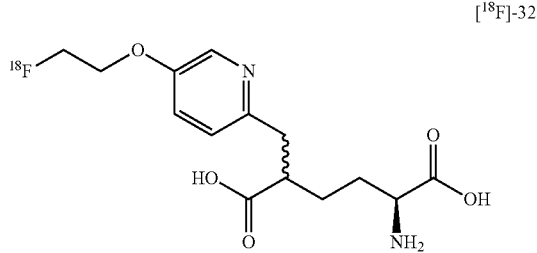 [SMILES: N[C@@H](CCC(Cc1ccc(OCC[18F])cn1)C(=O)O)C(=O)O]

[$^{18}$F]-32

[$^{18}$F]Fluoride (2482 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of di-tert-butyl (2S)-2-[(tert-butoxycarbonyl)amino]-5-{[5-(2-{[(4-methylphenyl)sulfonyl]oxy}ethoxy)pyridin-2-yl]methyl}hexanedioate in 1 mL acetonitrile were added to the dried residue. The resulting mixture was stirred at 120° C. for 10 min. After cooling to rt, 2M HCl (1 mL) was added and the mixture was stirred at 120° C. for 5 min. The crude product was diluted with 30 mL water (pH 2) and passed through a preconditioned Strata-X-C cartridge (200 mg, Phenomenex). The cartridge was washed with 20 mL water (pH 2) and 20 mL ethanol. The cartridge was eluted with 5 mL phosphate buffer (7 g Na$_2$HPO$_4$.2H$_2$O; 6 g NaCl in 1 L water) yielding 307 MBq (19% d.c.) (2S)-2-Amino-5-{[5-(2-[$^{18}$F]fluoroethoxy)pyridin-2-yl]methyl}hexanedioic acid ([$^{18}$F]-32) in a fraction of 1 ml buffer. Radiochemical purity was determined to be >99% ($t_R$=2.8 min, analytical HPLC method F).

Example 35

(4R)-4-{[5-(2-fluoroethoxy)-1-oxidopyridin-2-yl]methyl}-L-glutamic acid

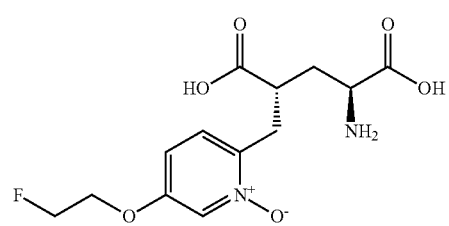

a) di-tert-Butyl (4R)—N-(tert-butoxycarbonyl)-4-{[5-(2-fluoroethoxy)-1-oxidopyridin-2-yl]methyl}-L-glutamate

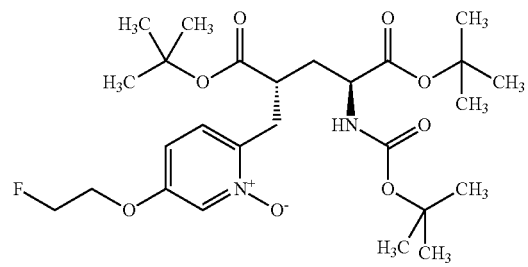 [SMILES: CC(C)(C)OC(=O)N[C@@H](C[C@H](Cc1ccc(OCCF)c[n+]1[O-])C(=O)OC(C)(C)C)C(=O)OC(C)(C)C]

To a solution of 350 mg di-tert-butyl (4R)—N-(tert-butoxycarbonyl)-4-{[5-(2-fluoroethoxy)pyridin-2-yl]methyl}-L-glutamate (0.68 mmol; see Example 17d) in dichloromethane (5 mL) was added 185 mg meta-chloro peroxybenzoic acid (70%), and the mixture was stirred for 1 h at room temperature. The mixture was extracted with aqueous sodium bicarbonate, followed by re-extraction of the aqueous layer with dichloromethane. The combined organic layers were concentrated in vacuo, and the residue was purified by preparative HPLC (Method D) to give 340 mg of the target compound (93% yield).

$^1$H-NMR (300 MHz, CHLOROFORM-d): δ [ppm]=1.35 (s, 9H), 1.43 (s, 9H), 1.47 (s, 9H), 1.86-2.14 (m, 2H), 2.88-3.23 (m, 3H), 4.10-4.31 (m, 3H), 4.62-4.89 (d, 2H), 5.12 (d br, 1H), 6.84 (dd, 1H), 7.13 (d, 1H), 8.04 (d, 1H).

ESI+ m/z 529 (M+H).

b) (4R)-4-{[5-(2-fluoroethoxy)-1-oxidopyridin-2-yl]methyl}-L-glutamic acid

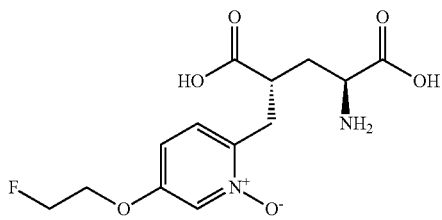

To a solution of 170 mg of di-tert-butyl (4R)—N-(tert-butoxycarbonyl)-4-{[5-(2-fluoroethoxy)-1-oxidopyridin-2-yl]methyl}-L-glutamate (0.32 mmol) in dichloromethane (10 mL) was added trifluoroacetic acid (124 µL, 5 eq) and the mixture was stirred for 2 h at room temperature. LC/MS revealed substantial quantities of starting material were present; hence an additional 5 eq of trifluoroacetic acid were added and stirring at room temperature was continued overnight. Repeated LC/MS still showed incomplete removal of the protecting groups. The mixture was evaporated, re-dissolved in trifluoroacetic acid and dichloromethane (2 mL each) and stirred at room temperature for another 2 h, whereupon the reaction was complete. The mixture was evaporated and the residue was purified by preparative HPLC (Method E), followed by lyophilisation to give 95 mg of the target compound as light brown lyophilisate in approx. 90% purity (84% purity adjusted yield).

$^1$H-NMR (300 MHz, DMSO-$d_6$): δ [ppm]=1.60-1.94 (m, 2H), 2.73-2.87 (m, 1H), 2.92-3.06 (m, 1H), 3.08-3.25 (m, 1H), 3.51-3.65 (m, 1H), 4.18-4.45 (m, 2H), 4.56-4.90 (m, 2H), 7.05 (dd, 1H), 7.30 (d, 1H), 8.11 (d, 1H).

ESI+ m/z 317 (M+H).

Example 36

Di-tert-butyl (4R)—N-(tert-butoxycarbonyl)-4-{[5-(2-{[(4-methylphenyl)sulfonyl]oxy}ethoxy)-1-oxidopyridin-2-yl]methyl}-L-glutamate

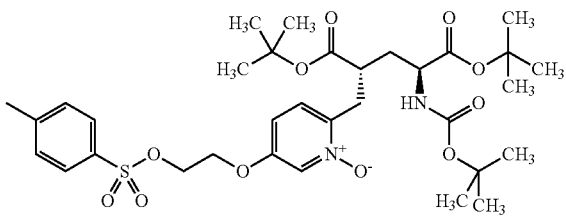 [SMILES: Cc1ccc(S(=O)(=O)OCCOc2ccc(C[C@@H](C[C@H](NC(=O)OC(C)(C)C)C(=O)OC(C)(C)C)C(=O)OC(C)(C)C)[n+]([O-])c2)cc1]

To a solution of 125 mg di-tert-butyl (4R)—N-(tert-butoxycarbonyl)-4-{[5-(2-{[(4-methylphenyl)sulfonyl]oxy}ethoxy)pyridin-2-yl]methyl}-L-glutamate (0.19 mmol; see Example XB) in dichloromethane (10 mL) was added 51 mg meta-chloro peroxybenzoic acid (70%), and the mixture was stirred for 3 h at room temperature. The mixture was extracted with aqueous sodium bicarbonate, followed by re-extraction of the aqueous layer with dichloromethane. The combined organic layers were dried over magnesium sulfate and concentrated in vacuo, and the residue was purified by preparative HPLC. (Method D) to give 104 mg of the target compound as colourless foam (81% yield).

$^1$H-NMR (300 MHz, CHLOROFORM-d): δ [ppm]=1.35 (s, 9H), 1.43 (s, 9H), 1.47 (s, 9H), 1.84-2.13 (m, 2H), 2.48 (s, 3H), 2.89-3.18 (m, 3H), 4.08-4.26 (m, 3H), 4.32-4.41 (m, 2H), 5.11 (d br, 1H), 6.68-6.76 (m, 1H), 7.09 (d, 1H), 7.38 (d, 2H), 7.78-7.89 (m, 3H).

ESI+ m/z 681 (M+H).

Example 37

4-{[5-(2-[$^{18}$F]fluoroethoxy)-1-oxidopyridin-2-yl]methyl}-L-glutamic acid

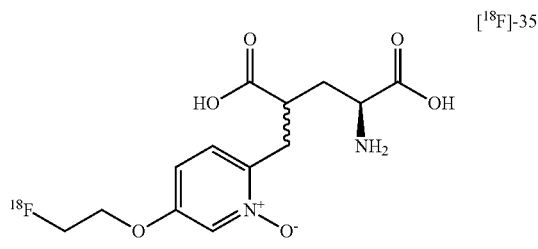 [SMILES: N[C@@H](CC(Cc1ccc(OCC[18F])c[n+]1[O-])C(=O)O)C(=O)O]

[$^{18}$F]-35

[$^{18}$F]Fluoride (2500 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of di-tert-butyl (4R)—N-(tert-butoxycarbonyl)-4-{[5-(2-{[(4-methylphenyl)sulfonyl]oxy}ethoxy)-1-oxidopyridin-2-yl]methyl}-L-glutamate in 1 mL acetonitrile were added to the dried residue. The resulting mixture was stirred at 120° C. for 10 min. After cooling to rt, 2M HCl (1 mL) was added and the mixture was stirred at 120° C. for 5 min. The crude product was diluted to 30 mL with water (pH 2) and passed through a preconditioned Strata-X-C cartridge (200 mg, Phenomenex). The cartridge was washed with 30 mL water (pH 2) and 50 mL ethanol. The cartridge was eluted with 5 mL phosphate buffer (7 g Na$_2$HPO$_4$.2H$_2$O; 6 g NaCl in 1 L water) yielding 765 MBq (45% d.c.) 4-{[5-(2-[$^{18}$F]fluoroethoxy)-1-oxidopyridin-2-yl]methyl}-L-glutamic acid ([$^{18}$F]-35) in a fraction of 2 ml buffer. Radiochemical purity was determined to be >93% ($t_R$=2.8 min, analytical HPLC method F). Further purification via an additional OASIS MCX cartridge (OASIS MCX plus, Waters) afforded a fraction of 24 MBq [$^{18}$F]-35 in 1 mL buffer with a radiochemical purity of >97%.

Example 38

(2S)-2-amino-5-{2-[4-(2-fluoroethoxy)phenyl]ethyl}hexanedioic acid

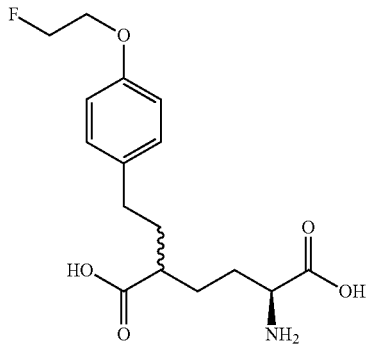

a) 1-(Benzyloxy)-4-(2-bromoethyl)benzene

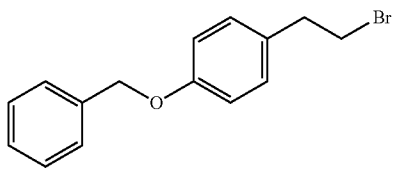 [SMILES: BrCCc1ccc(OCc2ccccc2)cc1]

To a cooled (0° C.) solution of 3.00 g 4-benzyloxy phenethyl alcohol (13.1 mmol) in dichloromethane (132 mL) were added subsequently 5.17 g of triphenylphosphine (19.7 mmol) and 6.54 g carbon tetrabromide (19.7 mmol). The resulting mixture was stirred for 2 h at room temperature and was then evaporated. The residue was triturated with diethyl ether at −20° C. for 30 minutes, and then all solids were removed by filtration. and the filtrate was concentrated in vacuo. The residue was subjected to column chromatography on silica gel (1%→10% ethyl acetate in hexane) to give 2.80 g of the target compound (73% yield) as a pale yellow oil crystallizing upon standing.

$^1$H-NMR (400 MHz, CHLOROFORM-d): δ [ppm]=3.11 (t, 2H), 3.54 (t, 2H), 5.06 (s, 2H), 6.91-6.98 (m, 2H), 7.10-7.18 (m, 2H), 7.30-7.48 (m, 5H).

b) 4-Benzyl 1,4-di-tert-butyl (1S)-6-[4-(benzyloxy)phenyl]-1-[(tert-butoxycarbonyl)amino]hexane-1,4,4-tricarboxylate

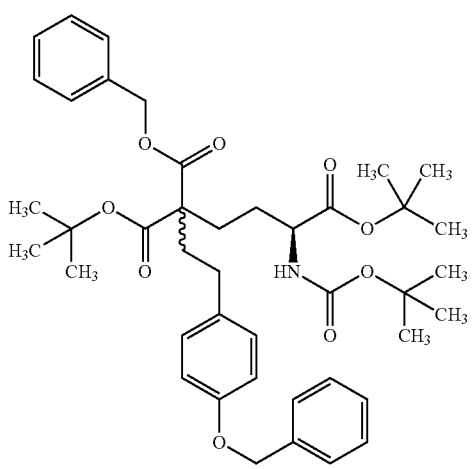 [SMILES: CC(C)(C)OC(=O)N[C@@H](CCC(CCc1ccc(OCc2ccccc2)cc1)(C(=O)OCc1ccccc1)C(=O)OC(C)(C)C)C(=O)OC(C)(C)C]

To a solution of 1.11 g di-tert-butyl (5S)-2-(benzyloxycarbonyl)-5-[(tert-butoxycarbonyl)-amino]hexanedioate (2.19 mmol; see example 12f) in N,N-dimethyl formamide (30 mL) was added under argon atmosphere 96 mg of sodium hydride (60% in oil, 2.40 mmol), and the mixture was stirred for 30 min at room temperature. Subsequently, a solution of 700 mg of 1-(benzyloxy)-4-(2-bromoethyl)benzene (2.40 mmol) in N,N-dimethyl formamide (15 mL) was added, an the mixture was stirred at 60° C. for 3 hours. The mixture was concentrated in vacuo, partitioned between water and ethyl acetate, and the organic layer was washed with brine, dried over sodium sulfate, and evaporated. The residue was purified by preparative HPLC (Method A) to give 413 mg of the target compound in approx. 90% purity (26% purity adjusted yield).

$^1$H-NMR (300 MHz, CHLOROFORM-d): δ [ppm]=1.33-1.39 (m, 9H), 1.41-1.51 (m, 18H), 1.57-2.14 (m, 6H), 2.29-2.48 (m, 2H), 4.15-4.26 (m, 1H), 5.00-5.25 (m, 5H), 6.84-6.91 (m, 2H), 6.98-7.06 (m, 2H), 7.28-7.47 (m, 10H).

ESI+ m/z 718 (M+H);

ESI− m/z 762 (M+HCOO⁻).

c) (5S)-6-tert-Butoxy-2-(tert-butoxycarbonyl)-5-[(tert-butoxycarbonyl)amino]-2-[2-(4-hydroxyphenyl)ethyl]-6-oxohexanoic acid

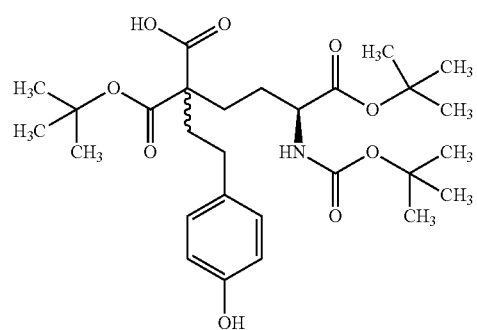 [SMILES: CC(C)(C)OC(=O)N[C@@H](CCC(CCc1ccc(O)cc1)(C(=O)O)C(=O)OC(C)(C)C)C(=O)OC(C)(C)C]

To a solution of 125 mg of 4-benzyl 1,4-di-tert-butyl (1S)-6-[4-(benzyloxy)phenyl]-1-[(tert-butoxycarbonyl)amino]hexane-1,4,4-tricarboxylate (0.18 mmol) in methanol (5 mL) was added 10% palladium on charcoal (15 mg) and the mixture was stirred under an atmosphere of hydrogen for 16 h at room temperature. The catalyst was removed by filtration, and the filtrate was evaporated to give the target compound (84 mg, 89% yield) which was used without further purification.

$^1$H-NMR (400 MHz, CHLOROFORM-d): δ [ppm]=1.44 (s, 9H). 1.47 (s, 9H), 1.54 (s, 9H), 1.59-2.44 (m, 7H), 2.46-2.57 (m, 1H), 4.09-4.25 (m, 1H), 5.08-5.20 (m, 1H), 6.75 (m, 2H), 6.95-7.03 (m, 2H).

ESI+ m/z 538 (M+H).

d) Di-tert-butyl (2S)-2-[(tert-butoxycarbonyl)amino]-5-[2-(4-hydroxyphenyl)ethyl]hexanedioate

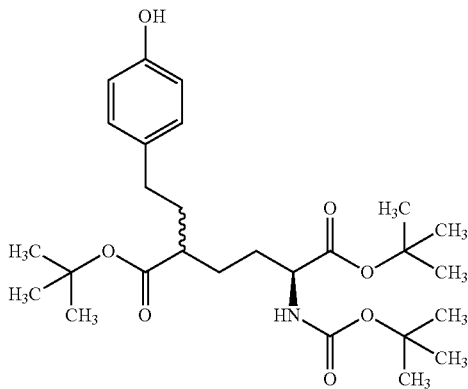 [SMILES: CC(C)(C)OC(=O)N[C@@H](CCC(CCc1ccc(O)cc1)C(=O)OC(C)(C)C)C(=O)OC(C)(C)C]

To a solution of 370 mg (5S)-6-tert-butoxy-2-(tert-butoxycarbonyl)-5-[(tert-butoxycarbonyl)amino]-2-[2-(4-hydroxyphenyl)ethyl]-6-oxohexanoic acid (0.69 mmol) in 1,4-dioxane (30 mL) was added 210 mg of 4-N,N-dimethylaminopyridine (1.72 mmol) and the mixture was stirred overnight at 100° C. (bath temperature), followed by refluxing for another 18 h. After cooling to room temperature, the mixture was concentrated in vacuo. The residue was purified by preparative HPLC (Method A) to give 169 mg (50% yield) of the target compound. In addition, 38 mg of unreacted starting material were recovered.

$^1$H-NMR (400 MHz, CHLOROFORM-d): δ [ppm]=1.42-1.51 (m, 27H), 1.53-1.82 (m, 5H), 1.82-1.94 (m, 1H), 2.19-2.35 (m, 1H), 2.43-2.61 (m, 2H), 4.10-4.24 (m, 1H), 4.85 (s br, 1H), 5.04 (d br, 1H), 6.76 (d, 2H), 7.03 (d, 2H).

ESI+ m/z 494 (M+H).

e) (2S)-2-tert.-Butoxycarbonylamino-5-{2-[4-(2-fluoro-ethoxy)-phenyl]-ethyl}-hexanedioic acid di-tert.-butyl ester

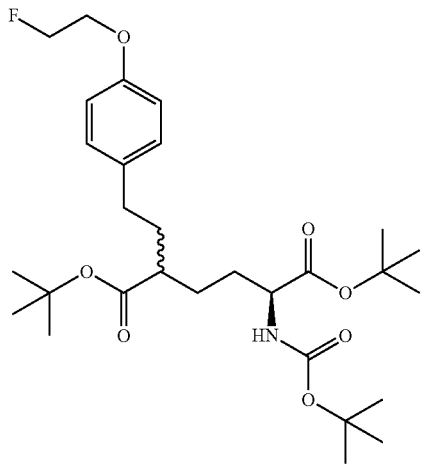 [SMILES: CC(C)(C)OC(=O)N[C@@H](CCC(CCc1ccc(OCCF)cc1)C(=O)OC(C)(C)C)C(=O)OC(C)(C)C]

53 mg (0.30 mmol) 1-Fluoro-2-iodoethane were dissolved in 5 ml dimethylformamide 98 mg (0.71 mmol) potassium carbonate and 100 mg (0.20 mmol) (2S,5RS)-2-tert.-Butoxycarbonylamino-5-[2-(4-hydroxy-phenyl)-ethyl]-hexanedioic acid di-tert.-butyl ester added. The mixture was stirred at room temperature over night. For workup, water and ethyl acetate were added, the phases separated and the water extracted with ethyl acetate twice. Combined organic phases were dried (Na2SO4), filtered and evaporated. The raw product was absorbed on Isolute and chromatographed on a Biotage Isolera system (SNAP NH 110 g, A=n-hexane, B=ethyl acetate, A 2 CV, A to 47% B in 9.4 CV, 5 CV 50% B, 50 mL/min, Fr. a 22 mL). Fractions 29 to 32 were collected to give 65 mg (59%) of (2S,5RS)-2-tert.-Butoxycarbonylamino-5-{2-[4-(2-fluoro-ethoxy)-phenyl]-ethyl}-hexanedioic acid di-tert.-butyl ester as clear oil.

MS (ESI$^+$): m/e=562 (M–Na$^+$), 540 (M–H$^+$), 440 (M+H$^+$—C$_4$H$_8$—CO$_2$), 328 (M+H$^+$-3C$_4$H$_8$—CO$_2$), 310 (328-H$_2$O).

$^{19}$F NMR (376 MHz, CHLOROFORM-d): δ ppm −223.9 (tt, J=47.0, 27.5 Hz).

$^1$H NMR (CHLOROFORM-d, 400 MHz): δ (ppm) 7.09 (d, J=8.6 Hz, 2H, Ar—H), 6.85 (d, J=8.6 Hz, 2H, Ar—H), 5.03 (d, J=7.3 Hz, 1H, NH), 4.74 (dt, $^2J_{HF}$=47.5 Hz, J=3.8 Hz, 2H, CH$_2$F), 4.10-4.27 (m, 1H), 4.20 (dt, $^3J_{HF}$=27.8 Hz, J=4.3 Hz, 2H, CH$_2$O), 2.45-2.64 (m, 1H), 2.18-2.36 (m, 1H), 1.83-1.96 (m, 1H), 1.71-1.82 (m, 1H), 1.64 (s, 5H), 1.41-1.52 (m, 27H, tBu).

$^{13}$C NMR (CHLOROFORM-d, 101 MHz): δ (ppm) 175.0, 174.8 (C-6), 171.7, 171.7 (C–1), 156.7, 156.7 (Ar C-4), 155.4, 155.3 (2 C-1), 134.6, 134.5 (Ar C-1), 129.4 (Ar C-2/6), 114.7 (Ar C-3/5), 82.0 (d, $^1J_{CF}$=171.0 Hz, CH$_2$F), 81.9, 81.9 (6 C-1), 80.4, 80.4 (1 C-1), 79.6 (2C-2), 67.2 (d, $^2J_{CF}$=20.8 Hz, CH$_2$O), 54.0, 53.6 (C-2), 45.8, 45.4 (C-5), 34.7, 34.5 (5-CH$_2$), 32.7 (Ar CH$_2$), 30.7, 30.5 (C-3), 28.4 (2 C-3), 28.2, 28.2 (6 C-2), 28.0 (1 C-2), 27.9 (C-4).

The sample is a mixture of the diastereomers.

f) (2S)-2-amino-5-{2-[4-(2-fluoroethoxy)phenyl]ethyl}hexanedioic acid

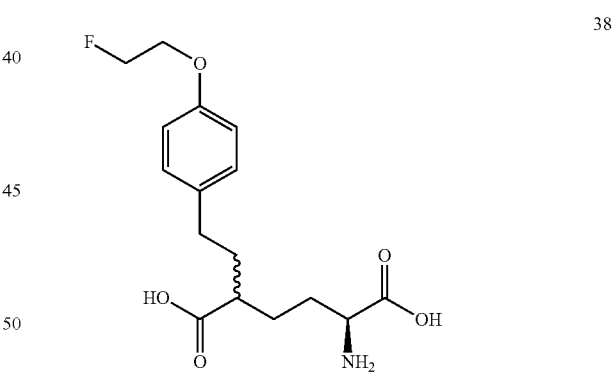

38

20 mg (37 μmol) of (2S)-2-tert.-Butoxycarbonylamino-5-{2-[4-(2-fluoro-ethoxy)-phenyl]-ethyl}-hexanedioic acid di-tert.-butyl ester were dissolved in 2 mL dichloromethane (dried over 4Å molecular sieve) and 1 mL trifluoroacetic acid were added. The reaction was stirred at room temperature for 30 min, after which the solution was directly applied to reversed phase chromatography on a Biotage system (Flash 12+M cartridge, A=water, B=acetonitrile, A 1 CV, A to 50% B in 10 CV, 2 CV 50% B, 12 mL/min). Fraction 6 was lyophilized to give 2 mg (11%) of (2R,5RS)-2-Amino-5-{2-[4-(2-fluoro-ethoxy)-phenyl]-ethyl}-hexanedioic acid as the Tfa-salt.

$^{19}$F NMR (376 MHz, DMSO-d6): δ ppm −73.5 (s. br., 3F, Tfa), −222.0 (tt, J=47.0, 29.8 Hz, 1F).

Example 39

(2S)-2-red.-Butoxycarbonylamino-5-(2-{4-[2-(toluene-4-sulfonyloxy)-ethoxy]-phenyl}-ethyl)-hexanedioic acid di-red.-butyl ester

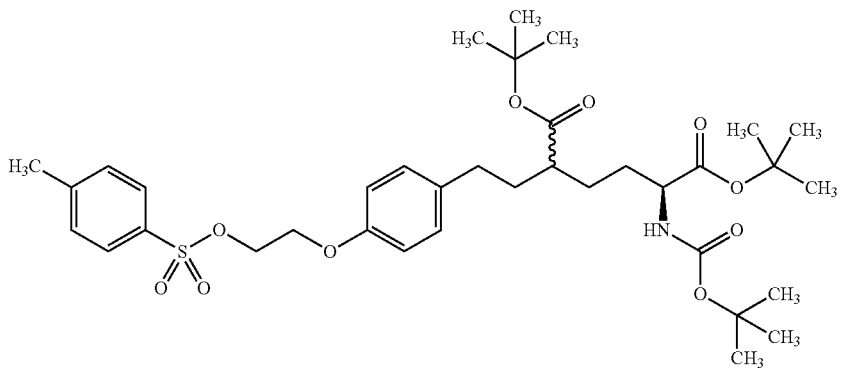 [SMILES: Cc1ccc(S(=O)(=O)OCCOc2ccc(CCC(CC[C@H](NC(=O)OC(C)(C)C)C(=O)OC(C)(C)C)C(=O)OC(C)(C)C)cc2)cc1]

90 mg (0.18 mmol) (2S)-2-tert.-Butoxycarbonylamino-5-[2-(4-hydroxy-phenyl)-ethyl]-hexanedioic acid di-tert.-butyl ester were dissolved in 10 ml dimethylformamide, 208 mg (0.64 mmol) cesium carbonate and 473 mg (1.28 mmol) ethylene glycol di-(p-toluolsulfonate) added and the mixture stirred at room temperature for 1 h. The solvent was evaporated, the mixture taken up in ethyl acetate and absorbed on Isolute. Chromatography on a Biotage Isolera system (SNAP 10 g, A=n-hexane, B=ethyl acetate, A 2 CV, A to 47% B in 10 CV, 3 CV 50% B, 12 mL/min, Fr. a 22 mL) gave 82 mg material, which still contained ethylene ditosylate. The compound was further purified by preparative HPLC. (Agilent: Prep 1200, 2×Prep Pump, DLA, MWD, ELSD, Prep FC) XBrigde C18 5 µm 100×30 mm; A=$H_2O$; B=Acetonitrile; 0-17.5 min 65-100% B, 17.5-20 min 100% B; 38 mL/min; RT; 82 mg/2.4 mL DMSO/MeCN 1:2; 2×1.2 mL; MWD 210 nm). The fractions eluting at 10.0-11.5 min were collected to give 73 mg (58%) (2S,5RS)-2-tert.-Butoxycarbonylamino-5-(2-{4-[2-(toluene-4-sulfonyloxy)-ethoxy]-phenyl}-ethyl)-hexanedioic acid di-tert.-butyl ester in >99% purity.

$^1$H NMR (CHLOROFORM-d, 400 MHz): δ (ppm) 7.81 (d, J=8.1 Hz, 2H, Ts-H), 7.33 (d, J=8.1 Hz, 2H, Ts-H), 7.03 (d, J=8.6 Hz, 2H, Ar—H), 6.70 (d, J=8.2 Hz, 2H, Ar—H), 5.03 (d, br., J=7.8 Hz, 1H, NH), 4.35 (t, J=4.5 Hz, 2H, $OCH_2$), 4.18 (s, 1H, 2-H), 4.11 (t, J=4.8 Hz, 2H, $OCH_2$), 2.46-2.62 (m, 2H, $ArCH_2$), 2.44 (s, 3H, $TsCH3$), 2.17-2.33 (m, 1H), 1.80-1.93 (m, 1H), 1.71-1.80 (m, 1H), 1.52-1.66 (m, 3H), 1.38-1.51 (m, 28H).

$^{13}$C NMR (CHLOROFORM-d, 101 MHz): δ (ppm) 175.0, 174.8 (C-6), 171.7, 1717 (C-1), 156.3, 156.3 (Ar C-4), 155.4, 155.3 (2 C-1), 144.9 (Ts C-4), 134.7, 134.7 (Ar C-1), 133.0 (Ts C-2), 129.9 (Ts C-3/5), 129.4 (Ar C-2/6), 128.1 (Ts C-216), 114.6, 114.6 (Ar C-3/5), 81.9, 81.9 (1 C-1), 80.5, 80.4 (6 C-1), 79.6 (br., 2 C-2), 68.2 ($OCH_2$), 65.6 ($OCH_2$), 54.0, 53.6 (C-2), 45.8, 45.4 (C-5), 34.6, 34.5 (5 $CH_2$), 32.7 ($ArCH_2$), 30.7, 30.5 (C-3), 28.4 (1 C-2), 28.2, 28.2 (6 C-1), 28.0 (br., 2 C-3), 27.9 (C-4), 21.7 (Ts-$CH_3$).

The compound is a mixture of diastereomers.

Example 40

(2S)-2-amino-5-{2-[4-(2-fluoroethoxy)phenyl]ethyl}hexanedioic acid

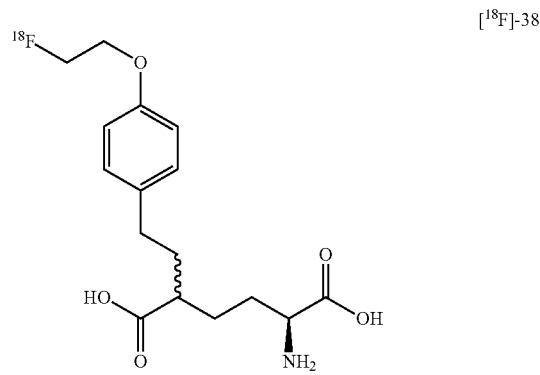 [SMILES: N[C@@H](CCC(CCc1ccc(OCC[18F])cc1)C(=O)O)C(=O)O]

[$^{18}$F]-38

[$^{18}$F]Fluoride (750 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of (2S)-2-tert.-Butoxycarbonylamino-5-(2-{4-[2-(toluene-4-sulfonyloxy)-ethoxy]-phenyl}-ethyl)-hexanedioic acid di-tert.-butyl ester in 1 mL acetonitrile were added to the dried residue. The resulting mixture was stirred at 120° C. for 10 min. After cooling to rt, 2M HCl (1 mL) was added and the mixture was stirred at 120° C. for 10 min. The crude product was diluted to 30 mL with water (pH 2) and passed through a preconditioned Strata-X-C cartridge (200 mg, Phenomenex). The cartridge was washed with 20 mL water (pH 2). The cartridge was eluted with 15 mL phosphate buffer (7 g $Na_2HPO_4.2H_2O$; 6 g NaCl in 1 L water) yielding 134 MBq (31% d.c.) (2S)-2-amino-5-{2-[4-(2-fluoroethoxy)phenyl]ethyl}hexanedioic acid ([$^{18}$F]-38). Radiochemical purity was determined to be >96% ($t_R$=3.2 min, analytical HPLC method E; $t_R$=21.8, 23.3 min*, analytical HPLC method G). *The two isomers (2S,5S)-2-amino-5-{2-[4-(2-fluoroethoxy)phenyl]ethyl}hexanedioic acid ([$^{18}$F]-38a) and (2S,5R)-2-amino-5-{2-[4-(2-fluoroethoxy)phenyl]ethyl}hexanedioic acid ([$^{18}$F]-38b) can be separated by analytical HPLC method G ("OPA-derivatization").

Example 41

(2S)-2-amino-5-[4-(fluoromethoxy)benzyl]hexanedioic acid

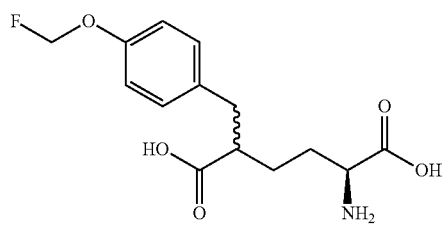

a) (2S)-5-Benzyloxycarbonyl-6-(4-benzyloxy-phenyl)-5-tert.-butoxycarbonyl-2-tert.-butoxycarbonylamino-hexanoic acid tert.-butyl ester

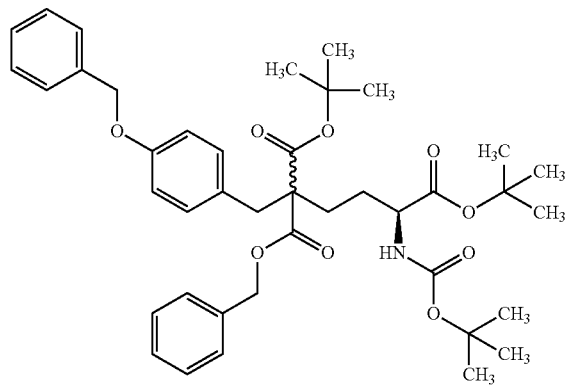 [SMILES: CC(C)(C)OC(=O)N[C@@H](CCC(Cc1ccc(OCc2ccccc2)cc1)(C(=O)OCc1ccccc1)C(=O)OC(C)(C)C)C(=O)OC(C)(C)C]

1.00 g (1.97 mmol) (2S)-2-Benzyloxycarbonyl-5-tert.-butoxycarbonylamino-hexane dioic acid di-tert.-butyl ester were dissolved in 25 mL dimethylformamide, 87 mg (2.2 mmol) NaH (60% in mineral oil) added and stirred at room temperature for 30 min. 601 mg (2.17 mmol) 4-benzloxy benzyl bromide 1 mL dimethylformamide were added and the reaction stirred for 1 h at 60° C. The solvent was removed i. vac. And the residue partitioned between ethyl acetate and brine. The organic phase was adsorbed on Isolute and directly chromatographed on a Biotage Isolera system (SNAP 100 g, A=n-Hexane, B=ethyl acetate. A 3 CV, A to 25% B in 10 CV, 4.7 CV 25% B, 50 mL/min, Fr. a 18 mL). Fractions 68 to 75 were collected to give 1.09 g (79%) of (2S,5SR)-5-Benzyloxycarbonyl-6-(4-benzyloxy-phenyl)-5-tert.-butoxycarbonyl-2-tert.-butoxycarbonylamino-hexanoic acid tert.-butyl ester.

MS (ESI$^+$): m/e=726 (M+Na$^+$), 704 (M–H+), 648 (M+H$^+$—C$_4$H$_8$), 592 (M+H$^+$-2C$_4$H$_8$), 536 (M+H$^+$-3C$_4$H$_8$), 492 (M+H$^+$-3 C$_4$H$_8$—CO$_2$).

$^1$H NMR (CHLOROFORM-d, 400 MHz): δ (ppm) 7.30-7.45 (m, 10H, Bn-H), 6.92-7.00 (m, 2H, Ar 2-H), 6.78-6.85 (m, 2H, Ar 3-H), 5.07-5.20 (m, 2H, 5-OCH$_2$), 4.96-5.06 (m, 3H, 6-OCH$_2$, NH), 4.14-4.21 (m, 1H), 3.19 (d, br., J=14.4 Hz, 1H, 6-H), 3.07 (d, br., J=13.9 Hz, 1H, 6-H), 1.61-1.91 (m, 4H, 3-H, 4-H), 1.38-1.48 (m, 18H, tBu), 1.31-1.37 (m, 9H, tBu).

$^{13}$C NMR (CHLOROFORM-d, 101 MHz): δ (ppm) 171.3, 171.3 (5 Cl Bn), 171.1, 171.0 (5C-1 tBu), 169.8, 169.7 (C–1), 157.8 (Ph C-4), 155.2 (br., 2 C-1), 137.1 (6 Bn C-2), 135.4 (5 C-2), 131.0, 131.0 (Ph C-2/6), 128.7 (br., 5 Bn C-3/7), 128.6 (6 Bn C-3/7), 128.6 (6 Bn C-4/6), 128.4, 128.4 (5 Bn C-4/6), 128.3 (br., Ph C-1), 128.0 (5 Bn C-5), 127.5 (6 Bn C-5), 114.7, 114.7 (Ph C-3/5), 82.1 (1 C-2), 82.0 (5 C-2 tBu), 79.6 (2 C-2), 70.0 (6 Bn C-1), 66.9 (br., 5 Bn C-1), 59.0, 59.0 (C-5), 53.8 (C-2), 37.6, 37.1 (C-6), 28.4 (2 C-3), 28.0, 28.0 (6 C-3 tBu), 27.8, 27.8 (1 C-2), 27.7 (C-4), 27.5, 27.4 (C-3).

The material is a mixture of diastereomers.

The preparation was repeated with 6.00 g (11.8 mmol) 2S,5RS)-2-Benzyloxycarbonyl-5-tert.-butoxycarbonylamino-hexanedioic acid di-tert.-butyl ester and 3.60 g 4-benzyloxy benzyl bromide to give 6 g raw product which was used in the next steps without further purification.

b) (2S)-2-tert.-Butoxycarbonylamino-5-(4-hydroxybenzyl)-hexanedioic acid di-tert.-butyl ester

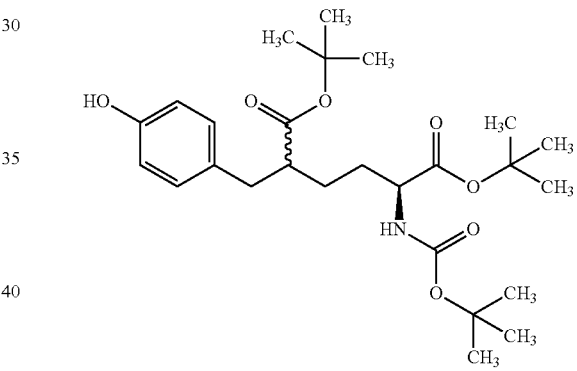

Hydrogenation:

The raw material obtained above 6.00 g (8.52 mmol) was dissolved in 50 mL methanol and 900 mg Pd/C 10% added under Argon atmosphere. The argon was replaced by hydrogen and the mixture hydrogenated for 3 h at room temperature (H$_2$ being supplied by a balloon under normal pressure), after which UPLC-MS indicated the reaction to be complete. The catalyst was filtered off over a PTFE-filter and the resulting clear solution evaporated i. vac. 8.8 g (>100%) raw product were obtained.

Decarboxylation:

The material was dissolved in 400 mL Dioxan, 5.13 g (42.0 mmol) 4-dimethylamino-pyridine added and stirred over night at 100° C. The resulting yellowish suspension was evaporated i. vac., the material dissolved in ethyl acetate and absorbed on Isolute.

Test: chromatography of a small amount (Biotage Isolera system; SNAP 25 g, A=n-Hexane, B=ethyl acetate. A 2 CV, A to 50% B in 10 CV, 3 CV 25% B, 25 mL/min, Fr. a 12 mL) gave 980 mg.

Main Chromatography. (Biotage Isolera system; SNAP 100 g, A=n-Hexane, B=ethyl acetate. A 2 CV, A to 50% B in 10 CV, 3 CV 25% B, 50 mL/min, Fr. a 12 mL) gave 3.46 g.

Combined yield: 4.44 g (79%) of (2S,5RS)-2-tert.-Butoxycarbonylamino-5-(4-hydroxy-benzyl)-hexanedioic acid di-tert.-butyl ester.

$^1$H NMR (CHLOROFORM-d, 400 MHz): δ (ppm) 6.97-7.06 (m, 2H, Ph 2/6-H), 6.72 (d, J=8.3 Hz, 2H, Ph 3/5-H), 5.43 (br. s., 1H, NH), 5.00-5.11 (m, 1H, 2-H), 4.12-4.23 (m, 1H, 5-H), 2.75-2.86 (m, 1H, PhCH$_2$), 2.57-2.67 (m, 1H, PhCH$_2$), 2.43-2.57 (m, 1H, 3-H), 1.72-1.87 (m, 1H, 3-H), 1.53-1.65 (m, 2H, 4-H$_2$), 1.45 (s, 18H, OtBu), 1.33-1.39 (m, 9H, Boc).

$^{13}$C NMR (CHLOROFORM-d, 101 MHz): δ (ppm) 174.7, 174.6 (C-6), 171.8, 171.6 (C−1), 155.5, 155.4 (2 C-1), 154.4 (Ph C-4), 131.1 (Ph C-1), 130.1 (Ph C-2/6), 115.2, 115.2 (Ph C-3/5), 82.0, 82.0 (1 C-1), 80.6, 80.5 (6 C-1), 79.8 (2 C-2), 53.9, 53.6 (C-2), 48.4, 47.9 (C-5), 37.9, 37.7 (PhCH$_2$), 30.7, 30.5 (C-4), 28.4 (2 C-3), 28.1 (6 C-2), 28.0 (1 C-2), 27.7, 27.7 (C-3).

The material is a mixture of diastereomers.

c) (2S)-2-amino-5-(4-hydroxybenzyl)hexanedioic acid

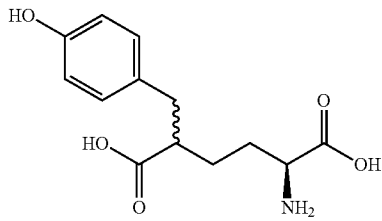 [SMILES: N[C@@H](CCC(Cc1ccc(O)cc1)C(=O)O)C(=O)O]

(2S)-2-tert.-Butoxycarbonylamino-5-(4-hydroxy-benzyl)-hexanedioic acid di-tert.-butyl ester (159 mg, 332 µmol) was solved in formic acid (20 ml) and the solution was stirred at 63° C. for one hour. The solvent was removed under reduced pressure and the residue was taken up in methanol and concentrated and dried in vacuo. The product was taken up in water and lyophilized to yield 78 mg (79%) of the title compound (contains 0.4 eq formic acid and traces of methanol).

$^1$H-NMR (300 MHz, DEUTERIUM OXIDE): δ [ppm]=1.52-1.91 (m, 4H), 2.59-2.72 (m, 1H), 2.73-2.84 (m, 2H), 3.63-3.80 (m, 1H), 6.54-6.92 (m, 2H), 6.95-7.22 (m, 2H).

MS (ESI$^+$): m/e=268.1 (M+H$^+$), 250.1 (M+H$^+$—H$_2$O).
The material is a mixture of diastereomers.

d) dimethyl (2S)-2-amino-5-(4-hydroxybenzyl)hexanedioate hydrochloride

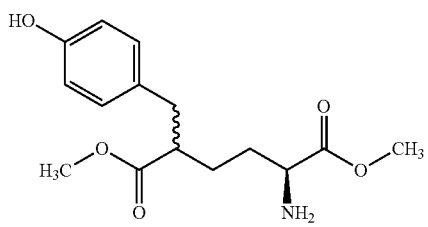 [SMILES: COC(=O)C(CC[C@H](N)C(=O)OC)Cc1ccc(O)cc1]

(2S)-2-amino-5-(4-hydroxybenzyl)hexanedioic acid (Example 42) (994 mg, 2.98 mmol) was solved in methanol (20 ml) and at 0° C. thionyl dichloride (1.17 ml, 15.97 mmol) were added slowly. After complete addition, the cooling bath was removed and the reaction was stirred for three days at room temperature. The solvent was removed and the residue was dried in vacuo to yield 828 mg (86%) of white foam. The crude product was used in the following step without further purification.

MS (ESI+): m/e=296.2 (M+H$^+$), 264.1 (M+H$^+$—CH$_3$OH).
The material is a mixture of diastereomers.

d) dimethyl (2S)-2-amino-5-[4-(fluoromethoxy)benzyl]hexanedioate

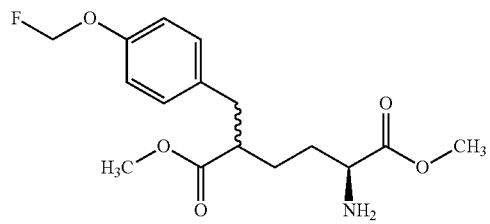 [SMILES: COC(=O)C(CC[C@H](N)C(=O)OC)Cc1ccc(OCF)cc1]

Dimethyl (2S)-2-amino-5-(4-hydroxybenzyl)hexanedioate hydrochloride (200 mg, 0.54 mmol) were solved in DMF (5 ml) and at 0° C. sodium hydride (34 mg, 1.14 mmol) were added. After 30 min, bromofluoromethane (1.35 mmol) were added and the resulting mixture was stirred at 0° C. for one hour. The mixture was then poured into water and extracted three times with methylene chloride. The organic phase was dried with sodium sulfate and concentrated in vacuo. The residue was purified by silica gel chromatography to yield 37 mg (20.8%) of the product.

MS (ESI$^+$): m/e=328.1 (M+H$^+$).
The material is a mixture of diastereomers.

e) (2S)-2-amino-5-[4-(fluoromethoxy)benzyl]hexanedioic acid

41

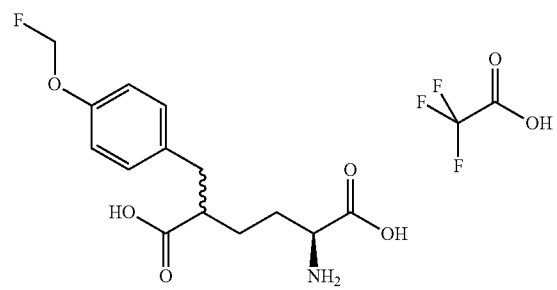

Dimethyl (2S)-2-amino-5-[4-(fluoromethoxy)benzyl]hexanedioate (37 mg, 113 µmol) was solved in 2 ml of a mixture of tetrahydrofurane and water (2:1), and to the solution, four drops of 1N sodium hydroxide were added. The mixture was stirred at room temperature for 14 h and then concentrated in vacuo. The residue was purified by preparative HPLC and the according fractions were lyophilized to yield 2 mg (4.3%) of the title compound.

$^1$H NMR (400 MHz, DMSO-d$_6$) δ ppm 7.14 (d, J=8.8 Hz, 2H), 6.96 (d, J=8.6 Hz, 2H), 5.78 (d, J=54.8 Hz, 2H), 3.10-3.16 (m, 2H, overlaps with water signal), 2.73 (dd, J=13.6, 9.1 Hz, 1H), 2.61 (dd, J=13.6, 5.6 Hz, 1H), 1.51-1.79 (m, 4H).

MS (ESI$^+$): m/e=300.0 (M+H$^+$).
The material is a mixture of diastereomers.

Example 42

(2S)-2-amino-5-(4-hydroxybenzyl)hexanedioic acid a) (2S)-2-amino-5-(4-hydroxybenzyl)hexanedioic acid mixture of isomers at C5

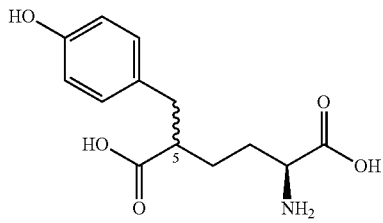 [SMILES: N[C@@H](CCC(Cc1ccc(O)cc1)C(=O)O)C(=O)O]

See Example 41c b) (2S)-2-amino-5-(4-hydroxybenzyl)hexanedioic acid—Separation of Isomers C5-1 and C5-2

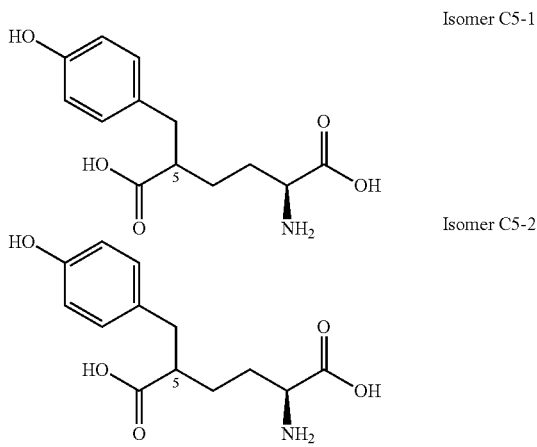

Isomer C5-1

Isomer C5-2

1.56 g (3.25 mmol) (2S)-2-tert.-Butoxycarbonylamino-5-(4-hydroxy-benzyl)-hexanedioic acid di-tert.-butyl ester (Example 41b) were purified by chiral HPLC (Chiralpak AD-H 5 μm 250×300 mm; hexan/2-propanol; 40 mL7 min). Two isomers were isolated (isomer 1: 362 mg and isomer 2: 424 mg). 0.15 g (0.31 mmol) isomer 1 and 0.15 g (0.31 mmol) isomer 2 were individually deprotected according to the procedure described in Example 41c, yielding 42 mg (51%) (2S)-2-amino-5-(4-hydroxybenzyl)hexanedioic acid—Isomers C5-1 and 40 mg (48%) (2S)-2-amino-5-(4-hydroxybenzyl)hexanedioic acid—Isomers C5-2.

Example 43

(2S)-2-amino-5-[4-(fluoromethoxy)benzyl]hexanedioic acid a) (2S)-2-amino-5-[4-(fluoromethoxy)benzyl]hexanedioic acid—Mixture of isomers C5-1 and C5-1 (Performed on Eckert & Ziegler Modular Lab)

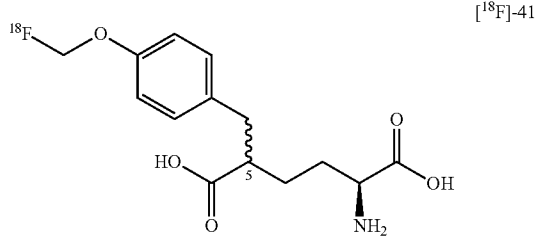 [SMILES: N[C@@H](CCC(Cc1ccc(OC[18F])cc1)C(=O)O)C(=O)O]

[$^{18}$F]-41

[$^{18}$F]Fluoride (43500 MBq) was trapped on a preconditioned QMA cartridge (Sep Pak Light. Accell Plus QMA, Waters). The activity was eluted with potassium carbonate/kryptofix solution (in acetonitrile/water) into the reaction vessel 1. The mixture was dried under gentle nitrogen stream at 120° C. Drying was repeated after addition of acetonitrile (1×1 mL). 100 μL dibromo methane in 0.9 mL acetonitrile were added to the dried residue. The resulting mixture was stirred at 130° C. for 5 min. The reaction vessel 1 was cooled to 50° C. and bromo [$^{18}$F]fluoromethane was distilled through 4 silica cartridges (Silica plus, Waters) into reaction vessel 2 containing 700 μL DMSO. A solution of 2.1 mg (2S)-2-amino-5-(4-hydroxybenzyl)hexanedioic acid, 100 μL water, 10 μL 10% NaOH solution in 400 μL DMSO was added after distillation was complete. The resulting mixture was heated at 110° C. for 5 min. After cooling to 50° C., the crude product was diluted with 50 mL water (pH 2) and passed through a preconditioned C18 cartridge (C18 plus, waters). The cartridge was washed with 20 mL water (pH 2) and the activity was eluted with 5 mL ethanol through a Strata-X-C cartridge (200 mg, Phenomenex). Activity was eluted from the SCX cartridge with 5 mL phosphate buffer (7 g Na$_2$HPO$_4$.2H$_2$O; 6 g NaCl in 1 L water) yielding 4100 MBq (15% d.c.) (2S)-2-amino-5-[4-(fluoromethoxy)benzyl]hexanedioic acid ([$^{18}$F]-41). Radiochemical purity was determined to be >99% ($t_R$=3.0 min, analytical HPLC method C; $t_R$=6.2 min, analytical HPLC method H, $t_R$=19.6, 20.7 min*, analytical HPLC method G). *The two isomers (2S)-2-amino-5-[4-(fluoromethoxy)benzyl]hexanedioic acid ([$^{18}$F]-41 C5-1) and ([$^{18}$F]-41 C5-2) can be separated by analytical HPLC method G ("OPA-derivatization").

b) (2S)-2-amino-5-[4-(fluoromethoxy)benzyl]hexanedioic acid—Isomer C5-1

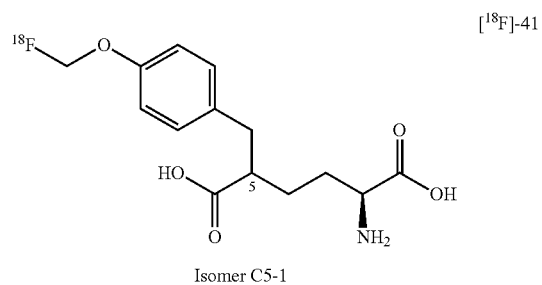 [SMILES: N[C@@H](CCC(Cc1ccc(OC[18F])cc1)C(=O)O)C(=O)O]

[$^{18}$F]-41

Isomer C5-1

[$^{18}$F]Fluoride (10000 MBq) was trapped on a preconditioned QMA cartridge (Sep Pak Light. Accell Plus QMA, Waters). The activity was eluted with potassium carbonate/kryptofix solution (in acetonitrile/water) into the reaction vessel 1. The mixture was dried under gentle nitrogen stream at 120° C. Drying was repeated after addition of acetonitrile (1×1 mL). 100 μL dibromo methane in 0.9 mL acetonitrile were added to the dried residue. The resulting mixture was stirred at 130° C. for 5 min. The reaction vessel 1 was coiled to 50° C. and bromo [$^{18}$F]fluoromethane was distilled through 4 silica cartridges (Silica plus, Waters) into reaction vessel 2 containing 700 μL DMSO. A solution of 2.1 mg (2S)-2-amino-5-(4-hydroxybenzyl)hexanedioic acid (isomer 1), 100 μL water, 10 μL 10% NaOH solution in 400 μL DMSO was added after distillation was complete. The resulting mixture was heated at 110° C. for 5 min. The crude product was diluted up to 30 mL with water (pH 2) and passed through a preconditioned C18 cartridge (C18 plus, waters). The cartridge was washed with 20 mL water (pH 2) and the activity was eluted with ethanol in 1 mL fractions. Fraction 1 (containing 799 MBq) was diluted with 30 mL water and passed through a Strata-X-C cartridge (200 mg, Phenomenex). The cartridge was washed with 20 mL ethanol and the activity was eluted from the SCX cartridge with 5 mL phosphate buffer (7 g $Na_2HPO_4.2H_2O$; 6 g NaCl in 1 L water) in fractions of 1 mL, yielding 642 MBq (15% d.c.) (2S)-2-amino-5-[4-(fluoromethoxy)benzyl]hexanedioic acid ([$^{18}$F]-41 isomer C5-1) in 1 mL buffer (fraction 3). Radiochemical purity was determined to be >99% ($t_R$=3.0 min, analytical HPLC method C; $t_R$=6.4 min, analytical HPLC method H, $t_R$=19.5, analytical HPLC method G).

c) (2S)-2-amino-5-[4-(fluoromethoxy)benzyl]hexanedioic acid—Isomer C5-2

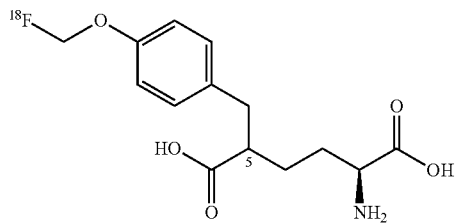

Isomer C5-2

[$^{18}$F]Fluoride (16500 MBq) was trapped on a preconditioned QMA cartridge (Sep Pak Light. Accell Plus QMA, Waters). The activity was eluted with potassium carbonate/kryptofix solution (in acetonitrile/water) into the reaction vessel 1. The mixture was dried under gentle nitrogen stream at 120° C. Drying was repeated after addition of acetonitrile (1×1 mL). 100 µL dibromo methane in 0.9 mL acetonitrile were added to the dried residue. The resulting mixture was stirred at 130° C. for 5 min. The reaction vessel 1 was cooled to 50° C. and bromo [$^{18}$F]fluoromethane was distilled through 4 silica cartridges (Silica plus, Waters) into reaction vessel 2 containing 1000 µL DMF. To 500 µL of the solution of bromo [$^{18}$F]fluoromethane in DMF were added 2.1 mg (2S)-2-amino-5-(4-hydroxybenzyl)hexanedioic acid (isomer 2), 100 µL water, 10 µL 10% NaOH and 500 µL DMF. The resulting mixture was heated at 110° C. for 5 min. The crude product was diluted up to 30 mL with water (pH 2) and passed through a preconditioned C18 cartridge (C18 plus, waters). The cartridge was washed with 10 mL water (pH 2) and the activity was etuted with ethanol in 1 mL fractions. Fraction 1 (containing 308 MBq) was diluted with 30 mL water and passed through a Strata-X-C cartridge (200 mg, Phenomenex). The cartridge was washed with 10 mL ethanol and the activity was eluted from the SCX cartridge with 5 mL phosphate buffer (7 g $Na_2HPO_4.2H_2O$; 6 g NaCl in 1 L water) in fractions of 1 mL, yielding 204 MBq (2S)-2-amino-5-[4-(fluoromethoxy)benzyl]hexanedioic acid ([$^{18}$F]-41 isomer C5-2) in 1 mL buffer (fraction 3). Radiochemical purity was determined to be >99% ($t_R$=2.9 min, analytical HPLC method C; $t_R$=20.6, analytical HPLC method G).

Example 44

(4S)-4-[4-(2-fluoroethoxy)-3-hydroxybenzyl]-L-glutamic acid

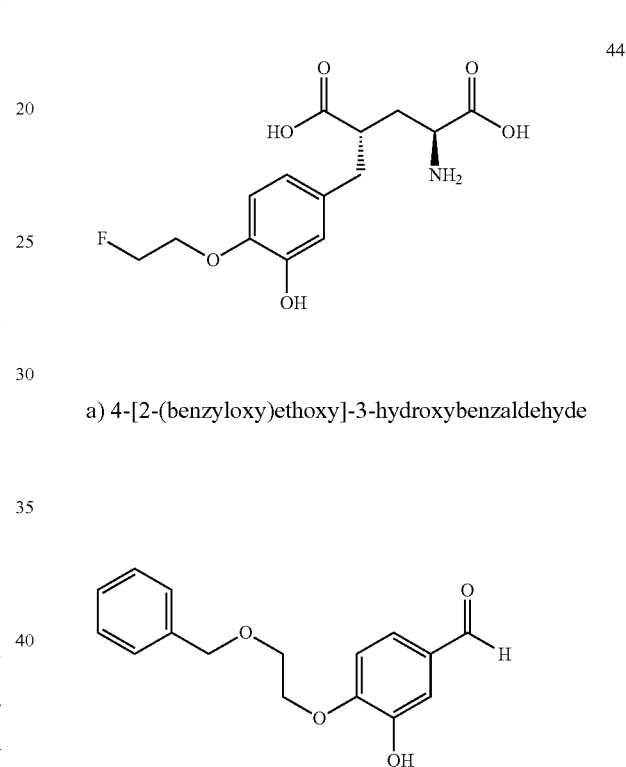

a) 4-[2-(benzyloxy)ethoxy]-3-hydroxybenzaldehyde

A solution of commercially available 3,4-dihydroxybenzaldehyde (17.04 g, 123.7 mmol) in 150 ml DMF and 14.9 g (107.5 mmol) potassium carbonate was stirred at 60° C. for 4 hours. 30.8 g (14.2 mmol) [(2-bromoethoxy)methyl]benzene was added at room temperature. The reaction mixture was stirred over night. The volume of the reaction mixture is reduced to half volume in vacuo. Aqueous saturated ammonium chloride solution and ethyl acetate is added to the reaction mixture. The organic phase is separated, washed twice with saturated aqueous sodium chloride solution, dried with magnesium sulfate filtered and concentrated in vacuo. The crude product is purified by column chromatography (silica gel, hexane/ethylacetate gradient: 7:1→1:2). The desired product was obtained in 22.2% yield (8.27 g, 27.3 mmol).

$^1$H NMR (300 MHz, CHLOROFORM-d) δ ppm 3.85 (dd, 2H) 4.28 (dd, 2H) 4.62 (s, 2H) 6.23 (s, 1H) 6.99 (d, 1H) 7.34-7.44 (m, 7H) 9.84 (s, 1H)

LC-MS (ESI)=M$^+$+1 (60) 272, →1.08 min b) 4-[2-(benzyloxy)ethoxy]-3-tert-butoxybenzaldehyde

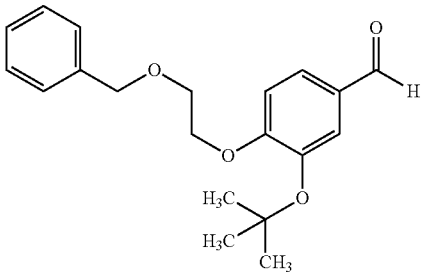 [SMILES: CC(C)(C)Oc1cc(C=O)ccc1OCCOCc1ccccc1]

To a stirred solution of 2.95 g (10.8 mmol) 4-[2-(benzyloxy)ethoxy]-3-hydroxybenzaldehyde in 20 ml toluene was added 17.6 g (86. mmol) 1,1-di-tert-butoxy-N,N-dimethylmethanamine drop by drop. The reaction mixture was stirred at room temperature over night. The reaction mixture is diluted with dichloromethane, washed with aqueous sodium hydroxide solution (1N), dried with sodium sulfate and concentrated in vacuo. The crude product is purified by column chromatography (silica gel, hexane/ethylacetate gradient: 7:1→1:99). The desired product was obtained in 43% yield (8.27 g, 27. mmol).

$^1$H NMR (400 MHz, CHLOROFORM-d) δ ppm 1.38 (s, 9H) 3.90 (dd, J=5.31, 4.29 Hz, 2H) 4.19-4.27 (m, 2H) 4.64 (s, 2H) 7.00 (d, J=8.34 Hz, 1H) 7.27-7.34 (m, 1H) 7.34-7.39 (m, 4H) 7.48-7.64 (m, 2H) 9.84 (s, 1H)

LC-MS (ESI)=M$^+$+1, 329, (95)

c) {4-[2-(benzyloxy)ethoxy]-3-tert-butoxyphenyl}methanol

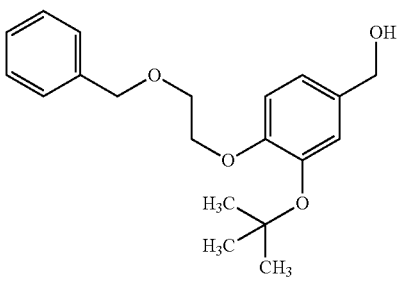 [SMILES: CC(C)(C)Oc1cc(CO)ccc1OCCOCc1ccccc1]

To a stirred mixture of 1.00 g (26.5 mmol) sodium borohydride in 80 ml THF was added 2, 0.9 g (8.83 mmol) 4-[2-(benzyloxy)ethoxy]-3-tert-butoxybenzaldehyde diluted in 40 ml THF drop by drop. The reaction mixture was stirred for 10 min. Methanol (5.8 ml) was added to this mixture drop by drop. The reaction mixture was stirred for 2 hours and poured onto ~200 ml stirred ice-cooled saturated aqueous ammonium chloride solution. The solution was extracted trice with dichloromethane. The combined organic phases were dried with sodium sulfate and concentrated in vacuo. The crude product was used in the following reaction without further purification.

$^1$H NMR (300 MHz, CHLOROFORM-d) δ ppm 1.35 (s, 9H) 3.81-3.91 (m, 2H) 4.09-4.21 (m, 2H) 4.54-4.62 (m, 2H) 4.63 (s, 2H) 6.85-6.92 (m, 1H) 6.98-7.02 (m, 1H) 7.03 (s, 1H) 7.27-7.34 (m, 2H) 7.34-7.41 (m, 3H)

LC-MS (ESI): M$^+$+18 (50), 1.27 min d) 1-[2-(benzyloxy)ethoxy]-4-(bromomethyl)-2-tert-butoxybenzene

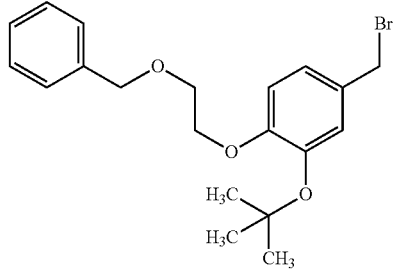 [SMILES: CC(C)(C)Oc1cc(CBr)ccc1OCCOCc1ccccc1]

To a stirred solution of 0.9 g (2.2 mmol) {4-[2-(benzyloxy)ethoxy]-3-tert-butoxyphenyl}methanol and 976 mg (2.94 mmol) tetrabromo methane in 9 ml THF was added 775 mg (2.96 mmol) triphenylphosphin diluted in 4.5 ml THF at 0° C. dropwisly. The reaction mixture was stirred for 1 h at 0° C. The suspension was filtrated. The filter cake was washed with THF. The combined filtrates were concentrated in vacua. The crude product is purified by column chromatography (silica gel, hexane/ethylacetate gradient: 99:1→1:99). The desired product was obtained in 28% yield (313 mg, 0.76 mmol).

$^1$H NMR (400 MHz, CHLOROFORM-d) δ ppm 1.36 (s, 9H) 3.80-3.91 (m, 2H) 4.09-4.21 (m, 2H) 4.46 (s, 2H) 4.63 (s, 2H) 6.81-6.89 (m, 1H) 6.99-7.09 (m, 2H) 7.27-7.34 (m, 1H) 7.35-7.40 (m, 3H)

e) di-tert-butyl (4S)-4-{4-[2-(benzyloxy)ethoxy]-3-tert-butoxybenzyl}-N-(tert-butoxycarbonyl)-L-glutamate

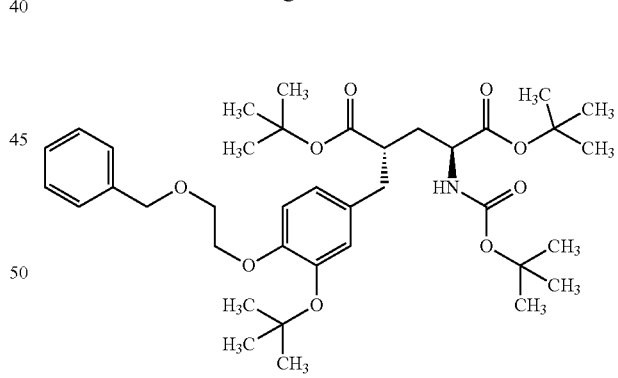

To a solution of 327 mg (0.91 mmol) di-tert-butyl N-(tert-butoxycarbonyl)-L-glutamate in 10 ml THF was added 2 ml (2 mmol) lithium bis(trimethylsilyl)amide solution in THF drop by drop at −78° C. The reaction mixture was stirred for 2 hours. 300 mg (0.76 mmol) 1-[2-(benzyloxy)ethoxy]-4-(bromomethyl)-2-tert-butoxybenzene in 2 ml THF were added at −78° C. The reaction mixture was stirred for 2 hours. 4.5 ml aqueous hydrogen chloride solution (2N) is added drop by drop. The solution was allowed to be warmed to room temperature. The solution was extracted repeatedly with dichloro methane. The combined organic phases were washed with water, dried with sodium sulfate and concentrated in vacuo. The crude product is purified twice by column chromatography (silica gel, hexane/ethylacetate gradient: 7:1→1:1). The desired product was obtained in 48.7% yield (358 mg, 0.45 mmol).

$^1$H NMR (300 MHz, CHLOROFORM-d) δ ppm 1.31 (s, 9H) 1.33 (s, 9H) 1.43 (s, 9H) 1.44 (s, 9H) 1.87 (t, J=7.72 Hz, 2H) 2.53-2.68 (m, 1H) 2.75 (d, J=6.78 Hz, 2H) 3.80-3.89 (m, 2H) 4.09-4.17 (m, 2H) 4.25-4.40 (m, 1H) 4.62 (s, 2H) 4.88 (d, J=9.04 Hz, 1H) 6.80 (s, 2H) 6.83 (s, 1H) 7.28-7.44 (m, 5H)

LC-MS (ESI): M$^+$+1, 672 (30), →1.81 min f) di-tert-butyl (4S)—N-(tert-butoxycarbonyl)-4-[3-tert-butoxy-4-(2-hydroxyethoxy)benzyl]-L-glutamate

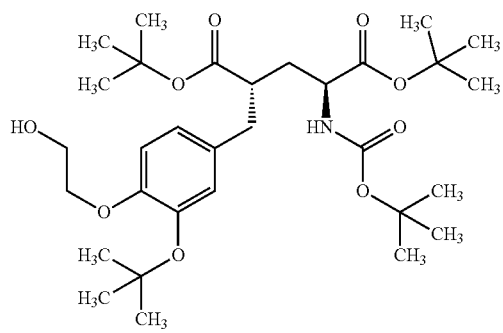 [SMILES: CC(C)(C)OC(=O)N[C@@H](C[C@H](Cc1ccc(OCCO)c(OC(C)(C)C)c1)C(=O)OC(C)(C)C)C(=O)OC(C)(C)C]

To a solution of 340 mg (0.506 mmol) di-tert-butyl (4S)-4-{4-[2-(benzyloxy)ethoxy]-3-tert-butoxybenzyl}-N-(tert-butoxycarbonyl)-L-glutamate in 5 ml methanol was added a little amount of palladium on carbon. The solution is stirred in hydrogen atmosphere for 4 hours. The reaction mixture is filtrated. The filtrate is concentrated. The crude product is concentrated in vacuo. The crude product (310 mg) was used in the following reaction without further purification.

$^1$H NMR (400 MHz, CHLOROFORM-d) δ ppm 1.32 (s, 9H) 1.35 (s, 9H) 1.44 (s, 9H) 1.45 (s, 9H) 1.85-1.88 (m, 2H) 2.55-2.67 (m, 1H) 2.68-2.85 (m, 2H) 2.93 (br. s., 1H) 3.49 (br. s., 4H) 3.74-3.85 (m, 2H) 4.01-4.10 (m, 2H) 4.18 (d, J=7.83 Hz, 1H) 4.89 (d, J=8.34 Hz, 1H) 6.76-6.93 (m, 3H)

LC-MS (ESI): M$^+$+1, 582 (100), 1.56 min g) di-tert-butyl (4S)—N-(tert-butoxycarbonyl)-4-[3-tert-butoxy-4-(2-fluoroethoxy)benzyl]-L-glutamate

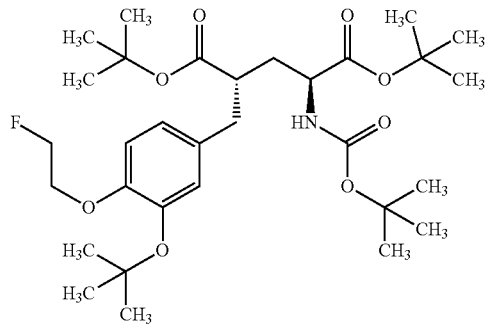 [SMILES: CC(C)(C)OC(=O)N[C@@H](C[C@H](Cc1ccc(OCCF)c(OC(C)(C)C)c1)C(=O)OC(C)(C)C)C(=O)OC(C)(C)C]

To a stirred solution of 64 mg (0.11 mmol) di-tert-butyl (4S)—N-(tert-butoxycarbonyl)-4-[3-tert-butoxy-4-(2-hydroxyethoxy)benzyl]-L-glutamate in 0.5 ml THF was added 102.7 mg (0.34 mmol) nonafluoro 1-butanesulphonic acid fluoride, 54.8 mg (0.34 mmol) triethylamine trihydrofluoride and 102 mg (1.01 mmol) triethyl amine. The reaction mixture is stirred for 3 days. Further 34 mg (0.11 mmol) nonafluoro 1-butanesulphonic acid fluoride, 18 mg (0.11 mmol) triethylamine trihydrofluoride and 34 mg (0.33 mmol) triethyl amine were added. The reaction mixture is stirred for 3 hours and is concentrated in vacuo. The crude product is purified by column chromatography (silica gel, hexane/ethylacetate gradient: 12:1→1:1). The desired product was obtained in 37.4% yield (64.2 mg, 0.04 mmol).

$^1$H NMR (400 MHz, CHLOROFORM-d) δ ppm 1.29-1.33 (m, 9H) 1.34 (s, 9H) 1.44 (s, 9H) 1.48 (s, 9H) 1.88 (t, 2H) 2.57-2.66 (m, 1H) 2.69-2.85 (m, 2H) 4.18 (br. s., 1H) 4.22 (dd, 1H) 4.64-4.70 (m, 1H) 4.76-4.82 (m, 1H) 4.89 (d, 1H) 6.76-6.89 (m, 3H)

h) (4S)-4-[4-(2-fluoroethoxy)-3-hydroxybenzyl]-L-glutamic acid

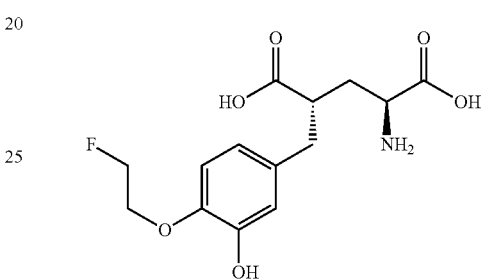

44

A solution of hydrogen chloride in dioxane (0.25 ml, 4M) is added to 24 mg (0.041 mmol) di-tert-butyl (4S)—N-(tert-butoxycarbonyl)-4-[3-tert-butoxy-4-(2-fluoroethoxy)benzyl]-L-glutamate. The reaction mixture is stirred for 4 hours and stored at −25° C. over night. The reaction mixture is concentrated in vacuo. Co. 3 ml dichloro methane is added and the solution is concentrate in vacuo. The last step is repeated. The crude product is purified by HPLC (column, XBrigde, C18, 5 μm 100×30 mm, H$_2$O+0.1% trifluoroacetic acid, acetonitrile, flow 38 mL/min).

$^1$H NMR (400 MHz, DEUTERIUM OXIDE) δ ppm 1.90-2.05 (m, 1H) 2.06-2.17 (m, 1H) 2.81-2.92 (m, 2H) 2.94-3.06 (m, 1H) 3.80 (dd, 1H) 4.24-4.32 (m, 1H) 4.33-4.40 (m, 1H) 4.83-4.91 (m, 1H) 6.79 (dd, 1H) 6.83 (d, 1H) 6.98-7.01 (m, 1H)

$^{19}$F NMR (376 MHz, DEUTERIUM OXIDE) δ ppm −75.42 (s, 1F)

Example 45 di-tert-butyl (4S)—N-(tert-butoxycarbonyl)-4-(3-tert-butoxy-4-{2-[(methylsulfonyl)oxy]ethoxy}benzyl)-L-glutamate

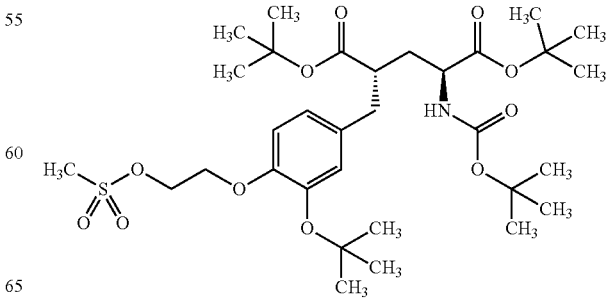

To a stirred solution of 100 mg (0.172 mmol) di-tert-butyl (4S)—N-(tert-butoxycarbonyl)-4-[3-tert-butoxy-4-(2-hydroxyethoxy)benzyl]-L-glutamate, 25.6 mg (0.253 mmol) triethylamine in ca. 1 ml dichloromethane was added 25.5 mg (0.222 mmol) methane sulphonic acid chloride at 0° C. The reaction mixture was stirred at room temperature for 4 hours. Further 25.6 mg (0.253 mmol) triethylamine and 25.5 mg (0.222 mmol) methane sulphonic acid chloride were added. The reaction mixture is stirred for another 4 hours. The reaction mixture is diluted with dichloro methane. The organic phase washed with saturated aqueous ammonium chloride, saturated aqueous sodium hydrogen carbonate solution, dried with sodium sulfate and concentrated in vacuo. The crude product is purified by column chromatography (silica gel, hexane/ethylacetate gradient: 5:1→1:99). The desired product was obtained in 79.6% yield (99 mg, 0.14 mmol).

$^1$H NMR (400 MHz, CHLOROFORM-d) δ ppm 1.33 (s, 9H) 1.34-1.38 (m, 9H) 1.44 (s, 9H) 1.45 (s, 9H) 1.87 (t, 2H) 2.55-2.67 (m, 1H) 2.71-2.84 (m, 2H) 3.12 (s, 3H) 4.14-4.19 (m, 1H) 4.19-4.24 (m, 2H) 4.50-4.61 (m, 2H) 4.89 (d, 1H) 6.73-6.90 (m, 3H)

LC-MS (ESI): M$^+$+1, 660, (35), →1.60 min

Example 46

4-[4-(2-[$^{18}$F]fluoroethoxy)-3-hydroxybenzyl]-L-glutamic acid

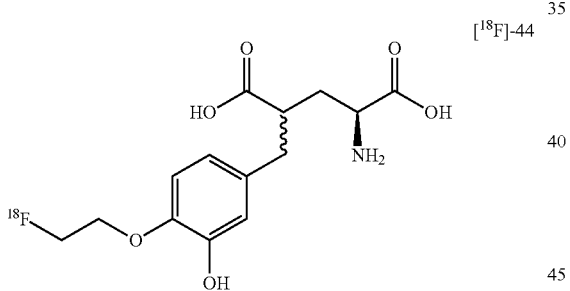

[$^{18}$F]-44

[$^{18}$F]Fluoride (1092 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of di-tert-butyl (4S)—N-(tert-butoxycarbonyl)-4-(3-tert-butoxy-4-{2-[(methylsulfonyl)oxy]ethoxy}benzyl)-L-glutamate in 1 mL acetonitrile were added to the dried residue. The resulting mixture was stirred at 120° C. for 10 min. After cooling to rt, 2M HCl (1 mL) was added and the mixture was stirred at 120° C. for 10 min. The crude product was diluted with 30 mL water (pH 2) and passed through a preconditioned Strata-X-C cartridge (200 mg, Phenomenex). The cartridge was washed with 20 mL water (pH 2) and 30 mL ethanol. The cartridge was eluted with 5 mL phosphate buffer (7 g Na$_2$HPO$_4$.2H$_2$O; 6 g NaCl in 1 L water) yielding 208 MBq (40% d.c.) 4-[4-(2-[$^{18}$F]fluoroethoxy)-3-hydroxybenzyl]-L-glutamic acid ([$^{18}$F]-44) in a fraction of 1 ml buffer. Radiochemical purity was determined to be >99% ($t_R$=2.7 min, analytical HPLC method C).

Example 47

(4S)-4-[4-Hydroxybenzyl]-L-glutamic acid

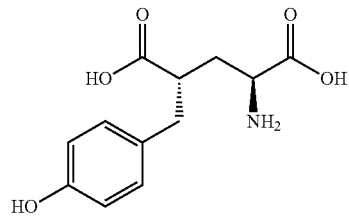 [SMILES: N[C@@H](C[C@H](Cc1ccc(O)cc1)C(=O)O)C(=O)O]

To 0.35 g (0.75 mmol) of di-tert-butyl (4S)—N-(tert-butoxycarbonyl)-4-(4-hydroxybenzyl)-L-glutamate were added 10 mL of trifluoro acetic acid and the solution was stirred for 2 days at room temperature. The excess of trifluoro acetic acid was evaporated and the residue was taken up three times in tetrahydrofuran and then evaporated. The resulting oil was chromatographed on C-18 reversed phase silica gel using a water/acetonitrile gradient, the appropriate fractions were combined and concentrated.

Yield: 145 mg (76.3%)

$^1$H-NMR (400 MHz, DIMETHYLSULFOXIDE-d6): δ [ppm]=1.64-1.68 (m, 2H), 2.38-2.43 (m, 1H), 2.78-2.87 (m, 2H), 3.44-3.49 (m, 1H), 6.63-6.66 (d, 2H), 6.94-6.96 (d, 2H).

ESI+ m/z 254 (M+H).

Example 48

(4S)-4-{4-[($^{18}$F)fluoromethoxy]benzyl}-L-glutamic acid

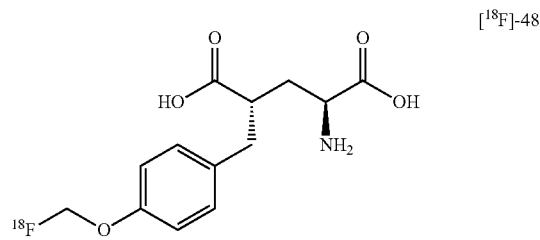 [SMILES: N[C@@H](C[C@H](Cc1ccc(OC[18F])cc1)C(=O)O)C(=O)O]

[$^{18}$F]-48

[$^{18}$F]Fluoride (15000 MBq) was trapped on a preconditioned QMA cartridge (Sep Pak Light. Accell Plus QMA, Waters). The activity was eluted with potassium carbonate/kryptofix solution (in acetonitrile/water) into the reaction vessel 1. The mixture was dried under gentle nitrogen stream at 120° C. Drying was repeated after addition of acetonitrile (1×1 mL). 100 μL dibromo methane in 0.9 mL acetonitrile were added to the dried residue. The resulting mixture was stirred at 130° C. for 5 min. The reaction vessel 1 was coiled to 50° C. and bromo [$^{18}$F]fluoromethane was distilled through 4 silica cartridges (Silica plus, Waters) into reaction vessel 2 containing 1000 μL DMSO.

800 μL of the solution of bromo [$^{18}$F]fluoromethane in DMSO were mixed with 2.1 mg (4S)-4-[4-Hydroxybenzyl]-L-glutamic acid, 200 μL water and 10 μL NaOH (10%). The resulting mixture was heated at 110° C. for 5 min. After cooling to rt, the crude product was diluted with 30 mL water (pH 2) and passed through a preconditioned C18 cartridge (C18 plus, waters). The cartridge was washed with 10 mL water (pH 2) and the activity was eluted with 1 mL fractions ethanol. Fractions 1 and 2 were combined (470 MBq), dilute with 30 mL water (pH 2) and passed through a Strata-X-C cartridge (200 mg, Phenomenex). The cartridge was washed with ethanol (20 mL) and the activity was eluted with 1 mL fractions phosphate buffer (7 g $Na_2HPO_4.2H_2O$; 6 g NaCl in 1 L water) yielding 344 MBq ((4S)-4-{4-[($^{18}$F)fluoromethoxy]benzyl}-L-glutamic acid ([$^{18}$F]-48) in 1 ml buffer (fraction 3). Radiochemical purity was determined to be >99% ($t_R$=2.7 min, analytical HPLC method C; $t_R$=14.7, analytical HPLC method G).

Example 49

(4R)-4-[4-Hydroxybenzyl]-L-glutamic acid

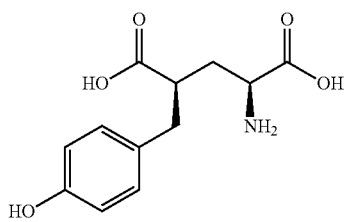 [SMILES: N[C@@H](C[C@@H](Cc1ccc(O)cc1)C(=O)O)C(=O)O]

a) di-tert-butyl 4-[4-(benzyloxy)benzyl]-N-trityl-L-glutamate

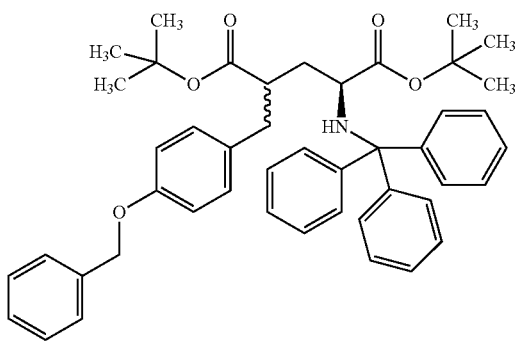 [SMILES: CC(C)(C)OC(=O)C(Cc1ccc(OCc2ccccc2)cc1)C[C@H](NC(c1ccccc1)(c1ccccc1)c1ccccc1)C(=O)OC(C)(C)C]

Di-tert-butyl N-trityl-L-glutamate (1.63 g, 3.25 mmol) was dissolved in tetrahydrofuran (12 ml) and the solution was cooled to −78° C. To the solution was added lithium 1,1,1,3,3,3-hexamethyldisilazide (1M in tetrahydrofuran, 7.14 ml) and, after stirring at −78° C. for 20 min, benzyl 4-(bromomethyl)phenyl ether (1.08 g, 3.90 mmol) in tetrahydrofuran (8 ml) was slowly added. The cooling bath was removed and the reaction mixture was stirred for 2 h. Then, 50 ml of 2 M aqueous hydrogen chloride solution were added and the mixture was extracted with dichloromethane. The organic phase was dried and concentrated under reduced pressure; the residue was purified by silica gel column chromatography to yield 813 mg (30%) of the product.

MS (ESI$^+$): m/e=698.3 (M+H$^+$).

The material is a mixture of diastereomers.

b) di-tert-butyl 4-(4-hydroxybenzyl)-L-glutamate

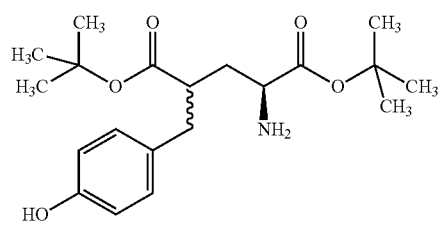 [SMILES: CC(C)(C)OC(=O)C(Cc1ccc(O)cc1)C[C@H](N)C(=O)OC(C)(C)C]

Di-tert-butyl 4-[4-(benzyloxy)benzyl]-N-trityl-L-glutamate (499 mg, 0.72 mmol) were dissolved in methanol (20 ml). Palladium (10% on charcoal) (228 mg; 214 μmol) was added and the suspension was shaken under a hydrogen atmosphere for 12 h. The reaction mixture was filtered through a pad of celite, concentrated under reduced pressure and the residue was purified by silica gel column chromatography to yield 75 mg (28.7%) of the product.

MS (ESI$^+$): m/e=366.1 (M+H+).

The material is a mixture of diastereomers.

c) (4R)-4-(4-hydroxybenzyl)-L-glutamic acid

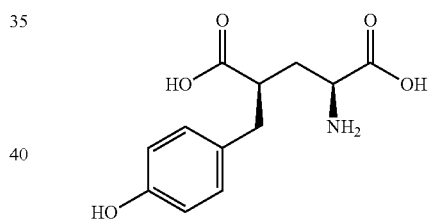

Di-tert-butyl 4-(4-hydroxybenzyl)-L-glutamate (27 mg, 58 μmol) was dissolved in trifluoroacetic acid (1 ml) and stirred at room temperature for 2 h. The mixture was then taken up in toluene and concentrated under reduced pressure. The residue was purified by preparative HPLC (RP-18; solvents: acetonitrile (+0.1% trifluoroacetic acid), water (+0.1% trifluoroacetic acid); gradient: 30%->40% acetonitrile (20 min)).

Two separate diastereomers of 4-(4-hydroxybenzyl)-L-glutamic acid were isolated:

| Compound | Retention time* |
|---|---|
| Major Isomer | 3.91 min |
| Minor Isomer | 3.94 min |
| Reference: (4S)-4[4-[Hydroxybenzyl]-L-glutamic acid (Example 47) | 3.94 min |

*analytical HPLC (RP-18; solvents: acetonitrile (+0.1% trifluoroacetic acid), water (+0.1% trifluoroacetic acid); gradient: 30% –> 40% acetonitrile (20 min))

The major isomer was isolated in 11.4 mg (77%) yield.

MS (ESI$^+$): m/e=254.1 (M+H$^+$).

$^1$H-NMR (400 MHz, DMSO-d$_6$): δ [ppm]=1.56-1.81 (m, 2H), 2.62-2.87 (m, 3H), 3.50-3.59 (m, 1H, overlaps with strong water signal), 6.65 (d, 2H), 6.96 (d, 2H), 9.05-9.30 (m, 1H).

Example 50

(4R)-4-{4-[($^{18}$F)fluoromethoxy]benzyl}-L-glutamic acid

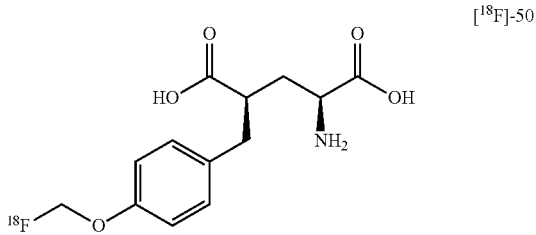 [SMILES: N[C@@H](C[C@@H](Cc1ccc(OC[18F])cc1)C(=O)O)C(=O)O]

[$^{18}$F]-50

[$^{18}$F]Fluoride (16000 MBq) was trapped on a preconditioned QMA cartridge (Sep Pak Light. Accell Plus QMA, Waters). The activity was eluted with potassium carbonate/kryptofix solution (in acetonitrile/water) into the reaction vessel 1. The mixture was dried under gentle nitrogen stream at 120° C. Drying was repeated after addition of acetonitrile (1×1 mL). 100 μL dibromo methane in 0.9 mL acetonitrile were added to the dried residue. The resulting mixture was stirred at 130° C. for 5 min. The reaction vessel 1 was cooled to 50° C. and bromo [$^{18}$F]fluoromethane was distilled through 4 silica cartridges (Silica plus, Waters) into reaction vessel 2 containing 1000 μL DMSO. 500 μL of the solution of bromo [$^{18}$F]fluoromethane in DMSO were mixed with 2.1 mg (4R)-4-[4-Hydroxybenzyl]-L-glutamic acid, 200 μL water, 300 μL DMSO and 10 μL NaOH (10%). The resulting mixture was heated at 110° C. for 5 min. After cooling to rt, the crude product was diluted with 30 mL water (pH 2) and passed through a preconditioned C18 cartridge (C18 plus, waters). The cartridge was washed with 10 mL water (pH 2) and the activity was eluted with 1 mL fractions ethanol. Fractions 1 and 2 were combined (209 MBq), dilute with 30 mL water (pH 2) and passed through a Strata-X-C cartridge (200 mg, Phenomenex). The cartridge was washed with ethanol (20 mL) and the activity was eluted with 1 mL fractions phosphate buffer (7 g Na$_2$HPO$_4$.2H$_2$O; 6 g NaCl in 1 L water) yielding 102 MBq ((4R)-4-{4-[($^{18}$F)fluoromethoxy]benzyl}-L-glutamic acid ([$^{18}$F]-50) in 1 ml buffer (fraction 4). Radiochemical purity was determined to be >99% ($t_R$=2.8 min, analytical HPLC method C).

Example 51

Di-tert-butyl (2S)-2-[(tert-butoxycarbonyl)amino]-5-{4-[(tert-butoxycarbonyl){2-[(methylsulfonyl)oxy]ethyl}amino]benzyl}hexanedioate

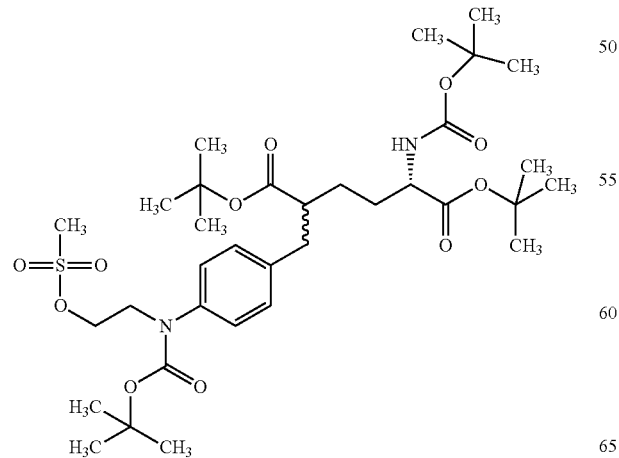

a) 4-benzyl 1,4-di-tert-butyl (1S,4S)-1-[(tert-butoxycarbonyl)amino]-5-(4-nitrophenyl)pentane-1,4,4-tricarboxylate

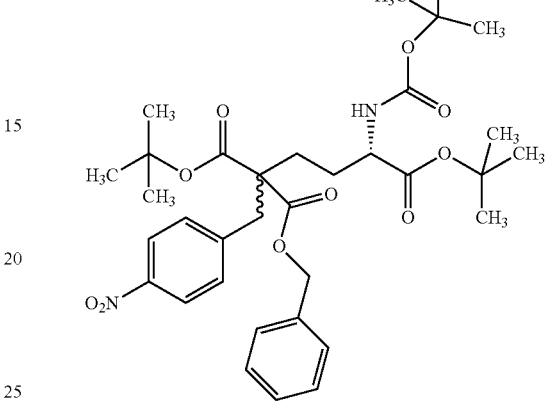

Di-tert-butyl (5S)-2-(benzyloxycarbonyl)-5-[(tert-butoxycarbonyl)amino]hexanedioate (1 g, 1.970 mmol) was dissolved in DMF (20 ml) and sodium hydride (53 mg, 1.773 mmol) was added. After stirring for 60 min, a solution of 4-nitrobenzyl bromide (426 mg, 1.970 mmol) in 10 ml DMF was added and the mixture was stirred at 60° C. for 90 min. The mixture was then concentrated in vacuo, the residue was taken up in water (50 ml) and ethyl acetate (100 ml), and the organic phase was washed with brine (3×50 ml), dried over magnesium sulfate and concentrated in vacuo. The crude product was chromatographed over silica gel (hexane, ethyl acetate) to yield 1.04 g (82%) of a clear oil.

MS (ESI$^+$): m/e=643.2 (M+H$^+$).

b) (5S)-2-(4-aminobenzyl)-6-tert-butoxy-2-(tert-butoxycarbonyl)-5-[(tert-butoxycarbonyl)amino]-6-oxohexanoic acid

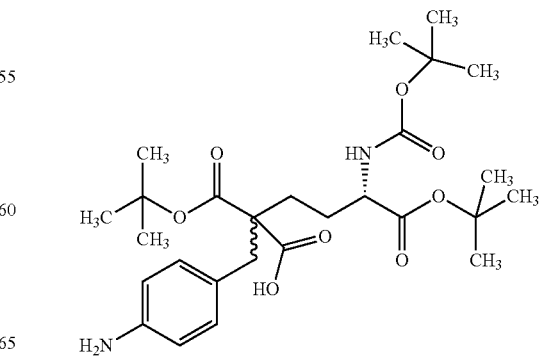

4-benzyl 1,4-di-tert-butyl (1S,4S)-1-[(tert-butoxycarbonyl)amino]-5-(4-nitrophenyl)-pentane-1,4,4-tricarboxylate (1.04 g, 1.618 mmol) were dissolved in methanol (20 ml). Palladium (10% on charcoal) (52 mg) was added and the suspension was shaken under a hydrogen atmosphere for 12 h. The catalyst was filtered off, the residue was concentrated in vacuo, and the product was obtained as white foam (864 mg, quant.).

MS (ESI$^+$): m/e=523.2 (M+H$^+$).

c) Di-tart-butyl (5S)-2-(4-aminobenzyl)-5-[(tert-butoxycarbonyl)amino]hexanedioate

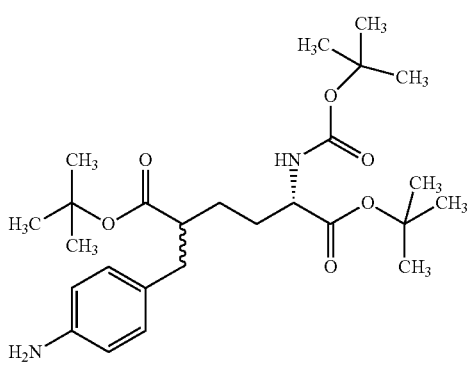 [SMILES: CC(C)(C)OC(=O)N[C@@H](CCC(Cc1ccc(N)cc1)C(=O)OC(C)(C)C)C(=O)OC(C)(C)C]

(5S)-2-(4-aminobenzyl)-6-tert-butoxy-2-(tert-butoxycarbonyl)-5-[(tert-butoxycarbonyl)-amino]-6-oxohexanoic acid (846 mg, 1.618 mmol) were dissolved in dioxane (25 ml). 4-(dimethylamino)pyridine (413 mg, 3.383 mmol) were added and the mixture was refluxed for 6 h. The mixture was concentrated in vacuo and the residue was chromatographed on silica gel (hexane/ethyl acetate) to yield 670 mg (87%) of a slightly yellow oil.

MS (ESI$^+$): m/e=479.2 (M+H$^+$).

d) Di-tert-butyl (5S)-2-(4-{[2-(benzyloxy)ethyl]amino}benzyl)-5-[(tert-butoxycarbonyl)amino]hexanedioate

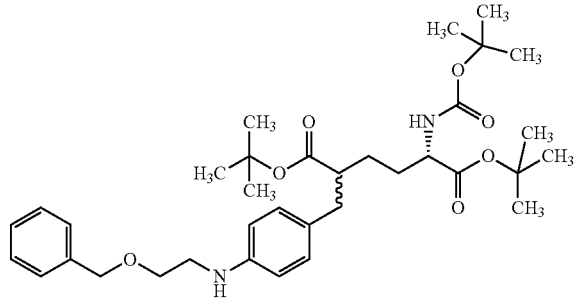 [SMILES: CC(C)(C)OC(=O)N[C@@H](CCC(Cc1ccc(NCCOCc2ccccc2)cc1)C(=O)OC(C)(C)C)C(=O)OC(C)(C)C]

Di-tert-butyl (5S)-2-(4-aminobenzyl)-5-[(tert-butoxycarbonyl)amino]hexanedioate (670 mg, 1.40 mmol) was dissolved in 1,2-dichloroethane (10 ml) and benzyloxyacetaldehyde (210 mg, 1.40 mmol) and sodium triacetoxyborohydride (415 mg, 1.96 mmol) were added. The mixture was stirred at room temperature for 4 h and than poured on 10 ml 1N aqueous sodium hydrogen carbonate solution. The aqueous phase was extracted with dichloromethane (2×10 ml) and the organic phases were washed with water (30 ml), dried over magnesium sulfate and concentrated in vacuo. Flash chromatography on silica gel (hexane, ethyl acetate) gave the product as slightly yellow oil (853 mg, 99%).

MS (ESI$^+$): m/e=613.3 (M+H$^+$).

e) Di-tert-butyl (5S)-2-(4-{[2-(benzyloxy)ethyl](tert-butoxycarbonyl)amino}benzyl)-5-[tert-butoxycarbonyl)amino]hexanedioate

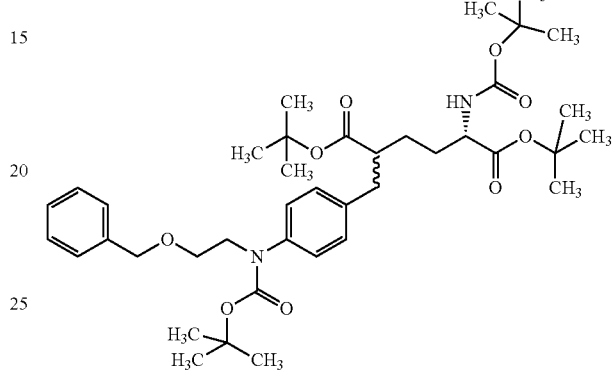

Di-tert-butyl (5S)-2-(4-{[2-(benzyloxy)ethyl]amino}benzyl)-5-[(tert-butoxycarbonyl)-amino]hexanedioate (853 mg, 1.39 mmol) was dissolved in dichloromethane (10 ml) and added slowly to a solution of di-tert-butyldicarbonate (608 mg, 2.78 mmol) in 10 ml dichloromethane. The mixture was stirred at room temperature for 2 d. The mixture was then concentrated and the residue was subjected to chromatography on silica gel (hexane, ethyl acetate) to yield 80 mg (8%) of a colourless oil.

MS (ESI$^+$): m/e=713.5 (M+H$^+$).

f) Di-tert-butyl (2S)-2-[(tert-butoxycarbonyl)amino]-5-{4-[(tert-butoxvcarbonyl)(2-hydroxyethyl)amino]benzyl}hexanedioate

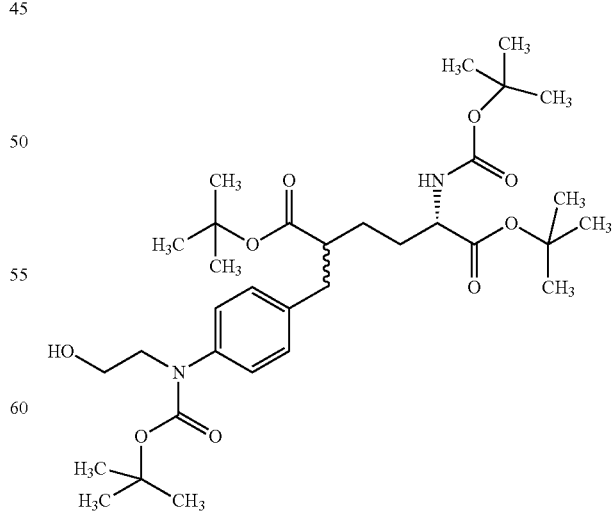

Di-tert-butyl (5S)-2-(4-{[2-(benzyloxy)ethyl](tert-butoxycarbonyl)amino}benzyl)-5-[((tert-butoxycarbonyl)

amino]hexanedioate (78 mg, 110 μmol) were dissolved in 10 ml methanol. Palladium (10% on charcoal) (15 mg) was added and the suspension was shaken under a hydrogen atmosphere for 27 h. The catalyst was filtered off, the residue was concentrated in vacuo to yield 65 mg (95%) of the product.

MS (ESI+): m/e=623.4 (M+H+).

g) Di-tert-butyl (2S)-2-[(tert-butoxycarbonyl)amino]-5-{4-[(tert-butoxycarbonyl){2-[(methylsulfonyl)oxy]ethyl}amino]benzyl}hexanedioate

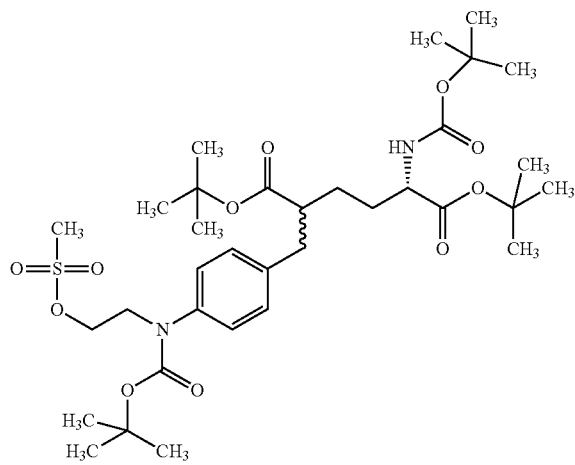 [SMILES: CC(C)(C)OC(=O)N[C@@H](CCC(Cc1ccc(N(CCOS(C)(=O)=O)C(=O)OC(C)(C)C)cc1)C(=O)OC(C)(C)C)C(=O)OC(C)(C)C]

Di-tert-butyl (2S)-2-[(tert-butoxycarbonyl)amino]-5-{4-[(tert-butoxycarbonyl)(2-hydroxy-ethyl)amino]benzyl}hexanedioate (30 mg, 48 μmol) was dissolved in 1 ml dichloromethane. The solution was cooled to 0° C. and triethylamine (200 μl, 1.43 mmol) and methanesulfonyl chloride (30 μl, 387 μmol) were slowly added. The mixture was stirred at 0° C. for 2 h and than for additional 12 h, while the temperature was allowed to rise to room temperature. The mixture was then concentrated in vacuo and the residue was chromatographed on silica gel (hexane, ethyl acetate) to give 10 mg (29%) of the mesylate.

MS (ESI+): m/e=701.5 (M+H+).

Example 52

(2S)-2-amino-5-(4-{[2-($^{18}$F)fluoroethyl]amino}benzyl)hexanedioic acid

[$^{18}$F]-52

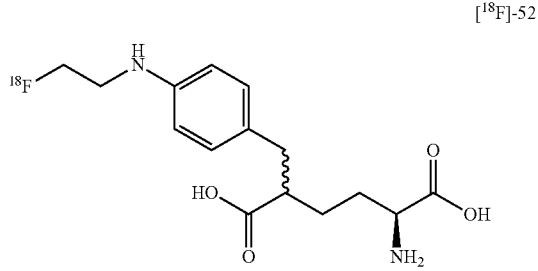 [SMILES: N[C@@H](CCC(Cc1ccc(NCC[18F])cc1)C(=O)O)C(=O)O]

[$^{18}$F]Fluoride (2775 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of di-tert-butyl (2S)-2-[(tert-butoxycarbonyl)amino]-5-{4-[(tert-butoxycarbonyl){2-[(methylsulfonyl)oxy]ethyl}amino]benzyl}hexanedioate in 1 mL acetonitrile were added to the dried residue. The resulting mixture was stirred at 120° C. for 10 min. After cooling to rt, 0.5 mL of the mixture were treated with 2M HCl (0.5 mL) and stirred at 100° C. for 10 min. The crude product was diluted with 30 mL water (pH 2) and passed through a preconditioned Strata-X-C cartridge (200 mg, Phenomenex). The cartridge was washed with 20 mL water (pH 1) and 10 mL ethanol. The cartridge was eluted with 5 mL phosphate buffer (7 g $Na_2HPO_4.2H_2O$; 6 g NaCl in 1 L water) yielding 19 MBq (2S)-2-amino-5-(4-{[2-($^{18}$F)fluoroethyl]amino}benzyl)hexanedioic acid ([$^{18}$F]-52) in a fraction of 1 ml buffer. Radiochemical purity was determined to be >99% ($t_R$=2.9 min, analytical HPLC method F).

Example 53 di-tert-butyl (2S)-2-[(tert-butoxycarbonyl)amino]-5-(4-{[(4S,5S)-2,2-dimethyl-5-({[(4-methylphenyl)sulfonyl]oxy}methyl)-1,3-dioxolan-4-yl]methoxy}benzyl)hexanedioate

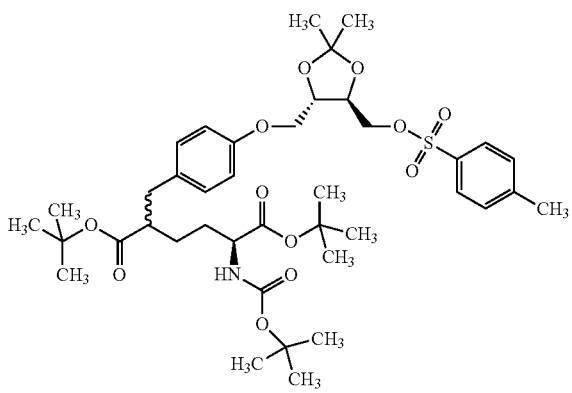 [SMILES: Cc1ccc(S(=O)(=O)OC[C@@H]2OC(C)(C)O[C@H]2COc2ccc(CC(CC[C@H](NC(=O)OC(C)(C)C)C(=O)OC(C)(C)C)C(=O)OC(C)(C)C)cc2)cc1]

500 mg (1.04 mmol) (2S)-2-tert.-Butoxycarbonylamino-5-(4-hydroxy-benzyl)-hexanedioic acid di-tert.-butyl ester, 144 mg (1.04 mmol) potassium carbonate and 491 mg (1.04 mmol) [(4S,5S)-2,2-dimethyl-1,3-dioxolane-4,5-diyl]bis(methylene) bis(4-methylbenzenesulfonate) in 12 mL DMF were heated in a microwave at 100° C. for 2 h. Brine (300 mL) was added and the mixture was extracted with dichloromethane (3×100 mL). The combined organic fractions were dried over sodium sulfate and concentracted. The crude product was purified by Flash chromatography (Silica, 2-40% ethyl acetate in hexane) to afford 430 mg (52%) di-tert-butyl (2S)-2-[(tert-butoxycarbonyl)amino]-5-(4-{[(4S,5S)-2,2-dimethyl-5-({[(4-methylphenyl)sulfonyl]oxy}methyl)-1,3-dioxolan-4-yl]methoxy}benzyl)hexanedioate.

$^1$H-NMR (400 MHz, CHLOROFORM-d): δ [ppm]=1.32-1.68 (m, 19H), 1.71-1.85 (m, 1H), 2.44 (s, 3H), 2.46-2.66 (m, 2H), 2.78-2.87 (m, 1H), 3.94 (dd, 1H), 4.06-4.29 (m, 6H), 5.03 (br. s, 1H), 6.74 (d, 2H), 7.06 (dd, 2H), 733 (d, 2H), 7.80 (d, 2H).

ES+ m/z 778 (M+H), 800 (M+Na).

Example 54

(2S)-2-amino-5-(4-{[(2S,3R)-4-($^{18}$F)fluoro-2,3-dihydroxybutyl]oxy}benzyl)hexanedioic acid

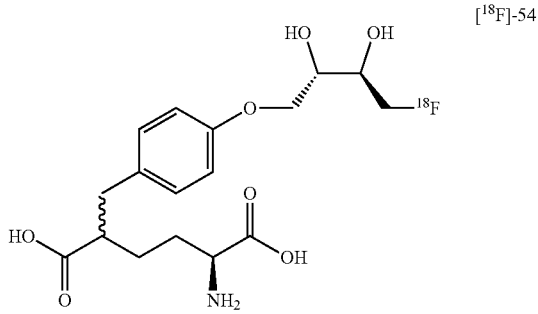 [SMILES: N[C@@H](CCC(Cc1ccc(OC[C@H](O)[C@@H](O)C[18F])cc1)C(=O)O)C(=O)O]

[$^{18}$F]-54

[$^{18}$F]Fluoride (850 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg of di-tert-butyl (2S)-2-[(tert-butoxycarbonyl)amino]-5-(4-{[(4S,5S)-2,2-dimethyl-5-({[(4-methylphenyl)sulfonyl]oxy}methyl)-1,3-dioxolan-4-yl]methoxy}benzyl)hexanedioate in 1 mL acetonitrile were added to the dried residue. The resulting mixture was stirred at 120° C. for 10 min. After cooling to rt 2M HCl (1 mL) and stirred at 120° C. for 10 min. The crude product was diluted with 30 mL water (pH 2) and passed through a preconditioned Strata-X-C cartridge (200 mg, Phenomenex). The cartridge was washed with 20 mL water (pH 2) and 20 mL ethanol. The cartridge was eluted in 1 mL fractions with phosphate buffer (7 g Na$_2$HPO$_4$.2H$_2$O; 6 g NaCl in 1 L water) yielding 74 MBq (22%, d.c.) (2S)-2-amino-5-(4-{[(2S,3R)-4-($^{18}$F)fluoro-2,3-dihydroxybutyl]oxy}benzyl)hexanedioic acid ([$^{18}$F]-54) in a fraction of 1 ml buffer (fraction 3). Radiochemical purity was determined to be >99% (t$_R$=2.6 min, analytical HPLC method C).

Example 55 di-tert-butyl (4S)—N-(tert-butoxycarbonyl)-4-(2,3-dihydro[1,3]oxazolo[3,2-a]pyridin-4-ium-6-ylmethyl)-L-glutamate 4-methylbenzenesulfonate

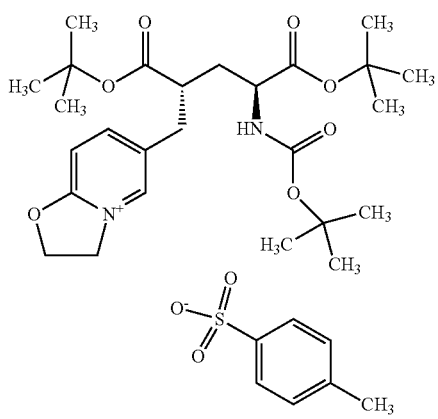 [SMILES: CC(C)(C)OC(=O)N[C@@H](C[C@H](Cc1ccc2[n+](c1)CCO2)C(=O)OC(C)(C)C)C(=O)OC(C)(C)C ; Cc1ccc(S(=O)(=O)[O-])cc1]

Di-tert-butyl (4S)—N-(tert-butoxycarbonyl)-4-{[6-(2-hydroxyethoxy)pyridin-3-yl]methyl}-L-glutamate (88 mg, 0.17 mmol) was dissolved in dichloromethane (10 mL) and treated with 2,6-lutidine (28 mg, 0.26 mmol) and p-toluenesulfonic anhydride (84 mg, 0.26 mmol). The mixture was stirred at room temperature over night, concentrated and purified by RP-HPLC (70-30% water (0.1% HCOOH) in acetonitrile).

81 mg (57%) di-tert-butyl (4S)—N-(tert-butoxycarbonyl)-4-(2,3-dihydro[1,3]oxazolo[3,2-a]pyridin-4-ium-6-ylmethyl)-L-glutamate 4-methylbenzenesulfonate were obtained.

$^1$H-NMR (400 MHz, CHLOROFORM-d): δ [ppm]=1.32-2.00 (m, 30H), 2.33 (s, 3H), 2.87-3.08 (m, 2H), 4.10-4.23 (m, 1H), 5.18-5.31 (m, 3H), 5.31-5.49 (m, 2H), 7.08-7.17 (m, 3H), 7.71 (d, 2H), 8.10-8.14 (m, 1H), 8.76 (s, 1H).

Example 56

4-({6-[2-($^{18}$F)fluoroethoxy]pyridin-3-yl}methyl)-L-glutamic acid

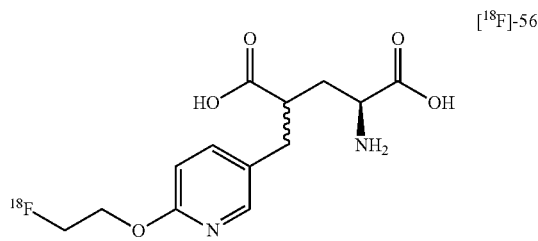 [SMILES: N[C@@H](CC(Cc1ccc(OCC[18F])nc1)C(=O)O)C(=O)O]

[$^{18}$F]-56

[$^{18}$F]Fluoride (2702 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg di-tert-butyl (4S)—N-(tert-butoxycarbonyl)-4-(2,3-dihydro[1,3]oxazolo[3,2-a]pyridin-4-ium-6-ylmethyl)-L-glutamate 4-methylbenzenesulfonate in 1 mL acetonitrile were added to the dried residue. The resulting mixture was stirred at 120° C. for 10 min. After cooling to rt 2M HCl (1 mL) and stirred at 120° C. for 5 min. The crude product was diluted with 30 mL water (pH 2) and passed through a preconditioned Strata-X-C cartridge (200 mg, Phenomenex). The cartridge was washed with 40 mL water (pH 2) and 30 mL ethanol. The cartridge was eluted in 1 mL fractions with phosphate buffer (7 g Na$_2$HPO$_4$.2H$_2$O; 6 g NaCl in 1 L water) yielding 338 MBq (21%, d.c.) 4-({6-[2-($^{18}$F)fluoroethoxy]pyridin-3-yl}methyl)-L-glutamic acid ([$^{18}$F]-56) in a fraction of 1 ml buffer (fraction 3). Radiochemical purity was determined to be >99% (t$_R$=2.7 min, analytical HPLC method F).

Example 57 di-tert-butyl (4S)—N-(tert-butoxycarbonyl)-4-(4-{[(4S,5S)-2,2-dimethyl-5-({[(4-methylphenyl)sulfonyl]oxy}methyl)-1,3-dioxolan-4-yl]methoxy}benzyl)-L-glutamate

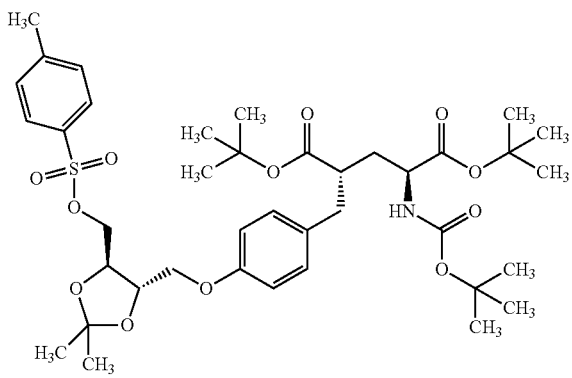 [SMILES: Cc1ccc(S(=O)(=O)OC[C@@H]2OC(C)(C)O[C@H]2COc2ccc(C[C@@H](C[C@H](NC(=O)OC(C)(C)C)C(=O)OC(C)(C)C)C(=O)OC(C)(C)C)cc2)cc1]

To 0.47 g (1 mmol) (4S)—N-(tert-butoxycarbonyl)-4-(4-hydroxybenzyl)-L-glutamate and 0.47 g (1 mmol) [(4S,5S)-2,2-dimethyl-1,3-dioxolane-4,5-diyl]dimethanediyl bis(4-methylbenzenesulfonate) in 15 mL DMF was added potassium carbonate (0.28 g, 2 mmol). The mixture was heated in a microwave for 2 h at 100° C. Water was added and the mixture was extracted with dichloromethane. The organic phase was dried over sodium sulfate, filtered and concentrated. The crude product was purified by flash chromatography (silica, 20% ethyl acetate in hexane) to afford 0.25 g (33%) di-tert-butyl (4S)—N-(tert-butoxycarbonyl)-4-(4-{[(4S,5S)-2,2-dimethyl-5-({[(4-methylphenyl)sulfonyl]oxy}methyl)-1,3-dioxolan-4-yl]methoxy}benzyl)-L-glutamate.

$^1$H-NMR (400 MHz, CHLOROFORM-d): δ [ppm]=1.31 (s, 9H), 1.37-1.53 (m, 23H), 1.87 (t, 2H), 2.44 (s, 3H), 2.61 (quin, 1H), 2.81 (br. d, 2H), 3.92-3.97 (m, 1H), 4.06-4.29 (m, 7H), 4.88 (d, 1H), 6.74 (d, 2H), 7.08 (d, 2H), 7.33 (d, 2H), 7.80 (d, 2H).

Example 58

4-(4-{[(2S,3R)-4-($^{18}$F)fluoro-2,3-dihydroxybutyl]oxy}benzyl)-L-glutamic acid

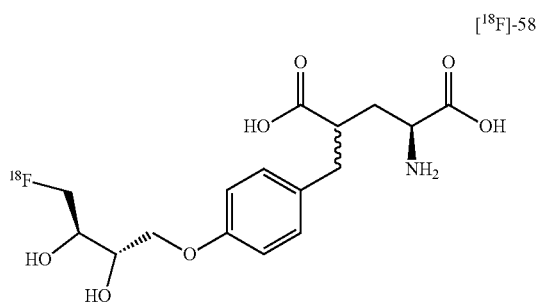 [SMILES: N[C@@H](CC(Cc1ccc(OC[C@H](O)[C@@H](O)C[18F])cc1)C(=O)O)C(=O)O]

[$^{18}$F]-58

[$^{18}$F]Fluoride (3565 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg di-tert-butyl (4S)—N-(tert-butoxycarbonyl)-4-(4-{[(4S,5S)-2,2-dimethyl-5-({[(4-methylphenyl)sulfonyl]oxy}methyl)-1,3-dioxolan-4-yl]methoxy}benzyl)-L-glutamate in 1 mL acetonitrile were added to the dried residue. The resulting mixture was stirred at 100° C. for 10 min. After cooling to rt 2M HCl (1 mL) and stirred at 120° C. for 10 min. The crude product was diluted with 30 mL water (pH 2) and passed through a preconditioned Strata-X-C cartridge (200 mg, Phenomenex). The cartridge was washed with 20 mL water (pH 2) and 20 mL ethanol. The cartridge was eluted in 1 mL fractions with phosphate buffer (7 g Na$_2$HPO$_4$.2H$_2$O; 6 g NaCl in 1 L water) yielding 545 MBq (23%, d.c.) 4-(4-{[(2S,3R)-4-($^{18}$F)fluoro-2,3-dihydroxybutyl]oxy}benzyl)-L-glutamic acid ([$^{18}$F]-58) in a fraction of 2 ml buffer (fraction 1+2). Radiochemical purity was determined to be >99% (t$_R$=2.6 min, analytical HPLC method C).

Example 59 di-tert-butyl (4S) N-(tert-butoxycarbonyl)-4-{4-[(1-hydroxy-3-{[(4-methylphenyl)sulfonyl]oxy}propan-2-yl)oxy]benzyl}-L-glutamate

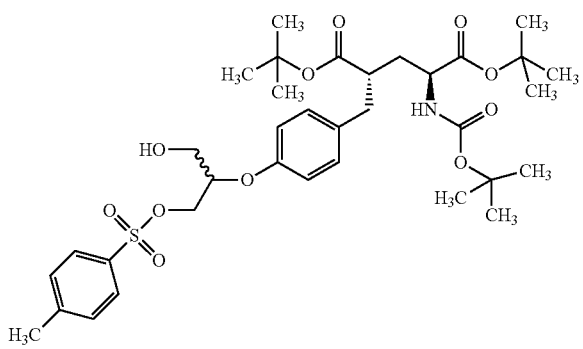 [SMILES: Cc1ccc(S(=O)(=O)OCC(CO)Oc2ccc(C[C@@H](C[C@H](NC(=O)OC(C)(C)C)C(=O)OC(C)(C)C)C(=O)OC(C)(C)C)cc2)cc1]

To 0.93 g (2 mmol) (4S)—N-(tert-butoxycarbonyl)-4-(4-hydroxybenzyl)-L-glutamate and 1.34 g (4 mmol) cis-2-phenyl-1,3-dioxan-5-yl 4-methylbenzenesulfonate in 18 mL was added potassium carbonate (0.55 g, 4 mmol). The mixture was heated in a microwave for 2 h at 100° C. Water was added and the mixture was extracted with ethyl acetate. The organic phase was dried over sodium sulfate, filtered and concentrated. The crude product was purified by flash chromatography to afford 0.165 g (13%) di-tert-butyl (4S)—N-(tert-butoxycarbonyl)-4-{4-[(trans-2-phenyl-1,3-dioxan-5-yl)oxy]benzyl}-L-glutamate. The benzylidene protected derivative (0.13 g, 0.2 mmoL)) was dissolved in methanol (15 mL) Palladium/C (10% Pd) was added and the mixture was stirred under hydrogen atmosphere over night. The mixture was filtered and the solvent was evaporated, yielding 0.11 g (100%) di-tert-butyl (4S)—N-(tert-butoxycarbonyl)-4-{4-[(1,3-dihydroxypropan-2-yl)oxy]benzyl}-L-glutamate.

The dihydroxy derivative (0.11 g, 0.2 mmol) was dissolved in dichloromethane (19 mL). Pyridiene (100 μL) and 4-methylbenzenesulfonyl chloride (38 mg, 0.2 mmol) were added at 0° C. The mixture was stirred for 2.5 h. The crude product was purified by flash-chromatography (silica, dichloromethane/methanol) yielding 55 mg (40%) di-tert-butyl (4S) N-(tert-butoxycarbonyl)-4-{4-[(1-hydroxy-3-{[(4-methylphenyl)sulfonyl]oxy}propan-2-yl)oxy]benzyl}-L-glutamate.

$^1$H-NMR (400 MHz, CHLOROFORM-d): δ [ppm]=1.32 (s, 9H), 1.38-1.98 (m, 20H), 1.87 (t, 2H), 2.45 (s, 3H), 2.60 (quin, 1H), 2.72-2.89 (m, 2H), 3.74-3.90 (m, 2H), 4.09-4.29 (m, 3H), 4.45 (m$_c$, 1H), 4.89 (d, 1H), 6.74-6.81 (m, 2H), 7.03-7.10 (m, 2H), 7.33 (d, 2H), 7.77 (d, 2H).

Example 60

4-(4-{[1-($^{18}$F)fluoro-3-hydroxypropan-2-yl]oxy}benzyl)-L-glutamic acid

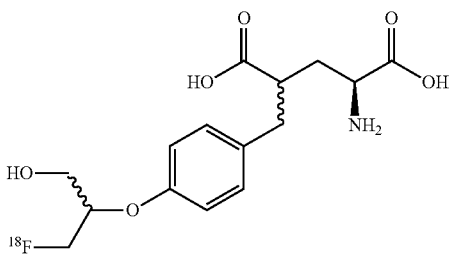

[$^{18}$F]-60

[$^{18}$F]Fluoride (3400 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg di-tert-butyl (4S) N-(tert-butoxycarbonyl)-4-{4-[(1-hydroxy-3-{[(4-methylphenyl)sulfonyl]oxy}propan-2-yl)oxy]benzyl}-L-glutamate in 1 mL DMSO were added to the dried residue. The resulting mixture was stirred at 120° C. for 15 min. After cooling to rt 2M HCl (1 mL) and stirred at 120° C. for 8 min. The crude product was diluted with 30 mL water (pH 2) and passed through a preconditioned Strata-X-C cartridge (200 mg, Phenomenex). The cartridge was washed with 30 mL water (pH 2) and 30 mL ethanol. The cartridge was eluted in 1 mL fractions with phosphate buffer (7 g Na$_2$HPO$_4$.2H$_2$O; 6 g NaCl in 1 L water) yielding 307 MBq (23%, d.c.) 4-(4-{[1-($^{18}$F)fluoro-3-hydroxypropan-2-yl]oxy}benzyl)-L-glutamic acid ([$^{18}$F]-60) in a fraction of 1 mL buffer (fraction 3). Radiochemical purity was determined to be >99% (t$_R$=2.7 min, analytical HPLC method C).

Example 61

(4R)-4-{[1-(2-fluoroethyl)-1H-1,2,3-triazol-4-yl]methyl}-L-glutamic acid

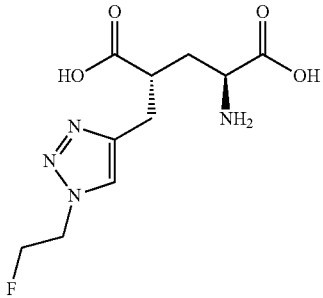

a) di-tert-butyl (4S)—N-(tert-butoxycarbonyl)-4-prop-2-yn-1-yl-L-glutamate

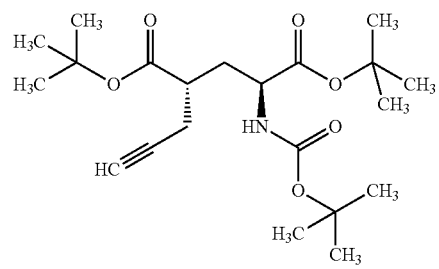 [SMILES: C#CC[C@@H](C[C@H](NC(=O)OC(C)(C)C)C(=O)OC(C)(C)C)C(=O)OC(C)(C)C]

Di-tert-butyl N-(tert-butoxycarbonyl)-L-glutamate (633 mg, 1.76 mmol) was dissolved in tetrahydrofuran (6 ml) and at −78° C., lithium bis(trimethylsilyl)amide (1M in tetrahydrofuran, 3.87 ml) were added dropwise. After 30 min, 3-bromo-1-(trimethylsilyl)-1-propyne (370 mg, 1.94 mmol) in tetrahydrofuran (2 ml) was added dropwise and the mixture was stirred at −78° C. for 3 h. The reaction was than warmed to 0° C. and 10 ml of 1 N hydrochloric acid were added. The mixture was extracted with dichloromethane, dried and concentrated in vacuo. The residue was purified by silica gel chromatography to give the intermediate TMS-protected alkyne. The intermediate was dissolved in 30 ml dichloromethane/methanol (1:1). Potassium carbonate (1 g) was added and the mixture was stirred for 1 h. Water (20 ml) was added and the mixture was extracted with dichloromethane, dried and concentrated in vacuo. The product (416 mg, 59%) was used in the following reaction without further purification.

MS (ESI$^+$): m/e=398.5 (M+H+).

b) di-tert-butyl (4R)—N-(tert-butoxycarbonyl)-4-{[1-(2-hydroxyethyl)-1H-1,2,3-triazol-4-yl]methyl}-L-glutamate

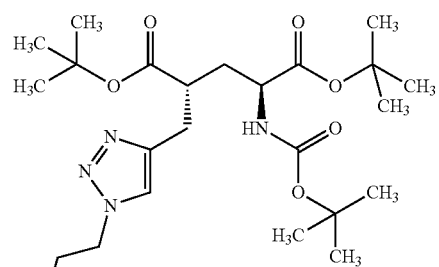

Di-tert-butyl (4S)—N-(tert-butoxycarbonyl)-4-prop-2-yn-1-yl-L-glutamate (150 mg, 377 μmol) and 2-azidoethanol (49 mg, 566 μmol) were dissolved in tetrahydrofuran (3.75 ml). To the solution, copper(I) iodide (7.2 mg, 38 μmol) and N,N-diisopropylethylamine (79 μl, 453 μmol) were added and the mixture was stirred for 12 h at room temperature. The mixture was then concentrated in vacuo and the residue was purified by preparative reversed phase HPLC to yield 62 mg (34%) of the product.

MS (ESI$^+$): m/e=485.2 (M+H$^+$).

c) di-tert-butyl (4R)—N-(tert-butoxycarbonyl)-4-{[1-(2-fluoroethyl)-1H-1,2,3-triazol-4-yl]methyl}-L-glutamate

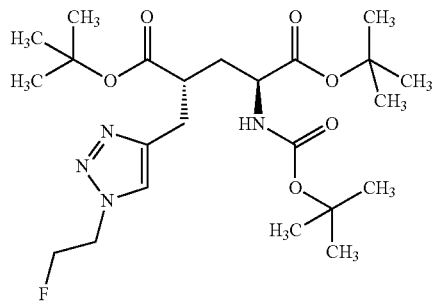 [SMILES: CC(C)(C)OC(=O)N[C@@H](C[C@H](Cc1cn(CCF)nn1)C(=O)OC(C)(C)C)C(=O)OC(C)(C)C]

Di-tert-butyl (4R)—N-(tert-butoxycarbonyl)-4-{[1-(2-hydroxyethyl)-1H-1,2,3-triazol-4-yl]methyl}-L-glutamate (74 mg, 152.7 μmol) was dissolved in tetrahydrofuran (5 ml) and triethyl amine (319 μl, 2.3 mmol), Nonafluorobutanesulfonyl fluoride (185 mg, 611 μmol), and Triethylamine trihydrofluoride (98 mg, 611 mmol) were added subsequently. The mixture was stirred at room temperature for 6 days. The mixture was than concentrated in vacuo, and the residue was purified by silica gel chromatography to yield 30 mg (40%) of slightly impure product, which was used in the following step.

MS (ESI+): m/e=487.2 (M+H+).

d) (4R)-4-{[1-(2-fluoroethyl)-1H-1,2,3-triazol-4-yl]methyl}-L-glutamic acid

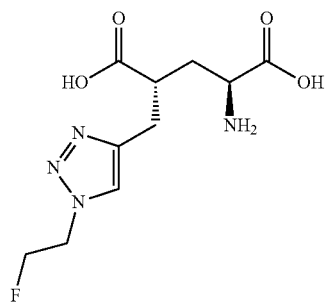

Di-tert-butyl (4R)—N-(tert-butoxycarbonyl)-4-{[1-CZ-fluoroethyl)-1H-1,2,3-triazol-4-yl]methyl}-L-glutamate (30 mg, 61.7 μmol) were stirred in trifluoroacetic acid (2 ml) for 12 h. To the reaction mixture was added dichloromethane (20 ml) and the mixture was concentrated in vacuo. The residue was purified by preparative reversed phase HPLC to yield 2 mg (11%) of the product.

MS (ESI−): m/e=273.5 (M−H+).

¹H-NMR (300 MHz, DEUTERIUM OXIDE): δ [ppm]=1.98-2.22 (m, 2H), 3.04-3.11 (m, 3H), 3.89-3.97 (m, 1H), 4.63-4.73 (m, 2H), 4.79-4.96 (m, 2H) (overlaps with solvent signal), 7.86-7.92 (m, 1H).

Example 62 di-tert-butyl (4R)—N-(tert-butoxycarbonyl)-4-[(1-{2-[(methylsulfonyl)oxy]ethyl}-1H-1,2,3-triazol-4-yl)methyl]-L-glutamate

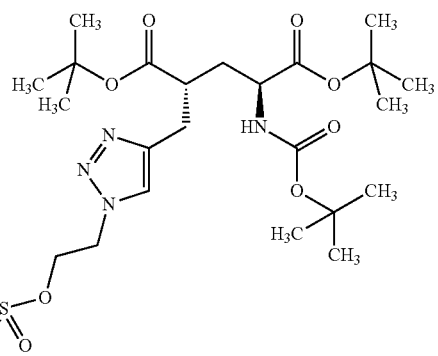

Di-tert-butyl (4S)—N-(tert-butoxycarbonyl)-4-prop-2-yn-1-yl-L-glutamate (60 mg, 151 μmol) and 2-azidoethyl methanesulfonate (37.4 mg, 226 μmol) were dissolved in tetrahydrofuran (4 ml). To the solution, copper(I) iodide (2.9 mg, 15 μmol) and N,N-diisopropylethylamine (32 μl, 181 μmol) were added and the mixture was stirred for 18 h at room temperature. The mixture was then concentrated in vacuo and the residue was purified by preparative reversed phase HPLC. The product fractions were collected, lyophilized, and purified again by silicagel chromatography to yield 50 mg (47%) of the product.

MS (ESI+): m/e=563.2 (M+H+).

¹H-NMR (400 MHz, DMSO-de): δ [ppm]=1.34 (s, 9H), 1.38 (s, 18H), 1.70-1.90 (m, 2H), 2.62-2.86 (m, 2H), 3.09 (s, 3H), 3.34 (br. s., 2H), 4.58 (m, 2H), 4.68 (m, 2H), 7.04-7.16 (m, 1H), 7.85 (s, 1H).

Example 63

4-({1-[2-(¹⁸F)fluoroethyl]-1H-1,2,3-triazol-4-yl}methyl)-L-glutamic acid

[¹⁸F]-62

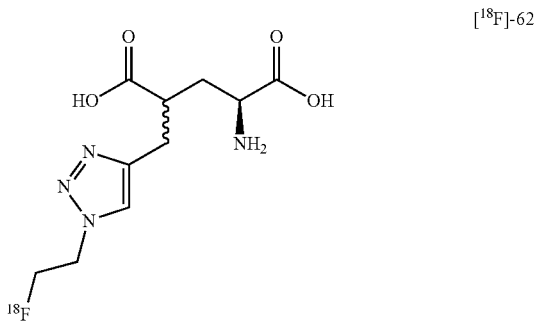 [SMILES: N[C@@H](CC(Cc1cn(CC[18F])nn1)C(=O)O)C(=O)O]

[¹⁸F]Fluoride (2188 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg di-tert-butyl (4R)—N-(tert-butoxycarbonyl)-4-[(1-{2-[(methylsulfonyl)oxy]ethyl}-1H-1,2,3-triazol-4-yl)methyl]-L-glutamate in 1 mL acetonitrile were added to the dried residue. The resulting mixture was stirred at 120° C. for 10 min. After cooling to rt 2M HCl (1 mL) and stirred at 120° C. for 10 min. The crude product was diluted with 30 mL water (pH 2) and passed through a preconditioned Strata-X-C cartridge (200 mg, Phenomenex). The cartridge was washed with 30 mL water (pH 2) and 30 mL ethanol. The cartridge was eluted in 1 mL fractions with phosphate buffer (7 g $Na_2HPO_4.2H_2O$; 6 g NaCl in 1 L water) yielding 278 MBq (20%, d.c.) 4-({1-[2-($^{18}F$)fluoroethyl]-1H-1,2,3-triazol-4-yl}methyl)-L-glutamic acid ([$^{18}F$]-62) in a fraction of 2 mL buffer (fraction 2+3). Radiochemical purity was determined to be >98% ($t_R$=3.8 min, analytical HPLC method F).

Example 64

(2S)-2-amino-5-[4-([$^{18}F$]fluoroethoxy)benzyl]hexanedioic acid—Isomer C5-1

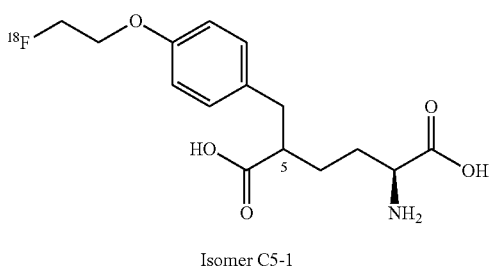

Isomer C5-1 a) 1-bromo-2-($^{18}F$)fluoroethane

[$^{18}F$]Fluoride (5492 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (1×1 mL). 10 mg 2-bromoethyl 4-nitrobenzenesulfonate in 0.5 mL 1,2-dichloro benzene were added to the dried residue. 1-bromo-2-($^{18}F$)fluoroethane was distilled of the reaction mixture into a second vial filled with 500 µL DMSO.

b) (2S)-2-amino-5-[4-([$^{18}F$]fluoroethoxy)benzyl] hexanedioic acid—Isomer C5-1

A solution of 124 MBq 1-bromo-2-($^{18}F$)fluoroethane in 250 µL DMSO was added to a mixture of 2.1 mg (2S)-2-amino-5-(4-hydroxybenzyl)hexanedioic acid (isomer 1), 100 µL water, 10 µL 10% NaOH solution and 400 µL DMSO. The resulting mixture was stirred at 120° C. for 15 min. The crude product was diluted with 30 mL water (pH 2) and passed through a preconditioned C18 cartridge (C18 plus, Waters). The cartridge was washed with 20 mL water (pH 2) and the activity was eluted with 5 mL ethanol. The ethanol fraction was diluted with 30 mL water (pH 2) and passed through a preconditioned Strata-X-C cartridge (200 mg, Phenomenex). The cartridge was washed with 20 mL water (pH 2) and 20 mL ethanol. The cartridge was eluted in 1 mL fractions with phosphate buffer (7 g $Na_2HPO_4.2H_2O$; 6 g NaCl in 1 L water) yielding 19 MBq (21%, d.c.) 4-({1-[2-($^{18}F$)fluoroethyl]-1H-1,2,3-triazol-4-yl}methyl)-L-glutamic acid ([$^{18}F$]-12 Isomer C1) in a fraction of 1 mL buffer (fraction 2). Radiochemical purity was determined to be >98% ($t_R$=2.5 min, analytical HPLC method I, $t_R$=19.1, analytical HPLC method G).

Example 65

(2S)-2-amino-5-[4-(fluoroethoxy)benzyl]hexanedioic acid—Isomer C5-2

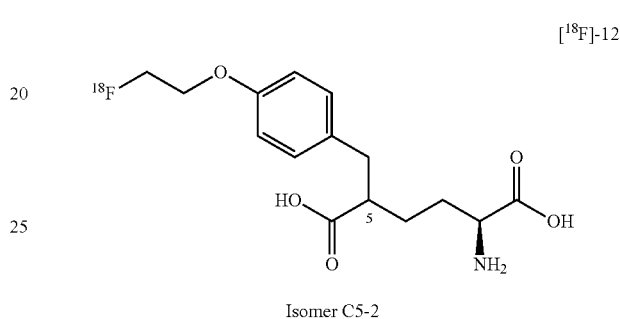

Isomer C5-2

A solution of 165 MBq 1-bromo-2-($^{18}F$)fluoroethane in 250 µL DMSO was added to a mixture of 2.1 mg (2S)-2-amino-5-(4-hydroxybenzyl)hexanedioic acid (isomer 2), 100 µL water, 10 µL 10% NaOH solution and 400 µL DMSO. The resulting mixture was stirred at 120° C. for 15 min. The crude product was diluted with 30 mL water (pH 2) and passed through a preconditioned C18 cartridge (C18 plus, Waters). The cartridge was washed with 20 mL water (pH 2) and the activity was eluted with 5 mL ethanol. The ethanol fraction was diluted with 30 mL water (pH 2) and passed through a preconditioned Strata-X-C cartridge (200 mg, Phenomenex). The cartridge was washed with 20 mL water (pH 2) and 20 mL ethanol. The cartridge was eluted in 1 mL fractions with phosphate buffer (7 g $Na_2HPO_4.2H_2O$; 6 g NaCl in 1 L water) yielding 28 MBq (21%, d.c.) 4-({1-[2-($^{18}F$)fluoroethyl]-1H-1,2,3-triazol-4-yl}methyl)-L-glutamic acid ([$^{18}F$]-12 Isomer C2) in a fraction of 2 mL buffer (fraction 2+3). Radiochemical purity was determined to be >98% ($t_R$=2.5 min, analytical HPLC method I, $t_R$=20.1, analytical HPLC method G).

Example 66 di-tert-butyl (4S)-4-[4-(bromomethyl)benzyl]-Nert-butoxycarbonyl)-L-glutamate

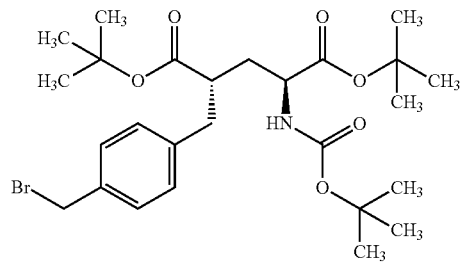 [SMILES: CC(C)(C)OC(=O)N[C@@H](C[C@H](Cc1ccc(CBr)cc1)C(=O)OC(C)(C)C)C(=O)OC(C)(C)C]

Di-tert-butyl N-(tert-butoxycarbonyl)-L-glutamate (1.0 g, 2.8 mmol) was dissolved in tetrahydrofuran (16 ml) and at −78° C., lithium bis(trimethylsilyl)amide (1M in tetrahydrofuran, 6.12 ml) were added dropwise. After 90 min, 1,4-bis (bromomethyl)benzene (1.3 mg, 3.7 mmol) was added and the mixture was stirred at −78° C. for 2.5 h. The reaction was then warmed to 0° C. and 14 ml of 2 N hydrochloric acid were added. The mixture was extracted with dichloromethane, dried and concentrated in vacuo. The residue was purified by silica gel (hexane/ethyl acetate) for afford 0.17 g (11%) di-tert-butyl (4S)-4-[4-(bromomethyl)benzyl]-Nert-butoxycarbonyl)-L-glutamate.

$^1$H-NMR (400 MHz, CHLOROFORM-d): δ [ppm]=1.30 (s, 9H), 1.40-1.50 (m, 18H), 1.89 (t, 2H), 2.65 (quin, 1H), 2.75-2.94 (m, 2H), 4.07-4.25 (m, 1H), 4.47 (s, 2H), 4.88 (d, 1H), 7.15 (d, 2H), 7.29 (d, 2H).

Example 67

4-{4-[($^{18}$F)fluoromethyl]benzyl}-L-glutamic acid

[$^{18}$F]-66

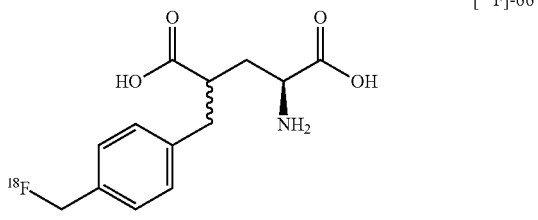

[$^{18}$F]Fluoride (3000 MBq) was trapped on a preconditioned QMA cartridge (Sep Pak Light. Accell Plus QMA, Waters). The activity was eluted with potassium carbonate/kryptofix solution (in acetonitrile/water) into the reaction vial. The mixture was dried under gentle nitrogen stream at 120° C. Drying was repeated after addition of acetonitrile (2×1 mL). 5 mg di-tert-butyl (45)-4-[4-(bromomethyl)benzyl]-Nert-butoxycarbonyl)-L-glutamate in 0.5 mL acetonitrile were added to the dried residue. The resulting mixture was stirred at 100° C. for 8 min.

150 μL of protected crude product mixture were added to 350 μL acetonitrile and 500 μL trifluoro acetic acid and the mixture was stirred at 50° C. for 10 min. The crude product was diluted with 30 mL water (pH 2) and passed through a preconditioned Strata-X-C cartridge (200 mg, Phenomenex). The cartridge was washed with 20 mL water (pH 2) and 20 mL ethanol. The cartridge was eluted in 1 mL fractions with phosphate buffer (7 g Na$_2$HPO$_4$.2H$_2$O; 6 g NaCl in 1 L water) yielding 31 MBq 4-{4-[($^{18}$F)fluoromethyl]benzyl}-L-glutamic acid ([$^{18}$F]-66) in a fraction of 1 mL buffer (fraction 3). Radiochemical purity was determined to be >99% ($t_R$=2.9 min, analytical HPLC method C).

Biology Examples

Example 68

In Vitro Cell-Uptake Study Blocking of Radiolabeled Glutamate Derivative Uptake Using Compounds from the Present Invention The ability of compounds from the present invention to compete with radiolabeled glutamate derivatives for uptake into tumor cells was examined. NCI-H460 (human NSCLC) cells, grown adherently in 48 well plates were used for these competition-experiments. Approximately 100.000 cells were co-incubated in PBS-buffer containing 0.1% BSA with a radiolabeled Glutamic acid derivative and several compounds, which were used at a concentration of 1 mM for 30 minutes. After this time, the cell bound radioactivity was determined. Interestingly, it was observed, that compounds from the invention are better competitors of radiolabeled glutamic acid derivative uptake into H460 cells than the naturally occurring L-glutamic acid.

TABLE 1

| Compound | Compound No | Uptake of radiolabeled glutamate-derivative (% of control)* |
|---|---|---|
| L-glutamic acid | — | 26.1 ± 0.3 |
| L-cystine | — | 10.7 ± 0.7 |
| (4S)-4-[4-(2-Fluoroethoxy)benzyl]-L-glutamic acid | 1 | 5.0 ± 0.2 |
| (4S)-4-[4-(3-Fluoropropoxy)benzyl]-L-glutamic acid | 4 | 3.0 ± 0.1 |
| 4-[4-(3-Fluoropropyl)benzyl]-L-glutamic acid | 9 | 14.2 ± 1.0 |
| (2S)-2-Amino-5-[4-(2-Fluoroethoxy)benzyl]-hexanedioic acid | 12 | 3.9 ± 0.3 |
| (4S)-4-{3-[4-(2-Fluoroethoxy)phenyl]propyl}-L-glutamic acid | 25 | 20.1 ± 0.4 |
| 4-{3-[4-(3-Fluoropropyl)phenyl]propyl}-L-glutamic acid | 19 | 6.6 ± 1.6 |
| (4R)-4-[4-(2-Fluoroethoxy)benzyl]-D-glutamic acid | 23 | 43.8 ± 3.2 |
| (4R)-4-[4-(3-Fluoropropoxy)benzyl]-D-glutamic acid | 24 | 36.5 ± 3.8 |

*Uptake of radiolabeled glutamate-derivative in H460 cells in the presence and absence of compounds from the invention (used at a concentration of 1 mM). Values are reported as % of control (mean ± SD). Uptake of radiolabeled glutamate-derivative without addition of compound is 100%.

Example 69

Cell Uptake Studies: 30 Min Uptake in H460 Cells

For determination of the biological activity, the F18 labeled derivatives were used as tracers in cell uptake experiments. NCI-H460 (human NSCLC) cells, grown adherently in 48 well plates were used for these uptake-experiments. Approximately 100.000 cells were incubated with 0.25 MBq of the tracers for 30 min in PBS-buffer containing 0.1% BSA. After this time, the cell-bound radioactivity was determined using a γ-counter. Interestingly, between 3 and 15% of the applied dose were taken up by the cells during this 30 min incubation period.

TABLE 2

| Compound | Compound No | 30 min uptake into H460 cells [%/100.000 cells] |
|---|---|---|
| 4-[4-(2-[$^{18}$F]Fluoroethoxy)benzyl]-L-glutamic acid | [$^{18}$F]-1 | 9.1 ± 0.6 |
| 4-[4-(3-[$^{18}$F]Fluoropropoxy)benzyl]-Lglutamic acid- | [$^{18}$F]-4 | 10.0 ± 0.3 |

TABLE 2-continued

| Compound | Compound No | 30 min uptake into H460 cells [%/100.000 cells] |
|---|---|---|
| 4-[4-(3-[$^{18}$F]fluoropropyl)benzyl]-L-glutamic acid | [$^{18}$F]-9 | 4.3 ± 0.2 |
| (2S)-2-amino-5-[4-(2-[$^{18}$F]fluoroethoxy)benzyl]-hexanedioic acid | [$^{18}$F]-12 | 10.5 ± 0.3 |
| 4-{4-[(3-[$^{18}$F]fluoropropyl)amino]benzyl}-L-glutamic acid | [$^{18}$F]-8 | 15.3 ± 0.1 |
| (4S)-4-{3-[4-(2-[$^{18}$F]Fluoroethoxy) phenyl]propyl}-L-glutamic acid | [$^{18}$F]-25 | 3.1 ± 01 |
| 4-{4-[(cis-3-[$^{18}$F]Fluorocyclobutyl) oxy]benzyl}-L-glutamic acid | [$^{18}$F]-22 | 4.2 ± 0.1 |

Example 70

Retention of 4-[4-(2-[$^{18}$F]fluoroethoxy)benzyl]-L-glutamic acid ([$^{18}$F]-1) in H460 Cells Over Time The retention of radioactivity in tumor cells was examined. Therefore. H460 cells were loaded with 0.25 MBq of the respective tracer for 30 minutes in PBS buffer, containing 0.1% BSA. After this uptake, the buffer was removed and the cells were washed with PBS. The cells were then reincubated with new PBS buffer, without radioactivity for up to 30 minutes. The release of activity into the supernatant as well as the retention of activity inside the cells was examined. As an example, results of [$^{18}$F]-1 are shown in FIG. 1. It was discovered, that only a limited amount of activity was released into the supernatant during the 30 minute efflux period. More than 80% of the activity were retained inside the tumor cells during the 30 minute incubation under these efflux conditions. Similar results were obtained by using [$^{18}$F]-4, [$^{18}$F]-9, [$^{18}$F]-12, [$^{18}$F]-8 and [$^{18}$F]-22.

Example 71

Competition Profile Indicating Uptake Via xCT (SLC7A11)

For determination of the responsible uptake mechanism, NCI-H460 tumor cells were co-incubated with the F-18 labeled tracer and several cold derivatives. These derivatives were used at a concentration of 1 mM, which is a large excess compared to the tracer. L-Glutamic acid, L-cystine, Carboxyphenylglycine (CPG) were used as competitors. In addition, also D-Glutamic acid, as well as L-aspartic acid and D-aspartic acid were used in this competition experiments. FIG. 2 shows one example which was obtained by using [$^{18}$F]-12. Interestingly, it was discovered, that the uptake of [$^{18}$F]-12 could be reduced by more than 90% by using an excess of L-Glutamic acid, L-cystine, Carboxyphenylglycine (CPG) and the corresponding F19-compound 12. D-Glutamic acid and L-aspartic and D-aspartic acid are less effective competitors. The strong competition of L-cystine and carboxy-phenylglycine (CPG), which is described to be a specific inhibitor for xCT (SLC7A11. Neuropharmacology 46 (2004) 273-284) clearly indicates specific uptake of [$^{18}$F]-12 via the sodium-independent glutamate/cystine exchanger xCT. Only minor competition was observed with either D- and L-aspartic acid which are both substrates for the Na$^+$-dependent excitatory amino acid transporter family, e.g., EAAT 1-5. Both derivatives are not as effective as cystine and CPG are in reducing the tracer uptake, indicating only potential minor involvement of other glutamate-transporters beside the xCT. The same experiments were performed using [$^{18}$F]-1, [$^{18}$F]-4, [$^{18}$F]-9, [$^{18}$F]-8, [$^{18}$F]-25 and [$^{18}$F]-22. For all tested derivatives, the identical competition profile was obtained, indicating that uptake of all examined derivatives takes place mainly via the xCT.

Example 72

In Vivo Biodistribution Data

To test the pharmacokinetic properties of compounds from the present invention, all F18-labeled compounds were examined by biodistribution studies in NCI-H460 tumor bearing mice. Female NMRI (nu/nu) mice were inoculated with 5×10$^6$ NCI-H460 tumor cells 8 to 10 days before the biodistribution studies. 185 kBq of activity of the fluorinated compound was injected and at least n=3 mice were used for every time point. After injection of the F18-labeled compound, mice were sacrificed at defined time-points. All organs were removed and radioactivity was determined using a γ-counter.

a) Biodistribution Data of [$^{18}$F]-1 are Summarized in Table 3

TABLE 3

| | Timepoint | | | | | | | | | |
|---|---|---|---|---|---|---|---|---|---|---|
| | 0.25 h | | 0.5 h | | 1.0 h | | 2.0 h | | 4.0 h | |
| % Dosis/g | | S.D. | | S.D. | | S.D. | | S.D. | | S.D. |
| Spleen | 2.36 | 0.08 | 2.60 | 0.08 | 1.36 | 0.26 | 0.76 | 0.19 | 0.36 | 0.04 |
| Liver | 4.04 | 0.69 | 2.31 | 0.44 | 0.71 | 0.18 | 0.25 | 0.02 | 0.13 | 0.06 |
| Kidney | 22.29 | 5.77 | 9.31 | 1.28 | 2.33 | 0.34 | 0.73 | 0.14 | 0.37 | 0.16 |
| Lung | 1.15 | 0.28 | 0.78 | 0.11 | 0.62 | 0.03 | 0.31 | 0.02 | 0.18 | 0.05 |
| Bone | 0.38 | 0.04 | 0.32 | 0.01 | 0.24 | 0.01 | 0.13 | 0.01 | 0.10 | 0.03 |
| Heart | 0.47 | 0.16 | 0.22 | 0.04 | 0.11 | 0.01 | 0.04 | 0.01 | 0.04 | 0.01 |
| Brain | 0.09 | 0.03 | 0.08 | 0.01 | 0.07 | 0.004 | 0.05 | 0.004 | 0.05 | 0.005 |
| Fat | 0.15 | 0.02 | 0.13 | 0.03 | 0.10 | 0.01 | 0.04 | 0.01 | 0.03 | 0.01 |
| Thyroid | 0.77 | 0.07 | 0.73 | 0.11 | 0.62 | 0.17 | 0.35 | 0.06 | 0.18 | 0.08 |
| Gallbladder | 3.80 | 0.65 | 3.95 | 0.47 | 5.76 | 2.22 | 3.34 | 0.95 | 2.84 | 0.56 |

TABLE 3-continued

| | \multicolumn{10}{c}{Timepoint} | | | | | | | | | |
|---|---|---|---|---|---|---|---|---|---|---|
| | 0.25 h | | 0.5 h | | 1.0 h | | 2.0 h | | 4.0 h | |
| Muscle | 0.20 | 0.02 | 0.15 | 0.035 | 0.08 | 0.01 | 0.04 | 0.002 | 0.05 | 0.01 |
| Tumor | 5.26 | 1.94 | 5.93 | 0.44 | 5.88 | 1.55 | 4.06 | 0.88 | 2.62 | 0.19 |
| Skin | 1.77 | 0.46 | 1.55 | 0.09 | 1.37 | 0.27 | 1.03 | 0.34 | 0.58 | 0.08 |
| Blood | 0.96 | 0.28 | 0.46 | 0.08 | 0.18 | 0.01 | 0.08 | 0.01 | 0.06 | 0.02 |
| Tail | 2.95 | 2.12 | 1.10 | 0.15 | 1.12 | 0.50 | 0.70 | 0.09 | 0.95 | 0.16 |
| Stomach | 4.01 | 1.27 | 2.33 | 0.64 | 1.21 | 0.06 | 0.45 | 0.09 | 0.35 | 0.28 |
| Uterus | 2.41 | 1.11 | 1.92 | 0.70 | 1.38 | 0.42 | 0.31 | 0.04 | 0.30 | 0.19 |
| Ovaries | 1.39 | 0.26 | 1.01 | 0.18 | 0.63 | 0.12 | 0.46 | 0.04 | 0.22 | 0.05 |
| Intestine | 1.21 | 0.13 | 1.11 | 0.22 | 0.89 | 0.12 | 0.72 | 0.17 | 1.00 | 0.43 |
| Pancreas | 9.31 | 2.47 | 5.73 | 0.42 | 2.68 | 0.59 | 0.60 | 0.12 | 0.24 | 0.10 |
| Adrenals | 0.85 | 0.29 | 0.38 | 0.07 | 0.26 | 0.03 | 0.18 | 0.05 | 0.37 | 0.09 |
| Bilanz/summary | | S.D. | | S.D. | | S.D. | | S.D. | | S.D. |
| Recovery | 89.50 | 3.01 | 98.41 | 0.53 | 98.62 | 2.45 | 92.58 | 5.31 | 91.01 | 8.09 |
| organs | 29.28 | 4.90 | 19.99 | 0.60 | 12.90 | 1.46 | 6.93 | 1.25 | 5.63 | 1.12 |
| Carcass | 7.09 | 1.71 | 6.60 | 1.55 | 5.55 | 2.92 | 2.29 | 0.32 | 1.66 | 0.46 |
| urine | 53.12 | 8.67 | 71.81 | 1.17 | 80.17 | 4.31 | 83.38 | 6.01 | 83.77 | 9.06 |
| faeces | 0.002 | 0.001 | 0.004 | 0.01 | 0.003 | 0.000 | 0.023 | 0.025 | 0.003 | 0.006 |
| Tumor/Tissue | | S.D. | | S.D. | | S.D. | | S.D. | | S.D. |
| Spleen | 2.24 | 0.88 | 2.29 | 0.22 | 4.59 | 2.21 | 5.54 | 1.58 | 7.29 | 0.87 |
| Liver | 1.30 | 0.38 | 2.62 | 0.40 | 8.87 | 4.35 | 16.59 | 4.38 | 21.31 | 6.98 |
| Kidney | 0.23 | 0.03 | 0.64 | 0.09 | 2.55 | 0.73 | 5.64 | 1.41 | 7.67 | 2.26 |
| Lung | 4.51 | 0.78 | 7.62 | 0.53 | 9.49 | 2.34 | 13.28 | 3.28 | 15.49 | 3.62 |
| Bone | 13.56 | 3.80 | 18.79 | 1.89 | 25.11 | 7.73 | 31.35 | 7.33 | 28.14 | 7.52 |
| Heart | 11.63 | 3.61 | 27.02 | 3.35 | 52.89 | 14.99 | 93.29 | 6.17 | 73.09 | 22.19 |
| Brain | 58.57 | 2.06 | 71.53 | 5.89 | 83.30 | 20.17 | 76.18 | 17.05 | 56.43 | 2.73 |
| Fat | 35.89 | 10.54 | 45.43 | 9.52 | 57.11 | 11.54 | 110.7 | 28.55 | 120.47 | 57.93 |
| Muscle | 25.83 | 7.33 | 40.88 | 7.19 | 72.45 | 14.29 | 101.5 | 25.71 | 60.50 | 22.20 |
| Skin | 2.99 | 0.74 | 3.85 | 0.53 | 4.38 | 1.16 | 4.13 | 0.92 | 4.59 | 0.75 |
| Blood | 5.47 | 1.00 | 13.00 | 1.34 | 32.50 | 6.28 | 50.76 | 8.91 | 48.51 | 13.88 |
| Stomach | 1.35 | 0.37 | 2.68 | 0.78 | 4.91 | 1.52 | 9.05 | 1.00 | 10.93 | 7.13 |
| Intestine | 4.35 | 1.58 | 5.51 | 1.12 | 6.75 | 2.31 | 5.78 | 1.59 | 2.97 | 1.24 |
| Thyroid | 6.90 | 2.82 | 8.25 | 1.30 | 9.58 | 0.7 | 11.49 | 2.04 | 16.89 | 6.9 |
| Uterus | 2.46 | 1.03 | 3.56 | 1.92 | 4.37 | 0.99 | 12.92 | 1.24 | 11.08 | 5.60 |
| Ovaries | 4.07 | 2.35 | 5.96 | 0.57 | 9.36 | 1.77 | 9.00 | 2.48 | 12.52 | 3.38 |
| Pancreas | 0.57 | 0.14 | 1.04 | 0.11 | 2.34 | 1.08 | 6.80 | 1.23 | 11.92 | 3.94 |
| Adrenals | 6.49 | 2.25 | 16.17 | 3.18 | 22.25 | 3.27 | 25.58 | 13.85 | 7.28 | 1.53 |

A high uptake into the tumor (5.88% ID/g+/−1.55 at 1 hp.i.) as well as a strong retention of activity (4.06% ID/g+/−0.88 at 2 h p.i. and 2.62% ID/g+/−0.19 at 4 h p.i.) was observed. Clearance of the compound takes place mainly via the kidneys, with 80.2% of activity being excreted at 1 h p.i. High tumor to blood (ratio 32.5) and tumor to muscle (ratio 72.5) ratios were observed, indicating excellent PET imaging properties of [$^{18}$F]-1. In addition, after high initial uptake into the pancreas (9.31% ID/g+/−2.47 at 0.25 h p.i.) a very fast clearance from this organ was observed (1 h p.i. 2.68% ID/g+/−0.59). Therefore already at 1 h p.i., the tumor-to-pancreas ratio was found to be 2.3 (see Table 3).

b) Biodistribution Data of [$^{18}$F]-12 are Summarized in Table 4

TABLE 4

| | \multicolumn{10}{c}{timepoint} | | | | | | | | | |
|---|---|---|---|---|---|---|---|---|---|---|
| Zeitpunkt | 0.25 h | | 0.5 h | | 1.0 h | | 2.0 h | | 4.0 h | |
| % Dosis/g | | S.D. | | S.D. | | S.D. | | S.D. | | S.D. |
| Spleen | 2.49 | 0.31 | 1.94 | 0.55 | 1.54 | 0.40 | 1.29 | 0.23 | 0.59 | 0.07 |
| Liver | 9.02 | 0.38 | 5.93 | 3.43 | 2.17 | 0.33 | 0.87 | 0.27 | 0.33 | 0.15 |
| Kidney | 18.02 | 5.47 | 8.61 | 2.46 | 2.11 | 0.25 | 0.64 | 0.11 | 0.20 | 0.05 |
| Lung | 1.45 | 0.06 | 0.91 | 0.32 | 0.36 | 0.00 | 0.26 | 0.11 | 0.13 | 0.11 |
| Bone | 0.39 | 0.04 | 0.30 | 0.04 | 0.16 | 0.06 | 0.14 | 0.05 | 0.06 | 0.01 |
| Heart | 0.58 | 0.04 | 0.38 | 0.20 | 0.11 | 0.01 | 0.06 | 0.01 | 0.04 | 0.02 |
| Brain | 0.09 | 0.02 | 0.07 | 0.01 | 0.05 | 0.01 | 0.05 | 0.01 | 0.02 | 0.00 |
| Fat | 0.16 | 0.05 | 0.12 | 0.04 | 0.03 | 0.02 | 0.02 | 0.01 | 0.01 | 0.02 |
| Thyroid | 0.78 | 0.13 | 0.65 | 0.26 | 0.29 | 0.08 | 0.26 | 0.13 | 0.08 | 0.01 |
| Gallbladder | 2.53 | 0.25 | 5.25 | 1.21 | 8.20 | 4.16 | 8.93 | 0.53 | 6.45 | 4.13 |
| Muscle | 0.26 | 0.07 | 0.15 | 0.02 | 0.07 | 0.02 | 0.05 | 0.03 | 0.03 | 0.01 |
| Tumor | 5.55 | 2.32 | 6.91 | 2.41 | 6.47 | 1.02 | 7.21 | 1.56 | 5.17 | 2.89 |
| Skin | 1.58 | 0.25 | 1.08 | 0.28 | 0.61 | 0.03 | 0.43 | 0.36 | 0.37 | 0.15 |
| Blood | 1.28 | 0.17 | 0.74 | 0.36 | 0.19 | 0.01 | 0.08 | 0.01 | 0.04 | 0.01 |
| Tail | 3.02 | 1.10 | 1.81 | 0.38 | 0.41 | 0.02 | 1.44 | 2.08 | 0.55 | 0.46 |
| Stomach | 3.08 | 0.46 | 4.18 | 3.66 | 0.94 | 0.12 | 0.46 | 0.11 | 0.21 | 0.04 |
| Uterus | 2.54 | 0.39 | 1.38 | 1.00 | 0.97 | 0.68 | 0.50 | 0.19 | 0.21 | 0.11 |
| Ovaries | 1.25 | 0.25 | 1.06 | 0.38 | 0.79 | 0.26 | 0.54 | 0.14 | 0.24 | 0.08 |
| Intestine | 1.10 | 0.14 | 4.00 | 5.46 | 0.91 | 0.34 | 1.12 | 0.11 | 0.93 | 0.30 |

TABLE 4-continued

| Zeitpunkt | 0.25 h | | 0.5 h | | 1.0 h | | 2.0 h | | 4.0 h | |
|---|---|---|---|---|---|---|---|---|---|---|
| Pancreas | 11.45 | 1.65 | 9.94 | 1.47 | 3.62 | 0.62 | 1.48 | 0.37 | 0.27 | 0.05 |
| Adrenals | 0.69 | 0.30 | 0.57 | 0.24 | 0.27 | 0.05 | 0.27 | 0.07 | 0.16 | 0.08 |
| Summary | | S.D. | | S.D. | | S.D. | | S.D. | | S.D. |
| Recovery | 96.96 | 1.75 | 97.82 | 1.26 | 98.57 | 6.62 | 99.00 | 8.38 | 100.1 | 6.23 |
| Organs | 36.92 | 2.29 | 33.35 | 20.62 | 12.93 | 1.39 | 8.77 | 0.54 | 6.12 | 1.33 |
| Carcass | 9.55 | 2.14 | 7.31 | 3.78 | 3.58 | 1.47 | 5.26 | 5.87 | 1.09 | 0.43 |
| urine | 50.49 | 4.49 | 57.06 | 24.65 | 82.05 | 7.30 | 83.35 | 12.59 | 92.66 | 7.95 |
| faeces | — | — | 0.10 | 0.16 | 0.01 | 0.00 | 1.74 | 2.99 | 0.25 | 0.22 |
| Tumor/Tissue | | S.D. | | S.D. | | S.D. | | S.D. | | S.D. |
| Spleen | 2.27 | 1.10 | 3.60 | 0.87 | 4.32 | 0.73 | 5.82 | 2.18 | 8.58 | 4.37 |
| Liver | 0.62 | 0.27 | 1.27 | 0.35 | 2.99 | 0.26 | 8.46 | 0.87 | 18.60 | 11.50 |
| Kidney | 0.36 | 0.26 | 0.79 | 0.06 | 3.12 | 0.78 | 11.24 | 1.68 | 28.19 | 17.92 |
| Lung | 3.79 | 1.46 | 7.67 | 1.21 | 18.22 | 2.79 | 29.67 | 9.98 | 227.5 | 361.9 |
| Bone | 14.61 | 6.84 | 22.54 | 4.65 | 41.80 | 8.84 | 57.86 | 34.89 | 91.73 | 64.38 |
| Heart | 9.67 | 4.48 | 20.04 | 7.34 | 58.14 | 11.29 | 126.5 | 5.16 | 153.2 | 153.7 |
| Brain | 62.27 | 14.14 | 92.44 | 27.03 | 142.1 | 19.26 | 161.0 | 66.01 | 237.6 | 97.49 |
| Fat | 37.81 | 24.45 | 64.26 | 25.50 | 302.3 | 185.6 | 396.0 | 267.5 | 2513 | 2056 |
| Muscle | 20.90 | 4.78 | 45.35 | 9.82 | 103.4 | 17.84 | 169.9 | 73.29 | 185.7 | 80.73 |
| Skin | 3.71 | 2.03 | 6.42 | 1.53 | 10.56 | 1.14 | 39.91 | 45.18 | 16.05 | 9.69 |
| Blood | 4.49 | 2.42 | 9.81 | 1.82 | 33.90 | 4.11 | 86.51 | 9.87 | 148.1 | 81.13 |
| Stomach | 1.75 | 0.52 | 2.18 | 0.97 | 6.88 | 0.61 | 16.25 | 5.70 | 24.28 | 10.80 |
| Intestine | 4.93 | 1.53 | 4.66 | 3.29 | 7.45 | 1.39 | 6.58 | 1.95 | 5.57 | 2.41 |
| Thyroid | 7.48 | 3.80 | 10.73 | 0.71 | 22.49 | 2.37 | 35.78 | 25.99 | 64.78 | 30.88 |
| Uterus | 2.31 | 1.31 | 5.85 | 1.80 | 8.25 | 3.42 | 15.37 | 3.32 | 23.55 | 2.71 |
| Ovaries | 4.55 | 1.94 | 6.59 | 1.07 | 8.99 | 3.54 | 13.81 | 3.26 | 21.39 | 9.50 |
| Pancreas | 0.49 | 0.21 | 0.68 | 0.13 | 1.82 | 0.35 | 4.90 | 0.38 | 19.41 | 10.50 |
| Adrenals | 8.53 | 3.68 | 13.61 | 6.40 | 23.74 | 1.63 | 27.83 | 5.69 | 41.62 | 29.33 |
| Gallbladder | 2.19 | 0.95 | 1.36 | 0.57 | 0.88 | 0.26 | 0.81 | 0.20 | 1.11 | 0.94 |

A high uptake into the tumor (6.47% ID/g+/−1.02 at 1 h p.i.) as well as a strong retention of activity (7.21% ID/g+/−1.56 at 2 h p.i. and 5.17% ID/g+/−2.89 at 4 h p.i.) was observed. Clearance of the compound takes place mainly via the kidneys, with 82.1% of activity being excreted into the urine at 1 h p.i. High tumor to blood (ratio 33.9) and tumor to muscle (ratio 103.4) ratios were observed, indicating excellent PET imaging properties of [$^{18}$F]-12. In addition, after high initial uptake into the pancreas (11.45% ID/g+/−1.65 at 0.25 h p.i.) a very fast clearance from this organ was observed (1 h p.i. 3.62% ID/g+/−0.62). Therefore already at 1 h p.i., the tumor-to-pancreas ratio was found to be 1.8 (see Table 4).

Example 73

In Vivo Tumor Retention

To compare the tumor uptake and retention of radioactivity of different $^{18}$F-labeled derivatives from the present invention, biodistribution studies were performed in NCI-H460 tumor bearing NMRI (nu/nu) mice as described above. The tumor uptake in 96 injected dose per gram of tissue (% ID/g) is shown in FIG. 3. Surprisingly, all examined compounds show good (more than 3% ID/g) or excellent uptake (more than 6% ID/g) into the H460-tumors. Additionally, strong retention of activity over time was observed with all derivatives examined.

Example 74

In Vivo Kidney Clearance

To compare the kidney clearance of several $^{18}$F-labeled derivatives from the present invention, biodistribution studies were performed in NCI-H460 tumor bearing female NMRI (nu/nu) mice as described above. The uptake of activity in the kidneys in % Dig is shown in FIG. 4. Surprisingly, all examined compounds show very fast decrease of kidney activity. After 2 h p.i., less than 1% ID/g can be found in the kidneys.

Example 75

In Vivo Pancreas Clearance

For comparison of pancreas uptake and clearance of several $^{18}$F-labeled derivatives from the present invention, biodistribution studies were performed in NCI-H460 tumor bearing NMRI (nu/nu) mice as described above. The uptake of activity in the pancreas in % ID/g is shown in FIG. 5. All examined compounds initially show uptake of about 10% ID/g at 0.25 h p.i. into the pancreas, which was surprisingly followed by a fast washout. After 2 h p.i., less than 2% ID/g can be found in the pancreas.

Example 76

PET Imaging Studies a) [$^{18}$F]-1 was examined in NCI-H460 tumor bearing nude-mice using PET-imaging. Approx. 10 MBq of the tracer was injected into the animals and PET images were acquired at 60 min p.i. for 10 minutes. The H460-tumor was very well visible in the images with 3.6% ID/g as was determined by region of interest (ROI) analysis. Except of some uptake into the bladder due to the renal excretion, no uptake into non target tissues was observed.

b) [$^{18}$F]-12 was examined in the same animal model in mice as described above. Approx. 10 MBq was injected into the animals and PET images were obtained at 60 min p.i. for 10 min. The NCI-H460 tumor was very well visible and uptake of 2.7% ID/g into the tumor was calculated by ROI analysis. Except of some uptake into the gallbladder due to a partial hepatobiliary clearance of this derivative, the majority of activity is excreted renally, resulting in a strong PET signal from the bladder. No uptake in other non-target tissues was observed.

c) Beside PET-imaging studies in mice, also the imaging properties of [$^{18}$F]-12 in rats were examined. NCI-H460 tumor cells were inoculated into the right flank of nude-rats (RH-Foxn1 nu/nu) 8 to 10 days before the PET study. PET images were acquired at 60 min after injection of approximately 10 MBq for 10 minutes. The H460 tumor was nicely visible (0.9% ID/g as determined by ROI analysis). Beside some minor uptake into the liver and kidneys due to the excretion of the compound, no uptake into other non-target tissues was observed.

Example 77

In Vivo Biodistribution Data

To test the pharmacokinetic properties of compounds from the present invention, all F18-labeled compounds were examined by biodistribution studies in NCI-H460 tumor bearing mice. Female NMRI (nu/nu) mice were inoculated with 5×10$^6$ NCI-H460 tumor cells 8 to 10 days before the biodistribution studies. 185 kBq of activity of the fluorinated compound was injected and at least n=3 mice were used and sacrificed at defined time-points raning from 15 min pi up to 2 h p.i. All organs were removed and radioactivity was determined using a γ-counter. Data from 1 h post injection are shown in Table 5. Interestingly, all examined compounds were taken up in the tumor. High tumor uptake values of >3% ID/g were obtained with various compounds from the present invention. A favorable clearance profile with high tumor-to-blood and tumor-to-muscle values was observed for all compounds with makes them useful for tumor detection in PET imaging studies.

sis was performed and activity in tumor, liver and kidney was determined. Interestingly, all examined compounds were able to visualize the tumor. High tumor uptake values of >1% Dig in this rat model were obtained with various compounds from the present invention. A favorable clearance profile of all compounds enables excellent tumor detection in PET imaging studies in tumor bearing rats.

TABLE 6

| Compound | Tumor (Mean % ID/g at 1 h p.i.) | Tumor (Max % ID/g at 1 h p.i.) | Liver (% ID/g at 1 h p.i.) | Kidney (% ID/g at 1 h p.i.) |
|---|---|---|---|---|
| [$^{18}$F]-1 | 1 | 1.7 | 0.2 | 0.37 |
| [$^{18}$F]-4 | 0.7 | 1 | 1.1 | 1.2 |
| [$^{18}$F]-12 | 0.9 | 2.2 | 0.8 | 0.9 |
| [$^{18}$F]-12 C5-1 | 1.3 | 3.4 | 1.2 | 0.8 |
| [$^{18}$F]-12 C5-2 | 1.6 | 3.7 | 0.5 | 0.4 |
| [$^{18}$F]-16 | 0.8 | 2.1 | 2.3 | 1.7 |
| [$^{18}$F]-17 | 1.2 | 2.6 | 0.9 | 2.4 |
| [$^{18}$F]-22 | 0.3 | 0.9 | 0.6 | 0.5 |
| [$^{18}$F]-35 | 0.2 | 0.5 | 0.2 | 3.1 |
| [$^{18}$F]-41 | 1.6 | 3.7 | 0.4 | 0.5 |
| [$^{18}$F]-41 C5-1 | 1.2 | 3.2 | 0.4 | 0.5 |
| [$^{18}$F]-41 C5-2 | 2.0 | 4.4 | 0.2 | 0.2 |
| [$^{18}$F]-48 | 0.8 | 1.6 | 0.2 | 0.9 |
| [$^{18}$F]-50 | 1.1 | 2.4 | 0.2 | 1.0 |
| [$^{18}$F]-58 | 0.3 | 0.63 | 1.7 | 4.6 |
| [$^{18}$F]-60 | 1.0 | 2.2 | 0.9 | 2.2 |
| [$^{18}$F]-66 | 0.7 | 1.3 | 1.7 | 2.9 |

Example 79

In Vitro Cell-Uptake and Retention Study Blocking of [$^{18}$F]-41 Uptake Using 41

NCI-H460 (human NSCLC) cells, grown adherently in 48 well plates were used for these experiments. Approximately

TABLE 5

| Compound | Tumor (% ID/g at 1 h p.i.) | T/Blood | T/Muscle | Pancreas (% ID/g at 1 h p.i.) | Liver (% ID/g at 1 h p.i.) | Kidney (% ID/g at 1 h p.i.) | Urine (% ID at 1 h p.i.) |
|---|---|---|---|---|---|---|---|
| [$^{18}$F]-1 | 5.9 ± 1.6 | 32.5 | 72.5 | 2.7 ± 0.6 | 0.7 ± 0.2 | 2.3 ± 0.3 | 80.2 ± 4.3 |
| [$^{18}$F]-4 | 2.8 ± 1.8 | 14.5 | 38.8 | 0.8 ± 0.1 | 1.5 ± 0.5 | 1.0 ± 0.3 | 79.8 ± 2.2 |
| [$^{18}$F]-8 | 4.6 ± 0.9 | 26.8 | 46.3 | 2.2 ± 0.4 | 1.3 ± 0.3 | 2.8 ± 0.6 | 92.7 ± 3.8 |
| [$^{18}$F]-9 | 1.8 ± 0.9 | 20.5 | 61.7 | 0.1 ± 0.01 | 0.2 ± 0.1 | 0.7 ± 0.04 | 86.3 ± 7.1 |
| [$^{18}$F]-12 | 6.5 ± 1.0 | 33.9 | 103.4 | 3.6 ± 0.6 | 2.2 ± 0.3 | 2.2 ± 0.3 | 82.1 ± 7.3 |
| [$^{18}$F]-16 | 3.6 ± 0.6 | 14.1 | 54.2 | 1.4 ± 0.1 | 3.3 ± 0.1 | 3.4 ± 0.3 | 74.5 ± 6.8 |
| [$^{18}$F]-22 | 1.3 ± 0.5 | 5.1 | 32.3 | 0.63 ± 0.04 | 4.1 ± 0.8 | 1.8 ± 0.6 | 64.9 ± 4.3 |
| [$^{18}$F]-25 | 0.5 ± 0.1 | 9.7 | 32.2 | 0.04 ± 0.01 | 0.2 ± 0.1 | 0.2 ± 0.05 | 86.6 ± 4.4 |
| [$^{18}$F]-32 | 2.3 ± 0.9 | 17.9 | 23.5 | 0.7 ± 0.1 | 2.3 ± 0.2 | 3.9 ± 1.0 | 81.0 ± 7.5 |
| [$^{18}$F]-41 | 6.8 ± 1.3 | 26.3 | 90.6 | 1.0 ± 0.5 | 0.3 ± 0.1 | 3.1 ± 0.4 | 69.3 ± 14.5 |
| [$^{18}$F]-41 C5-1 | 6.4 ± 1.4 | 23.4 | 94.2 | 2.2 ± 0.3 | 0.3 ± 0.1 | 3.5 ± 0.7 | 85.0 ± 7.7 |
| [$^{18}$F]-41 C5-2 | 8.7 ± 1.9 | 36.0 | 107.3 | 1.1 ± 0.2 | 0.3 ± 0.1 | 2.4 ± 0.8 | 83.5 ± 5.1 |
| [$^{18}$F]-44 | 3.3 ± 1.2 | 28.2 | 71.1 | 1.2 ± 0.1 | 0.95 ± 0.1 | 2.5 ± 0.7 | 80.6 ± 10.1 |
| [$^{18}$F]-48 | 2.8 ± 1.4 | 23.3 | 30.4 | 0.8 ± 0.1 | 0.2 ± 0.08 | 1.8 ± 0.4 | 79 ± 7.8 |
| [$^{18}$F]-52 | 8.2 ± 2.1 | 32.5 | 95.4 | 7.5 ± 1.1 | 2.6 ± 0.4 | 3.5 ± 1.1 | 66.8 ± 10.3 |
| [$^{18}$F]-56 | 1.0 ± 0.1 | 9.9 | 25 | 0.2 ± 0.03 | 0.7 ± 0.2 | 5.2 ± 1.1 | 77 ± 6.7 |

Example 78

PET Imaging Studies

To test the imaging properties, compounds from the present invention were evaluated in PET imaging studies using tumor bearing rats. NCI-H460 tumor cells were inoculated into the right flank of nude-rats (RH-Foxn1 nu/nu) 8 to 10 days before the PET study. PET images were acquired at 60 min after injection of approximately 10 MBq for 10 minutes. After the imaging study, region-of-interest (ROI) analy- 100.000 cells were incubated in PBS-buffer containing 0.1% BSA with 0.25 MBq [$^{18}$F]-41 for up to 60 minutes. A time-dependent uptake was observed during the 60 min incubation period. Approximately 13% of applied dose was taken up by the cells during the 60 min incubation period (FIG. 6). For the blocking study [$^{18}$F]-41 was co-incubated with 1 mM 41 for 30 minutes. After this time, the cell bound radioactivity was determined. Interestingly, it was observed, that 41 is a strong competitor for [$^{18}$F]-41, indicating specific transport of the [$^{18}$F]labeled derivative into the cells (FIG. 7).

In addition, the retention of radioactivity in tumor cells was examined. Therefore. H460 cells were loaded with 0.25 MBq of [$^{18}$F]-41 for 30 minutes in PBS buffer, containing 0.1% BSA. After this uptake, the buffer was removed and the cells were washed with PBS. The cells were then reincubated with new PBS buffer without radioactivity for 30 min. The release of activity into the supernatant as well as the retention of activity inside the cells was determined. It was discovered, that only a limited amount of activity was released into the supernatant during the 30 minute efflux period. More than 80% of the activity were retained inside the tumor cells during the 30 minute incubation under these efflux conditions (FIG. 7) indicating strong retention.

Example 80

Uptake of Compound [$^{18}$F]-41 in Inflammatory Lesions

To test the specificity of compounds from the present invention, compound [$^{18}$F]-41 was examined in an animal model of reactive lymph nodes in comparison to the clinically commonly used PET tracer FDG. Therefore, female immunocompetent NMRI mice (10 weeks old) were injected with streptozotocin (500 μg/40 μL PBS) in the right hind limb to induce an inflammatory reaction in the right popliteal and additional lymph nodes. PET imaging studies were performed 3 days after Streptozotocin injection. PET images were acquired dynamically for 1 h after injection of approximately 5-10 MBq. After the imaging study, region-of-interest (ROI) analysis was performed in the popliteal, inguinal and iliacal lymph nodes. At least 3 animals were examined per tracer. FIG. 8 shows the quantified activity in the lymph nodes and the time-course of compound [$^{18}$F]-41 in comparison to FDG. Interestingly it was observed, that the initial uptake of compound [$^{18}$F]-41 in the inflammatory lesions was already reduced compared to FDG. Additionally, whereas the activity of FDG in the reactive lymph nodes remained almost constant during the imaging period, a wash-out of radioactivity was observed during the PET study with compound [$^{18}$F]-41. In summary, these results indicate a higher specificity of compounds from the present invention due to lower uptake in inflammatory processes and wash-out from the lesions during the imaging period.

BRIEF DESCRIPTION OF THE DRAWINGS

Figures

Figure 1:
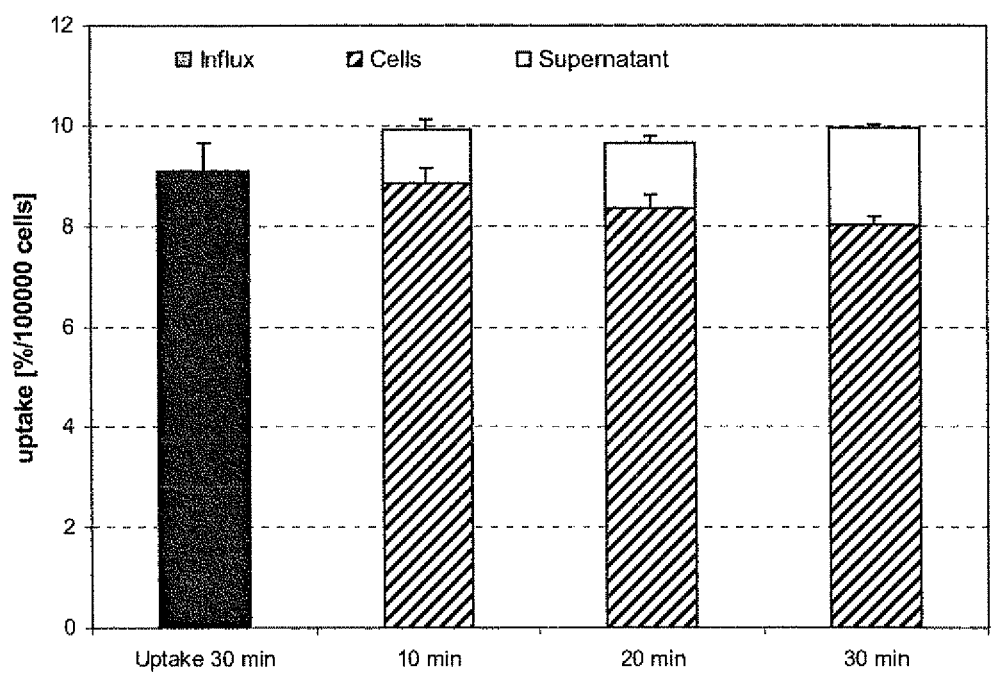
FIG. 1: Retention of 4-[4-(2-[$^{18}$F]fluoroethoxy)benzyl]-L-glutamic acid ([$^{18}$F]-1) in H460 cells over time
Figure 2:
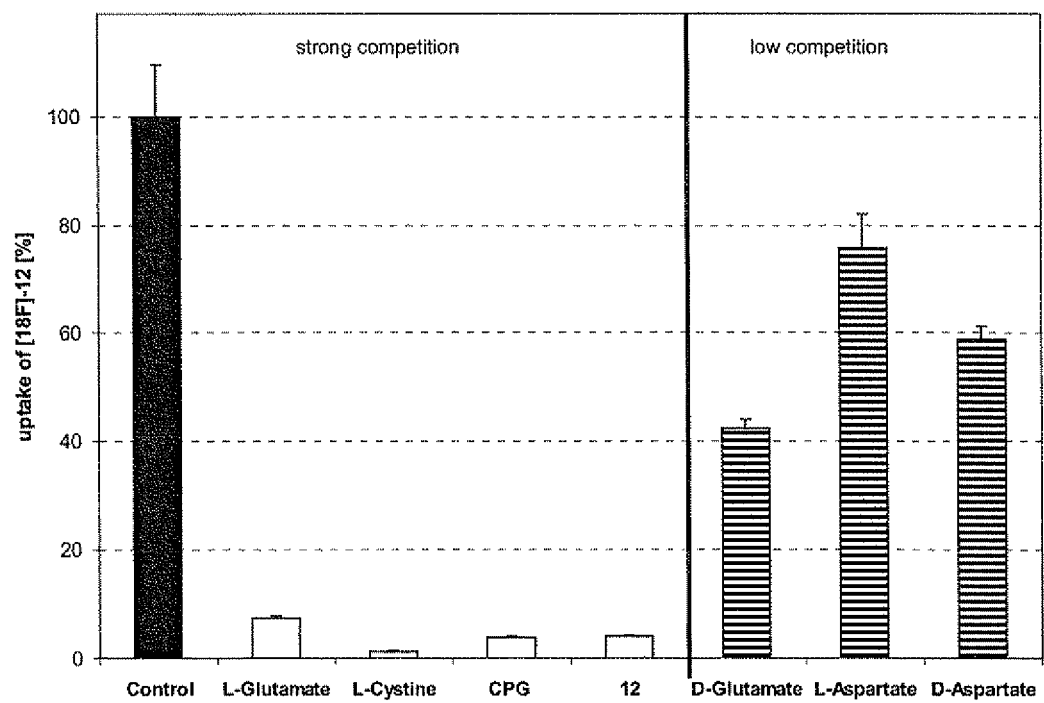
FIG. 2: Competition profile indicating uptake of (2S)-2-Amino-5-[4-(2-[$^{18}$F]fluoroethoxy)benzyl]hexanedioic acid ([$^{18}$F]-12) via xCT (SLC7A11)
Figure 3:
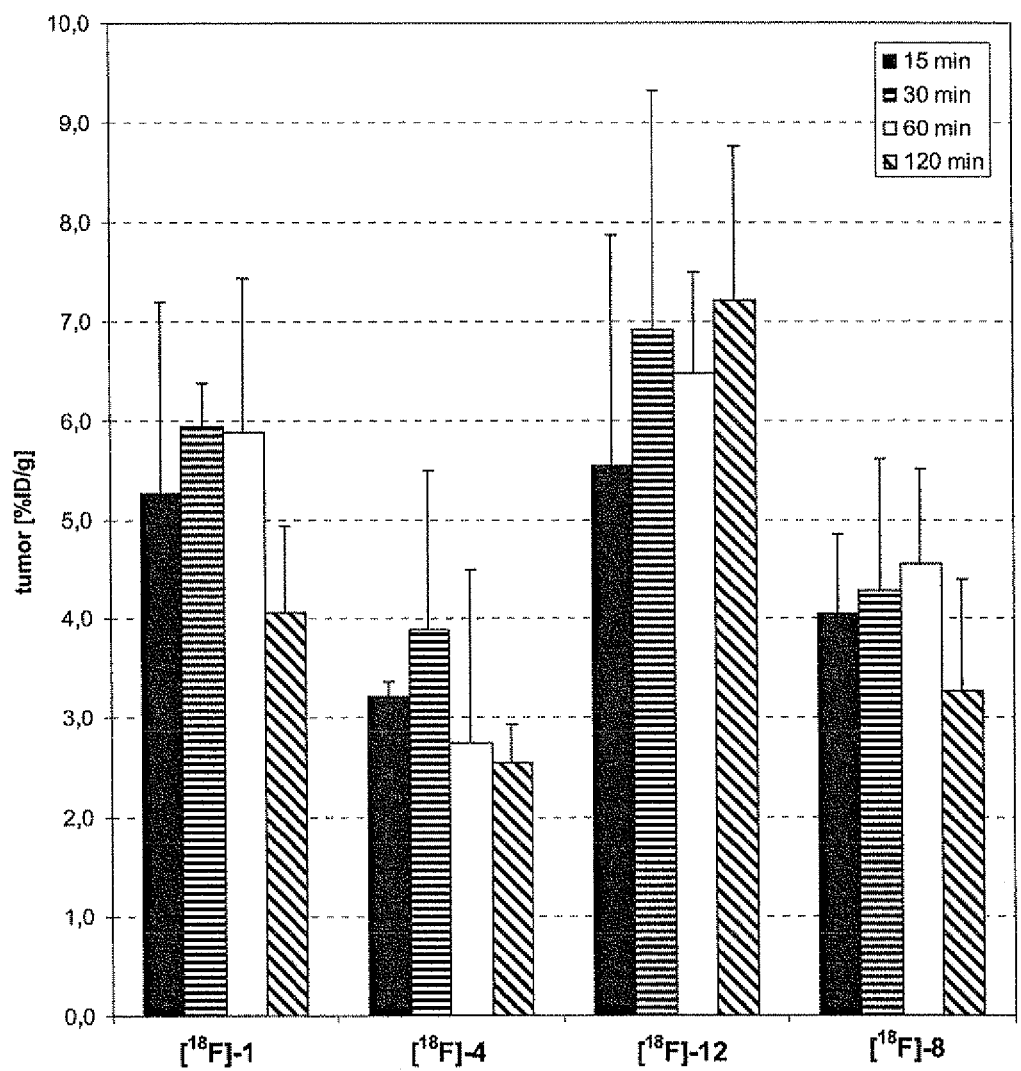
FIG. 3: in vivo tumor retention of [$^{18}$F]-1, [$^{18}$F]-4, [$^{18}$F]-12 and [$^{18}$F]-8 in H460 tumors
Figure 4:
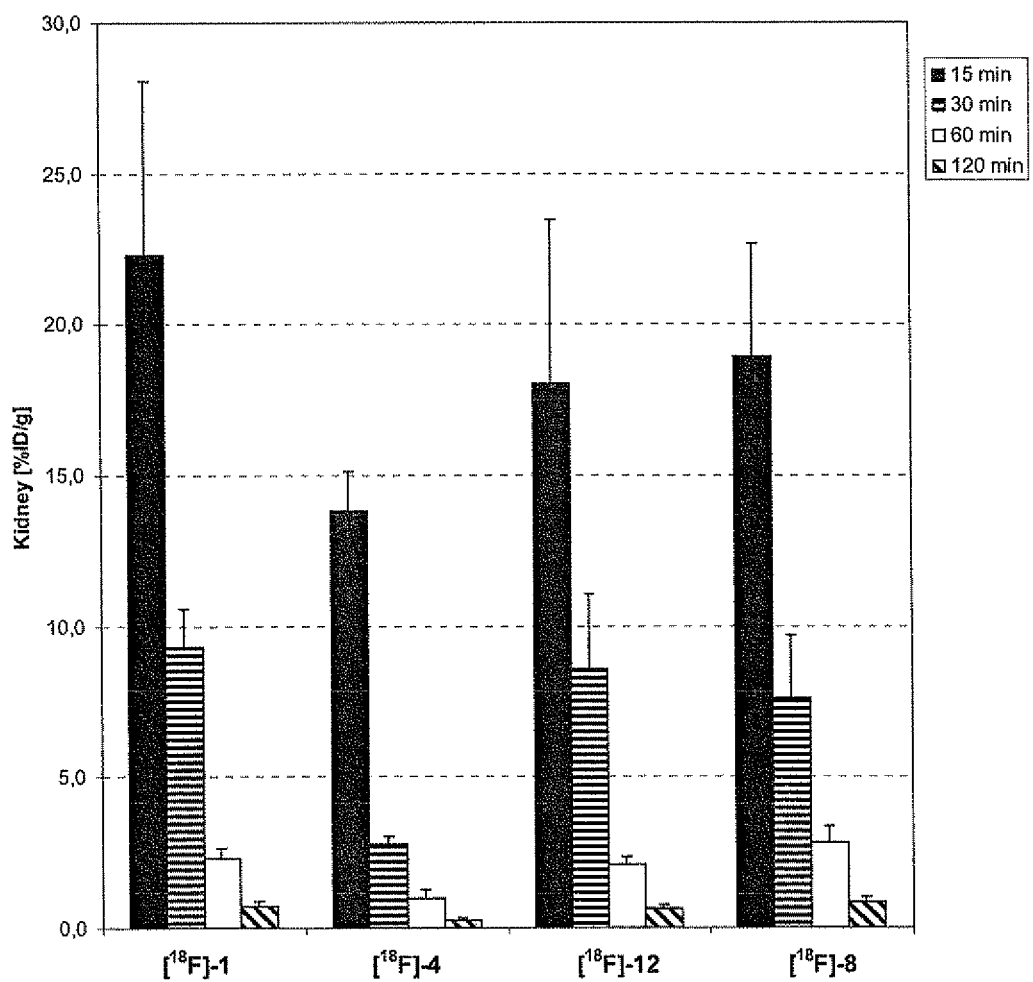
FIG. 4: in vivo kidney clearance of [$^{18}$F]-1, [$^{18}$F]-4, [$^{18}$F]-12 and [$^{18}$F]-8 in female NMRI (nu/nu) mice
Figure 5:
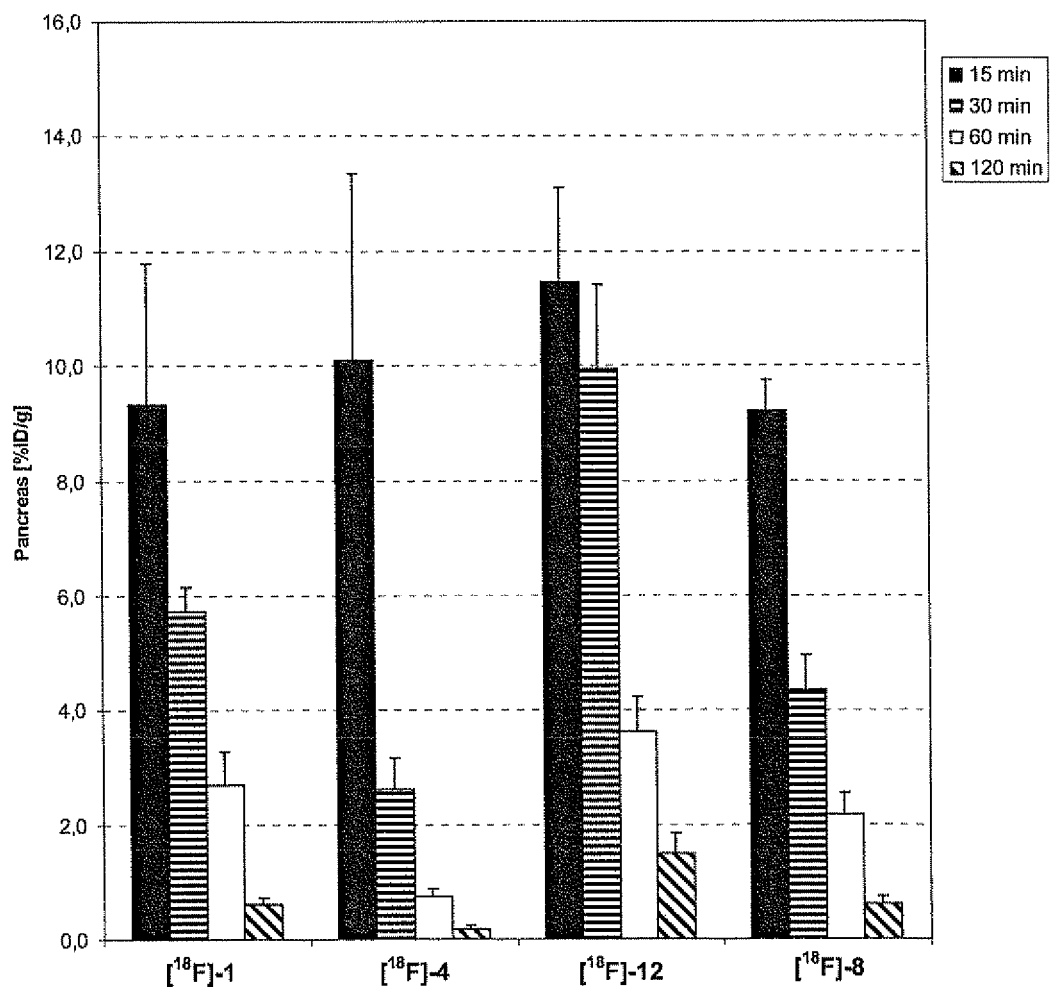
FIG. 5: in vivo pancreas clearance of [$^{18}$F]-1, [$^{18}$F]-4, [$^{18}$F]-12 and [$^{18}$F]-8 in female NMRI (nu/nu) mice
Figure 6:
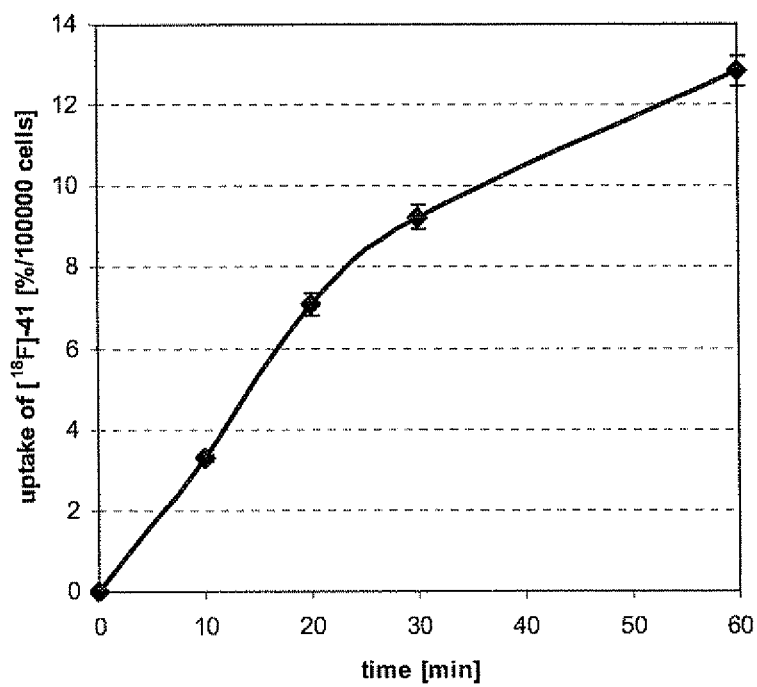
FIG. 6: Time-dependent uptake of [$^{18}$F]-41 in NCI-H460 cells
Figure 7:
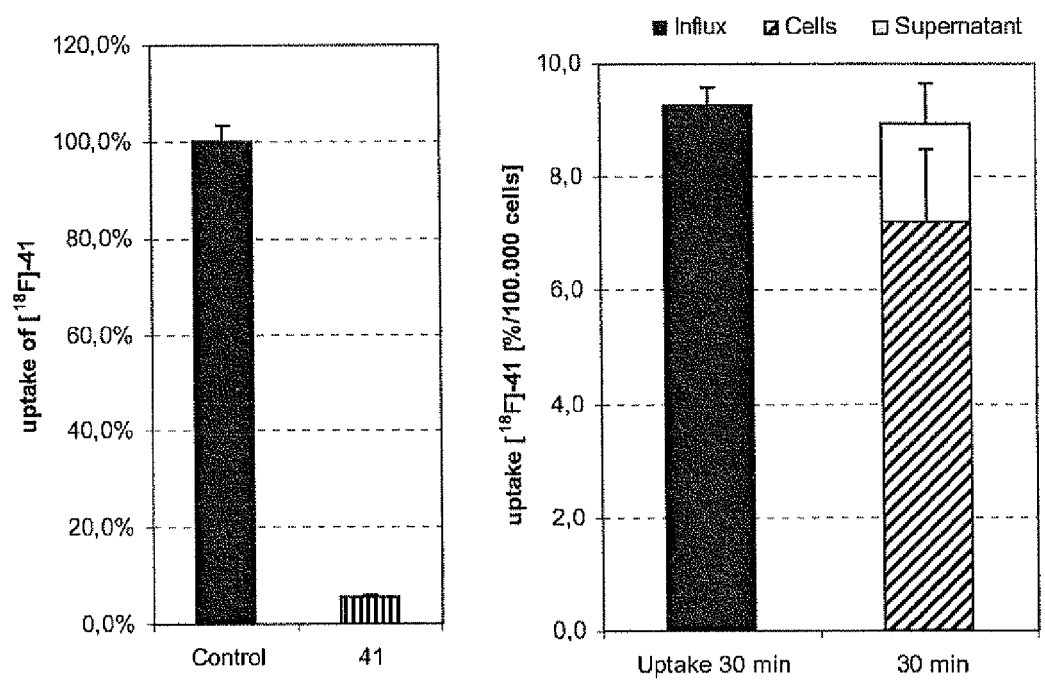
FIG. 7: Blocking and retention of [$^{18}$F]-41
Figure 8:
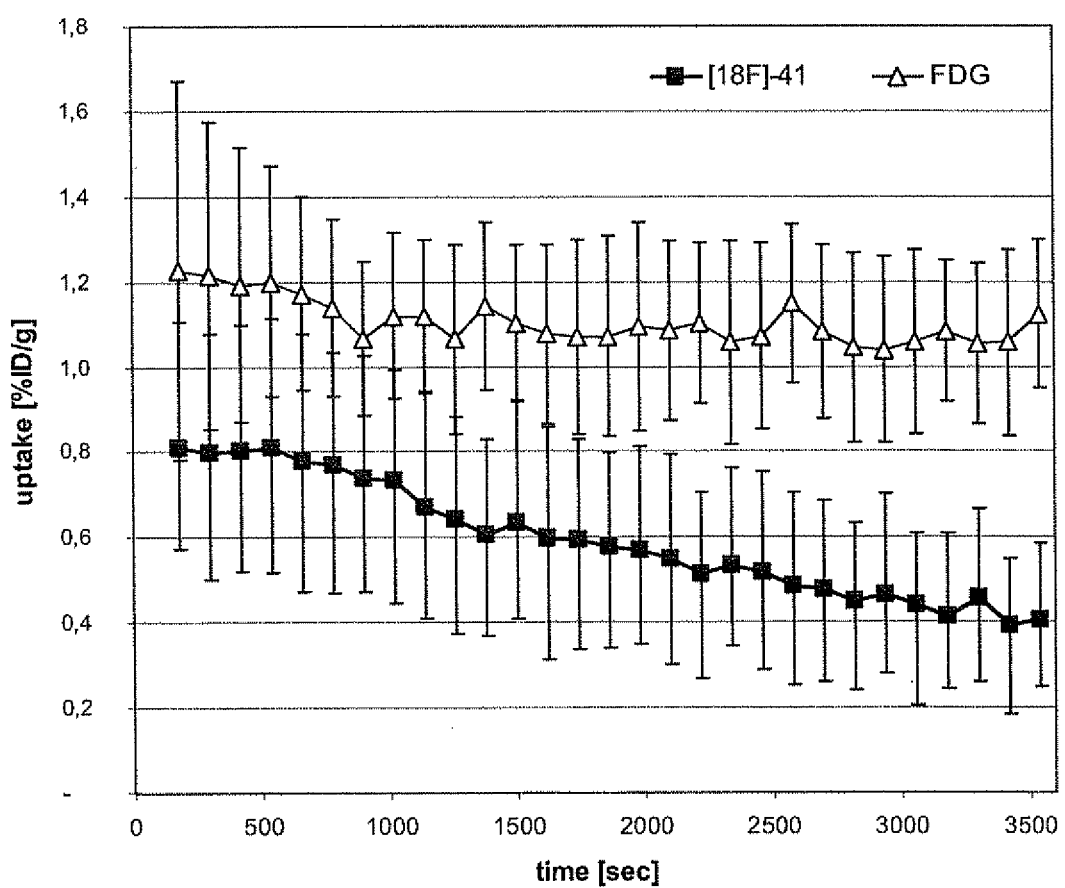
FIG. 8: Time-course of activity of FDG and [$^{18}$F]-41 in reactive lymph nodes caused by streptozotocin injection

The invention claimed is:

1. A compound of Formula III:

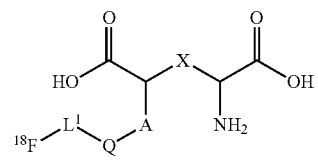

wherein

X is selected from:
  a) $CH_2$, and
  b) $CH_2$—$CH_2$,

A is alkylene,

Q is arylene or heteroarylene,

L$^1$ is selected from:
  a) alkylene,
  b) alkylene-O*,
  c) alkylene-N*H,
  d) cycloalkylene-O*,
  e) monohydroxyalkylene,
  f) monohydroxyalkylene-O*,
  g) dihydroxyalkylene,
  h) dihydroxyalkylene-O*, and
  i) $(CH_2CH_2O)_n$—$CH_2CH_2$—O* with n=1, 2 or 3,

* indicates the position of the bond to Q, or a tautomer, a diastereomer, an enantiomer, a stereoisomer, a stereoisomeric mixture, or mixtures thereof.

2. The compound according to claim 1, wherein Q is phenylene or pyridylene.

3. The compound according to claim 1, wherein said compound is selected from the group below:

4-[4-(2-[$^{18}$F]fluoroethoxy)benzyl]glutamic acid:

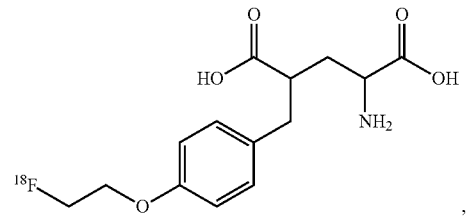 [SMILES: NC(CC(Cc1ccc(OCC[18F])cc1)C(=O)O)C(=O)O]

4-[4-(3-[$^{18}$F]fluoropropoxy)benzyl]glutamic acid:

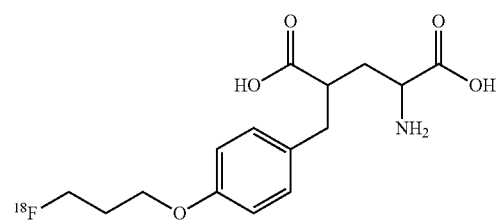

4-[4-(3-[18F]fluoropropyl)benzyl]glutamic acid:

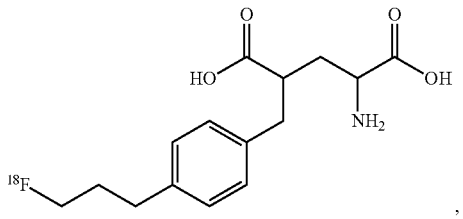

,

4-{4-{(3-[18F]fluoropropyl)amino]benzyl]glutamic acid:

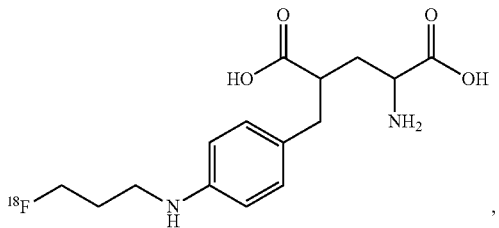 [SMILES: NC(CC(Cc1ccc(NCCC[18F])cc1)C(=O)O)C(=O)O]

,

4-{4-[(3-[18F]fluorocyclobutyl)oxy]benzyl}glutamic acid:

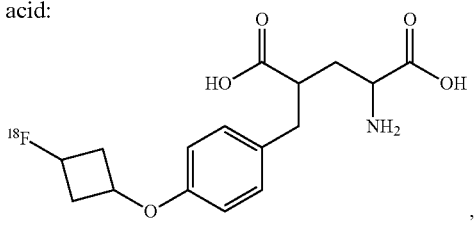

,

4-{3-[4-(2-[18F]fluoroethoxy)phenyl]propyl}glutamic acid:

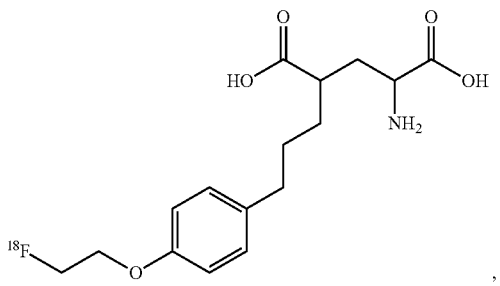 [SMILES: NC(CC(CCCc1ccc(OCC[18F])cc1)C(=O)O)C(=O)O]

, 2-amino-5-[4-(2-[18F]fluoroethoxy)benzyl]hexanedioic acid:

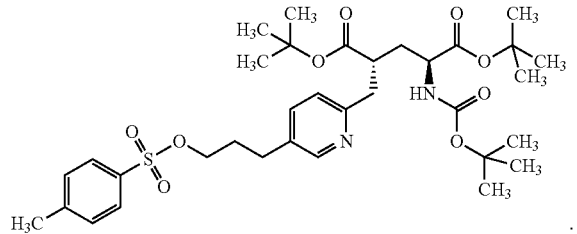 [SMILES: Cc1ccc(S(=O)(=O)OCCCc2ccc(C[C@@H](C[C@H](NC(=O)OC(C)(C)C)C(=O)OC(C)(C)C)C(=O)OC(C)(C)C)nc2)cc1]

4-[4-(2-[18F]fluoroethoxy)benzyl]-L-glutamic acid:

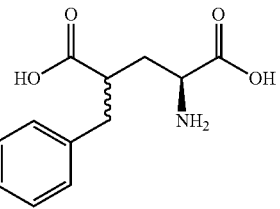

,

4-[4-(3-[18F]fluoropropoxy)benzyl]-L-glutamic acid:

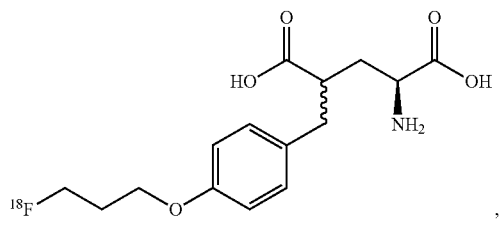 [SMILES: N[C@@H](CC(Cc1ccc(OCCC[18F])cc1)C(=O)O)C(=O)O]

,

4-[4-(3-[18F]fluoropropyl)benzyl]-L-glutamic acid:

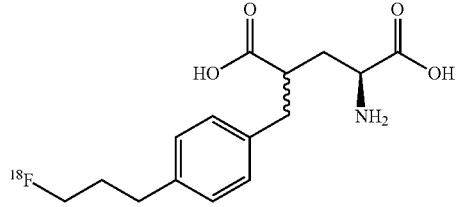

,

4-{4-[(3-[18F]fluoropropyl)amino]benzyl}-L-glutamic acid:

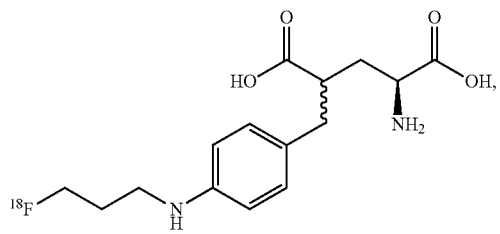

,

4-{4-[(cis-3-[18F]fluorocyclobutyl)oxy]benzyl}-L-glutamic acid:

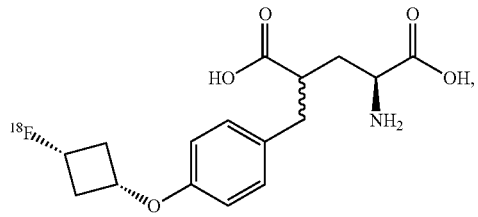

, (4S)-4-{3-[4-(2-[18F]fluoroethoxy)phenyl]propyl}-L-glutamic acid:

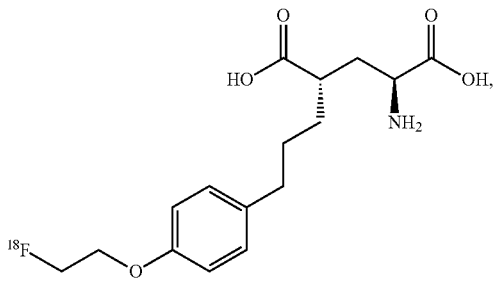 [SMILES: N[C@@H](C[C@H](CCCc1ccc(OCC[18F])cc1)C(=O)O)C(=O)O]

(2S)-2-amino-5-[4-(2-[18F]fluoroethoxy)benzyl]hexanedioic acid:

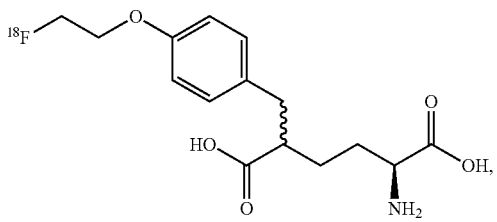 [SMILES: N[C@@H](CCC(Cc1ccc(OCC[18F])cc1)C(=O)O)C(=O)O]

(2R)-2-amino-5-[4-(2-[18F]fluoroethoxy)benzyl]hexanedioic acid:

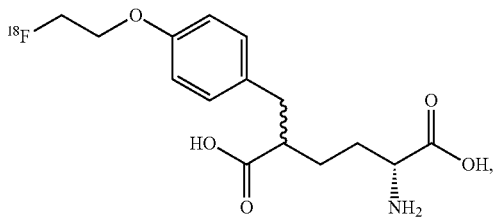

(4-{[5-(2-[18F]fluoroethoxy)pyridin-2-yl]methyl}-L-glutamic acid:

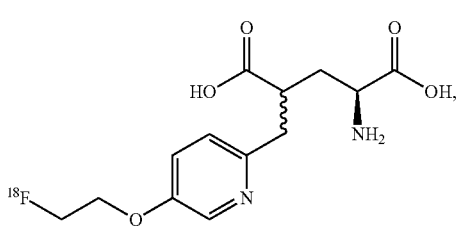

(2S)-2-Amino-5-{[5-(2-[18F]fluoroethoxy)pyridin-2-yl]methyl}hexanedioic acid:

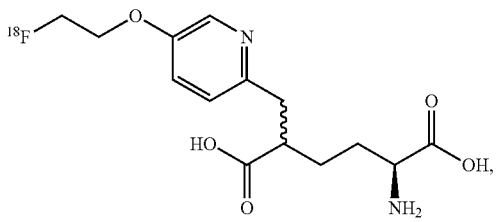

4-{[5-(2-[18F]fluoroethoxy)-1-oxidopyridin-2-yl]methyl}-L-glutamic acid:

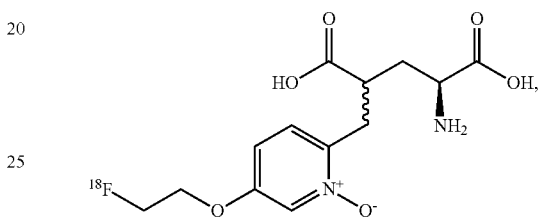

(2S)-2-amino-5-{2-[4-(2-[18F]fluoroethoxy)phenyl]ethyl}hexanedioic acid:

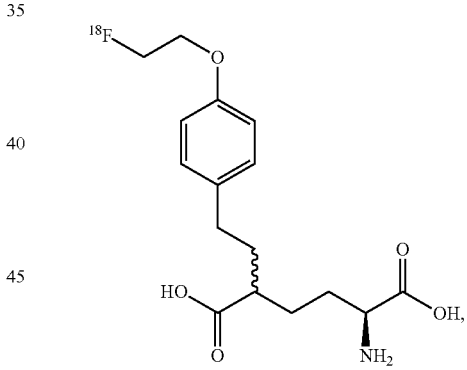

(2S)-2-amino-5-[4-([18F]fluoromethoxy)benzyl]hexanedioic acid:

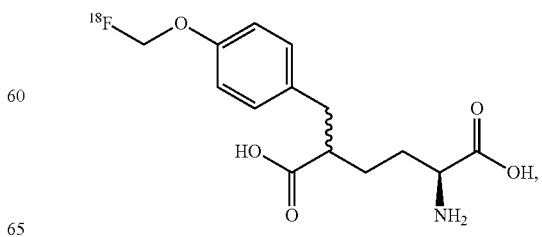

237

(2S,5R)-2-amino-5-[4-([^18F]fluoromethoxy)benzyl]hex-anedioic acid:

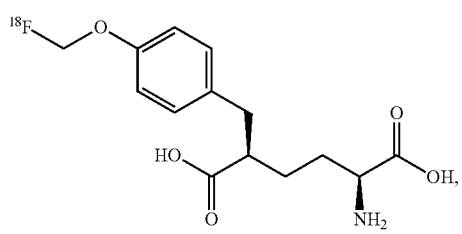

(2S,5S)-2-amino-5-[4-([^18F]fluoromethoxy)benzyl]hex-anedioic acid:

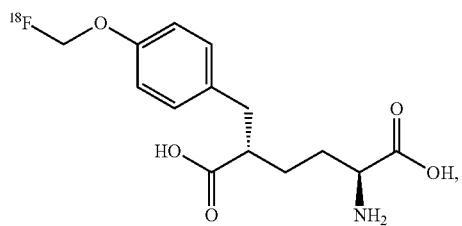

4-[4-(2-[^18F]fluoroethoxy)-3-hydroxybenzyl]-L-glutamic acid:

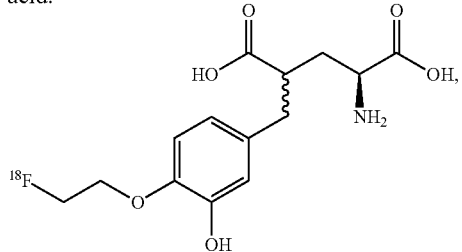

(4S)-4-{4-[(^18F)fluoromethoxy]benzyl}-L-glutamic acid:

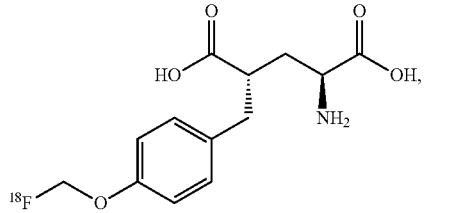 [SMILES: N[C@@H](C[C@H](Cc1ccc(OC[18F])cc1)C(=O)O)C(=O)O]

(4R)-4-{4-[(^18F)fluoromethoxy]benzyl}-L-glutamic acid:

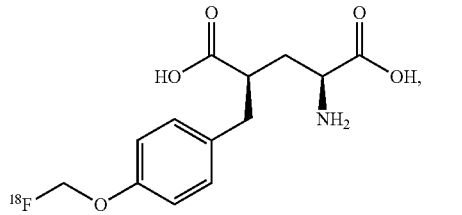 [SMILES: N[C@@H](C[C@@H](Cc1ccc(OC[18F])cc1)C(=O)O)C(=O)O]

238

(2S)-2-amino-5-(4-{[2-(^18F)fluoroethyl]amino}benzyl)hexanedioic acid:

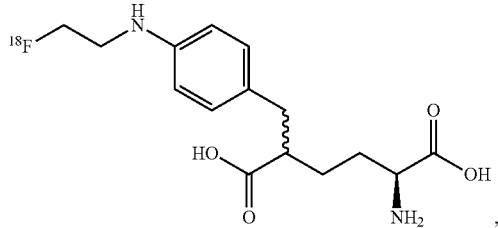

(2S)-2-amino-5-(4-{[(2S,3R)-4-(^18F)fluoro-2,3-dihydroxybutyl]oxy}benzyl)hexanedioic acid:

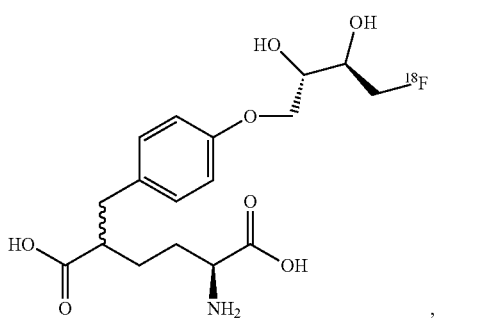 [SMILES: N[C@@H](CCC(Cc1ccc(OC[C@H](O)[C@@H](O)C[18F])cc1)C(=O)O)C(=O)O]

4-({6-[2-(^18F)fluoroethoxy]pyridin-3-yl}methyl)-L-glutamic acid:

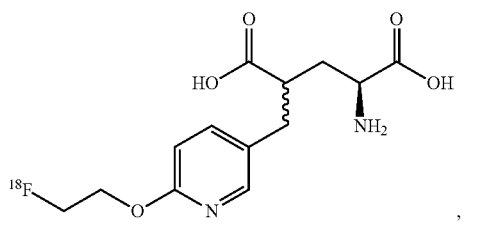 [SMILES: N[C@@H](CC(Cc1ccc(OCC[18F])nc1)C(=O)O)C(=O)O]

4-(4-{[2S,3R]-4-(^18F)fluoro-2,3-dihydroxybutyl]oxy}benzyl)-L-glutamic acid:

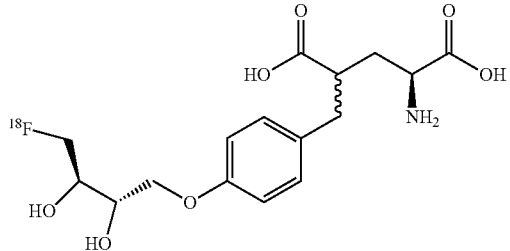

4-(4-{[1-($^{18}$F)fluoro-3-hydroxypropan-2-yl]oxy}benzyl)-L-glutamic acid:

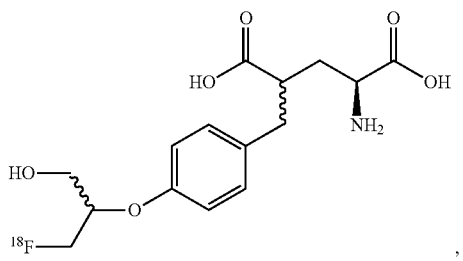 [SMILES: N[C@@H](CC(Cc1ccc(OC(CO)C[18F])cc1)C(=O)O)C(=O)O]

4-({1-[2-($^{18}$F)fluoroethyl]-1H-1,2,3-triazol-4-yl}methyl)-L-glutamic acid:

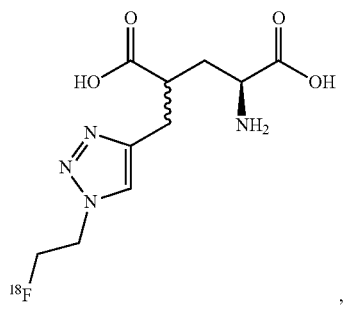

(2S,5R)-2-amino-5-[4-([$^{18}$F]fluoroethoxy)benzyl]hexanedioic acid:

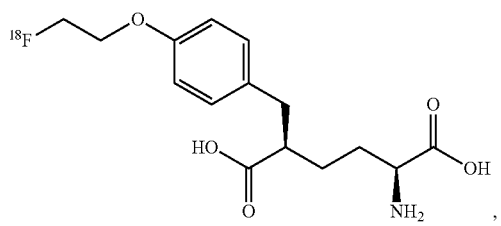 [SMILES: N[C@@H](CC[C@H](Cc1ccc(OCC[18F])cc1)C(=O)O)C(=O)O]

(2S,5S)-2-amino-5-[4-([$^{18}$F]fluoroethoxy)benzyl]hexanedioic acid:

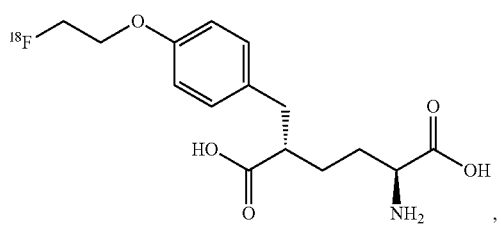 [SMILES: N[C@@H](CC[C@@H](Cc1ccc(OCC[18F])cc1)C(=O)O)C(=O)O]

and

4-{4-[($^{18}$F)fluoromethyl]benzyl}-L-glutamic acid:

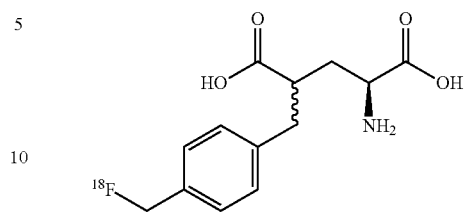

4. A method for preparation of a compound according to claim 1, wherein $L^1$ is alkylene-O, alkylene-NH or cycloalkylene-O, said method comprising:

(a) reacting of a compound of Formula IV,

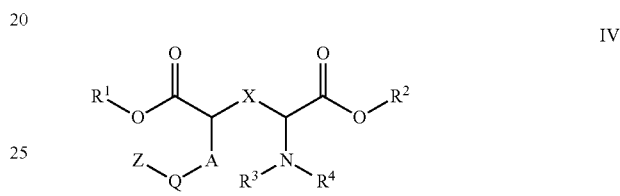

IV wherein
$R^1$ is a carboxyl protecting group or hydrogen,
$R^2$ is a carboxyl protecting group or hydrogen,
$R^3$ is hydrogen or an amine protecting group,
$R^4$ is hydrogen or an amine protecting group,
X is selected from:
  a) $CH_2$, and
  b) $CH_2$—$CH_2$,
A is alkylene,
Q is arylene or heteroarylene,
Z is OH or $NH_2$,
L is selected from:
  a) alkylene,
  b) alkylene-O*,
  c) alkylene-N*H,
  d) cycloalkylene-O*,
  e) ($R^5$—O)-substituted alkylene,
  f) ($R^5$—O)-substituted alkylene-O*,
  g) ($R^6$—O), ($R^7$—O)-disubstituted alkylene,
  h) ($R^6$—O), ($R^7$—O)-disubstituted alkylene-O*
  i) $(CH_2CH_2O)_n$—$CH_2CH_2$—O* with n=1, 2 or 3,
* indicates the position of the bond to Q,
$R^5$ is
  a) hydrogen or
  b) hydroxyl protecting group,
$R^6$ is
  a) hydrogen or
  b) hydroxyl protecting group,
$R^7$ is
  a) hydrogen or
  b) hydroxyl protecting group, and
with the proviso that Z is not OH if X is $CH_2$, and Q is phenyl;
with an 18F labeled building block of formula VII, $^{18}$F-L'-LG wherein
LG is a leaving group, and
L' is alkylene or cycloalkylene; and (b) cleaving protecting groups to obtain a compound of Formula III.

5. A pharmaceutical composition comprising a compound of according to claim 1, and at least one pharmaceutically acceptable carrier, diluent, adjuvant or excipient.

6. An imaging tracer or radiopharmaceutical agent for imaging proliferative diseases comprising a compound according to claim 1.

7. A composition comprising one or more compounds according to claim 1.

8. A method for imaging or diagnosing a proliferative disease in a mammal, comprising administering to said mammal an effective amount of a compound according to claim 1, obtaining an image of said mammal.

9. The compound according to claim 1, wherein A is —$CH_2$—, Q is phenylene, and L is —$CH_2CH_2$—O—.

10. The compound according to claim 9, wherein X is —$CH_2$—.

11. The compound according to claim 9, wherein X is $CH_2$—$CH_2$.

12. The compound according to claim 1, wherein X is —$CH_2$—.

13. The compound according to claim 1, wherein X is $CH_2$—$CH_2$.

14. The compound according to claim 1, wherein A is $C_1$-$C_6$ alkylene.

15. The compound according to claim 1, wherein A is $C_1$-$C_3$ alkylene.

16. The compound according to claim 1, wherein Q is phenylene.

17. The compound according to claim 1, wherein Q is triazolylene.

18. The compound according to claim 1, wherein Q is or pyridylene.

19. The compound according to claim 1, wherein L is $C_2$-$C_6$ alkylene, $C_2$-$C_6$ alkylene-O*, $C_2$-$C_6$ alkylene-N*H, $C_3$-$C_6$ cycloalkylene-O*, monohydroxy $C_2$-$C_6$ alkylene, monohydroxy $C_3$-$C_6$ alkylene-O*, dihydroxy $C_3$-$C_6$ alkylene, dihydroxy C4-$C_6$ alkylene-O*, or ($CH_2CH_2O)_n$—$CH_2CH_2$—O*, wherein n is 1, 2, or 3, and * indicates the position of the bond to Q.

20. The compound according to claim 1, wherein $L^1$ is propylene, propylene-O*, ethylene-O*, propylene-N*H, position of the bond to Q,

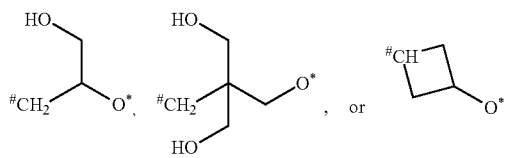

wherein n is 1, 2, or 3, and * indicates the position of the bond to Q and # indicates the position of the bond to $^{18}F$.

21. The compound according to claim 1, wherein
A is $C_1$-$C_6$ alkylene;
Q is phenylene, triazolylene, or pyridylene; and
$L^1$ is $C_2$-$C_6$ alkylene, $C_2$-$C_6$ alkylene-O*, $C_2$-$C_6$ alkylene-N*H, $C_3$-$C_6$ cycloalkylene-O*, monohydroxy $C_2$-$C_6$ alkylene, monohydroxy $C_3$-$C_6$ alkylene-O*, dihydroxy $C_3$-$C_6$ alkylene, dihydroxy C4-$C_6$ alkylene-O*, or ($CH_2CH_2O)_n$—$CH_2CH_2$—O*, wherein n is 1, 2, or 3, and * indicates the position of the bond to Q.

22. A compound according to claim 3, wherein said compound is:
4-[4-(2-[$^{18}F$]fluoroethoxy)benzyl]glutamic acid:

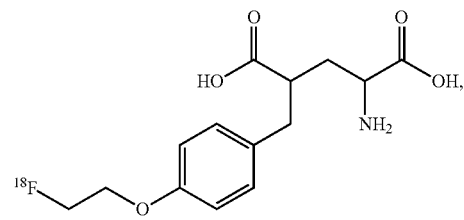 [SMILES: NC(CC(Cc1ccc(OCC[18F])cc1)C(=O)O)C(=O)O]

4-[4-(3-[$^{18}F$]fluoropropoxy)benzyl]glutamic acid:

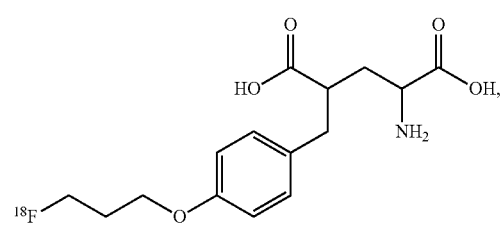 [SMILES: NC(CC(Cc1ccc(OCCC[18F])cc1)C(=O)O)C(=O)O]

4-[4-(3-[$^{18}F$]fluoropropyl)benzyl]glutamic acid:

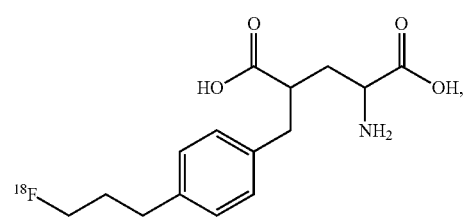 [SMILES: NC(CC(Cc1ccc(CCC[18F])cc1)C(=O)O)C(=O)O]

4-[4-{(3-[$^{18}F$]fluoropropyl)amino]benzyl]glutamic acid:

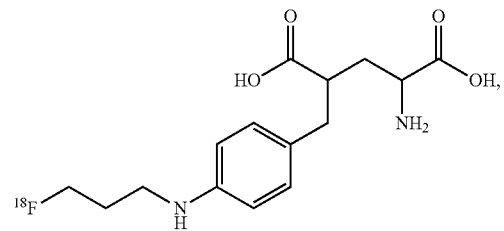 [SMILES: NC(CC(Cc1ccc(NCCC[18F])cc1)C(=O)O)C(=O)O]

or
4-{4-[(3-[$^{18}F$]fluorocyclobutyl)oxy]benzyl}glutamic acid:

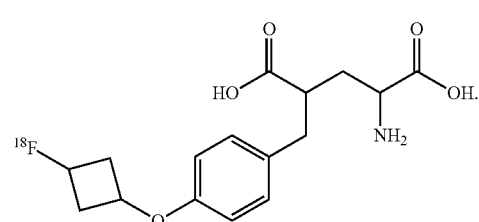

23. A compound according to claim 3, wherein said compound is:

4-{3-[4-(2-[¹⁸F]fluoroethoxy)phenyl]propyl}glutamic acid:

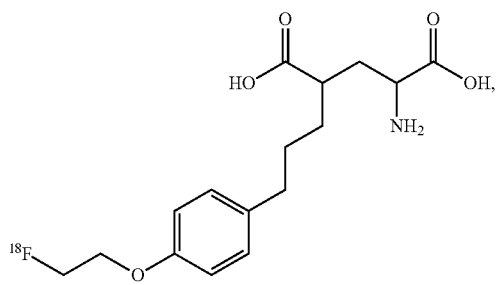 [SMILES: NC(CC(CCCc1ccc(OCC[18F])cc1)C(=O)O)C(=O)O]

2-amino-5-[4-(2-[¹⁸F]fluoroethoxy)benzyl]hexanedioic acid:

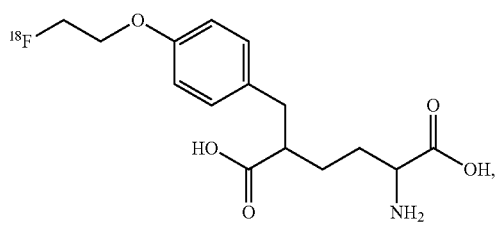

4-[4-(2-[¹⁸F]fluoroethoxy)benzyl]-L-glutamic acid:

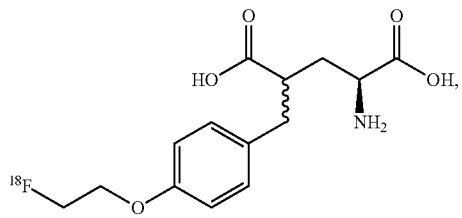

4-[4-(3-[¹⁸F]fluoropropoxy)benzyl]-L-glutamic acid:

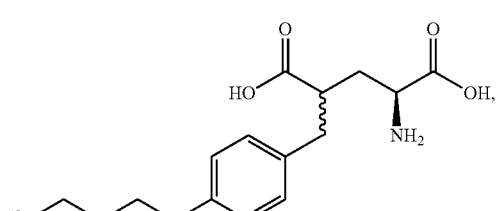

or

4-[4-(3-[¹⁸F]fluoropropyl)benzyl]-L-glutamic acid:

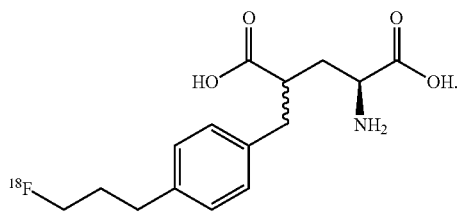 [SMILES: N[C@@H](CC(Cc1ccc(CCC[18F])cc1)C(=O)O)C(=O)O]

24. A compound according to claim 3, wherein said compound is:

4-{4-[(3-[¹⁸F]fluoropropyl)amino]benzyl}-L-glutamic acid:

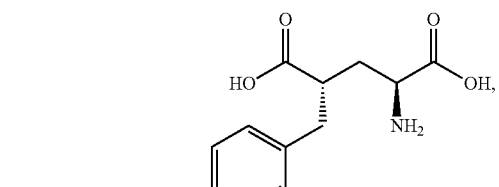

4-{4-[(cis-3-[¹⁸F]fluorocyclobutyl)oxy]benzyl}-L-glutamic acid:

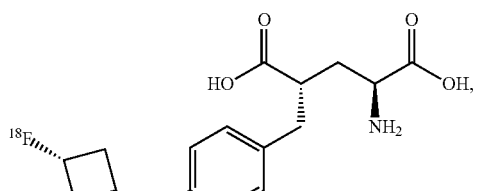

(4S)-4-{3-[4-(2-[¹⁸F]fluoroethoxy)phenyl]propyl}-L-glutamic acid:

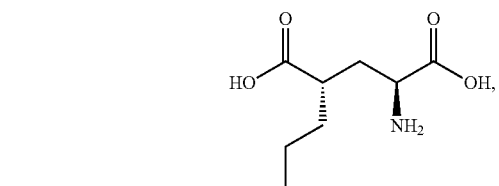
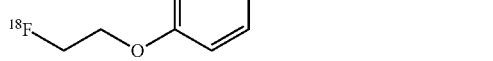

245

(2S)-2-amino-5-[4-(2-[$^{18}$F]fluoroethoxy)benzyl]hexanedioic acid:

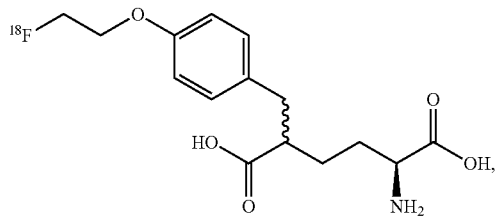

or (2R)-2-amino-5-[4-(2-[$^{18}$F]fluoroethoxy)benzyl]hexanedioic acid:

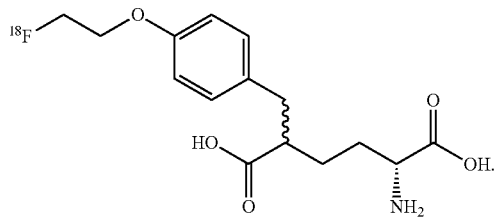

25. A compound according to claim 3, wherein said compound is:

(4-{[5-(2-[$^{18}$F]fluoroethoxy)pyridin-2-yl]methyl}-L-glutamic acid:

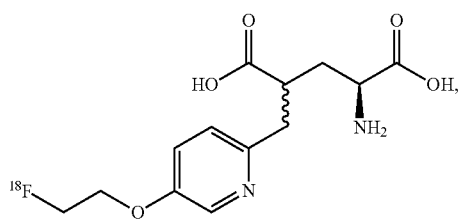

(2S)-2-Amino-5-{[5-(2-[$^{18}$F]fluoroethoxy)pyridin-2-yl]methyl}hexanedioic acid:

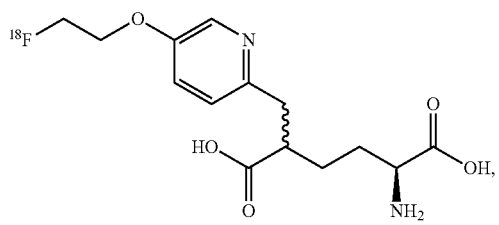

246

4-{[5-(2-[$^{18}$F]fluoroethoxy)-1-oxidopyridin-2-yl]methyl}-L-glutamic acid:

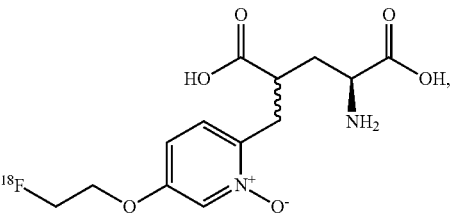 [SMILES: N[C@@H](CC(Cc1ccc(OCC[18F])c[n+]1[O-])C(=O)O)C(=O)O]

(2S)-2-amino-5-{2-[4-(2-[$^{18}$F]fluoroethoxy)phenyl]ethyl}hexanedioic acid:

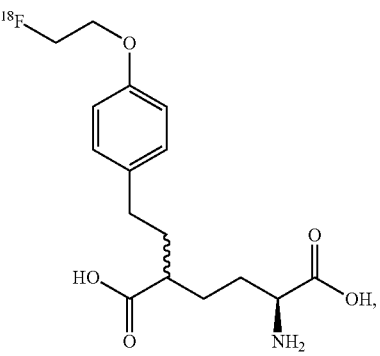 [SMILES: N[C@@H](CCC(CCc1ccc(OCC[18F])cc1)C(=O)O)C(=O)O]

or (2S)-2-amino-5-[4-([$^{18}$F]fluoromethoxy)benzyl]hexanedioic acid:

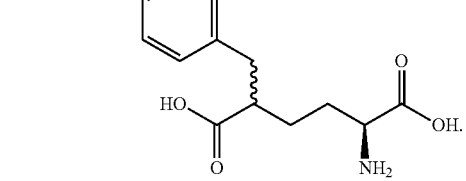

26. A compound according to claim 3, wherein said compound is:

(2S,5R)-2-amino-5-[4-([$^{18}$F]fluoromethoxy)benzyl]hexanedioic acid:

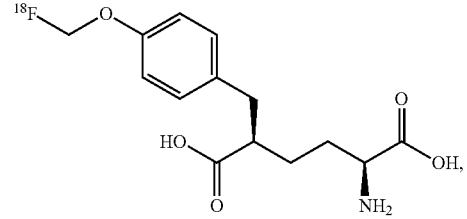

247

(2S,5S)-2-amino-5-[4-([$^{18}$F]fluoromethoxy)benzyl]hex-anedioic acid:

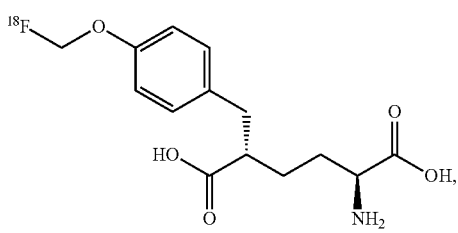

4-[4-(2-[$^{18}$F]fluoroethoxy)-3-hydroxybenzyl]-L-glutamic acid:)

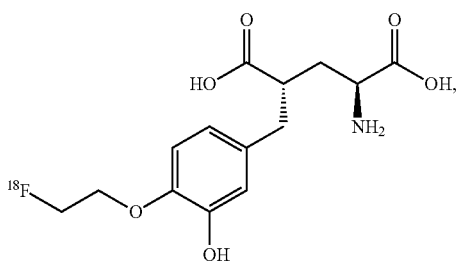 [SMILES: N[C@@H](C[C@H](Cc1ccc(OCC[18F])c(O)c1)C(=O)O)C(=O)O]

or (4S)-4-{4-[($^{18}$F)fluoromethoxy]benzyl}-L-glutamic acid:

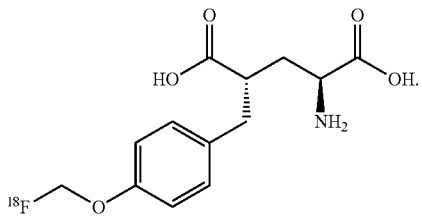

27. A compound according to claim 3, wherein said compound is:

(4R)-4-{4-[($^{18}$F)fluoromethoxy]benzyl}-L-glutamic acid:

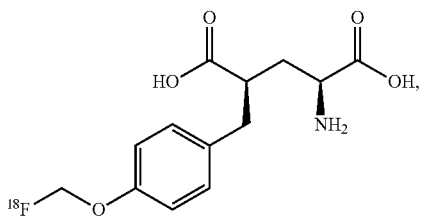 [SMILES: N[C@@H](C[C@@H](Cc1ccc(OC[18F])cc1)C(=O)O)C(=O)O]

248

(2S)-2-amino-5-(4-{[2-($^{18}$F)fluoroethyl]amino}benzyl)hexanedioic acid:

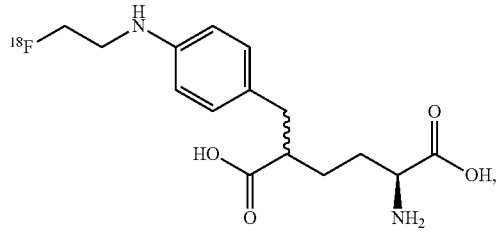 [SMILES: N[C@@H](CCC(Cc1ccc(NCC[18F])cc1)C(=O)O)C(=O)O]

(2S)-2-amino-5-(4-{[(2S,3R)-4-($^{18}$F)fluoro-2,3-dihydroxybutyl]oxy}benzyl)hexanedioic acid:

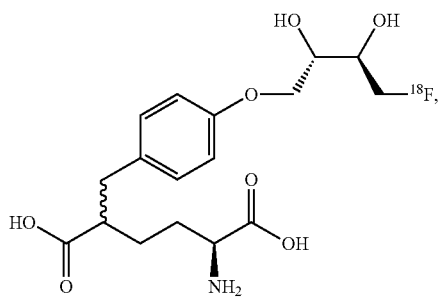

4-({6-[2-($^{18}$F)fluoroethoxy]pyridin-3-yl}methyl)-L-glutamic acid:

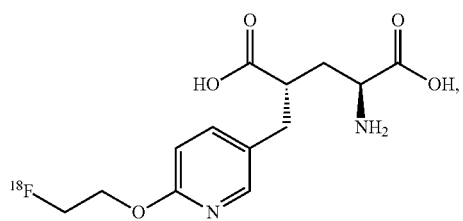

or 4-(4-{[2S,3R]-4-($^{18}$F)fluoro-2,3-dihydroxybutyl]oxy}benzyl)-L-glutamic acid:

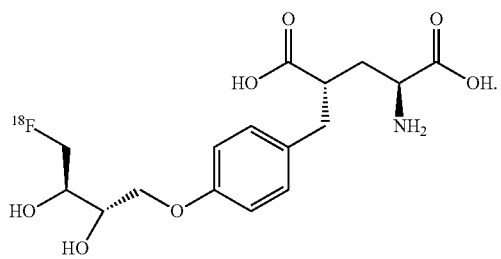 [SMILES: N[C@@H](C[C@H](Cc1ccc(OC[C@H](O)[C@@H](O)C[18F])cc1)C(=O)O)C(=O)O]

28. A compound according to claim 3, wherein said compound is:
4-(4-{[1-($^{18}$F)fluoro-3-hydroxypropan-2-yl]oxy}benzyl)-L-glutamic acid:
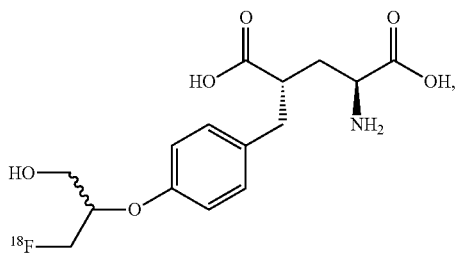 [SMILES: N[C@@H](C[C@H](Cc1ccc(OC(CO)C[18F])cc1)C(=O)O)C(=O)O]
4-({1-[2-($^{18}$F)fluoroethyl]-1H-1,2,3-triazol-4-yl}methyl)-L-glutamic acid:
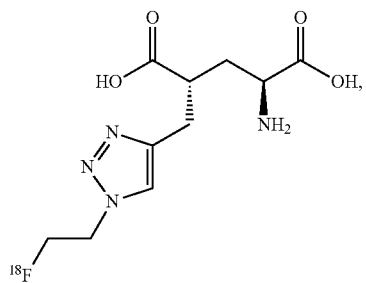 [SMILES: N[C@@H](C[C@H](Cc1cn(CC[18F])nn1)C(=O)O)C(=O)O]
(2S,5R)-2-amino-5-[4-([$^{18}$F]fluoroethoxy)benzyl]hexanedioic acid:
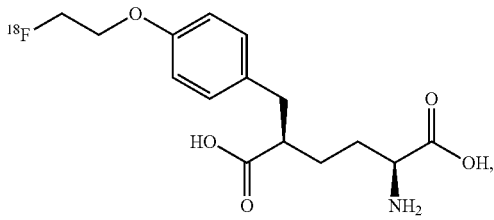
(2S,5S)-2-amino-5-[4-([$^{18}$F]fluoroethoxy)benzyl]hexanedioic acid:
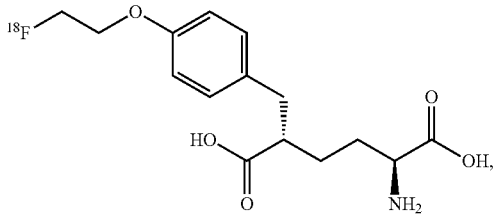
or
4-{4-[($^{18}$F)fluoromethyl]benzyl}-L-glutamic acid:
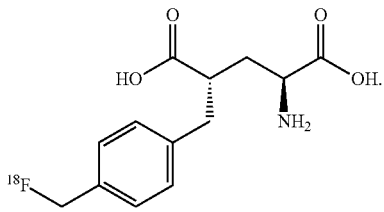 [SMILES: N[C@@H](C[C@H](Cc1ccc(C[18F])cc1)C(=O)O)C(=O)O]
* * * * *